(12) United States Patent
Shelton, IV et al.

(10) Patent No.: US 11,937,866 B2
(45) Date of Patent: Mar. 26, 2024

(54) METHOD FOR AN ELECTROSURGICAL PROCEDURE

(71) Applicant: Cilag GmbH International, Zug (CH)

(72) Inventors: Frederick E. Shelton, IV, Hillsboro, OH (US); Kevin M. Fiebig, Cincinnati, OH (US); Taylor W. Aronhalt, Loveland, OH (US); Jeffrey D. Messerly, Cincinnati, OH (US); Mark S. Zeiner, Mason, OH (US); Sarah A. Worthington, Cincinnati, OH (US); Joshua P. Morgan, Loveland, OH (US); Nicholas M. Morgan, Cincinnati, OH (US)

(73) Assignee: Cilag GmbH International, Zug (CH)

(*) Notice: Subject to any disclaimer, the term of this patent is extended or adjusted under 35 U.S.C. 154(b) by 402 days.

(21) Appl. No.: 16/885,813

(22) Filed: May 28, 2020

(65) Prior Publication Data

US 2021/0196354 A1    Jul. 1, 2021

Related U.S. Application Data

(60) Provisional application No. 62/955,299, filed on Dec. 30, 2019.

(51) Int. Cl.
*A61B 18/14* (2006.01)
*A61B 18/00* (2006.01)
*A61B 18/12* (2006.01)

(52) U.S. Cl.
CPC ...... *A61B 18/1445* (2013.01); *A61B 18/1206* (2013.01); *A61B 2018/00023* (2013.01);
(Continued)

(58) Field of Classification Search
CPC ............ A61B 18/1442; A61B 18/1445; A61B 18/1447; A61B 2018/1442;
(Continued)

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| CA | 2535467 A1 | 4/1993 |
| CN | 2460047 Y | 11/2001 |

(Continued)

OTHER PUBLICATIONS

Covidien Brochure, [Value Analysis Brief], LigaSure Advance™ Pistol Grip, dated Rev. Apr. 2010 (7 pages).
(Continued)

*Primary Examiner* — Joanne M Rodden
*Assistant Examiner* — Nora W Rhodes

(57) ABSTRACT

A method for performing an electrosurgical procedure using an electrosurgical instrument including an end effector is disclosed. The method comprises applying a bipolar energy to a target tissue grasped by the end effector in a tissue-feathering segment, applying an energy blend of the bipolar energy and a monopolar energy to the target tissue in a tissue-warming segment and a tissue-sealing segment following the tissue-warming segment, and discontinuing the bipolar energy but continuing to apply the monopolar energy to the target tissue in a tissue-cutting segment following the tissue-sealing segment.

17 Claims, 133 Drawing Sheets

(52) U.S. Cl.
CPC ............... *A61B 2018/00607* (2013.01); *A61B 2018/0063* (2013.01); *A61B 2018/00702* (2013.01); *A61B 2018/00791* (2013.01); *A61B 2018/00827* (2013.01); *A61B 2018/00875* (2013.01); *A61B 2018/00898* (2013.01); *A61B 2018/00958* (2013.01); *A61B 2018/00994* (2013.01); *A61B 2018/1253* (2013.01); *A61B 2018/126* (2013.01); *A61B 2018/1452* (2013.01)

(58) Field of Classification Search
CPC ...... A61B 2018/145; A61B 2018/1452; A61B 2018/1455; A61B 2018/1457; A61B 2018/146; A61B 2018/1462
See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,739,759 A * | 4/1988 | Rexroth ............ A61B 18/1206 606/39 |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |

(56) References Cited

U.S. PATENT DOCUMENTS

| | | |
|---|---|---|
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,926,860 A | 5/1990 | Stice et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,203,380 A | 4/1993 | Chikama |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |

(56) References Cited

U.S. PATENT DOCUMENTS

| | | |
|---|---|---|
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,536,267 A | 7/1996 | Edwards et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,042 A | 12/1997 | Boiarski et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |

(56) References Cited

U.S. PATENT DOCUMENTS

| | | |
|---|---|---|
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,238,384 B1 | 5/2001 | Peer |

(56) References Cited

U.S. PATENT DOCUMENTS

| | | |
|---|---|---|
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,558,380 B2 | 5/2003 | Lingenfelder et al. |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |

(56) References Cited

U.S. PATENT DOCUMENTS

| | | |
|---|---|---|
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |

(56) References Cited

U.S. PATENT DOCUMENTS

| | | |
|---|---|---|
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |

(56) References Cited

U.S. PATENT DOCUMENTS

| | | |
|---|---|---|
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,525,309 B2 | 4/2009 | Sherman et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |

(56) References Cited

U.S. PATENT DOCUMENTS

| | | |
|---|---|---|
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |

(56) References Cited

U.S. PATENT DOCUMENTS

| | | |
|---|---|---|
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,360,299 B2 | 1/2013 | Zemlok et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,398,674 B2 | 3/2013 | Prestel |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,036 B2 | 5/2013 | Shelton, IV |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |

(56) References Cited

U.S. PATENT DOCUMENTS

| | | |
|---|---|---|
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,521,331 B2 | 8/2013 | Itkowitz |
| 8,523,043 B2 | 9/2013 | Ullrich et al. |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,040 B2 | 1/2014 | Artsyukhovich et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |

(56) References Cited

U.S. PATENT DOCUMENTS

| | | |
|---|---|---|
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,807,414 B2 | 8/2014 | Ross et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,035 B2 | 5/2015 | Allen, IV et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,691 B2 | 5/2015 | Moua et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,230 B2 | 6/2015 | Morgan et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,083 B2 | 6/2015 | Yates et al. |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |

(56) References Cited

U.S. PATENT DOCUMENTS

| | | |
|---|---|---|
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,283,054 B2 | 3/2016 | Morgan et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,767 B2 | 5/2016 | Koch et al. |
| 9,326,787 B2 | 5/2016 | Sanai et al. |
| 9,326,788 B2 | 5/2016 | Batross et al. |
| 9,332,987 B2 | 5/2016 | Leimbach et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,727 B2 | 5/2016 | Leimbach et al. |
| 9,351,754 B2 | 5/2016 | Vakharia et al. |
| 9,352,173 B2 | 5/2016 | Yamada et al. |
| 9,358,003 B2 | 6/2016 | Hall et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,014 B2 | 8/2016 | Ingmanson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,438 B2 | 10/2016 | Baber et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,465 B1 | 1/2017 | Liu et al. |
| 9,554,794 B2 | 1/2017 | Baber et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,056 B2 | 3/2017 | Mozdzierz et al. |
| 9,592,072 B2 | 3/2017 | Akagane |
| 9,597,143 B2 | 3/2017 | Madan et al. |
| 9,603,669 B2 | 3/2017 | Govari et al. |

(56) References Cited

U.S. PATENT DOCUMENTS

| | | |
|---|---|---|
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,629,623 B2 | 4/2017 | Lytle, IV et al. |
| 9,629,629 B2 | 4/2017 | Leimbach et al. |
| 9,632,573 B2 | 4/2017 | Ogawa et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,230 B2 | 6/2017 | Leimbach et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,094 B2 | 8/2017 | Baber et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,733,663 B2 | 8/2017 | Leimbach et al. |
| 9,737,301 B2 | 8/2017 | Baber et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,757,128 B2 | 9/2017 | Baber et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,169 B2 | 10/2017 | Kimsey et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,626 B2 | 10/2017 | Parihar et al. |
| 9,801,648 B2 | 10/2017 | Houser et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,815,211 B2 | 11/2017 | Cao et al. |
| 9,820,738 B2 | 11/2017 | Lytle, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,826,977 B2 | 11/2017 | Leimbach et al. |
| 9,839,443 B2 | 12/2017 | Brockman et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,878,184 B2 | 1/2018 | Beaupre |
| 9,883,860 B2 | 2/2018 | Leimbach |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,901,321 B2 | 2/2018 | Harks et al. |
| 9,901,342 B2 | 2/2018 | Shelton, IV et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,642 B2 | 3/2018 | Leimbach et al. |
| 9,913,656 B2 | 3/2018 | Stulen |
| 9,913,680 B2 | 3/2018 | Voegele et al. |
| 9,918,730 B2 | 3/2018 | Trees et al. |
| 9,924,961 B2 | 3/2018 | Shelton, IV et al. |
| 9,925,003 B2 | 3/2018 | Parihar et al. |
| 9,931,118 B2 | 4/2018 | Shelton, IV et al. |
| 9,943,309 B2 | 4/2018 | Shelton, IV et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,968,355 B2 | 5/2018 | Shelton, IV et al. |
| 9,974,539 B2 | 5/2018 | Yates et al. |
| 9,987,000 B2 | 6/2018 | Shelton, IV et al. |
| 9,987,033 B2 | 6/2018 | Neurohr et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,501 B2 | 6/2018 | Shelton, IV et al. |
| 10,004,526 B2 | 6/2018 | Dycus et al. |
| 10,004,527 B2 | 6/2018 | Gee et al. |
| D822,206 S | 7/2018 | Shelton, IV et al. |
| 10,010,339 B2 | 7/2018 | Witt et al. |
| 10,010,341 B2 | 7/2018 | Houser et al. |
| 10,013,049 B2 | 7/2018 | Leimbach et al. |
| 10,016,199 B2 | 7/2018 | Baber et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| D826,405 S | 8/2018 | Shelton, IV et al. |
| 10,039,588 B2 | 8/2018 | Harper et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,052,044 B2 | 8/2018 | Shelton, IV et al. |

(56) References Cited

U.S. PATENT DOCUMENTS

| | | |
|---|---|---|
| 10,052,102 B2 | 8/2018 | Baxter, III et al. |
| 10,070,916 B2 | 9/2018 | Artale |
| 10,080,609 B2 | 9/2018 | Hancock et al. |
| 10,085,748 B2 | 10/2018 | Morgan et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,679 B2 | 10/2018 | Baber et al. |
| 10,111,699 B2 | 10/2018 | Boudreaux |
| 10,111,703 B2 | 10/2018 | Cosman, Jr. et al. |
| 10,117,649 B2 | 11/2018 | Baxter et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,154,848 B2 | 12/2018 | Chernov et al. |
| 10,154,852 B2 | 12/2018 | Conlon et al. |
| 10,159,483 B2 | 12/2018 | Beckman et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,178,992 B2 | 1/2019 | Wise et al. |
| 10,179,022 B2 | 1/2019 | Yates et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,455 B2 | 1/2019 | Hancock et al. |
| 10,194,907 B2 | 2/2019 | Marczyk et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,226,250 B2 | 3/2019 | Beckman et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,258,331 B2 | 4/2019 | Shelton, IV et al. |
| 10,258,505 B2 | 4/2019 | Ovchinnikov |
| 10,263,171 B2 | 4/2019 | Wiener et al. |
| 10,265,068 B2 | 4/2019 | Harris et al. |
| 10,265,117 B2 | 4/2019 | Wiener et al. |
| 10,265,118 B2 | 4/2019 | Gerhardt |
| 10,271,840 B2 | 4/2019 | Sapre |
| 10,271,851 B2 | 4/2019 | Shelton, IV et al. |
| D847,989 S | 5/2019 | Shelton, IV et al. |
| 10,278,721 B2 | 5/2019 | Dietz et al. |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,704 B2 | 5/2019 | Harris et al. |
| 10,299,810 B2 | 5/2019 | Robertson et al. |
| 10,299,821 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,579 B2 | 6/2019 | Chowaniec et al. |
| 10,314,582 B2 | 6/2019 | Shelton, IV et al. |
| 10,314,638 B2 | 6/2019 | Gee et al. |
| 10,321,907 B2 | 6/2019 | Shelton, IV et al. |
| 10,321,950 B2 | 6/2019 | Yates et al. |
| D854,151 S | 7/2019 | Shelton, IV et al. |
| 10,335,149 B2 | 7/2019 | Baxter, III et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,543 B2 | 7/2019 | Shelton, IV et al. |
| 10,342,602 B2 | 7/2019 | Strobl et al. |
| 10,342,606 B2 | 7/2019 | Cosman et al. |
| 10,342,623 B2 | 7/2019 | Huelman et al. |
| 10,348,941 B2 | 7/2019 | Elliot, Jr. et al. |
| 10,349,999 B2 | 7/2019 | Yates et al. |
| 10,350,016 B2 | 7/2019 | Burbank et al. |
| 10,350,025 B1 | 7/2019 | Loyd et al. |
| 10,357,246 B2 | 7/2019 | Shelton, IV et al. |
| 10,357,247 B2 | 7/2019 | Shelton, IV et al. |
| 10,357,303 B2 | 7/2019 | Conlon et al. |
| 10,363,084 B2 | 7/2019 | Friedrichs |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,376,305 B2 | 8/2019 | Yates et al. |
| 10,390,841 B2 | 8/2019 | Shelton, IV et al. |
| 10,398,439 B2 | 9/2019 | Cabrera et al. |
| 10,398,466 B2 | 9/2019 | Stulen et al. |
| 10,398,497 B2 | 9/2019 | Batross et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,413,352 B2 | 9/2019 | Thomas et al. |
| 10,413,353 B2 | 9/2019 | Kerr et al. |
| 10,420,552 B2 | 9/2019 | Shelton, IV et al. |
| 10,420,579 B2 | 9/2019 | Wiener et al. |
| 10,420,607 B2 | 9/2019 | Woloszko et al. |
| D865,175 S | 10/2019 | Widenhouse et al. |
| 10,426,471 B2 | 10/2019 | Shelton, IV et al. |
| 10,426,507 B2 | 10/2019 | Wiener et al. |
| 10,426,546 B2 | 10/2019 | Graham et al. |
| 10,426,978 B2 | 10/2019 | Akagane |
| 10,433,837 B2 | 10/2019 | Worthington et al. |
| 10,433,849 B2 | 10/2019 | Shelton, IV et al. |
| 10,433,865 B2 | 10/2019 | Witt et al. |
| 10,433,866 B2 | 10/2019 | Witt et al. |
| 10,433,900 B2 | 10/2019 | Harris et al. |
| 10,441,279 B2 | 10/2019 | Shelton, IV et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,448,986 B2 | 10/2019 | Zikorus et al. |
| 10,456,140 B2 | 10/2019 | Shelton, IV et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,470,762 B2 | 11/2019 | Leimbach et al. |
| 10,470,764 B2 | 11/2019 | Baxter, III et al. |
| 10,478,182 B2 | 11/2019 | Taylor |
| 10,478,190 B2 | 11/2019 | Miller et al. |
| 10,485,542 B2 | 11/2019 | Shelton, IV et al. |
| 10,485,543 B2 | 11/2019 | Shelton, IV et al. |
| 10,485,607 B2 | 11/2019 | Strobl et al. |
| D869,655 S | 12/2019 | Shelton, IV et al. |
| 10,492,785 B2 | 12/2019 | Overmyer et al. |
| 10,492,849 B2 | 12/2019 | Juergens et al. |
| 10,499,914 B2 | 12/2019 | Huang et al. |
| 10,507,033 B2 | 12/2019 | Dickerson et al. |
| 10,512,795 B2 | 12/2019 | Voegele et al. |
| 10,517,595 B2 | 12/2019 | Hunter et al. |

(56) References Cited

U.S. PATENT DOCUMENTS

| | | |
|---|---|---|
| 10,517,596 B2 | 12/2019 | Hunter et al. |
| 10,517,627 B2 | 12/2019 | Timm et al. |
| 10,524,787 B2 | 1/2020 | Shelton, IV et al. |
| 10,524,789 B2 | 1/2020 | Swayze et al. |
| 10,524,854 B2 | 1/2020 | Woodruff et al. |
| 10,524,872 B2 | 1/2020 | Stewart et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,543,008 B2 | 1/2020 | Vakharia et al. |
| 10,548,504 B2 | 2/2020 | Shelton, IV et al. |
| 10,548,655 B2 | 2/2020 | Scheib et al. |
| 10,555,769 B2 | 2/2020 | Worrell et al. |
| 10,561,560 B2 | 2/2020 | Boutoussov et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,892 B2 | 3/2020 | Danziger et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,929 B2 | 3/2020 | Boudreaux et al. |
| 10,595,930 B2 | 3/2020 | Scheib et al. |
| 10,603,036 B2 | 3/2020 | Hunter et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,420 B2 | 4/2020 | Shelton, IV et al. |
| 10,617,464 B2 | 4/2020 | Duppuis |
| 10,624,635 B2 | 4/2020 | Harris et al. |
| 10,624,691 B2 | 4/2020 | Wiener et al. |
| 10,631,858 B2 | 4/2020 | Burbank |
| 10,631,859 B2 | 4/2020 | Shelton, IV et al. |
| 10,632,630 B2 | 4/2020 | Cao et al. |
| RE47,996 E | 5/2020 | Turner et al. |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,639,092 B2 | 5/2020 | Corbett et al. |
| 10,639,098 B2 | 5/2020 | Cosman et al. |
| 10,646,269 B2 | 5/2020 | Worrell et al. |
| 10,646,292 B2 | 5/2020 | Solomon et al. |
| 10,653,413 B2 | 5/2020 | Worthington et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,677,764 B2 | 6/2020 | Ross et al. |
| 10,682,136 B2 | 6/2020 | Harris et al. |
| 10,682,138 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,688,321 B2 | 6/2020 | Wiener et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,119 B2 | 6/2020 | Smith |
| 10,702,270 B2 | 7/2020 | Shelton, IV et al. |
| 10,702,329 B2 | 7/2020 | Strobl et al. |
| 10,709,446 B2 | 7/2020 | Harris et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,233 B2 | 7/2020 | Wellman |
| D893,717 S | 8/2020 | Messerly et al. |
| 10,729,458 B2 | 8/2020 | Stoddard et al. |
| 10,729,494 B2 | 8/2020 | Parihar et al. |
| 10,736,629 B2 | 8/2020 | Shelton, IV et al. |
| 10,736,685 B2 | 8/2020 | Wiener et al. |
| 10,751,108 B2 | 8/2020 | Yates et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,294 B2 | 9/2020 | Jones |
| 10,765,427 B2 | 9/2020 | Shelton, IV et al. |
| 10,765,470 B2 | 9/2020 | Yates et al. |
| 10,772,629 B2 | 9/2020 | Shelton, IV et al. |
| 10,772,630 B2 | 9/2020 | Wixey |
| 10,779,821 B2 | 9/2020 | Harris et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,845 B2 | 9/2020 | Timm et al. |
| 10,779,849 B2 | 9/2020 | Shelton, IV et al. |
| 10,779,879 B2 | 9/2020 | Yates et al. |
| 10,786,253 B2 | 9/2020 | Shelton, IV et al. |
| 10,786,276 B2 | 9/2020 | Hirai et al. |
| 10,806,454 B2 | 10/2020 | Kopp |
| 10,813,638 B2 | 10/2020 | Shelton, IV et al. |
| 10,820,938 B2 | 11/2020 | Fischer et al. |
| 10,828,058 B2 | 11/2020 | Shelton, IV et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,307 B2 | 11/2020 | Shelton, IV et al. |
| 10,842,492 B2 | 11/2020 | Shelton, IV et al. |
| 10,842,523 B2 | 11/2020 | Shelton, IV et al. |
| 10,842,563 B2 | 11/2020 | Gilbert et al. |
| D906,355 S | 12/2020 | Messerly et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,856,896 B2 | 12/2020 | Eichmann et al. |
| 10,856,929 B2 | 12/2020 | Yates et al. |
| 10,856,934 B2 | 12/2020 | Trees et al. |
| 10,874,465 B2 | 12/2020 | Weir et al. |
| D908,216 S | 1/2021 | Messerly et al. |
| 10,881,399 B2 | 1/2021 | Shelton, IV et al. |
| 10,881,401 B2 | 1/2021 | Baber et al. |
| 10,881,409 B2 | 1/2021 | Cabrera |
| 10,881,449 B2 | 1/2021 | Boudreaux et al. |
| 10,888,322 B2 | 1/2021 | Morgan et al. |
| 10,888,347 B2 | 1/2021 | Witt et al. |
| 10,893,863 B2 | 1/2021 | Shelton, IV et al. |
| 10,893,864 B2 | 1/2021 | Harris et al. |
| 10,893,883 B2 | 1/2021 | Dannaher |
| 10,898,186 B2 | 1/2021 | Bakos et al. |
| 10,898,256 B2 | 1/2021 | Yates et al. |
| 10,912,559 B2 | 2/2021 | Harris et al. |
| 10,912,580 B2 | 2/2021 | Green et al. |
| 10,912,603 B2 | 2/2021 | Boudreaux et al. |
| 10,918,385 B2 | 2/2021 | Overmyer et al. |
| 10,925,659 B2 | 2/2021 | Shelton, IV et al. |
| D914,878 S | 3/2021 | Shelton, IV et al. |
| 10,932,766 B2 | 3/2021 | Tesar et al. |
| 10,932,847 B2 | 3/2021 | Yates et al. |
| 10,945,727 B2 | 3/2021 | Shelton, IV et al. |
| 10,952,788 B2 | 3/2021 | Asher et al. |
| 10,959,727 B2 | 3/2021 | Hunter et al. |
| 10,966,741 B2 | 4/2021 | Illizaliturri-Sanchez et al. |
| 10,966,747 B2 | 4/2021 | Worrell et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,980,536 B2 | 4/2021 | Weaner et al. |
| 10,987,123 B2 | 4/2021 | Weir et al. |
| 10,987,156 B2 | 4/2021 | Trees et al. |
| 10,993,715 B2 | 5/2021 | Shelton, IV et al. |
| 10,993,716 B2 | 5/2021 | Shelton, IV et al. |

(56) References Cited

U.S. PATENT DOCUMENTS

| | | |
|---|---|---|
| 10,993,763 B2 | 5/2021 | Batross et al. |
| 11,000,278 B2 | 5/2021 | Shelton, IV et al. |
| 11,000,279 B2 | 5/2021 | Shelton, IV et al. |
| 11,020,114 B2 | 6/2021 | Shelton, IV et al. |
| 11,020,140 B2 | 6/2021 | Gee et al. |
| 11,033,322 B2 | 6/2021 | Wiener et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,051,840 B2 | 7/2021 | Shelton, IV et al. |
| 11,051,873 B2 | 7/2021 | Wiener et al. |
| 11,058,424 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,064,997 B2 | 7/2021 | Shelton, IV et al. |
| 11,065,048 B2 | 7/2021 | Messerly et al. |
| 11,083,455 B2 | 8/2021 | Shelton, IV et al. |
| 11,083,458 B2 | 8/2021 | Harris et al. |
| 11,090,048 B2 | 8/2021 | Fanelli et al. |
| 11,090,049 B2 | 8/2021 | Bakos et al. |
| 11,090,104 B2 | 8/2021 | Wiener et al. |
| 11,096,688 B2 | 8/2021 | Shelton, IV et al. |
| 11,096,752 B2 | 8/2021 | Stulen et al. |
| 11,109,866 B2 | 9/2021 | Shelton, IV et al. |
| 11,129,611 B2 | 9/2021 | Shelton, IV et al. |
| 11,129,666 B2 | 9/2021 | Messerly et al. |
| 11,129,669 B2 | 9/2021 | Stulen et al. |
| 11,129,670 B2 | 9/2021 | Shelton, IV et al. |
| 11,134,942 B2 | 10/2021 | Harris et al. |
| 11,134,978 B2 | 10/2021 | Shelton, IV et al. |
| 11,141,154 B2 | 10/2021 | Shelton, IV et al. |
| 11,141,213 B2 | 10/2021 | Yates et al. |
| 11,147,551 B2 | 10/2021 | Shelton, IV |
| 11,147,553 B2 | 10/2021 | Shelton, IV |
| 11,160,551 B2 | 11/2021 | Shelton, IV et al. |
| 11,166,716 B2 | 11/2021 | Shelton, IV et al. |
| 11,172,929 B2 | 11/2021 | Shelton, IV |
| 11,179,155 B2 | 11/2021 | Shelton, IV et al. |
| 11,179,173 B2 | 11/2021 | Price et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,670 B2 | 12/2021 | Worrell et al. |
| 11,207,065 B2 | 12/2021 | Harris et al. |
| 11,207,067 B2 | 12/2021 | Shelton, IV et al. |
| 11,213,293 B2 | 1/2022 | Worthington et al. |
| 11,213,294 B2 | 1/2022 | Shelton, IV et al. |
| 11,219,453 B2 | 1/2022 | Shelton, IV et al. |
| 11,224,426 B2 | 1/2022 | Shelton, IV et al. |
| 11,224,497 B2 | 1/2022 | Shelton, IV et al. |
| 11,229,437 B2 | 1/2022 | Shelton, IV et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |
| 11,234,698 B2 | 2/2022 | Shelton, IV et al. |
| 11,241,235 B2 | 2/2022 | Shelton, IV et al. |
| 11,246,592 B2 | 2/2022 | Shelton, IV et al. |
| 11,246,625 B2 | 2/2022 | Kane et al. |
| 11,246,678 B2 | 2/2022 | Shelton, IV et al. |
| 11,253,256 B2 | 2/2022 | Harris et al. |
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,266,430 B2 | 3/2022 | Clauda et al. |
| 11,272,931 B2 | 3/2022 | Boudreaux et al. |
| 11,278,280 B2 | 3/2022 | Shelton, IV et al. |
| 11,284,890 B2 | 3/2022 | Nalagatla et al. |
| 11,291,440 B2 | 4/2022 | Harris et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,451 B2 | 4/2022 | Shelton, IV |
| 11,298,127 B2 | 4/2022 | Shelton, IV |
| 11,298,129 B2 | 4/2022 | Bakos et al. |
| 11,298,130 B2 | 4/2022 | Bakos et al. |
| 11,304,695 B2 | 4/2022 | Shelton, IV et al. |
| 11,304,696 B2 | 4/2022 | Shelton, IV et al. |
| 11,304,699 B2 | 4/2022 | Shelton, IV et al. |
| 11,311,306 B2 | 4/2022 | Shelton, IV et al. |
| 11,311,326 B2 | 4/2022 | Boudreaux |
| 11,311,342 B2 | 4/2022 | Parihar et al. |
| D950,728 S | 5/2022 | Bakos et al. |
| D952,144 S | 5/2022 | Boudreaux |
| 11,317,915 B2 | 5/2022 | Boudreaux et al. |
| 11,324,503 B2 | 5/2022 | Shelton, IV et al. |
| 11,324,527 B2 | 5/2022 | Aldridge et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,747 B2 | 5/2022 | Voegele et al. |
| 11,344,362 B2 | 5/2022 | Yates et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,369,377 B2 | 6/2022 | Boudreaux et al. |
| 11,376,098 B2 | 7/2022 | Shelton, IV et al. |
| 11,382,642 B2 | 7/2022 | Robertson et al. |
| 11,389,161 B2 | 7/2022 | Shelton, IV et al. |
| 11,389,164 B2 | 7/2022 | Yates et al. |
| 11,399,837 B2 | 8/2022 | Shelton, IV et al. |
| 11,399,855 B2 | 8/2022 | Boudreaux et al. |
| 11,406,382 B2 | 8/2022 | Shelton, IV et al. |
| 11,413,060 B2 | 8/2022 | Faller et al. |
| 11,419,606 B2 | 8/2022 | Overmyer et al. |
| 11,419,626 B2 | 8/2022 | Timm et al. |
| 11,424,027 B2 | 8/2022 | Shelton, IV |
| 11,426,167 B2 | 8/2022 | Shelton, IV et al. |
| 11,426,191 B2 | 8/2022 | Vakharia et al. |
| 11,446,029 B2 | 9/2022 | Shelton, IV et al. |
| 11,452,525 B2 | 9/2022 | Shelton, IV et al. |
| 11,464,511 B2 | 10/2022 | Timm et al. |
| 11,464,512 B2 | 10/2022 | Shelton, IV et al. |
| 11,464,601 B2 | 10/2022 | Shelton, IV et al. |
| 11,471,155 B2 | 10/2022 | Shelton, IV et al. |
| 11,471,156 B2 | 10/2022 | Shelton, IV et al. |
| 11,471,206 B2 | 10/2022 | Henderson et al. |
| 11,471,209 B2 | 10/2022 | Yates et al. |
| 11,478,242 B2 | 10/2022 | Shelton, IV et al. |
| 11,484,310 B2 | 11/2022 | Shelton, IV et al. |
| 11,504,122 B2 | 11/2022 | Shelton, IV et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0032452 A1 | 3/2002 | Tierney et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0133152 A1* | 9/2002 | Strul .................. A61B 18/1445 606/50 |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177862 A1 | 11/2002 | Aranyi et al. |
| 2003/0009164 A1 | 1/2003 | Woloszko et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0073981 A1 | 4/2003 | Whitman et al. |
| 2003/0109778 A1 | 6/2003 | Rashidi |

(56) References Cited

U.S. PATENT DOCUMENTS

| | | |
|---|---|---|
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0208186 A1 | 11/2003 | Moreyra |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0193153 A1 | 9/2004 | Sartor et al. |
| 2004/0193212 A1 | 9/2004 | Taniguchi et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217700 A1* | 9/2006 | Garito ............... A61B 18/1206 606/42 |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |

(56) References Cited

U.S. PATENT DOCUMENTS

| | | |
|---|---|---|
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0112206 A1 | 4/2009 | Dumbauld et al. |
| 2009/0118751 A1 | 5/2009 | Wiener et al. |
| 2009/0131885 A1 | 5/2009 | Akahoshi |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0248022 A1 | 10/2009 | Falkenstein et al. |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057081 A1 | 3/2010 | Hanna |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0015650 A1 | 1/2011 | Choi et al. |
| 2011/0022032 A1 | 1/2011 | Zemlok et al. |
| 2011/0028964 A1 | 2/2011 | Edwards |
| 2011/0071523 A1 | 3/2011 | Dickhans |
| 2011/0082494 A1 | 4/2011 | Kerr et al. |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0238079 A1 | 9/2011 | Hannaford et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |

(56) References Cited

U.S. PATENT DOCUMENTS

| | | |
|---|---|---|
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136347 A1 | 5/2012 | Brustad et al. |
| 2012/0136386 A1 | 5/2012 | Kishida et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0193396 A1 | 8/2012 | Zemlok et al. |
| 2012/0211542 A1 | 8/2012 | Racenet |
| 2012/0226266 A1 | 9/2012 | Ghosal et al. |
| 2012/0234893 A1 | 9/2012 | Schuckmann et al. |
| 2012/0253328 A1 | 10/2012 | Cunningham et al. |
| 2012/0265241 A1 | 10/2012 | Hart et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0085510 A1 | 4/2013 | Stefanchik et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0267874 A1 | 10/2013 | Marcotte et al. |
| 2013/0277410 A1 | 10/2013 | Fernandez et al. |
| 2013/0296843 A1 | 11/2013 | Boudreaux et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005663 A1 | 1/2014 | Heard et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0077426 A1 | 3/2014 | Park |
| 2014/0121569 A1 | 5/2014 | Schafer et al. |
| 2014/0135804 A1 | 5/2014 | Weisenburgh, II et al. |
| 2014/0163541 A1 | 6/2014 | Shelton, IV et al. |
| 2014/0163549 A1 | 6/2014 | Yates et al. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207124 A1 | 7/2014 | Aldridge et al. |
| 2014/0207135 A1 | 7/2014 | Winter |
| 2014/0221994 A1 | 8/2014 | Reschke |
| 2014/0246475 A1 | 9/2014 | Hall et al. |
| 2014/0249557 A1 | 9/2014 | Koch et al. |
| 2014/0263541 A1 | 9/2014 | Leimbach et al. |
| 2014/0263552 A1 | 9/2014 | Hall et al. |
| 2014/0276794 A1 | 9/2014 | Batchelor et al. |
| 2014/0276797 A1 | 9/2014 | Batchelor et al. |
| 2014/0276798 A1 | 9/2014 | Batchelor et al. |
| 2014/0373003 A1 | 12/2014 | Grez et al. |
| 2015/0014392 A1 | 1/2015 | Williams et al. |
| 2015/0032150 A1 | 1/2015 | Ishida et al. |
| 2015/0048140 A1 | 2/2015 | Penna et al. |
| 2015/0066027 A1 | 3/2015 | Garrison et al. |
| 2015/0080876 A1 | 3/2015 | Worrell et al. |
| 2015/0080887 A1 | 3/2015 | Sobajima et al. |
| 2015/0088122 A1 | 3/2015 | Jensen |
| 2015/0100056 A1 | 4/2015 | Nakamura |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0238260 A1 | 8/2015 | Nau, Jr. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2015/0317899 A1 | 11/2015 | Dumbauld et al. |
| 2015/0351765 A1 | 12/2015 | Valentine et al. |
| 2015/0351857 A1 | 12/2015 | Vander Poorten et al. |
| 2015/0374430 A1 | 12/2015 | Weiler et al. |
| 2016/0038228 A1 | 2/2016 | Daniel et al. |
| 2016/0044841 A1 | 2/2016 | Chamberlain |
| 2016/0045248 A1 | 2/2016 | Unger et al. |
| 2016/0051314 A1* | 2/2016 | Batchelor .......... A61B 18/1442 606/45 |
| 2016/0051316 A1 | 2/2016 | Boudreaux |
| 2016/0066913 A1 | 3/2016 | Swayze et al. |
| 2016/0175025 A1 | 6/2016 | Strobl |
| 2016/0175029 A1 | 6/2016 | Witt et al. |
| 2016/0206342 A1 | 7/2016 | Robertson et al. |
| 2016/0249910 A1 | 9/2016 | Shelton, IV et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0331455 A1* | 11/2016 | Hancock ............ A61B 18/1815 |
| 2016/0358849 A1 | 12/2016 | Jur et al. |
| 2017/0065331 A1 | 3/2017 | Mayer et al. |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0164997 A1 | 6/2017 | Johnson et al. |
| 2017/0189095 A1 | 7/2017 | Danziger et al. |
| 2017/0202595 A1 | 7/2017 | Shelton, IV |
| 2017/0224332 A1 | 8/2017 | Hunter et al. |
| 2017/0231628 A1 | 8/2017 | Shelton, IV et al. |
| 2017/0281186 A1 | 10/2017 | Shelton, IV et al. |
| 2017/0296177 A1 | 10/2017 | Harris et al. |
| 2017/0296180 A1 | 10/2017 | Harris et al. |
| 2017/0303954 A1 | 10/2017 | Ishii |
| 2017/0312018 A1 | 11/2017 | Trees et al. |
| 2017/0325874 A1 | 11/2017 | Noack et al. |
| 2017/0333073 A1 | 11/2017 | Faller et al. |
| 2017/0348044 A1 | 12/2017 | Wang et al. |
| 2018/0014872 A1 | 1/2018 | Dickerson |
| 2018/0132850 A1 | 5/2018 | Leimbach et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |

(56) References Cited

U.S. PATENT DOCUMENTS

| | | |
|---|---|---|
| 2018/0206904 A1 | 7/2018 | Felder et al. |
| 2018/0221045 A1 | 8/2018 | Zimmerman et al. |
| 2018/0289432 A1 | 10/2018 | Kostrzewski et al. |
| 2018/0303493 A1 | 10/2018 | Chapolini |
| 2018/0325517 A1 | 11/2018 | Wingardner et al. |
| 2018/0353245 A1 | 12/2018 | Mccloud et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0000475 A1 | 1/2019 | Shelton, IV et al. |
| 2019/0000477 A1 | 1/2019 | Shelton, IV et al. |
| 2019/0029746 A1 | 1/2019 | Dudhedia et al. |
| 2019/0038283 A1 | 2/2019 | Shelton, IV et al. |
| 2019/0104919 A1 | 4/2019 | Shelton, IV et al. |
| 2019/0125384 A1 | 5/2019 | Scheib et al. |
| 2019/0125390 A1 | 5/2019 | Shelton, IV et al. |
| 2019/0183504 A1 | 6/2019 | Shelton, IV et al. |
| 2019/0200844 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0201030 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201048 A1 | 7/2019 | Stulen et al. |
| 2019/0201104 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201594 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0209201 A1 | 7/2019 | Boudreaux et al. |
| 2019/0223941 A1 | 7/2019 | Kitamura et al. |
| 2019/0269455 A1 | 9/2019 | Mensch et al. |
| 2019/0290265 A1 | 9/2019 | Shelton, IV et al. |
| 2019/0298350 A1 | 10/2019 | Shelton, IV et al. |
| 2019/0298353 A1 | 10/2019 | Shelton, IV et al. |
| 2019/0366562 A1 | 12/2019 | Zhang et al. |
| 2019/0388091 A1 | 12/2019 | Eschbach et al. |
| 2020/0054321 A1 | 2/2020 | Harris et al. |
| 2020/0078076 A1 | 3/2020 | Henderson et al. |
| 2020/0078085 A1 | 3/2020 | Yates et al. |
| 2020/0078609 A1 | 3/2020 | Messerly et al. |
| 2020/0100825 A1 | 4/2020 | Henderson et al. |
| 2020/0100830 A1 | 4/2020 | Henderson et al. |
| 2020/0129261 A1 | 4/2020 | Eschbach |
| 2020/0138473 A1 | 5/2020 | Shelton, IV et al. |
| 2020/0188047 A1 | 6/2020 | Itkowitz et al. |
| 2020/0222111 A1 | 7/2020 | Yates et al. |
| 2020/0222112 A1 | 7/2020 | Hancock et al. |
| 2020/0229834 A1 | 7/2020 | Olson et al. |
| 2020/0237434 A1 | 7/2020 | Scheib et al. |
| 2020/0261078 A1 | 8/2020 | Bakos et al. |
| 2020/0261086 A1 | 8/2020 | Zeiner et al. |
| 2020/0261141 A1 | 8/2020 | Wiener et al. |
| 2020/0268433 A1 | 8/2020 | Wiener et al. |
| 2020/0305870 A1 | 10/2020 | Shelton, IV |
| 2020/0315623 A1 | 10/2020 | Eisinger et al. |
| 2020/0315712 A1 | 10/2020 | Jasperson et al. |
| 2020/0405296 A1 | 12/2020 | Shelton, IV et al. |
| 2020/0405302 A1 | 12/2020 | Shelton, IV et al. |
| 2020/0405316 A1 | 12/2020 | Shelton, IV et al. |
| 2020/0405409 A1 | 12/2020 | Shelton, IV et al. |
| 2020/0405410 A1 | 12/2020 | Shelton, IV |
| 2020/0405439 A1 | 12/2020 | Shelton, IV et al. |
| 2020/0410177 A1 | 12/2020 | Shelton, IV |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0177481 A1 | 6/2021 | Shelton, IV et al. |
| 2021/0177494 A1 | 6/2021 | Houser et al. |
| 2021/0177496 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186504 A1 | 6/2021 | Shelton, IV et al. |
| 2021/0186553 A1 | 6/2021 | Green et al. |
| 2021/0186554 A1 | 6/2021 | Green et al. |
| 2021/0196263 A1 | 7/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196301 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196350 A1 | 7/2021 | Fiebig et al. |
| 2021/0196351 A1 | 7/2021 | Sarley et al. |
| 2021/0196352 A1 | 7/2021 | Messerly et al. |
| 2021/0196353 A1 | 7/2021 | Gee et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196360 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |
| 2021/0393314 A1 | 12/2021 | Wiener et al. |
| 2021/0393319 A1 | 12/2021 | Shelton, IV et al. |
| 2022/0039891 A1 | 2/2022 | Stulen et al. |
| 2022/0071655 A1 | 3/2022 | Price et al. |
| 2022/0168005 A1 | 6/2022 | Aldridge et al. |
| 2022/0168039 A1 | 6/2022 | Worrell et al. |
| 2022/0226014 A1 | 7/2022 | Clauda, IV et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 201029899 Y | 3/2008 |
| CN | 101474081 A | 7/2009 |
| CN | 101516285 A | 8/2009 |
| CN | 101522112 A | 9/2009 |
| CN | 102100582 A | 6/2011 |
| CN | 102149312 A | 8/2011 |
| CN | 202027624 U | 11/2011 |
| CN | 102792181 A | 11/2012 |
| CN | 103281982 A | 9/2013 |
| CN | 103379853 A | 10/2013 |
| CN | 203468630 U | 3/2014 |
| CN | 104001276 A | 8/2014 |
| CN | 104013444 A | 9/2014 |

(56) References Cited

FOREIGN PATENT DOCUMENTS

| | | |
|---|---|---|
| CN | 104434298 A | 3/2015 |
| CN | 107374752 A | 11/2017 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 2510891 B1 | 6/2016 |
| EP | 3476302 A2 | 5/2019 |
| EP | 3476331 A1 | 5/2019 |
| EP | 3694298 A1 | 8/2020 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | H11169381 A | 6/1999 |
| JP | 2000210299 A | 8/2000 |
| JP | 2000271142 A | 10/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114070 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9840015 A2 | 9/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2006091494 A1 | 8/2006 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |
| WO | WO-2011060031 A1 | 5/2011 |
| WO | WO-2012044606 A2 | 4/2012 |
| WO | WO-2012061722 A2 | 5/2012 |
| WO | WO-2012088535 A1 | 6/2012 |
| WO | WO-2012150567 A1 | 11/2012 |
| WO | WO-2016130844 A1 | 8/2016 |

(56) References Cited

FOREIGN PATENT DOCUMENTS

| WO | WO-2019130090 A1 | 7/2019 |
|----|------------------|--------|
| WO | WO-2019130113 A1 | 7/2019 |

OTHER PUBLICATIONS

Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Jang, J. et al. "Neuro-fuzzy and Soft Computing." Prentice Hall, 1997, pp. 13-89, 199-293, 335-393, 453-496, 535-549.
Sullivan, "Optimal Choice for No. of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wall et al., "Thermal modification of collagen," J Shoulder Elbow Surg, No. 8, pp. 339-344 (Jul./Aug. 1999).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online on Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Douglas, S.C. "Introduction to Adaptive Filter". Digital Signal Processing Handbook. Ed. Vijay K. Madisetti and Douglas B. Williams. Boca Raton: CRC Press LLC, 1999.
Chen et al., "Heat-induced changes in the mechanics of a collagenous tissue: pseudoelastic behavior at 37° C.," Journal of Biomechanics, 31, pp. 211-216 (1998).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
http://www.apicalinstr.com/generators.htm.
http://www.dotmed.com/listing/electrosurical-unit/ethicon/ultracision-g110-/1466724.
http://www.ethicon.com/gb-en/healthcare-professionals/products/energy-devices/capital//ge . . . .
http://www.medicalexpo.com/medical-manufacturer/electrosurgical-generator-6951.html.
http://www.megadyne.com/es_generator.php.
http://www.valleylab.com/product/es/generators/index.html.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Walsh, S. J., White, R. G., "Vibrational Power Transmission in Curved Beams," Journal of Sound and Vibration, 233(3), 455-488 (2000).
Covidien 501(k) Summary Sonicision, dated Feb. 24, 2011 (7 pages).
Morley, L. S. D., "Elastic Waves in a Naturally Curved Rod," Quarterly Journal of Mechanics and Applied Mathematics, 14: 155-172 (1961).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Campbell et al., "Thermal Imaging in Surgery," p. 19-3, in Medical Infrared Imaging, N. A. Diakides and J. D. Bronzino, Eds. (2008).
Gerhard, Glen C., "Surgical Electrotechnology: Quo Vadis?," IEEE Transactions on Biomedical Engineering, vol. BME-31, No. 12, pp. 787-792, Dec. 1984.
http://www.4-traders.com/JOHNSON-JOHNSON-4832/news/Johnson-Johnson-Ethicon-E . . . .

(56) References Cited

OTHER PUBLICATIONS

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Kurt Gieck & Reiner Gieck, *Engineering Formulas* § Z.7 (7th ed. 1997).

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

Leonard I. Malis, M.D., "The Value of Irrigation During Bipolar Coagulation," 1989.

Covidien Brochure, The LigaSure Precise™ Instrument, dated Mar. 2011 (2 pages).

Glaser and Subak-Sharpe, Integrated Circuit Engineering, Addison-Wesley Publishing, Reading, MA (1979). (book—not attached).

Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.

Hörmann et al., "Reversible and irreversible denaturation of collagen fibers." Biochemistry, 10, pp. 932-937 (1971).

Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

Moraleda et al., A Temperature Sensor Based on a Polymer Optical Fiber Macro-Bend, Sensors 2013, 13, 13076-13089, doi: 10.3390/s131013076, ISSN 1424-8220.

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

Missinne, et al. "Stretchable Optical Waveguides," vol. 22, No. 4, Feb. 18, 2014, pp. 4168-4179 (12 pages).

\* cited by examiner

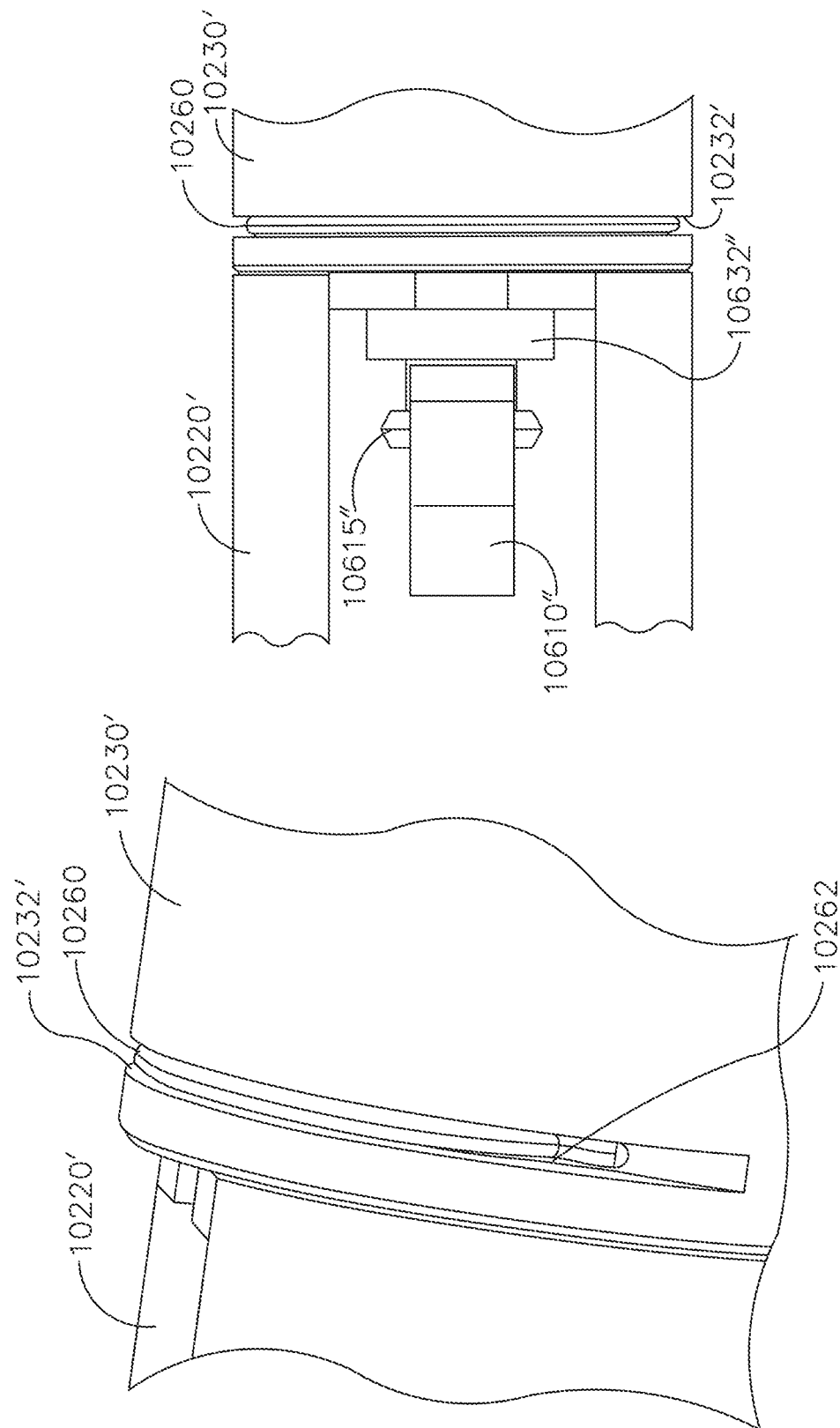

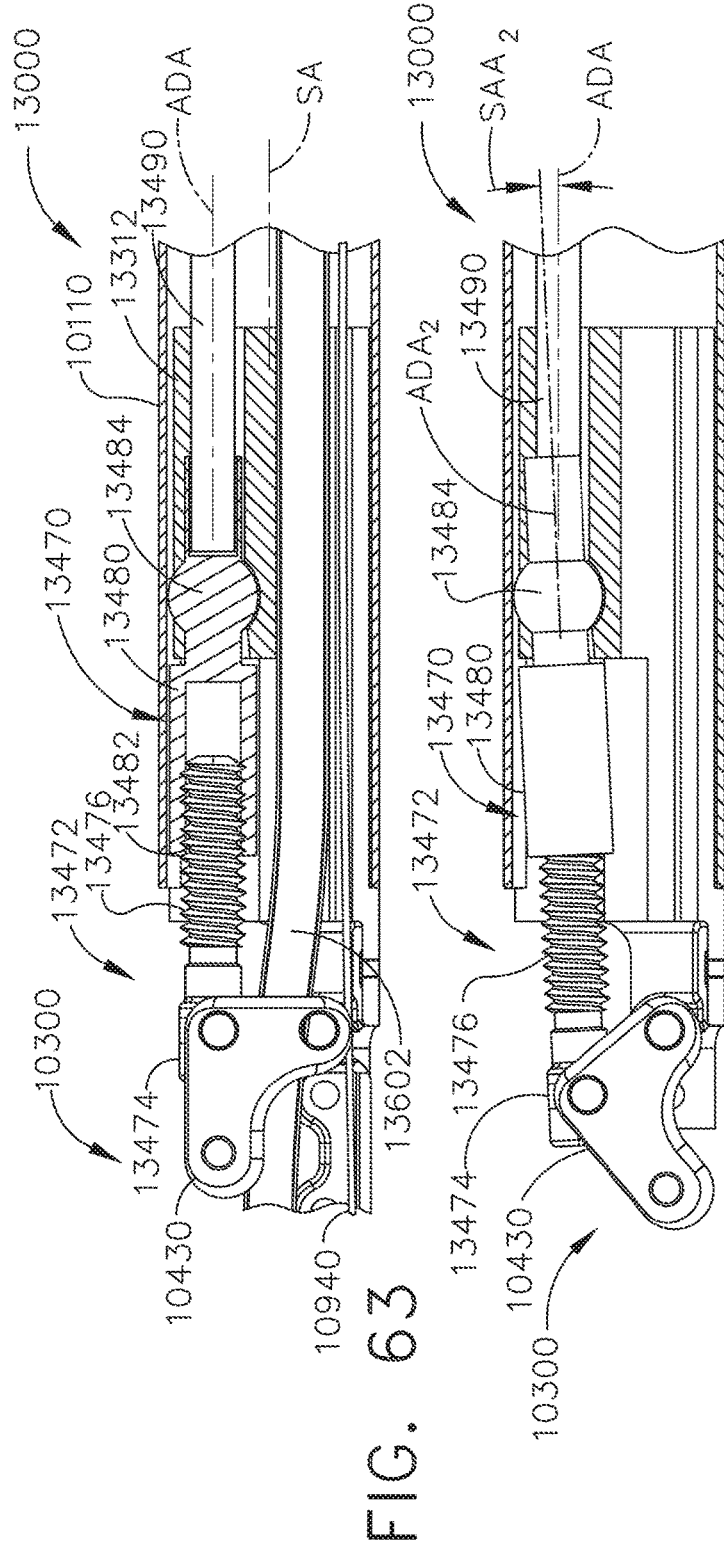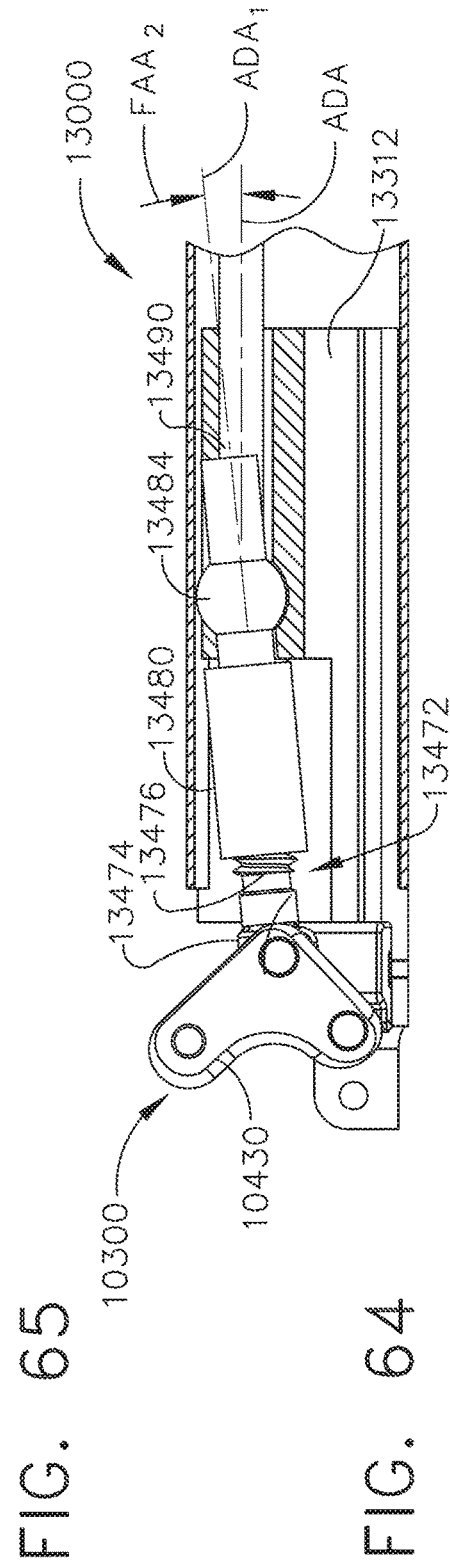

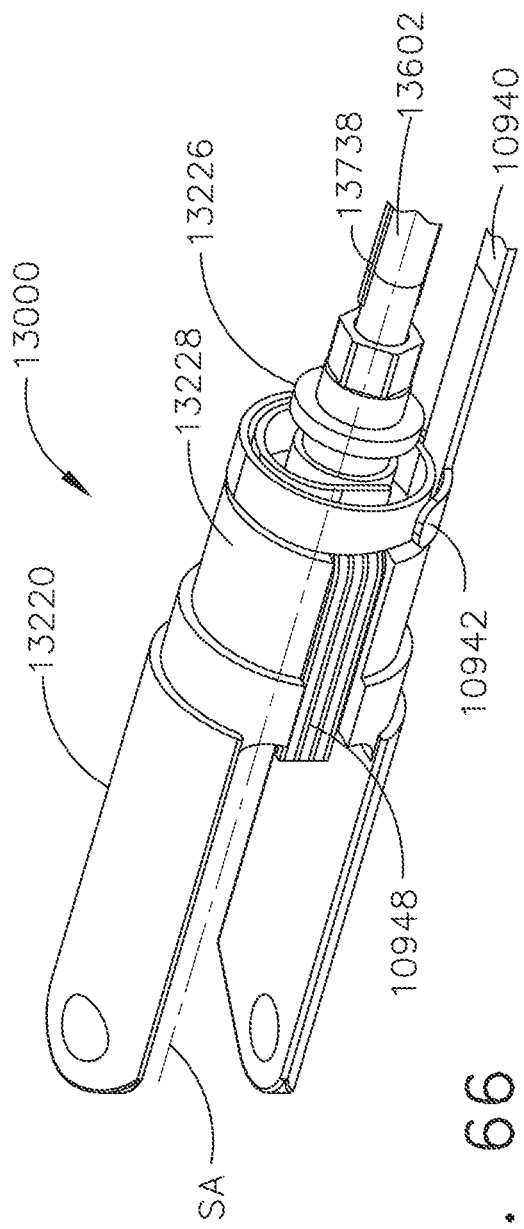
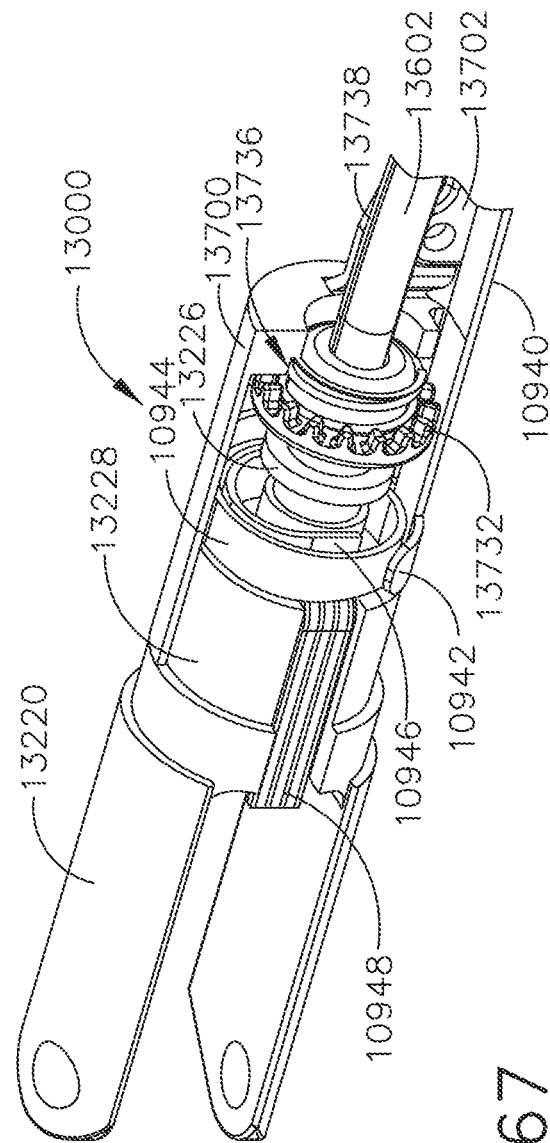

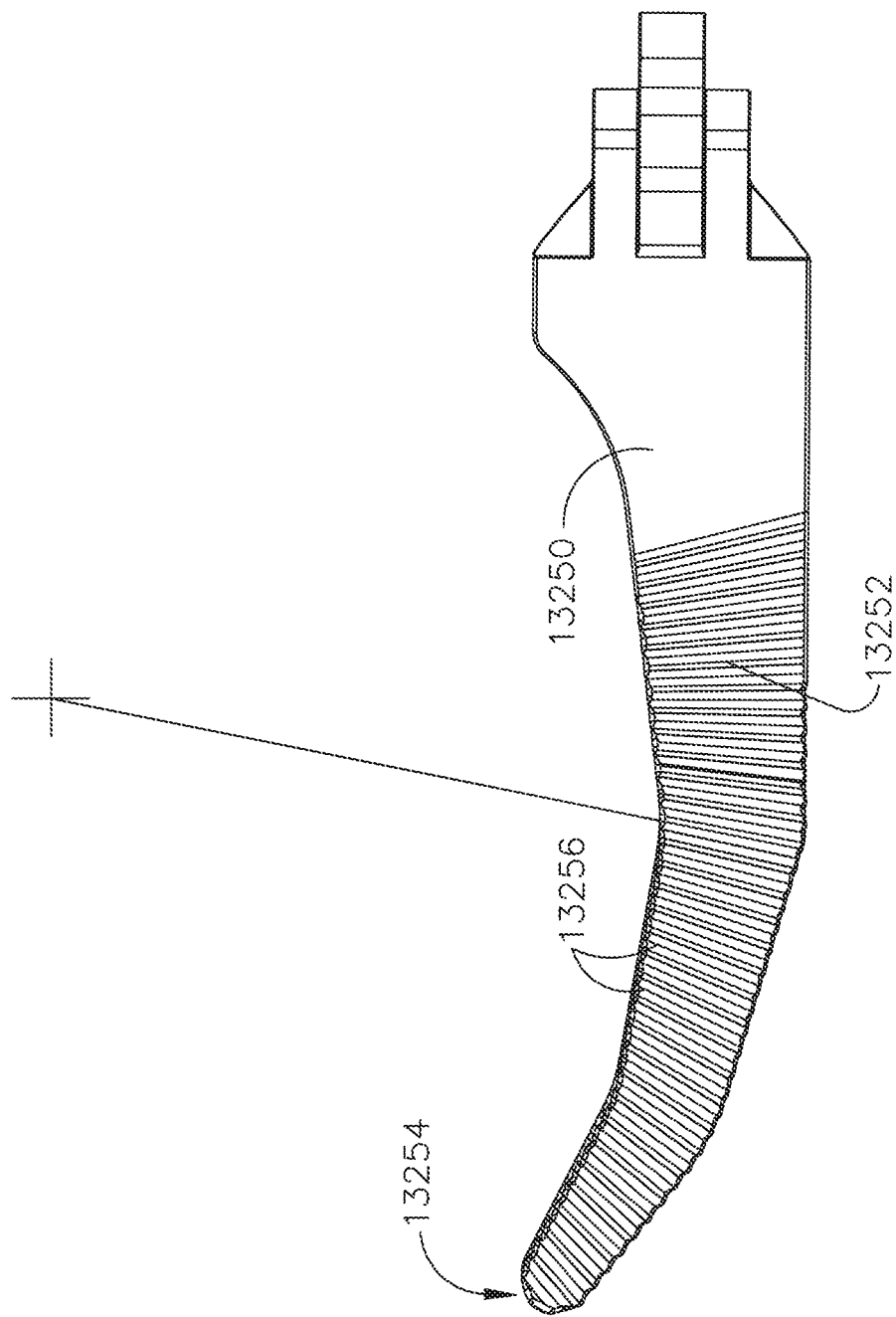

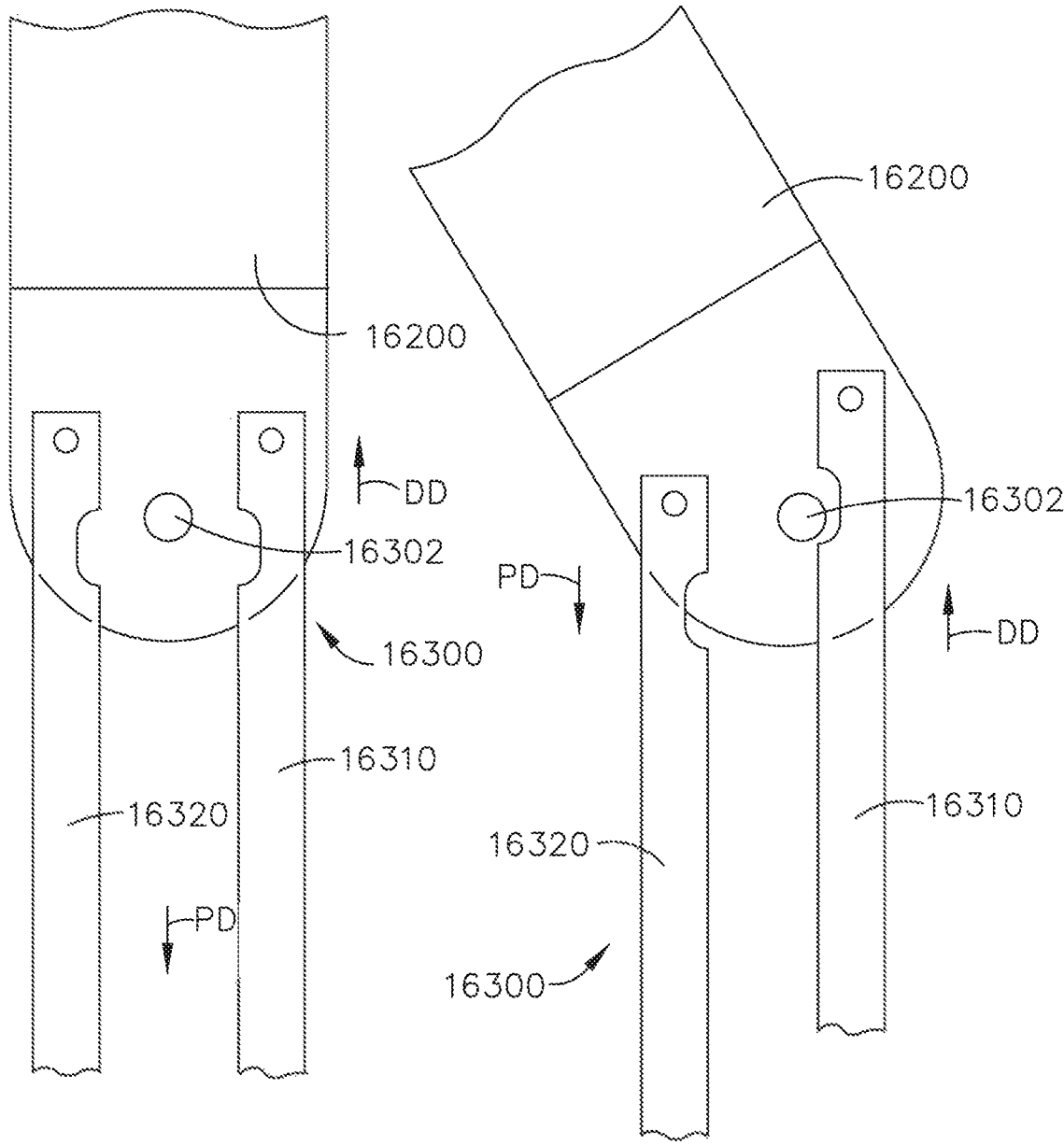

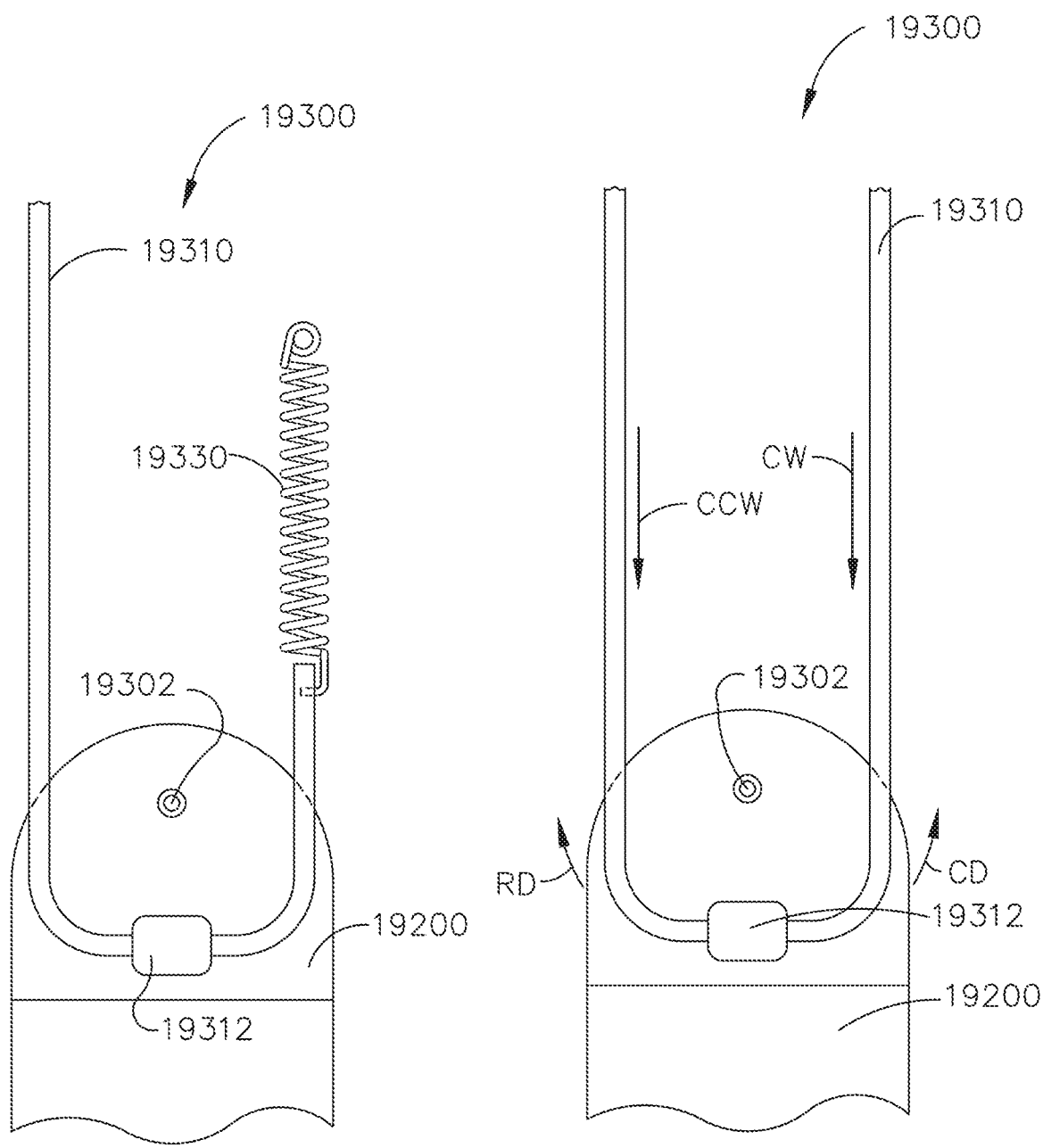

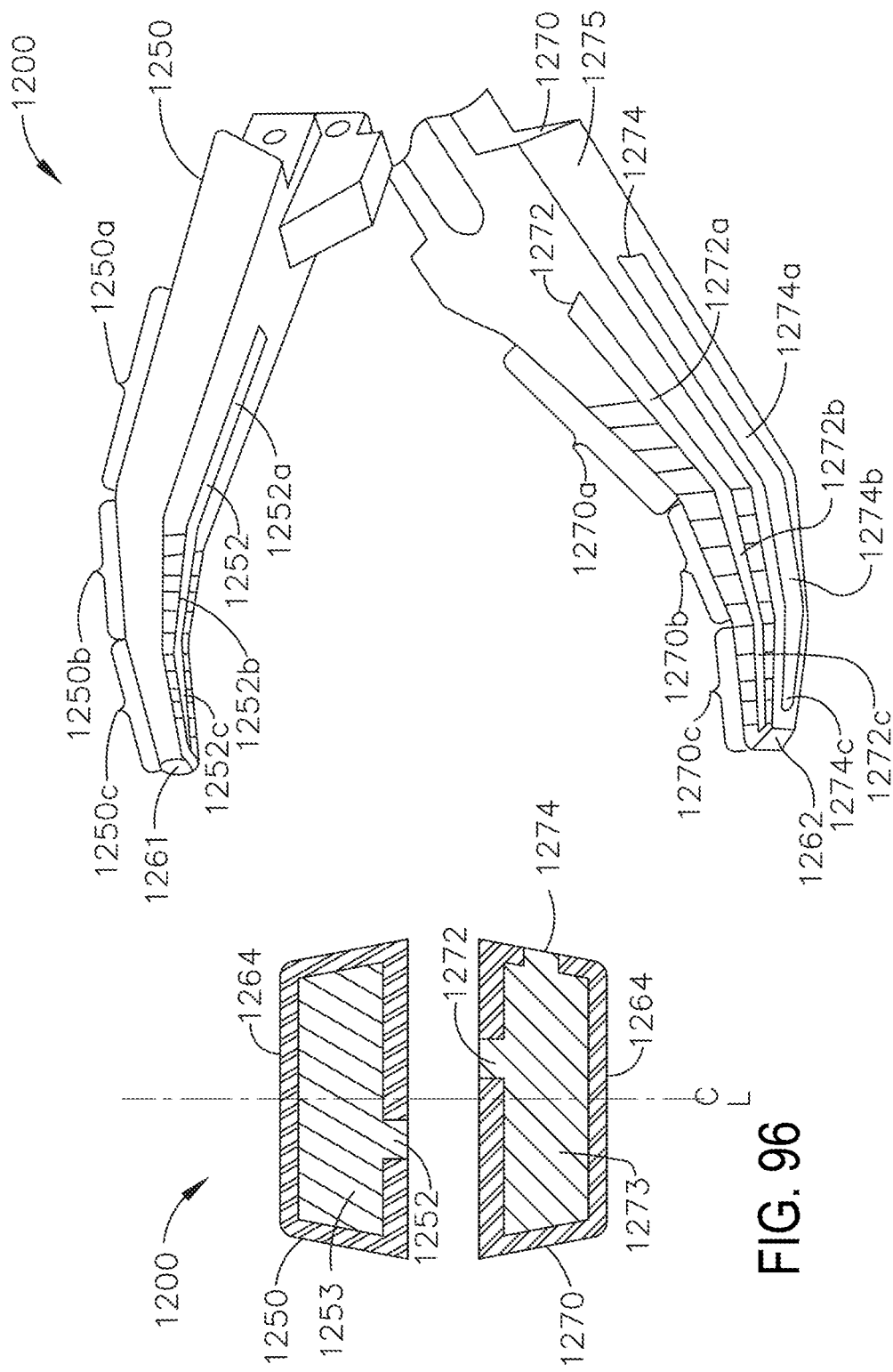
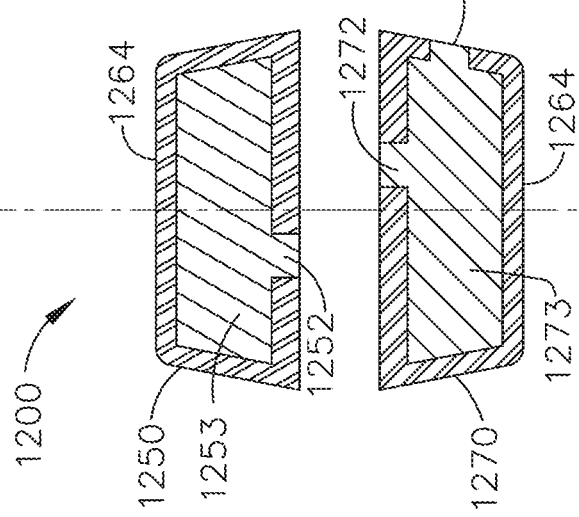
FIG. 95
FIG. 96

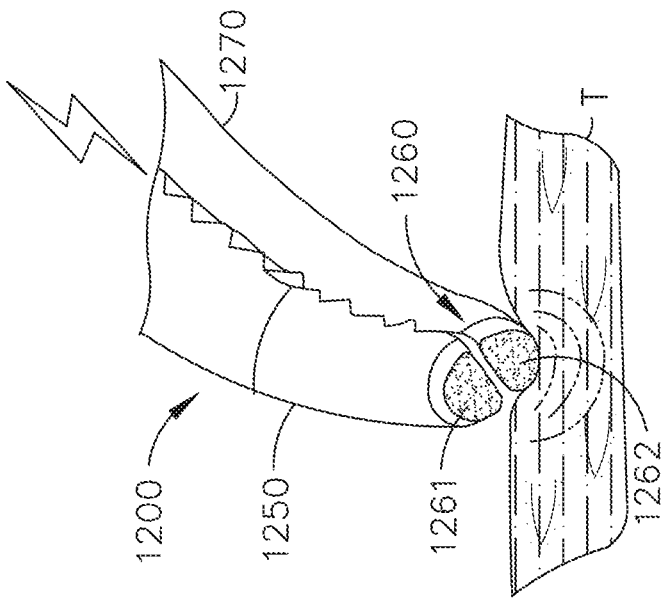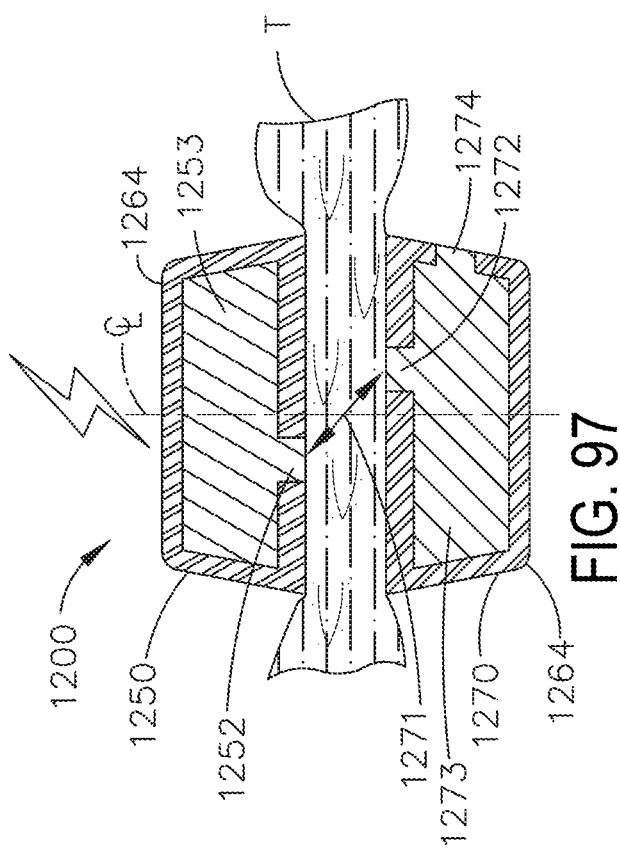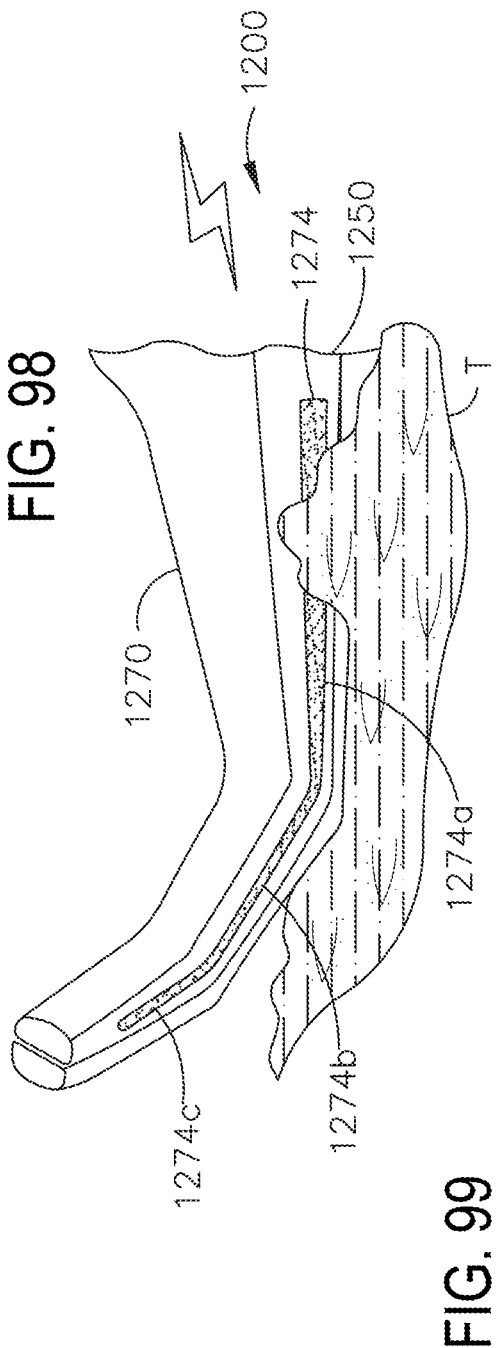
FIG. 98
FIG. 97
FIG. 99

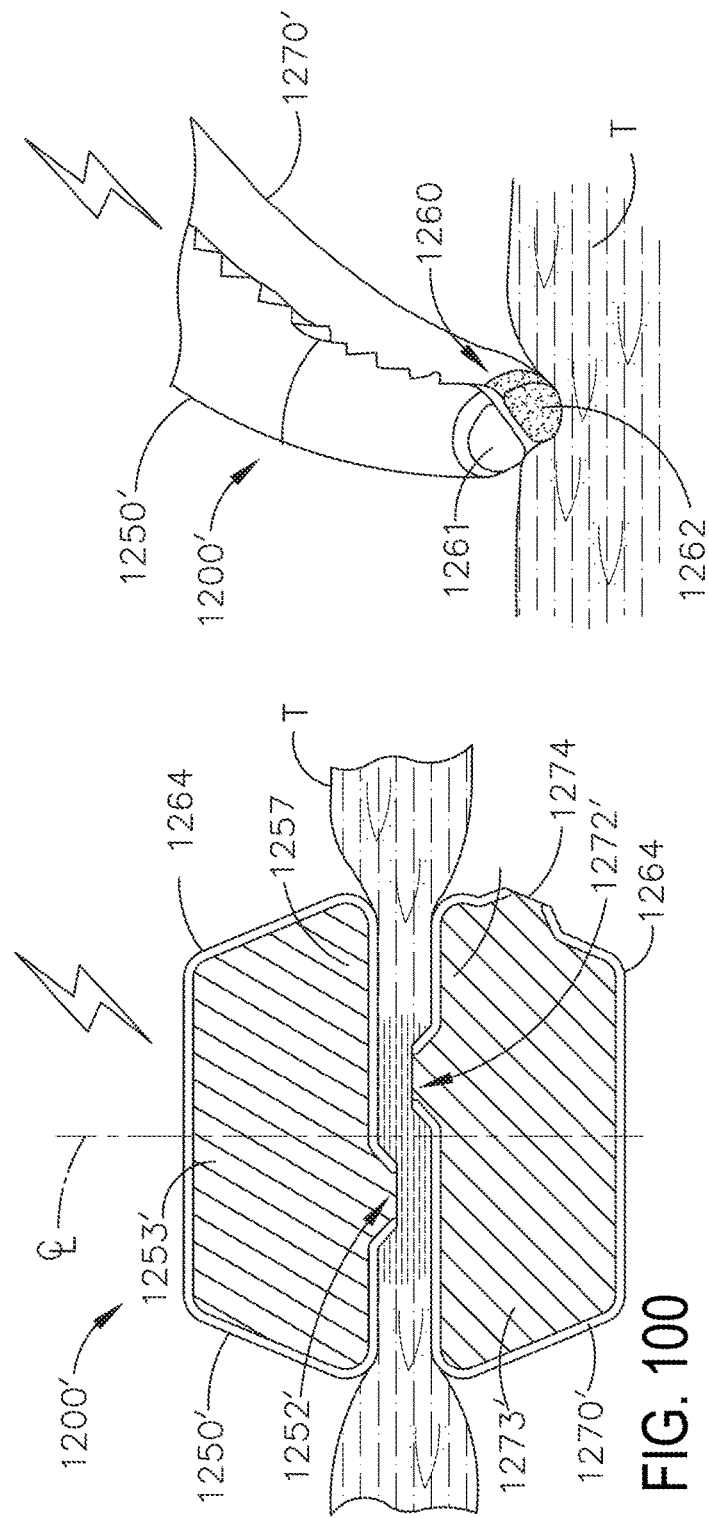
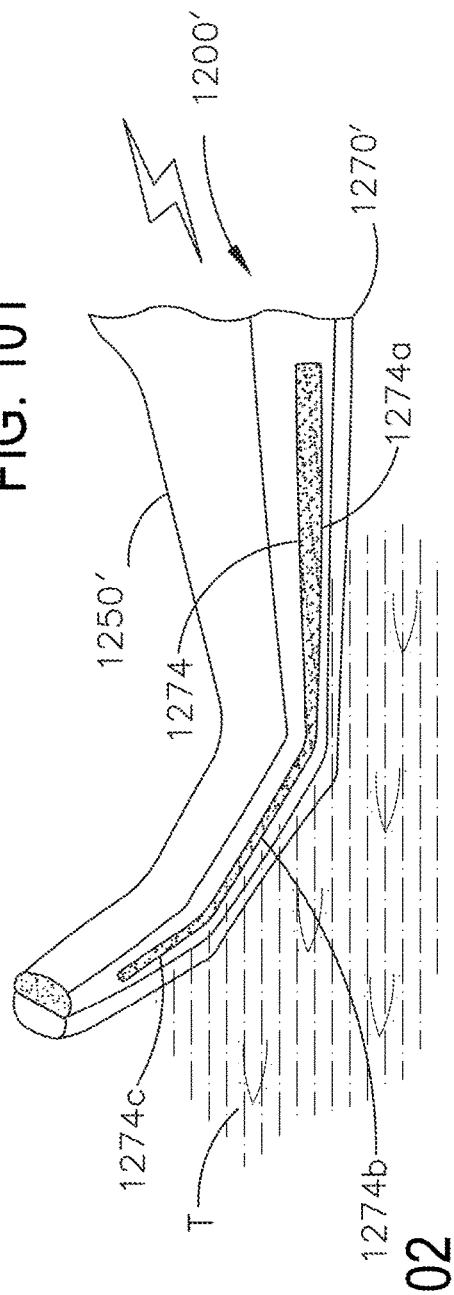
FIG. 100
FIG. 101
FIG. 102

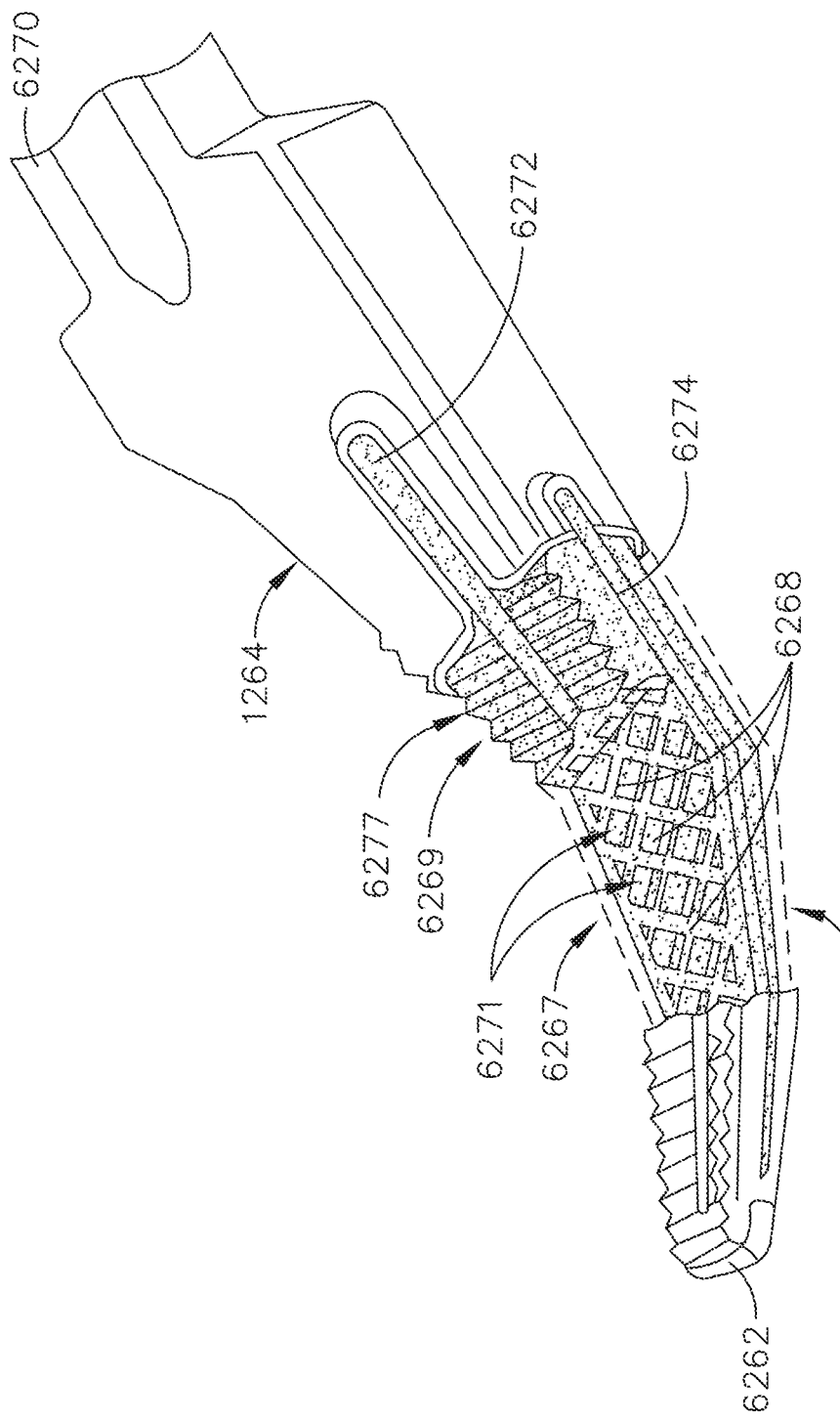

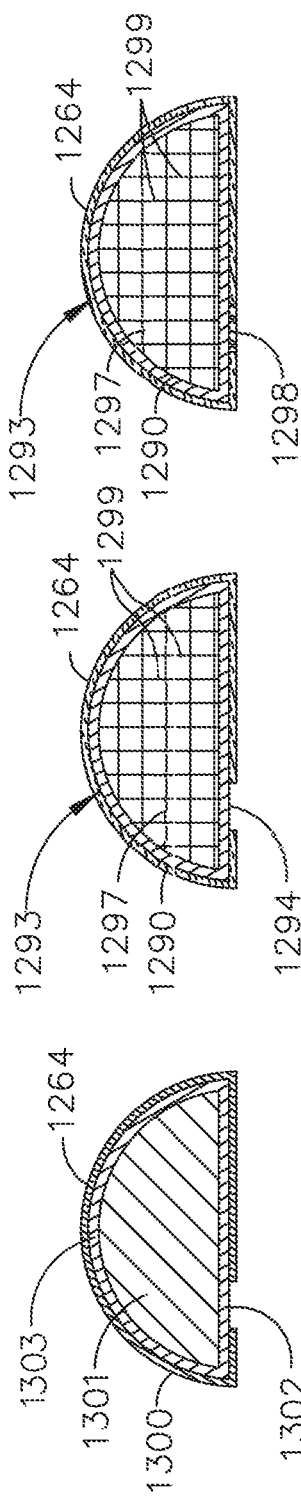
FIG. 111
FIG. 112
FIG. 114
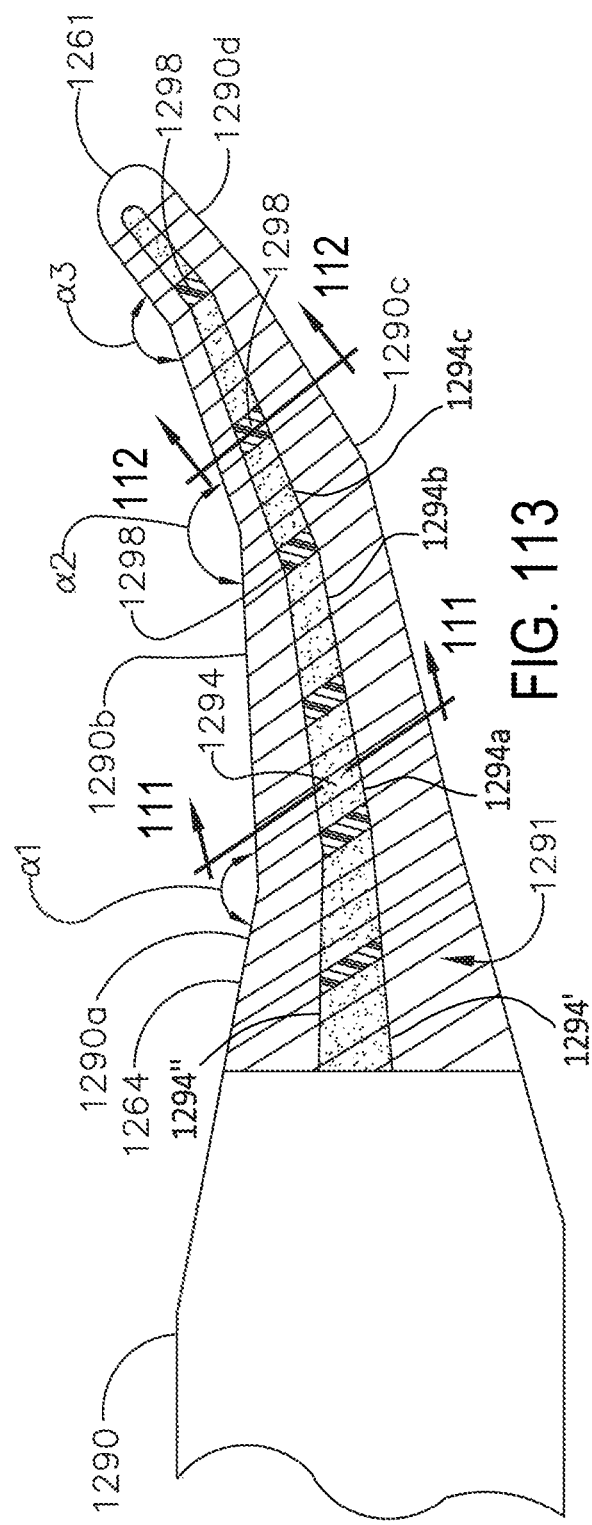
FIG. 113

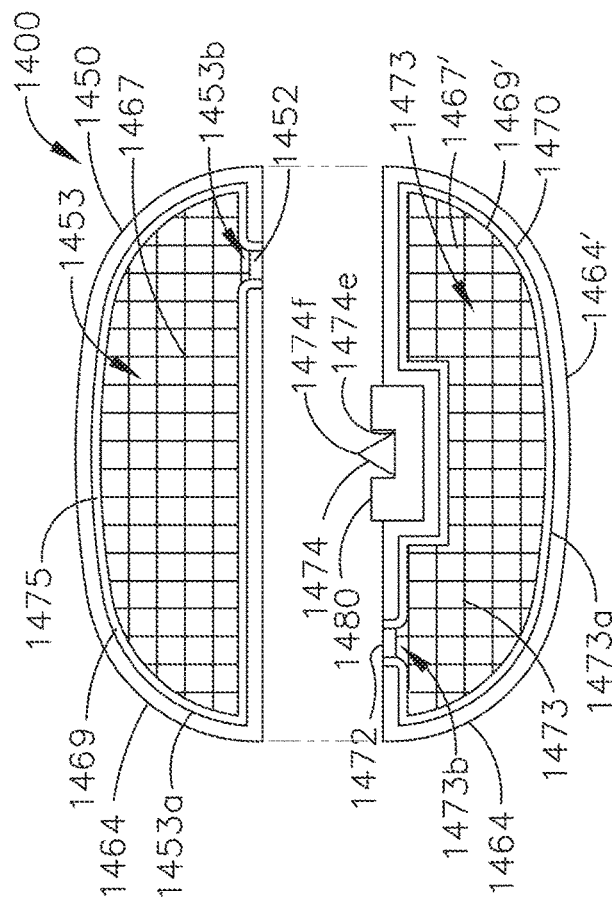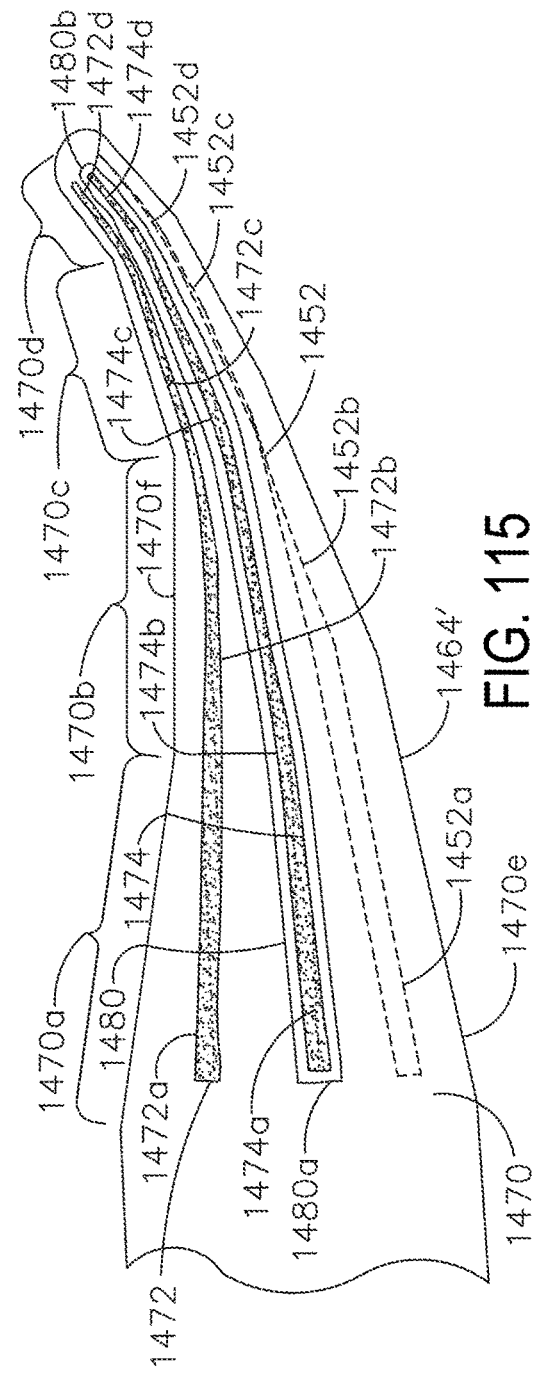

| Time | Tissue Operation | Energy type | Jaw aperture | Image |
|---|---|---|---|---|
| $t_0$ | No tissue contact | n/a | 0.700"–0.500" | $T_{t_0}$, $d_0$ 0.700" |
| $t_1$ | Feathering 3008 | Bipolar | 0.500"–0.030" | $T_{t_1}$, $d_1$ 0.500" |
| $t_2$ | Tissue Warming power 3009 | Bipolar & Monopolar | 0.030"–0.010" | $T_{t_2}$, $d_2$ 0.030" |
| $t_3$ | Sealing 3010 | Monopolar & Bipolar | 0.010"–0.003" | $T_{t_3}$, $d_3$ 0.010" |
| $t_4$ | Cutting 3007 | Monopolar | 0.010"–0.003" | $T_{t_4}$, $d_4$ 0.010" |

FIG. 128

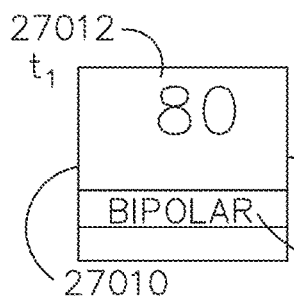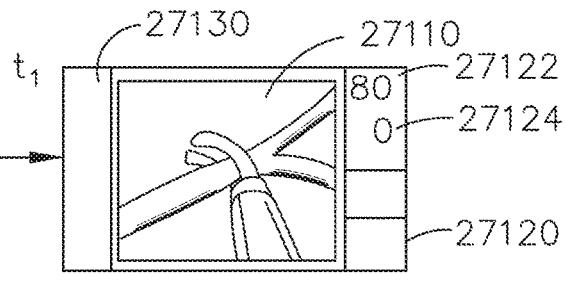
FIG. 142
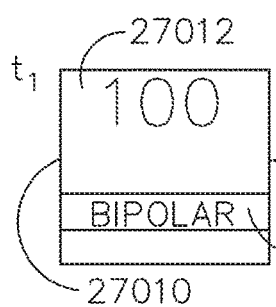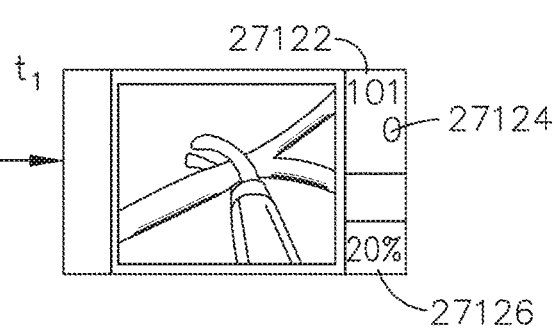
FIG. 143
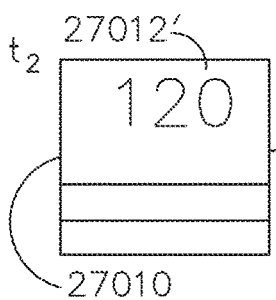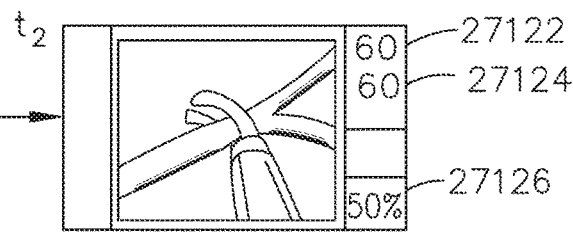
FIG. 144
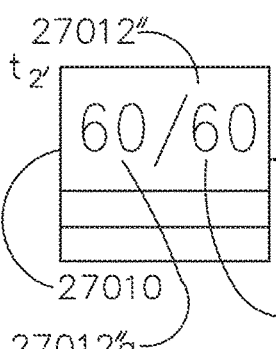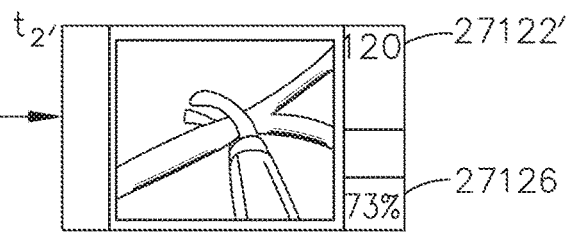
FIG. 145
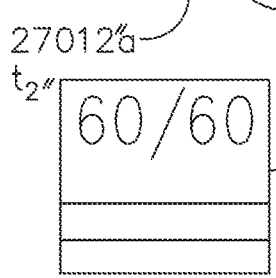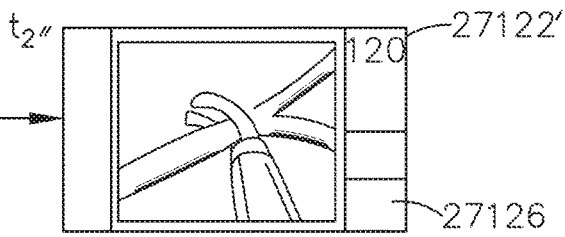
FIG. 146

| Time | Tissue Operation | Energy type | Jaw aperture | Image |
|---|---|---|---|---|
| $t_0$ | No tissue contact | n/a | 0.700″–0.500″ | $T_{t_0}$, $d_0$ 0.700″/0.500″ |
| $t_1$ | Feathering | Bipolar | 0.500″–0.030″ | $T_{t_1}$, $d_1$ 0.500″/0.030″ |
| $t_2$ | Tissue Warming power | Bipolar & Monopolar | 0.030″–0.010″ | $T_{t_2}$, $d_2$ 0.030″/0.010″ |
| $t_3$ | Sealing | Monopolar & Bipolar | 0.010″–0.003″ | $T_{t_3}$, $d_3$ 0.010″/0.003″ |
| $t_4$ | Cutting | Monopolar | 0.010″–0.003″ | $T_{t_4}$, $d_4$ 0.010″/0.003″ |

FIG. 153

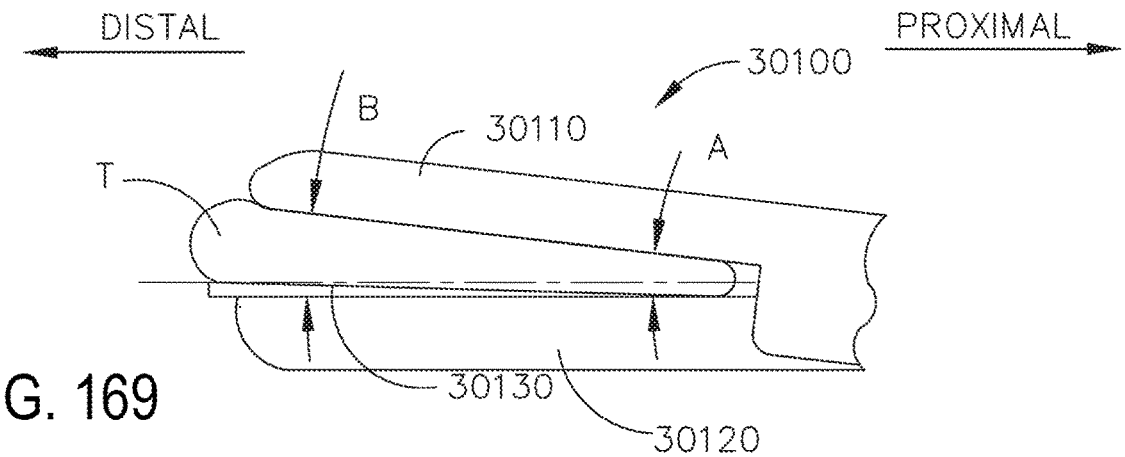
FIG. 169
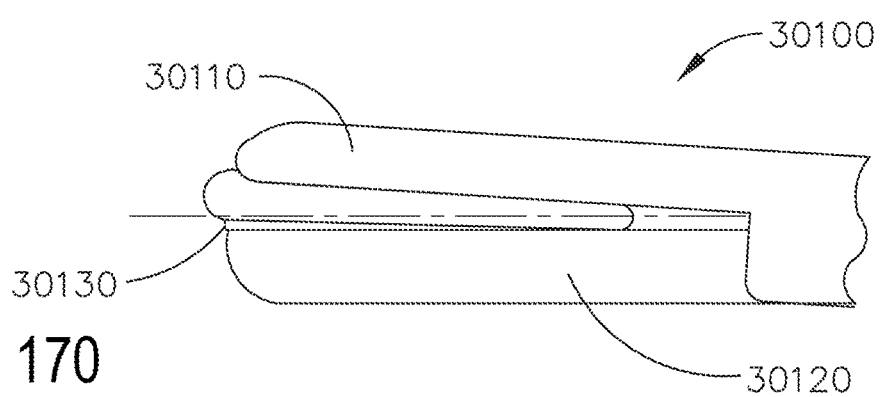
FIG. 170
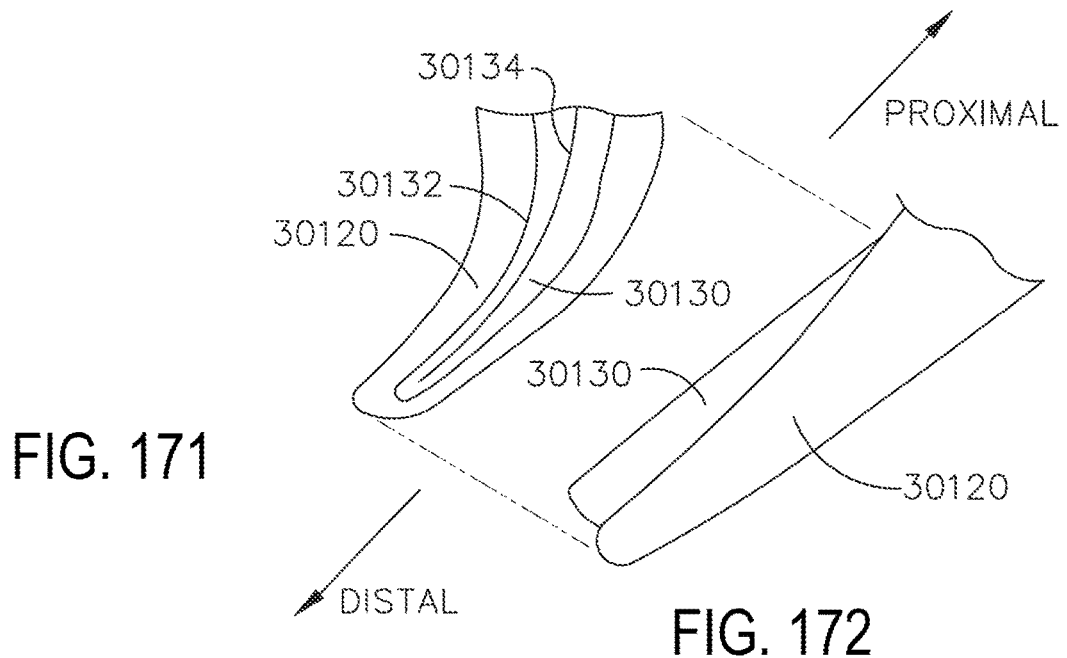
FIG. 171
FIG. 172

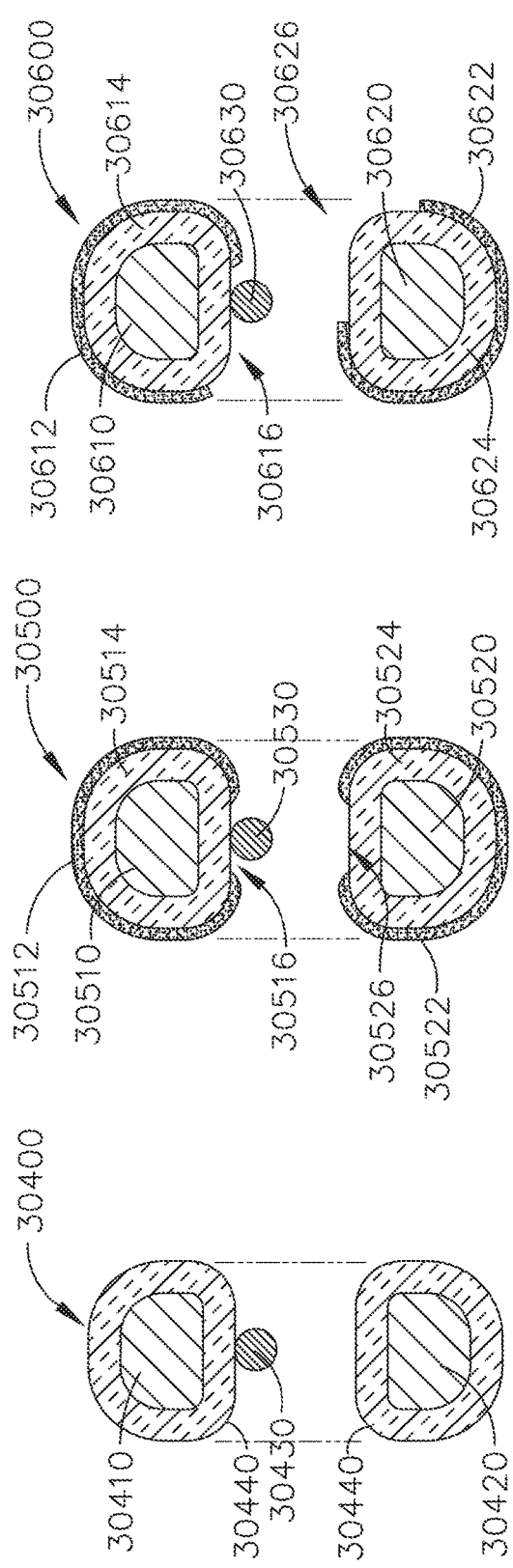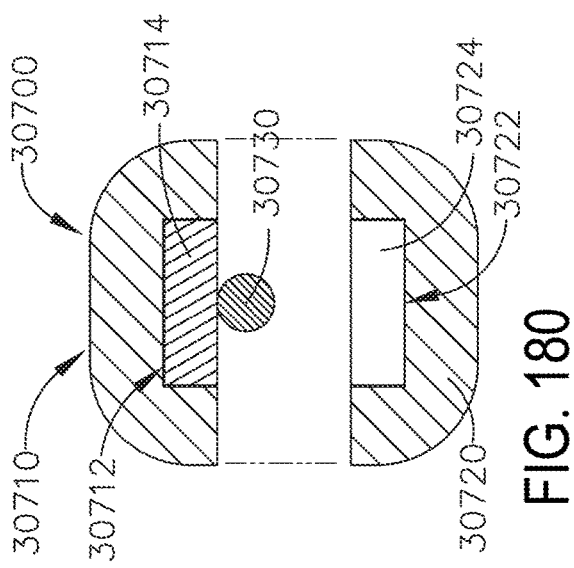

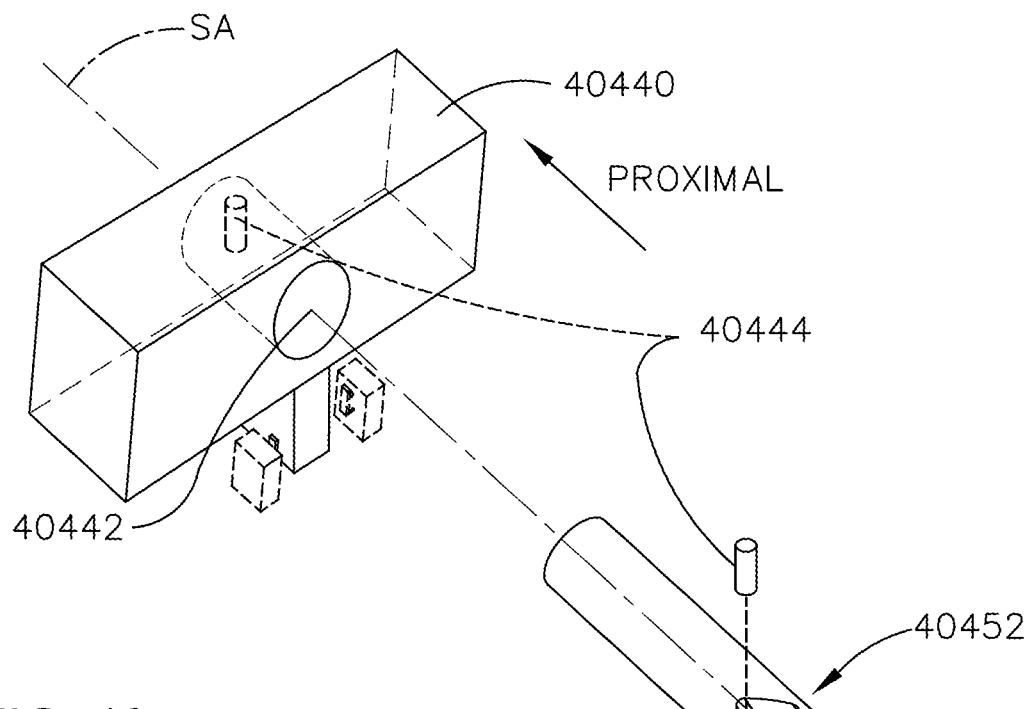
FIG. 195
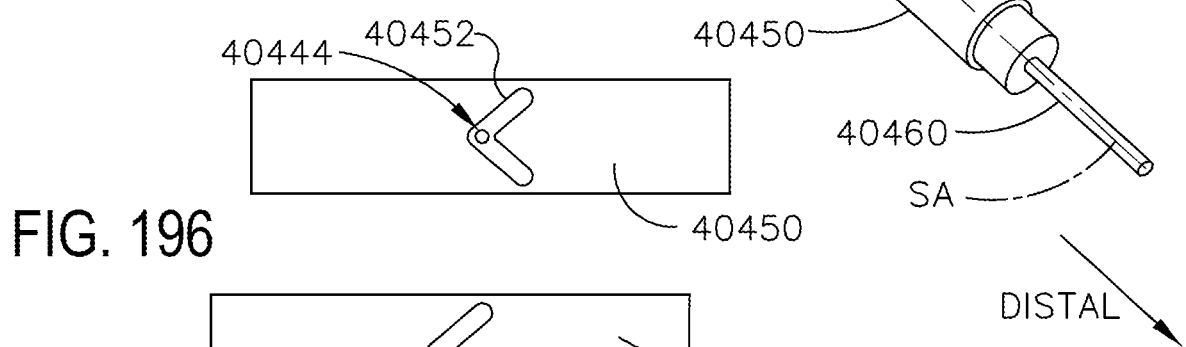
FIG. 196
FIG. 197
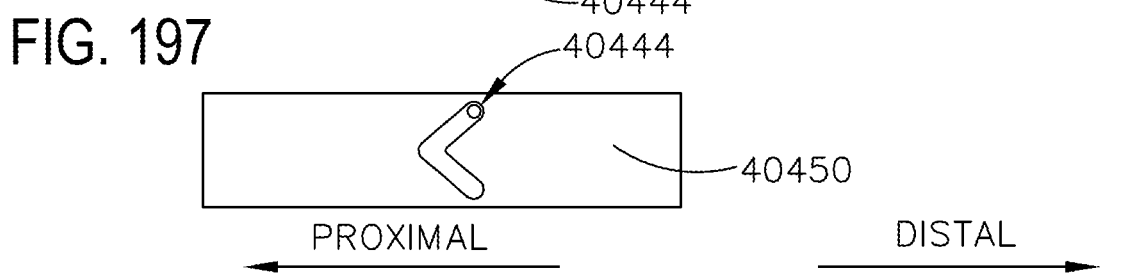
FIG. 198

METHOD FOR AN ELECTROSURGICAL PROCEDURE

CROSS REFERENCE TO RELATED APPLICATION

This non-provisional application claims the benefit under 35 U.S.C. § 119(e) of U.S. Provisional Patent Application Ser. No. 62/955,299, entitled DEVICES AND SYSTEMS FOR ELECTROSURGERY, filed Dec. 30, 2019, the disclosure of which is incorporated by reference herein in its entirety.

BACKGROUND

The present invention relates to surgical instruments designed to treat tissue, including but not limited to surgical instruments that are configured to cut and fasten tissue. The surgical instruments may include electrosurgical instruments powered by generators to effect tissue dissecting, cutting, and/or coagulation during surgical procedures. The surgical instruments may include instruments that are configured to cut and staple tissue using surgical staples and/or fasteners. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

SUMMARY

In various embodiments, a method for performing an electrosurgical procedure using an electrosurgical instrument is disclosed. The method comprises articulating an end effector of the electrosurgical instrument relative to a shaft of the electrosurgical instrument. The end effector is articulated toward a target tissue. The method further comprises causing the end effector to transition to a closed configuration. The target tissue is grasped by jaws of the end effector in the closed configuration. The method further comprises reversibly moving an electrode by the target tissue relative to the jaws of the end effector, and performing an energy treatment cycle to coagulate and cut the target tissue. The energy treatment cycle comprises applying a bipolar energy to the target tissue in a tissue-feathering segment, and applying an energy blend of the bipolar energy and a monopolar energy to the target tissue in a tissue-warming segment and a tissue-sealing segment following the tissue-warming segment. The monopolar energy is applied to the target tissue through the electrode. The energy treatment cycle further comprises discontinuing the bipolar energy but continuing to apply the monopolar energy to the target tissue in a tissue-cutting segment following the tissue-sealing segment.

In various embodiments, a method for performing an electrosurgical procedure using an electrosurgical instrument including an end effector is disclosed. The method comprises applying a bipolar energy to a target tissue grasped by the end effector in a tissue-feathering segment, applying an energy blend of the bipolar energy and a monopolar energy to the target tissue in a tissue-warming segment and a tissue-sealing segment following the tissue-warming segment, and discontinuing the bipolar energy but continuing to apply the monopolar energy to the target tissue in a tissue-cutting segment following the tissue-sealing segment.

In various embodiments, a method for operating an electrosurgical system in a tissue treatment cycle applied to a target tissue by an electrosurgical instrument of the electrosurgical system is disclosed. The method comprises gradually increasing a bipolar power level of a bipolar generator of the electrosurgical system to a predetermined bipolar power level in a first portion of a tissue-feathering segment of the tissue treatment cycle, maintaining the predetermined bipolar power level in a second portion of the tissue-feathering segment, gradually increasing a monopolar power level of a monopolar generator of the electrosurgical system to a predetermined monopolar power level in a first portion of a tissue-warming segment of the tissue treatment cycle, maintaining the predetermined bipolar power level and the predetermined monopolar power level in a second portion of the tissue-warming segment, gradually increasing the monopolar power level of the monopolar generator beyond the predetermined monopolar power level while gradually decreasing the bipolar power level of the bipolar generator below the predetermined bipolar power level in a tissue sealing segment of the tissue treatment cycle, and stepping up the monopolar power level of the monopolar generator in a tissue-cutting segment of the tissue treatment cycle.

DRAWINGS

The novel features of the various aspects are set forth with particularity in the appended claims. The described aspects, however, both as to organization and methods of operation, may be best understood by reference to the following description, taken in conjunction with the accompanying drawings in which:

FIG. 34 is a top view of a portion of a distal frame member and a proximal housing member of a surgical instrument, in accordance with at least one aspect of the present disclosure;

FIG. 35 is a partial perspective view of a spring clip used to support the proximal housing member on the distal frame member of FIG. 34;

FIG. 63 is a cross-sectional side elevational view of the proximal shaft segment of FIG. 56 with an articulation joint thereof in an unarticulated position;

FIG. 64 is another cross-sectional side elevational view of the proximal shaft segment of FIG. 56 with the articulation joint thereof articulated in a first direction;

FIG. 65 is another cross-sectional side elevational view of the proximal shaft segment of FIG. 56 articulated in a second direction;

FIG. 66 is a partial perspective view of a distal frame member and a flexible circuit arrangement of the surgical instrument of FIG. 56;

FIG. 67 is another partial perspective view of the distal frame member and flexible circuit arrangement of FIG. 66;

FIG. 77 is a top view of another first jaw, in accordance with at least one aspect of the present disclosure;

FIG. 89 is a partial view of another surgical instrument with a surgical end effector in an unarticulated position, in accordance with at least one aspect of the present disclosure;

FIG. 90 is another partial view of the surgical instrument of FIG. 89 with the surgical end effector thereof in an articulated position;

FIG. 93 is a partial view of another surgical instrument with a surgical end effector in an unarticulated position, in accordance with at least one aspect of the present disclosure;

FIG. 94 is a partial view of another surgical instrument with a surgical end effector in an unarticulated position, in accordance with at least one aspect of the present disclosure;

FIG. 95 is an exploded view of an end effector of an electro surgical instrument, in accordance with at least one aspect of the present disclosure;

FIG. 96 is a cross-sectional view of the of the end effector of FIG. 95;

FIGS. 97-99 depict three different operational modes of the end effector of FIG. 95 prior to energy application to tissue;

FIGS. 100-102 depict three different operational modes of the end effector of FIG. 95 during energy application to tissue;

FIG. 105 illustrates a partial perspective view of a jaw of an end effector of an electrosurgical instrument, in accordance with at least one aspect of the present disclosure;

FIG. 111 illustrates a cross-sectional view of a jaw of an end effector of an electrosurgical instrument taken through line 111-111 in FIG. 113, in accordance with at least one aspect of the present disclosure;

FIG. 112 illustrates a cross-sectional view of the jaw of the end effector of the electrosurgical instrument taken through line 112-112 in FIG. 113;

FIG. 113 illustrates a perspective view of the jaw of the end effector of the electrosurgical instrument of FIG. 111;

FIG. 114 illustrates a cross-sectional view of a jaw of an end effector of an electrosurgical instrument, in accordance with at least one aspect of the present disclosure;

FIG. 115 illustrates a partial perspective view of a jaw of an end effector of an electrosurgical instrument, in accordance with at least one aspect of the present disclosure;

FIG. 116 illustrates a cross-sectional view of an end effector of an electrosurgical instrument, in accordance with at least one aspect of the present disclosure;

FIG. 128 is a table illustrating a power scheme for coagulating and cutting a tissue treatment region in a treatment cycle applied by an end effector, in accordance with at least one aspect of the present disclosure;

FIG. 142 is a schematic representation of the corresponding views of the display screen of the surgical instrument and the display monitor of FIG. 141 in accordance with at least one embodiment;

FIG. 143 is a schematic representation of the corresponding views of the display screen of the surgical instrument and the display monitor of FIG. 141 in accordance with at least one embodiment;

FIG. 144 is a schematic representation of the corresponding views of the display screen of the surgical instrument and the display monitor of FIG. 141 in accordance with at least one embodiment;

FIG. 145 is a schematic representation of the corresponding views of the display screen of the surgical instrument and the display monitor of FIG. 141 in accordance with at least one embodiment;

FIG. 146 is a schematic representation of the corresponding views of the display screen of the surgical instrument and the display monitor of FIG. 141 in accordance with at least one embodiment;

Figure 22:
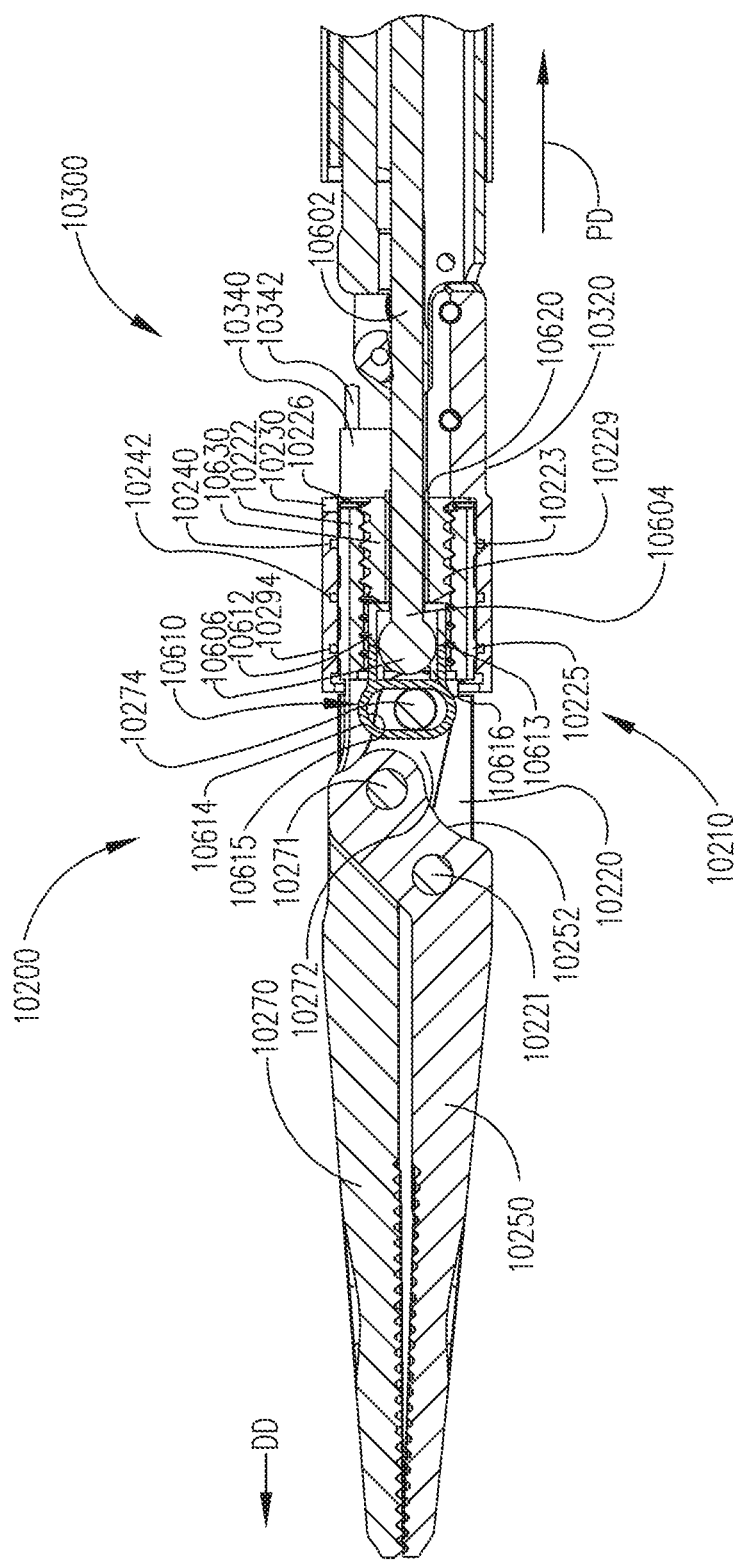
FIG. 22 is a cross-sectional side view of a portion of the surgical instrument of FIG. 4 with jaws thereof in a closed position.
Figure 23:
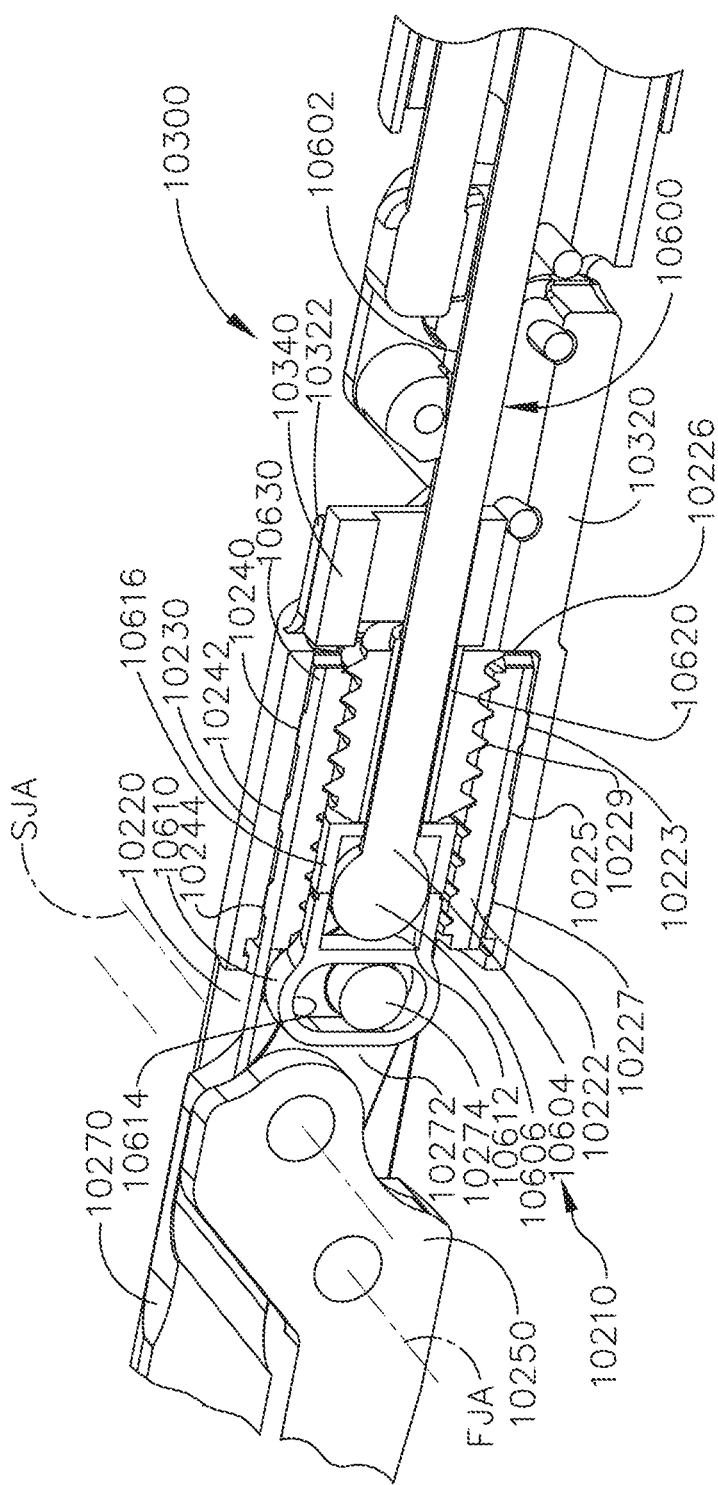
FIG. 23 is a cross-sectional perspective view of the portion of the surgical instrument of FIG. 22.
Figure 24:
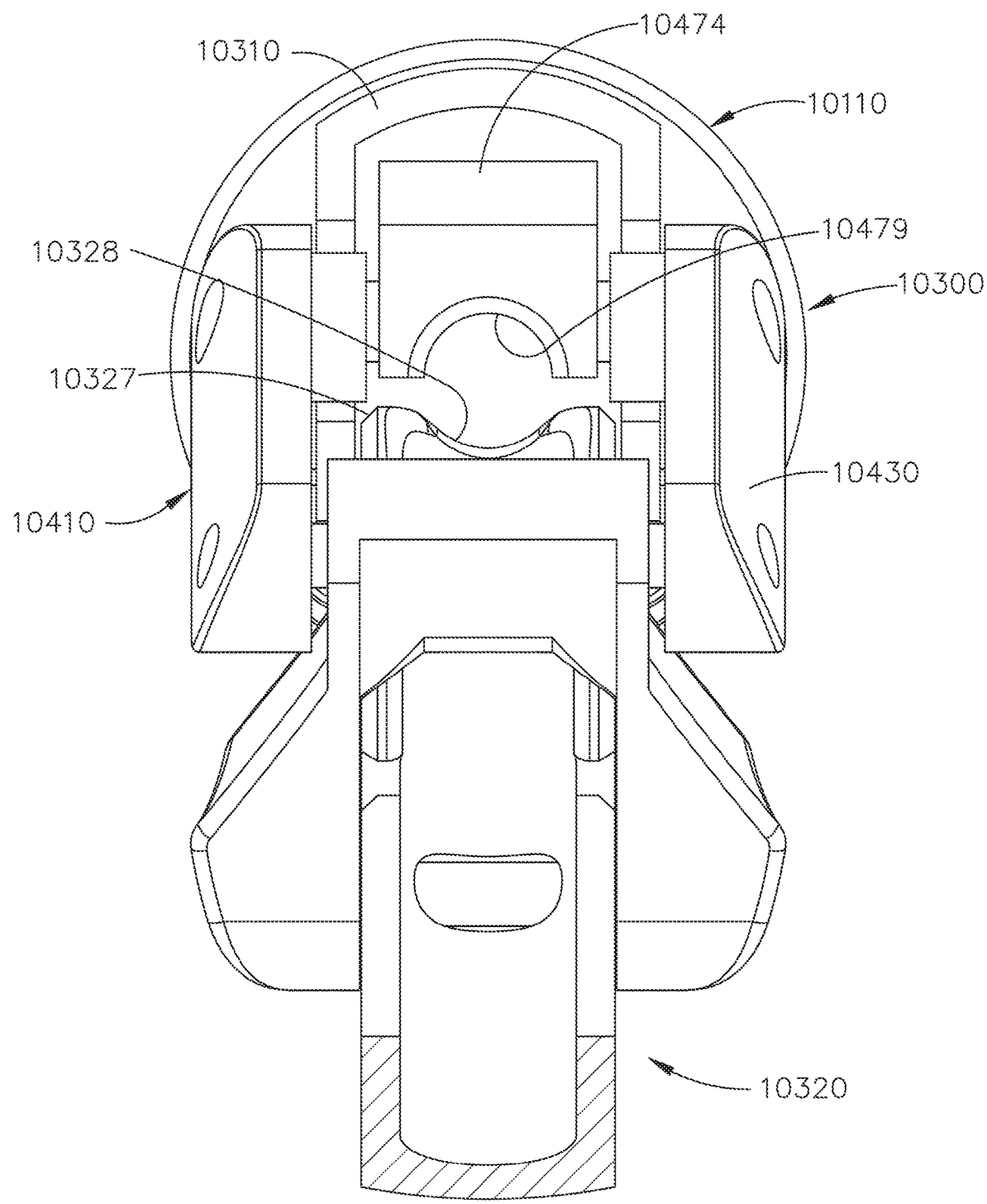
FIG. 24 is an end perspective view of the articulation joint of the surgical instrument of FIG. 4 with the articulation joint articulated in a second direction.
Figure 25:
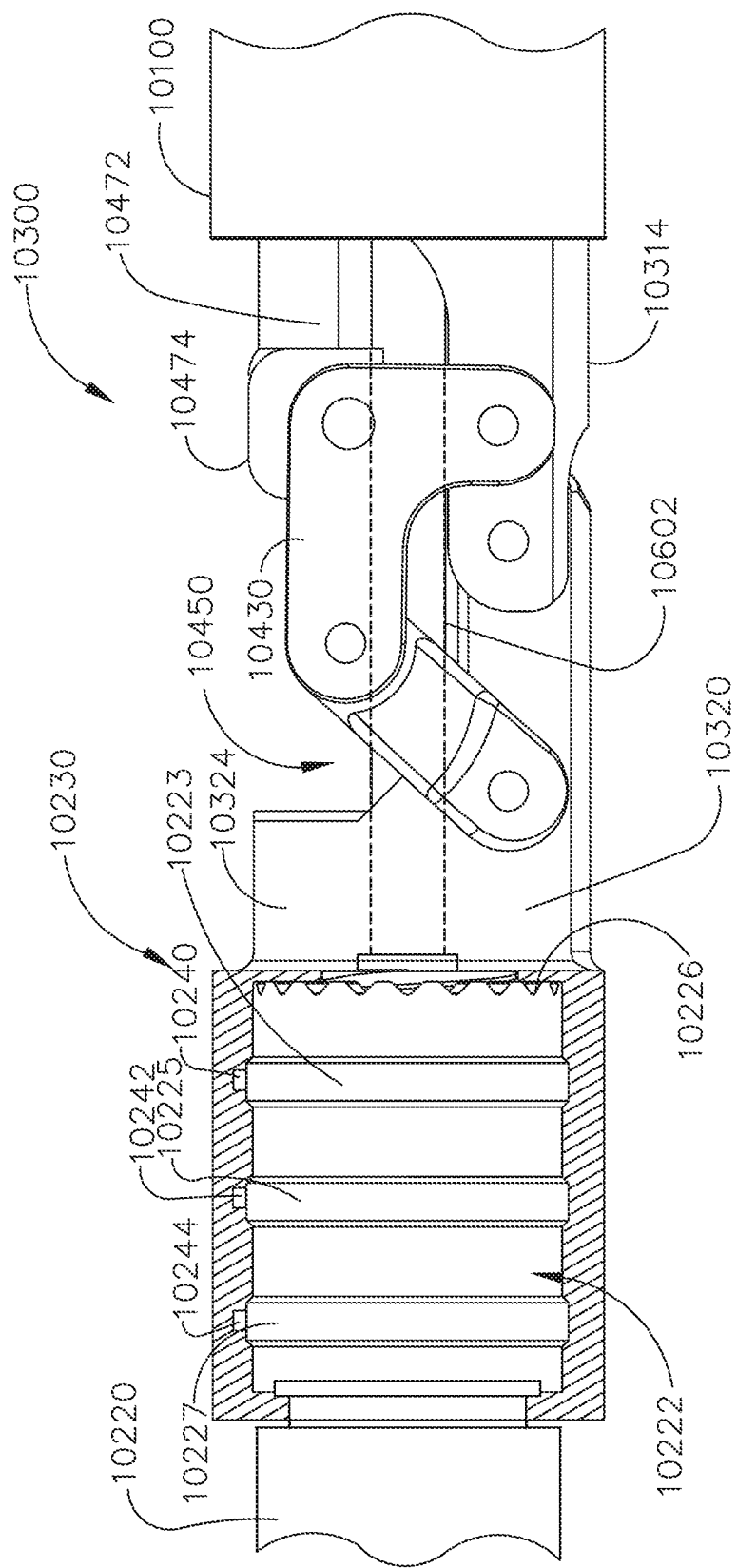
FIG. 25 is a side elevational view of a portion of the surgical instrument of FIG. 4 with portions thereof shown in phantom.
Figure 26:
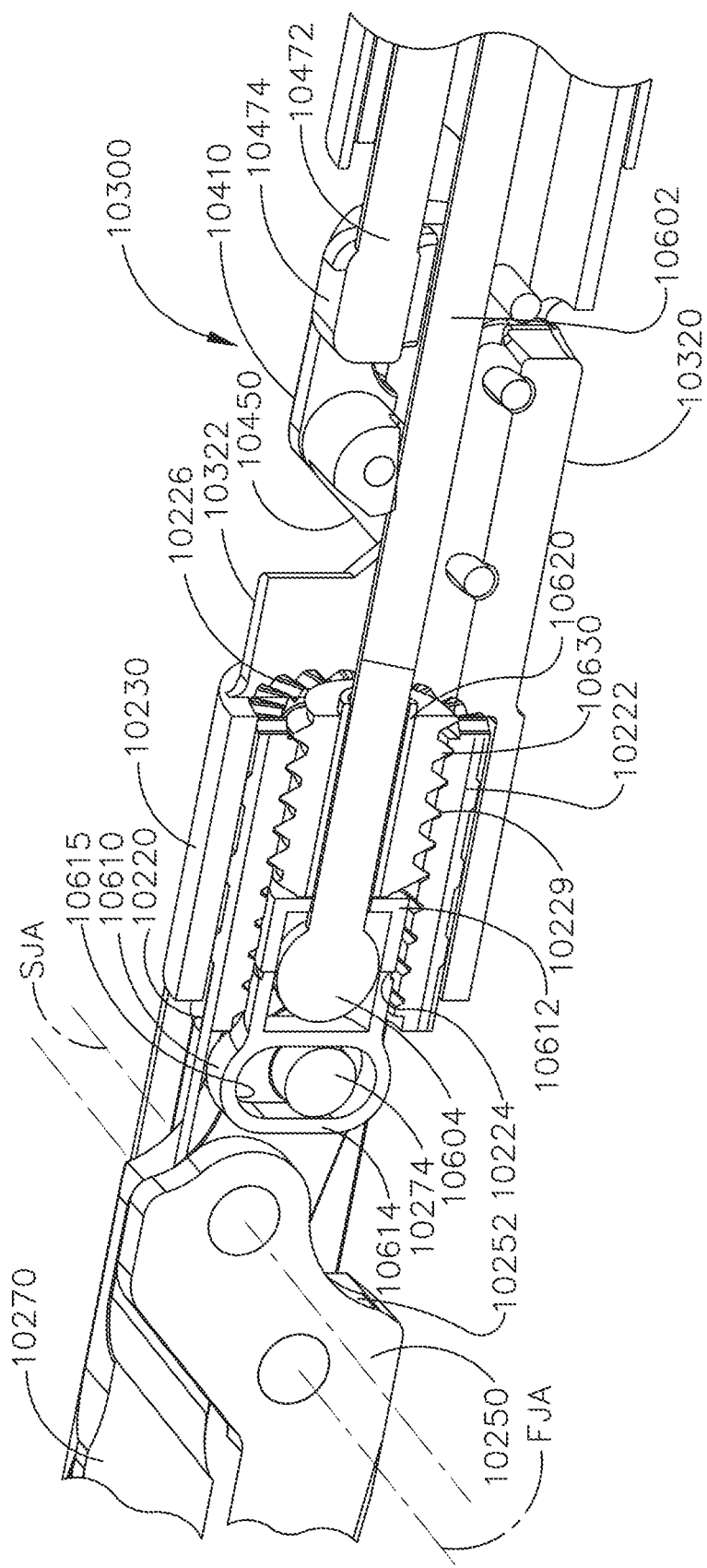
FIG. 26 is a cross-sectional perspective view of the surgical instrument of FIG. 25 with jaws thereof in a closed position.
Figure 27:
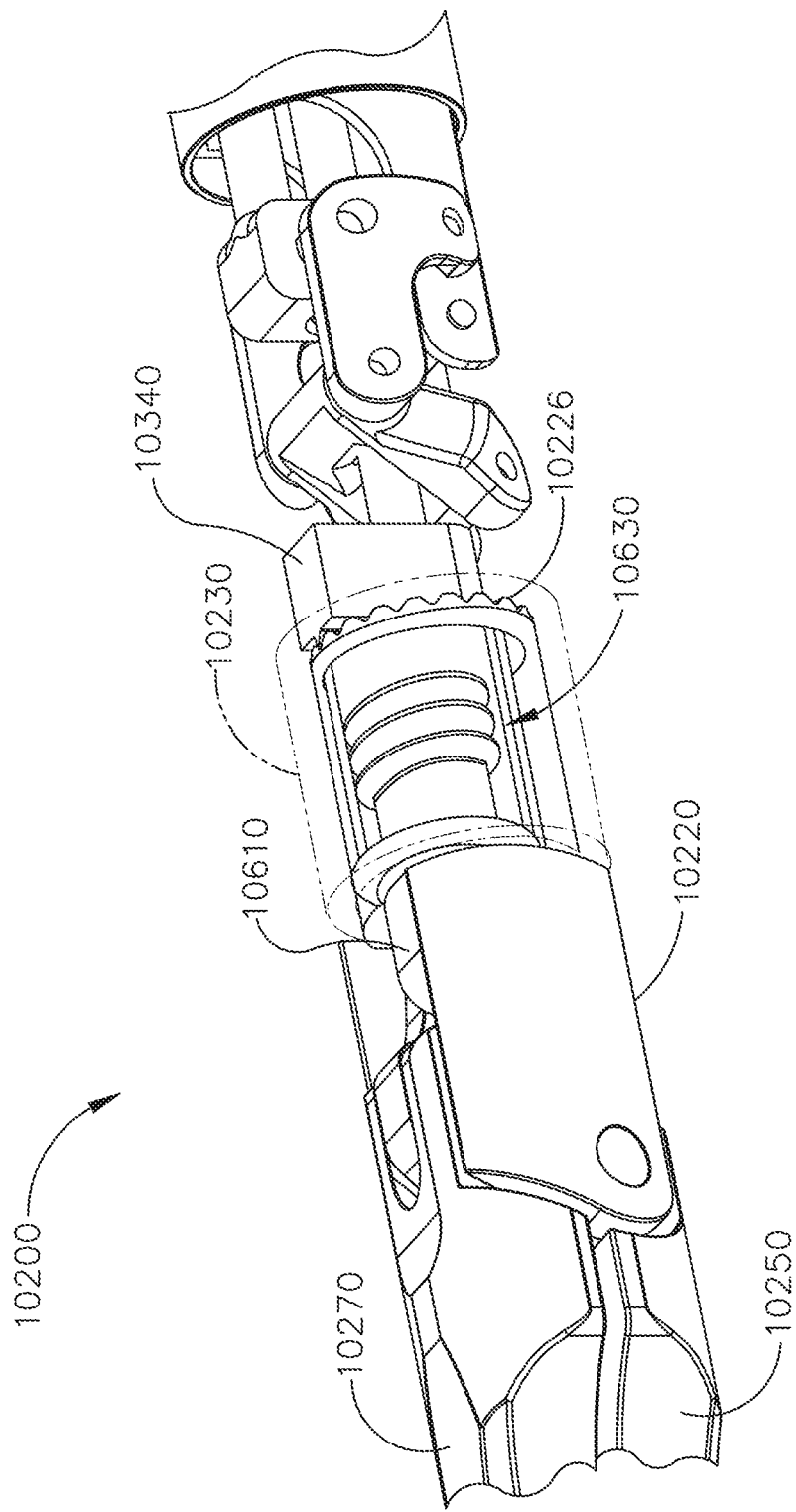
FIG. 27 is another perspective view of the surgical instrument of FIG. 26 with portions thereof shown in phantom.
Figure 28:
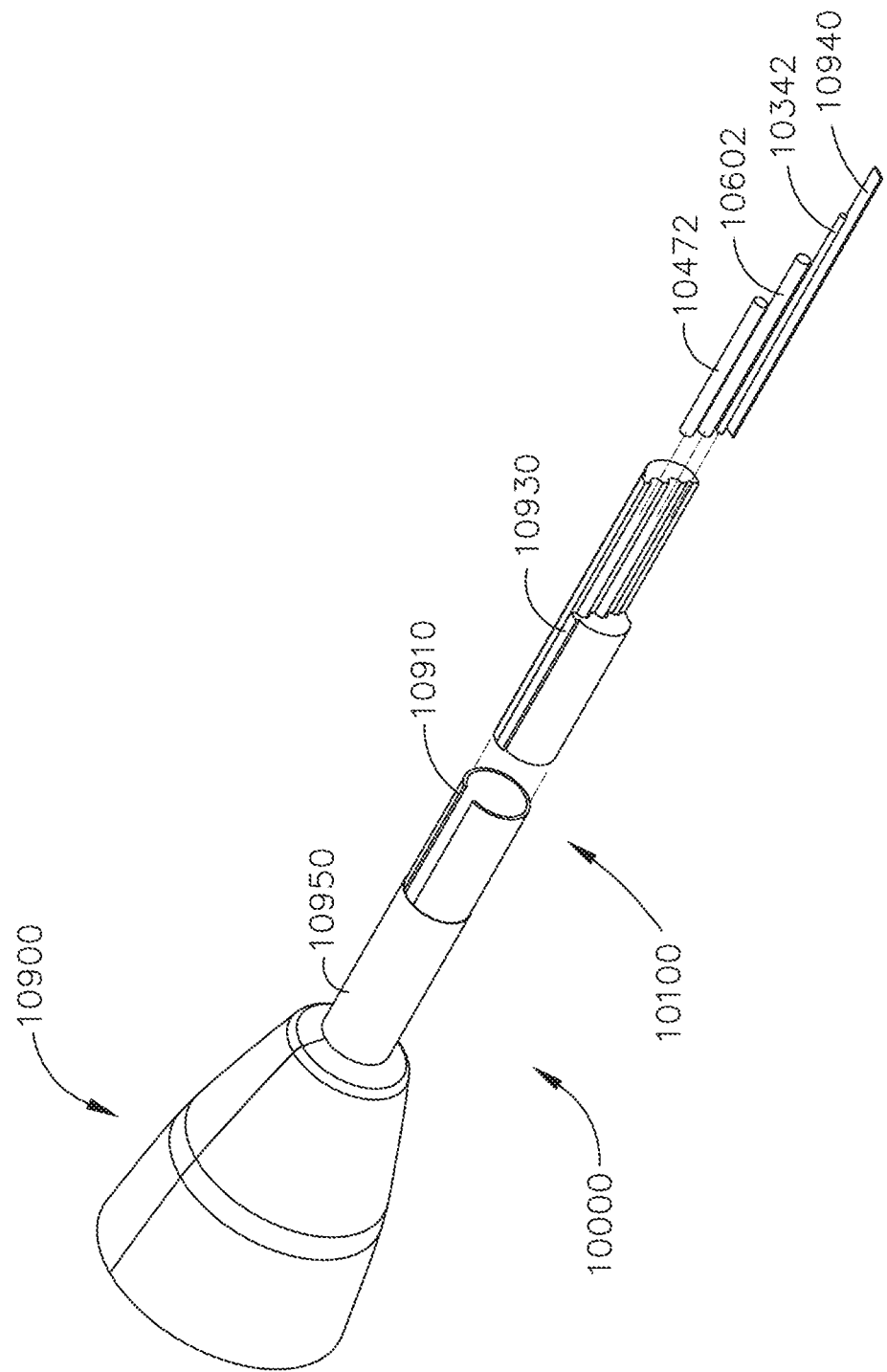
FIG. 28 is a partial cross-sectional perspective view of a proximal shaft segment embodiment, in accordance with at least one aspect of the present disclosure.
Figure 29:
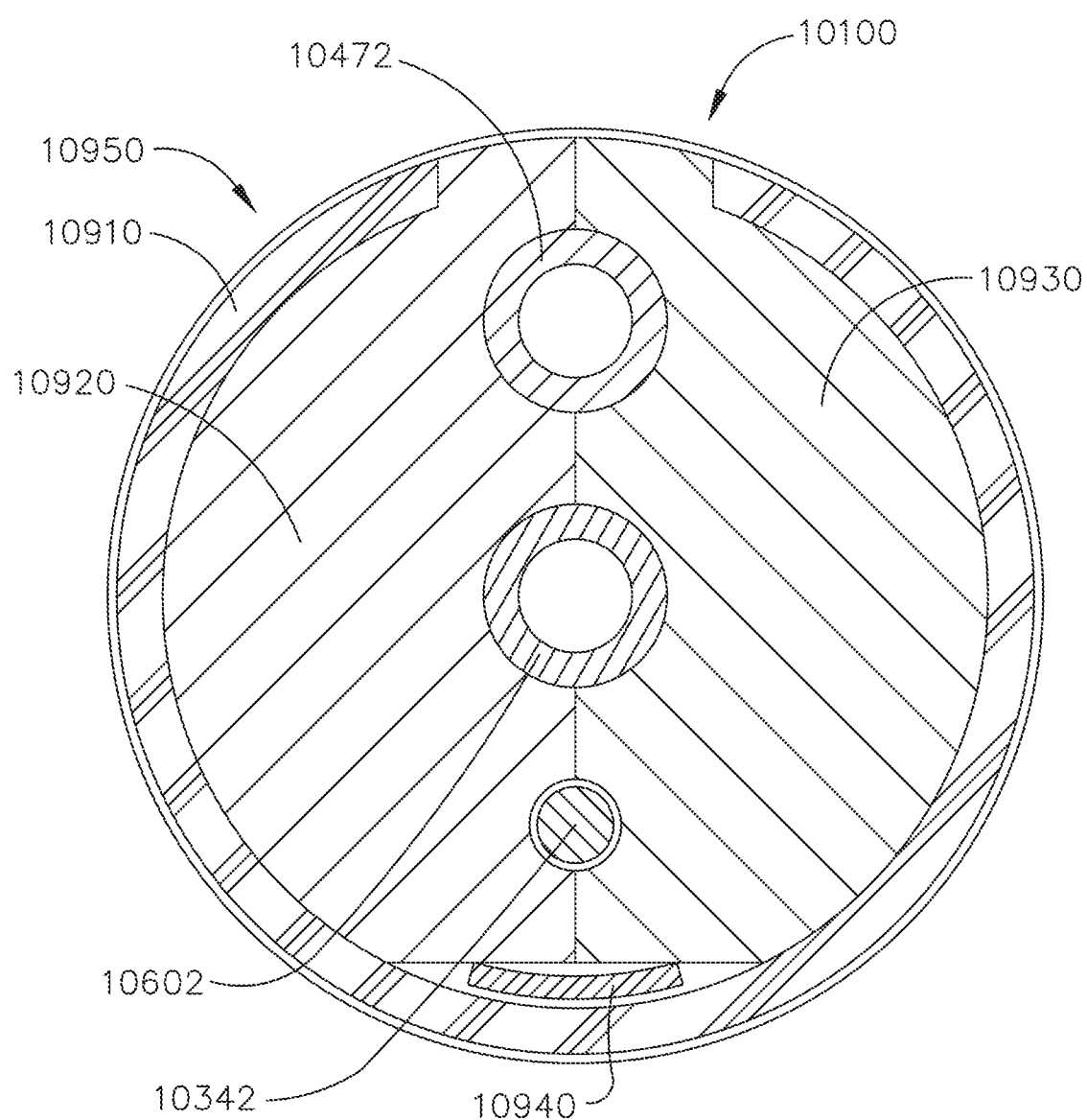
FIG. 29 is a cross-sectional end view of the proximal shaft segment of FIG. 28.
Figure 30:
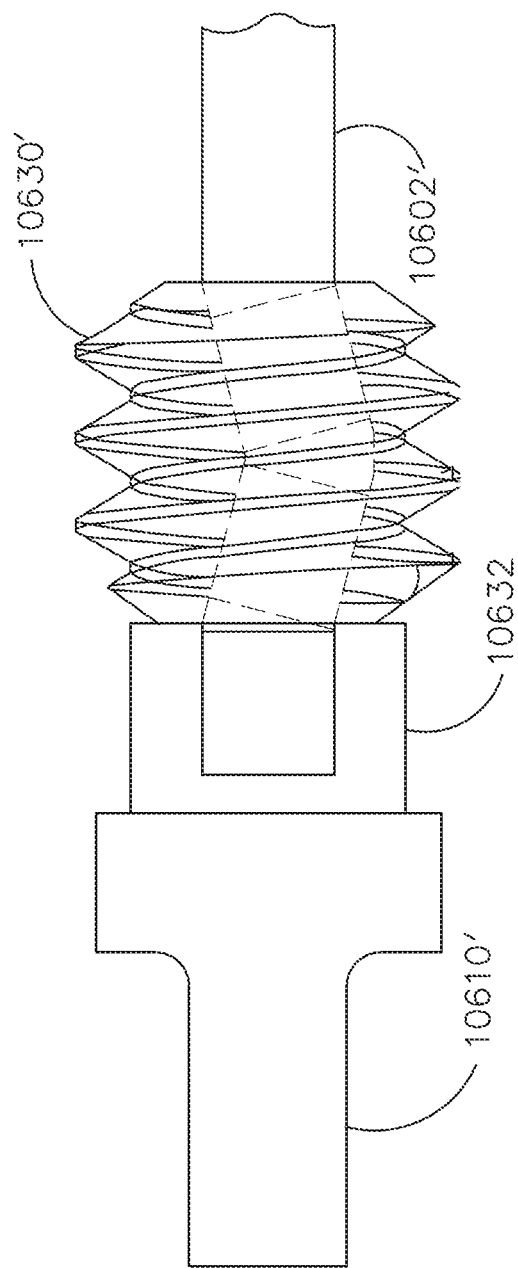
FIG. 30 is a top view of a portion of a rotary drive shaft, an actuation yoke assembly, and a threaded insert embodiment with portions of the rotary drive shaft shown in phantom, in accordance with at least one aspect of the present disclosure.
Figure 31:
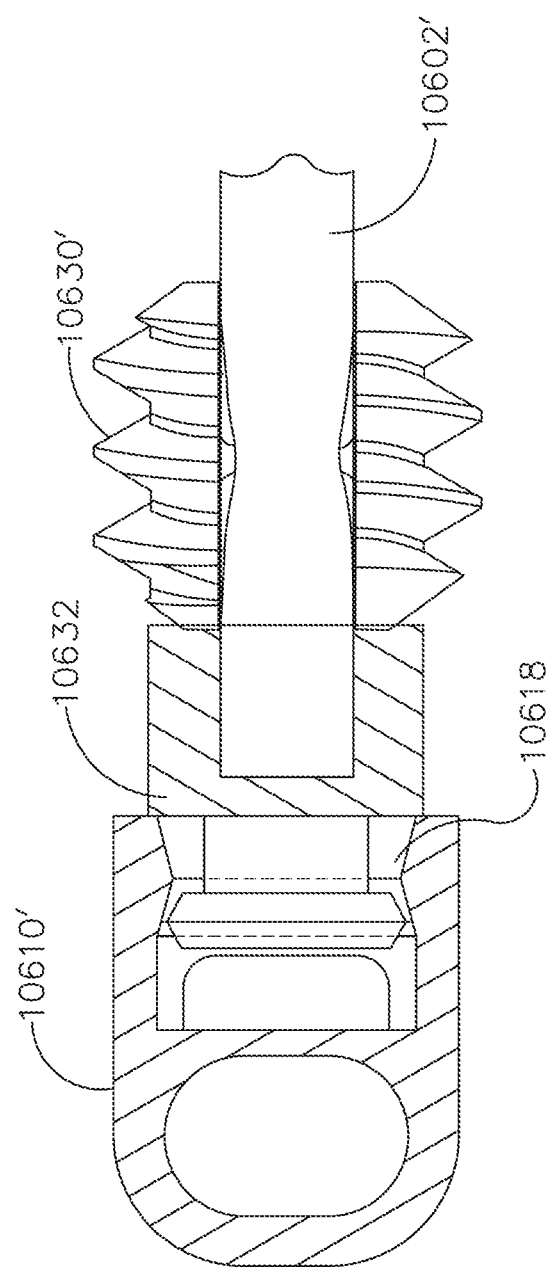
FIG. 31 is a side elevational view of the rotary drive shaft, actuation yoke assembly and threaded insert of FIG. 30.
Figure 32:
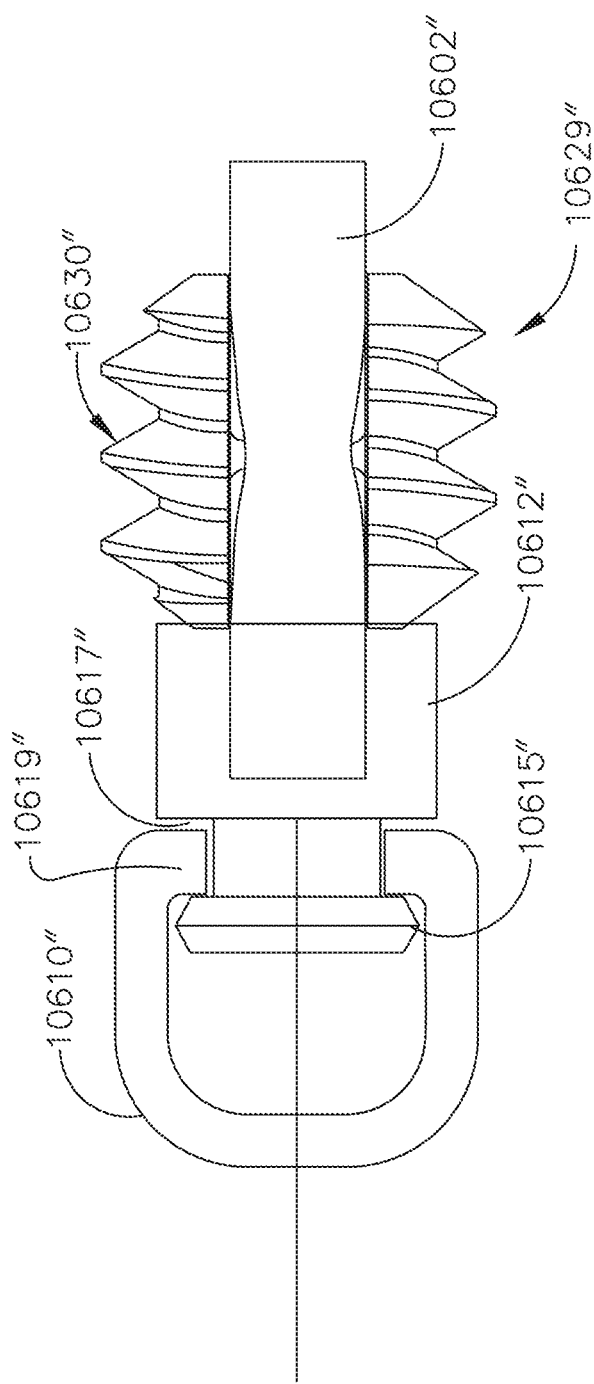
FIG. 32 is a side elevational view of a portion of another rotary drive shaft, another actuation yoke assembly, and another threaded insert embodiment, in accordance with at least one aspect of the present disclosure.
Figure 33:
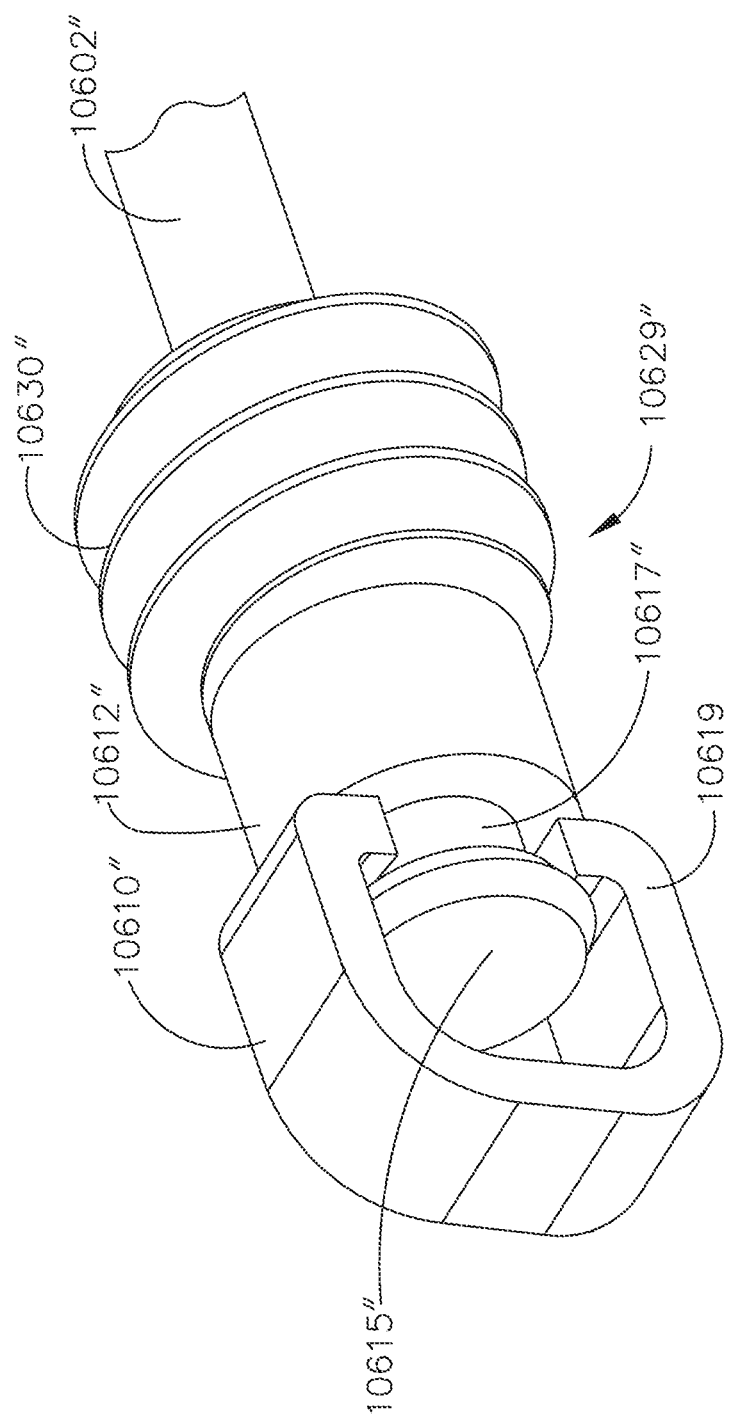
FIG. 33 is a perspective view of the rotary drive shaft, actuation yoke assembly, and threaded insert of FIG. 32.
Figure 37:
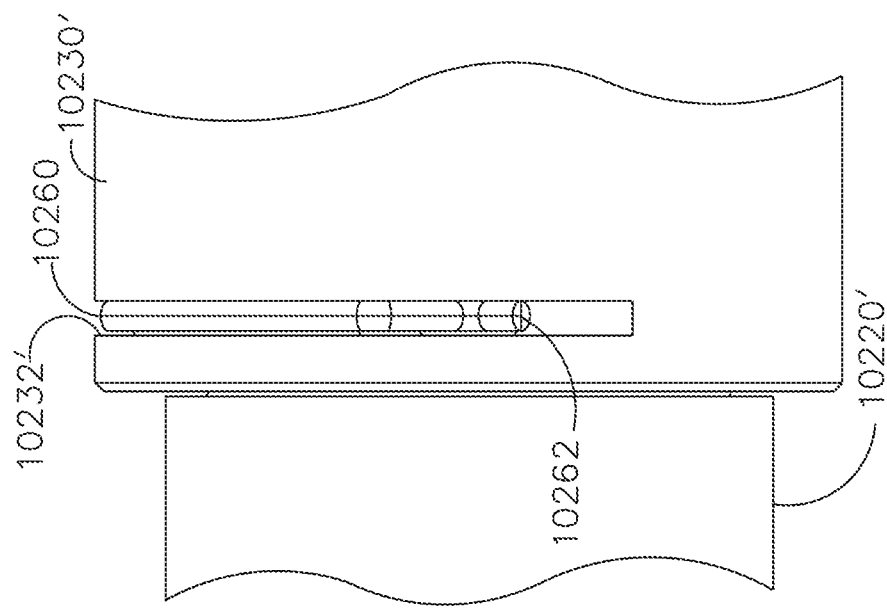
FIG. 37 is a side elevational view of a portion of the distal frame member and proximal housing member of FIG. 34.
Figure 36:
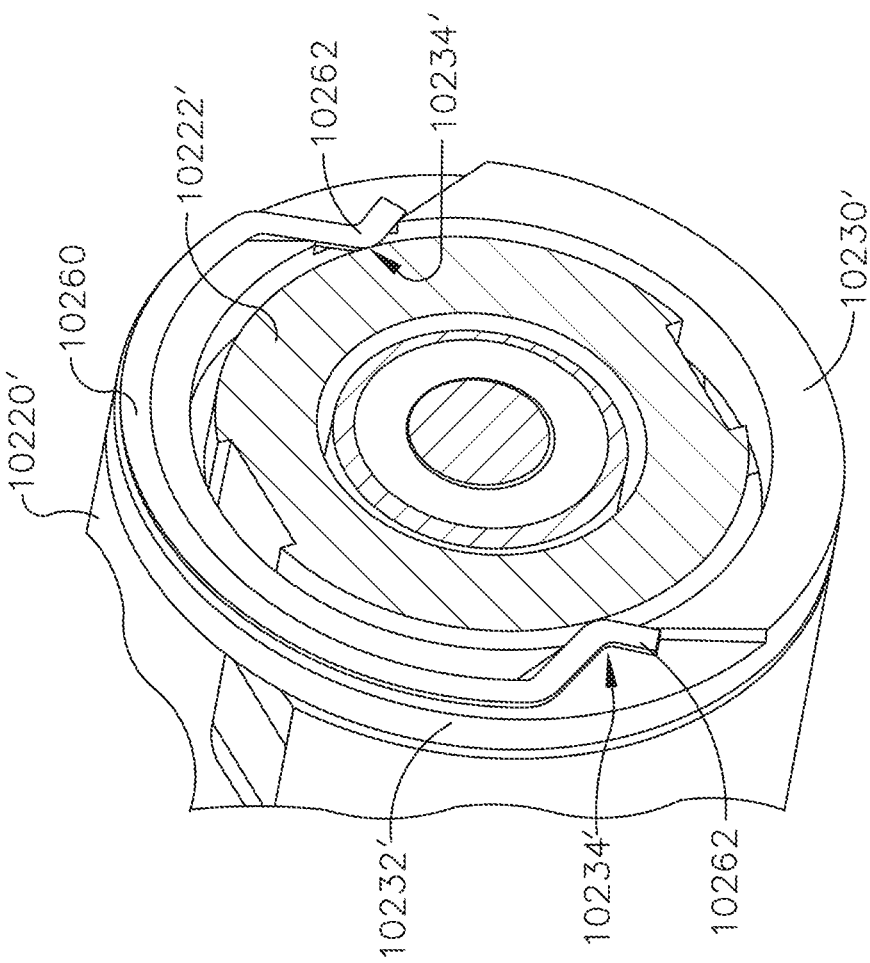
FIG. 36 is a cross-sectional end view of the distal frame member and proximal housing member of FIG. 34.
Figure 38:
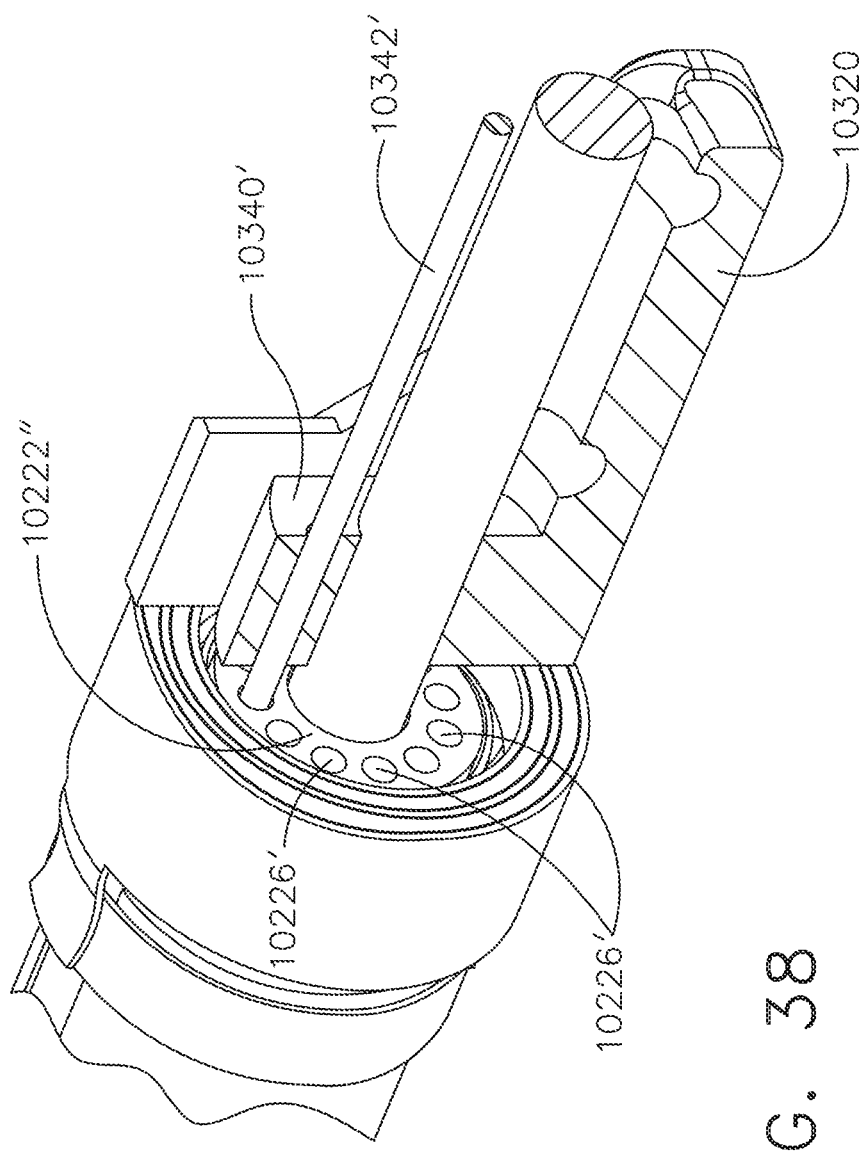
FIG. 38 is a partial cross-sectional perspective view of a portion of another surgical instrument, in accordance with at least one aspect of the present disclosure.
Figure 39:
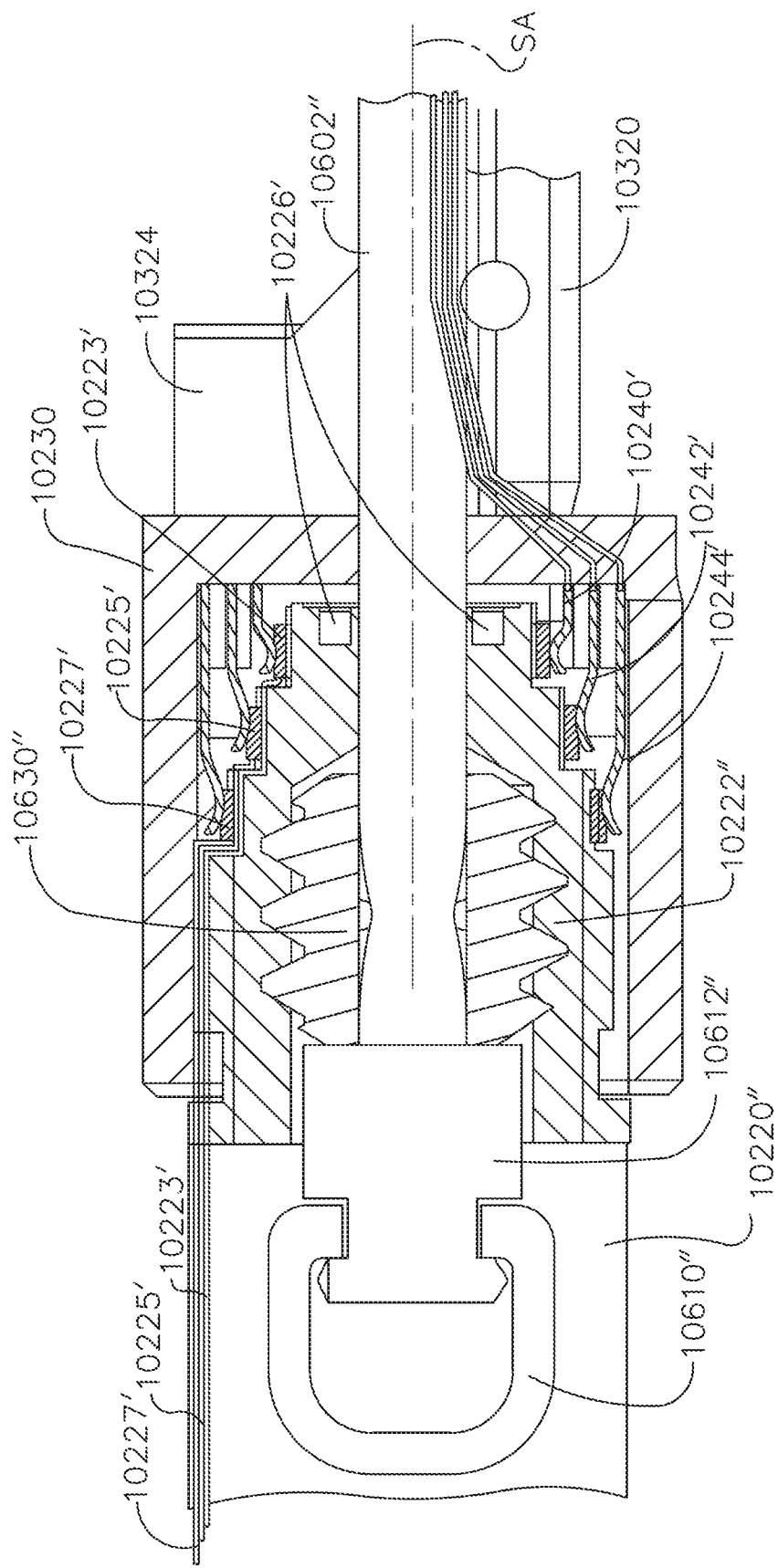
FIG. 39 is a cross-sectional side view of a portion of the surgical instrument of FIG. 38.
Figure 40:
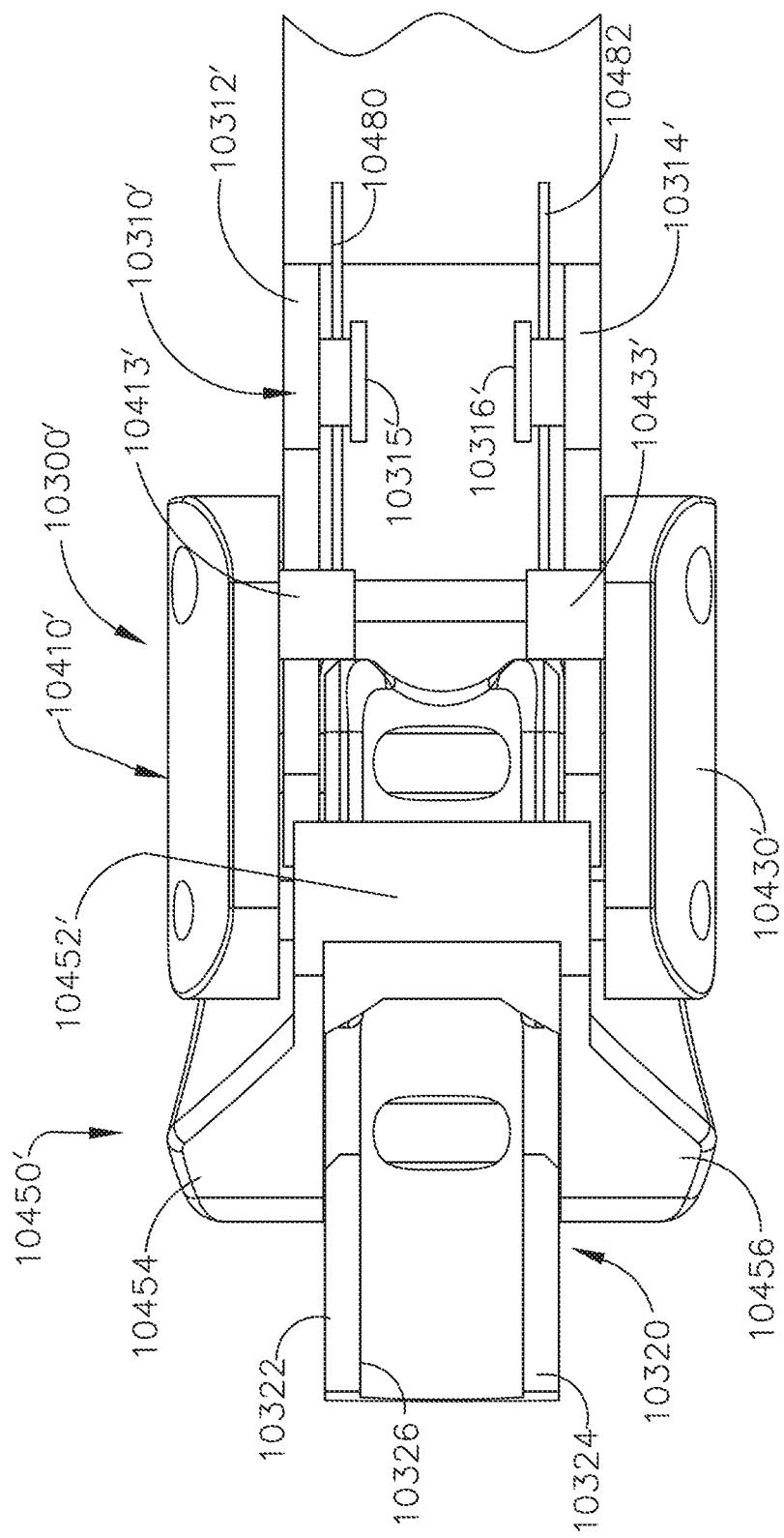
FIG. 40 is a top view of a portion of another articulation joint embodiment in an unarticulated position, in accordance with at least one aspect of the present disclosure.
Figure 41:
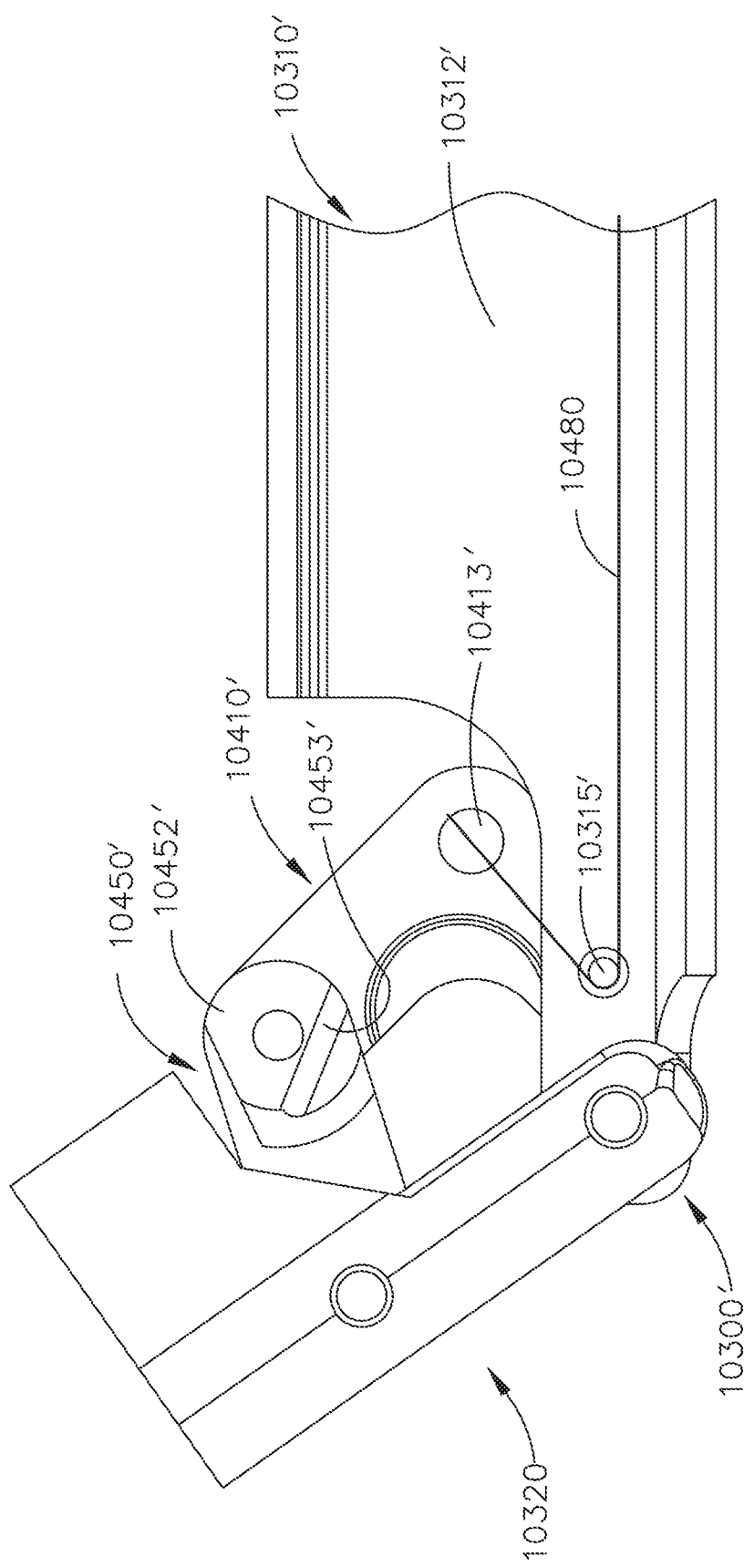
FIG. 41 is a partial cross-sectional side view of the articulation joint of FIG. 40 articulated in a first direction.
Figure 42:
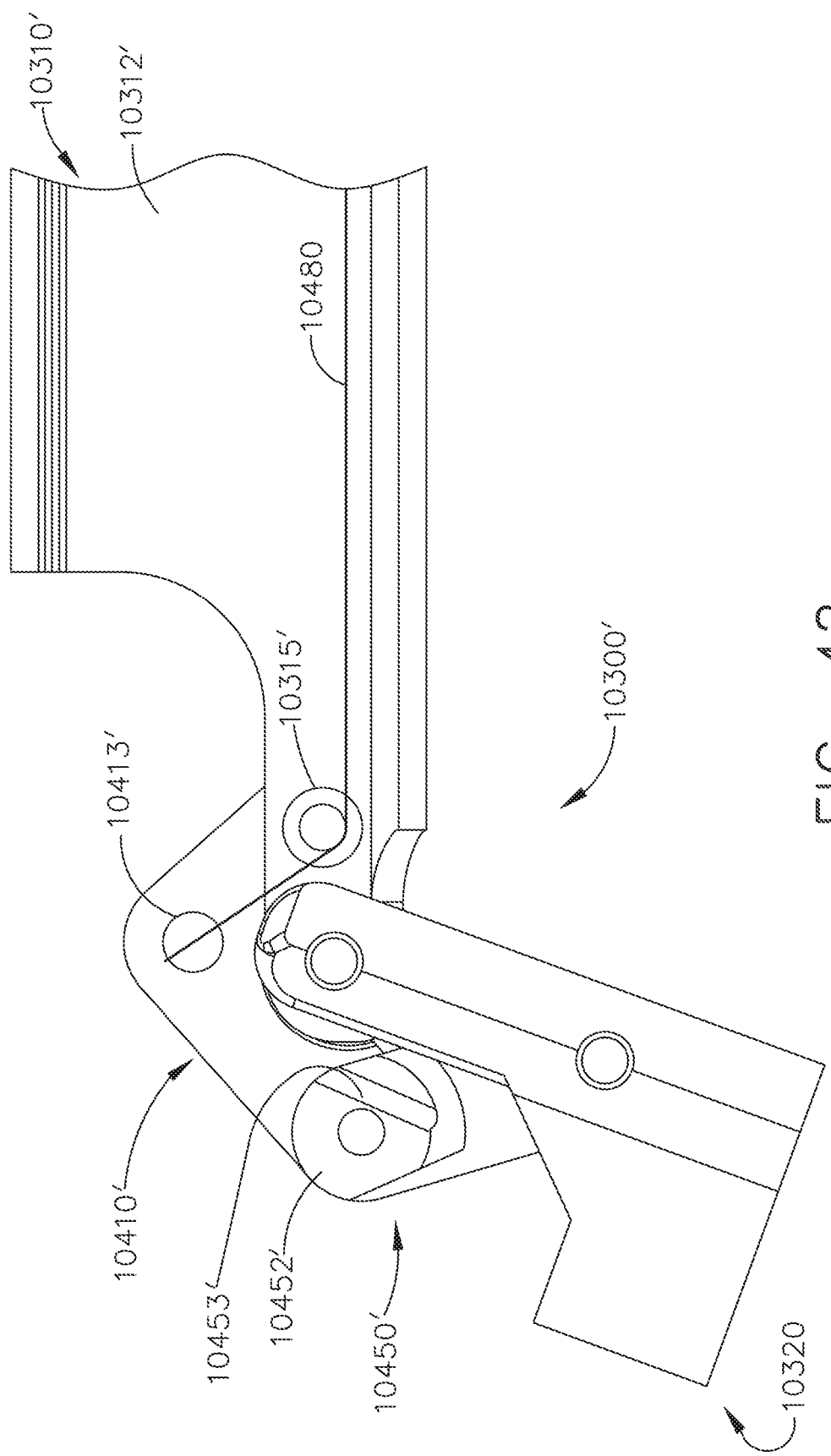
FIG. 42 is another partial cross-sectional side view of the articulation joint of FIG. 40 articulated in a second direction.
Figure 43:
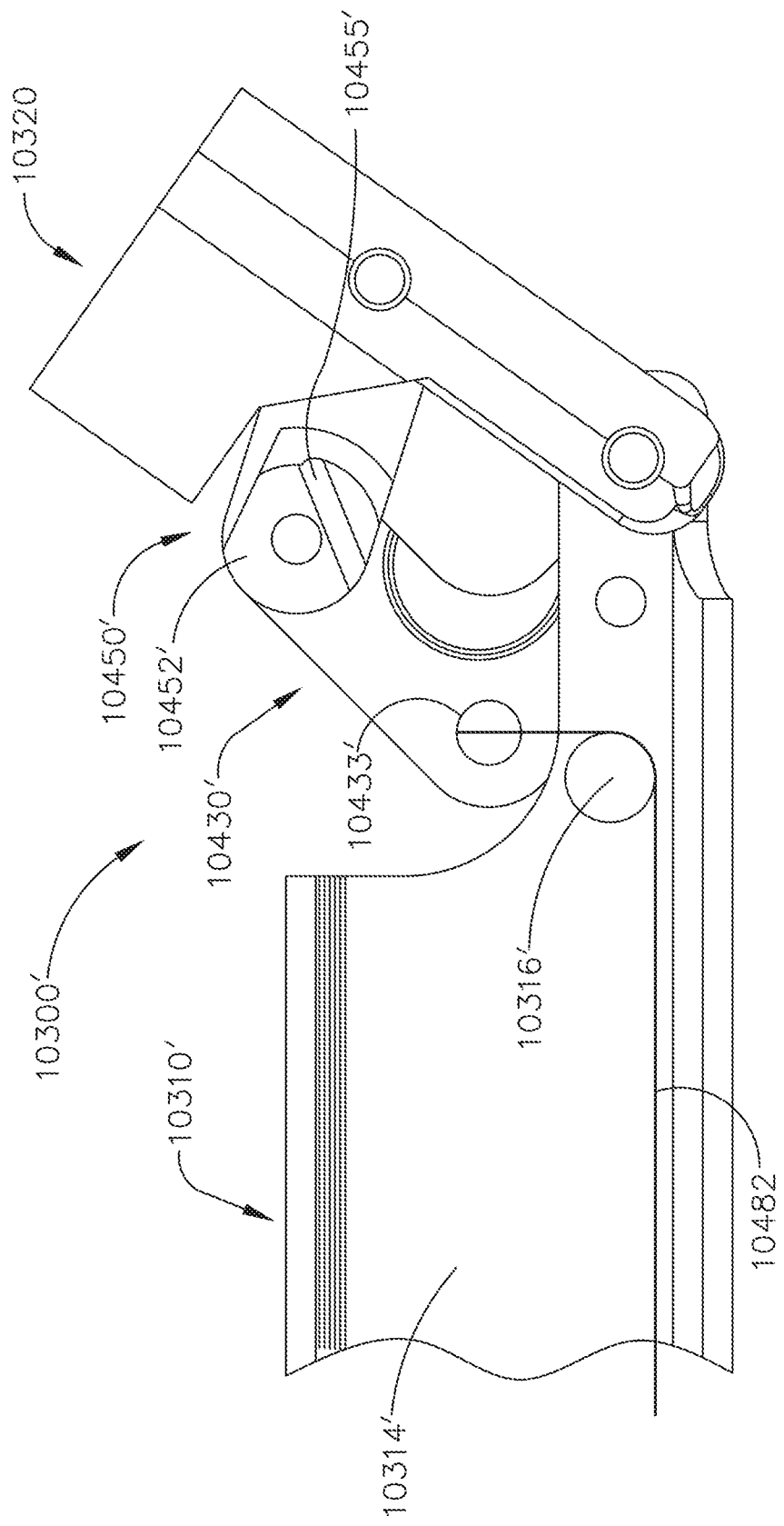
FIG. 43 is another partial cross-sectional side view of the articulation joint of FIG. 40 articulated in a first direction.
Figure 44:
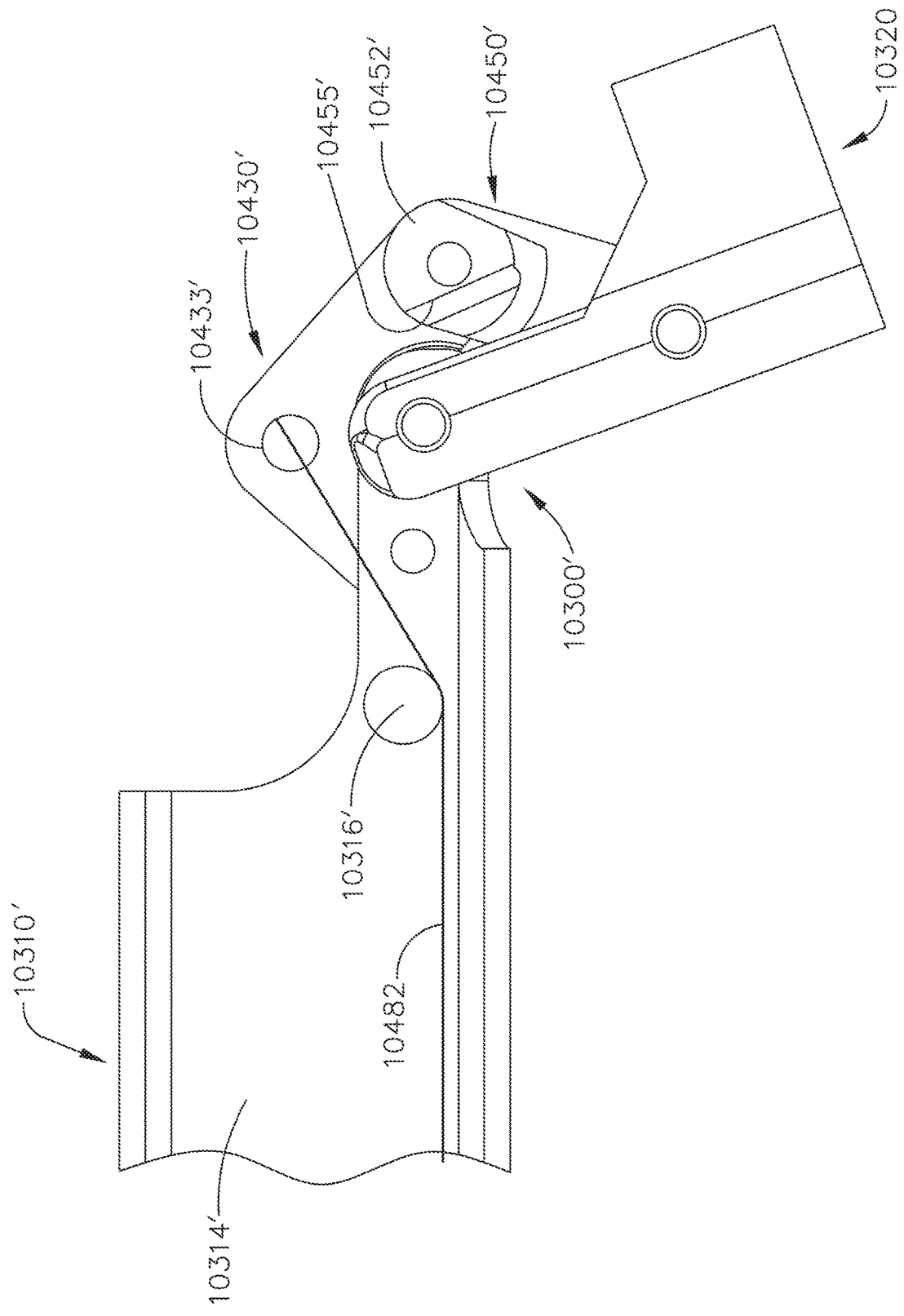
FIG. 44 is another partial cross-sectional side view of the articulation joint of FIG. 40 articulated in a second direction.
Figure 45:
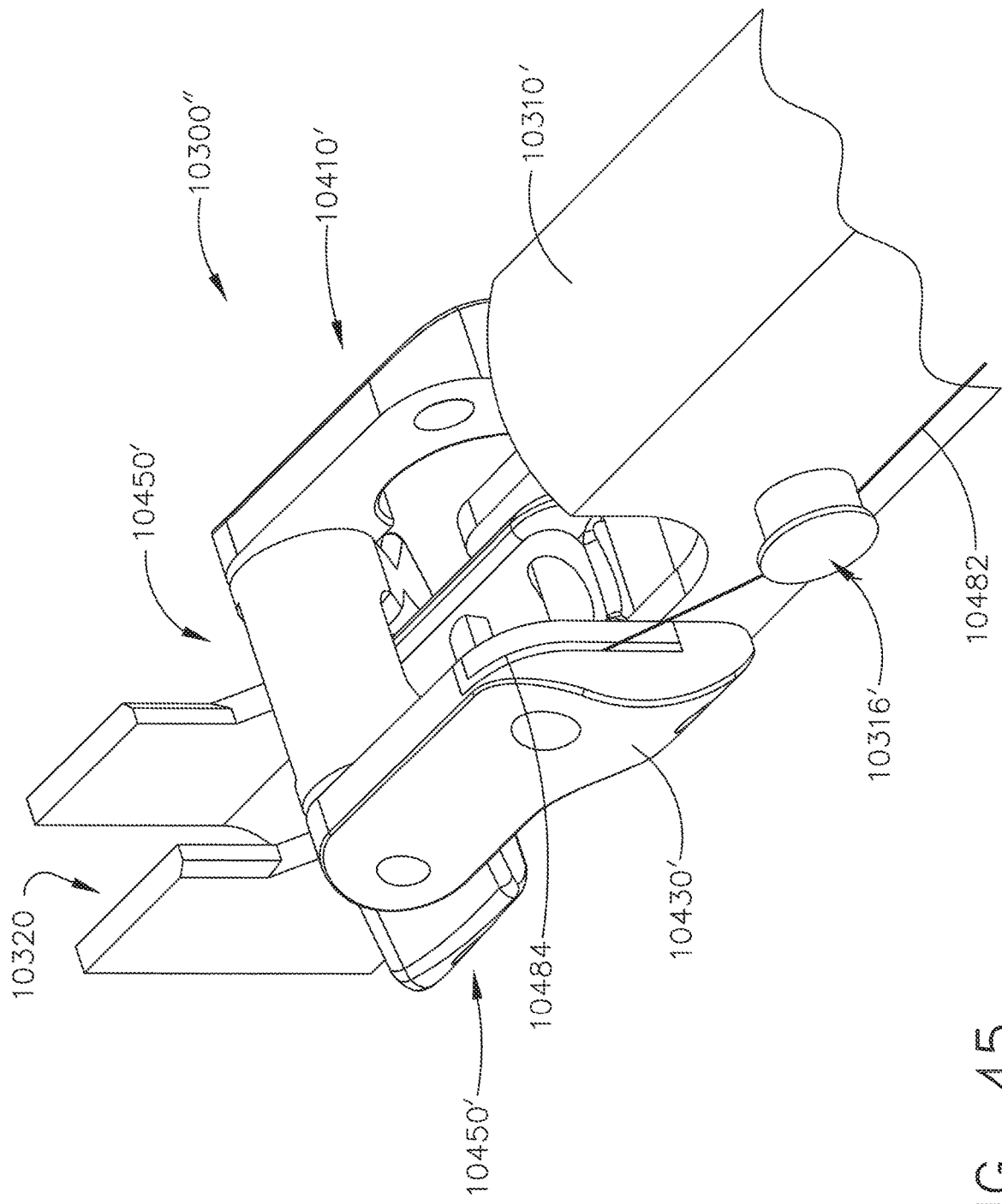
FIG. 45 is a partial perspective view of a portion of another articulation joint embodiment, in accordance with at least one aspect of the present disclosure.
Figure 46:
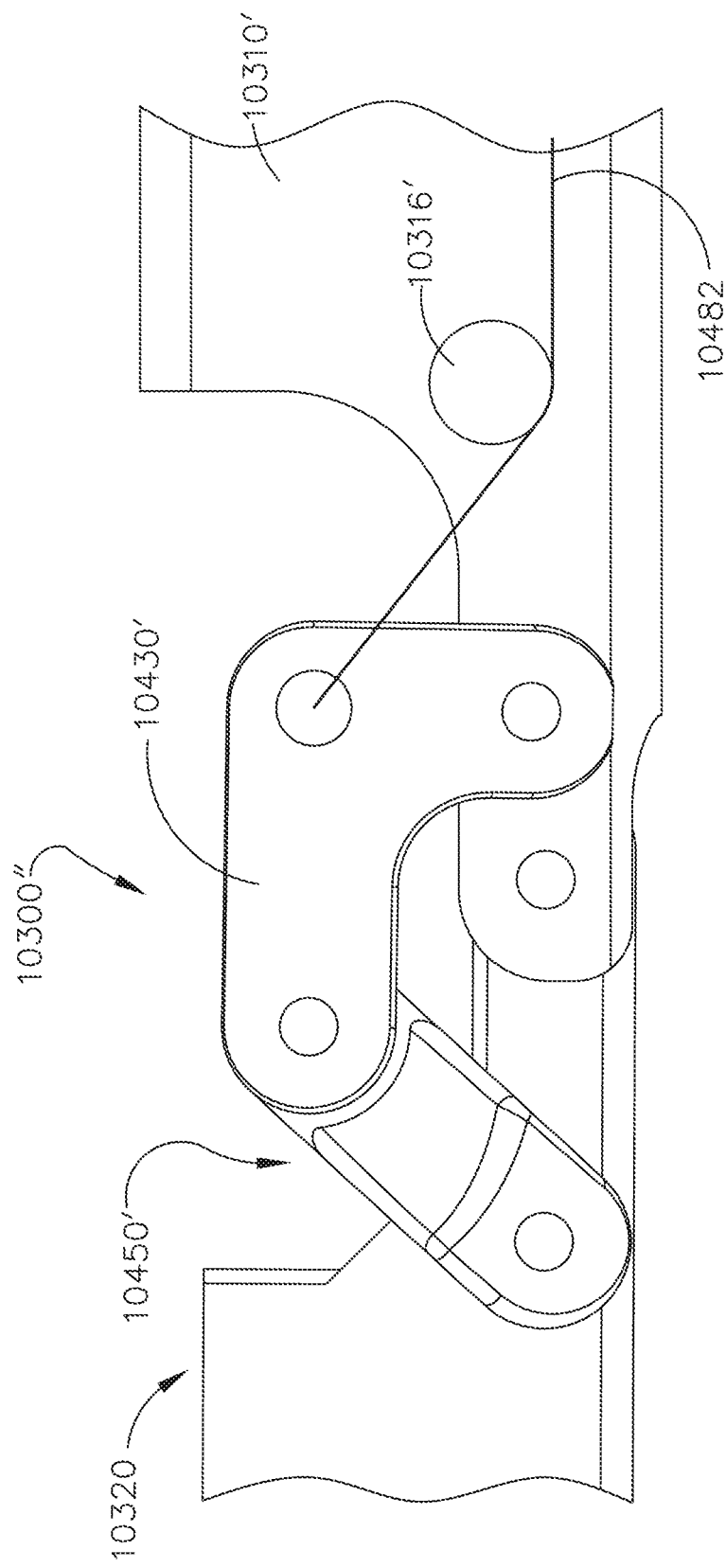
FIG. 46 is a side elevational view of the articulation joint of FIG. 45 in an unarticulated position.
Figure 47:
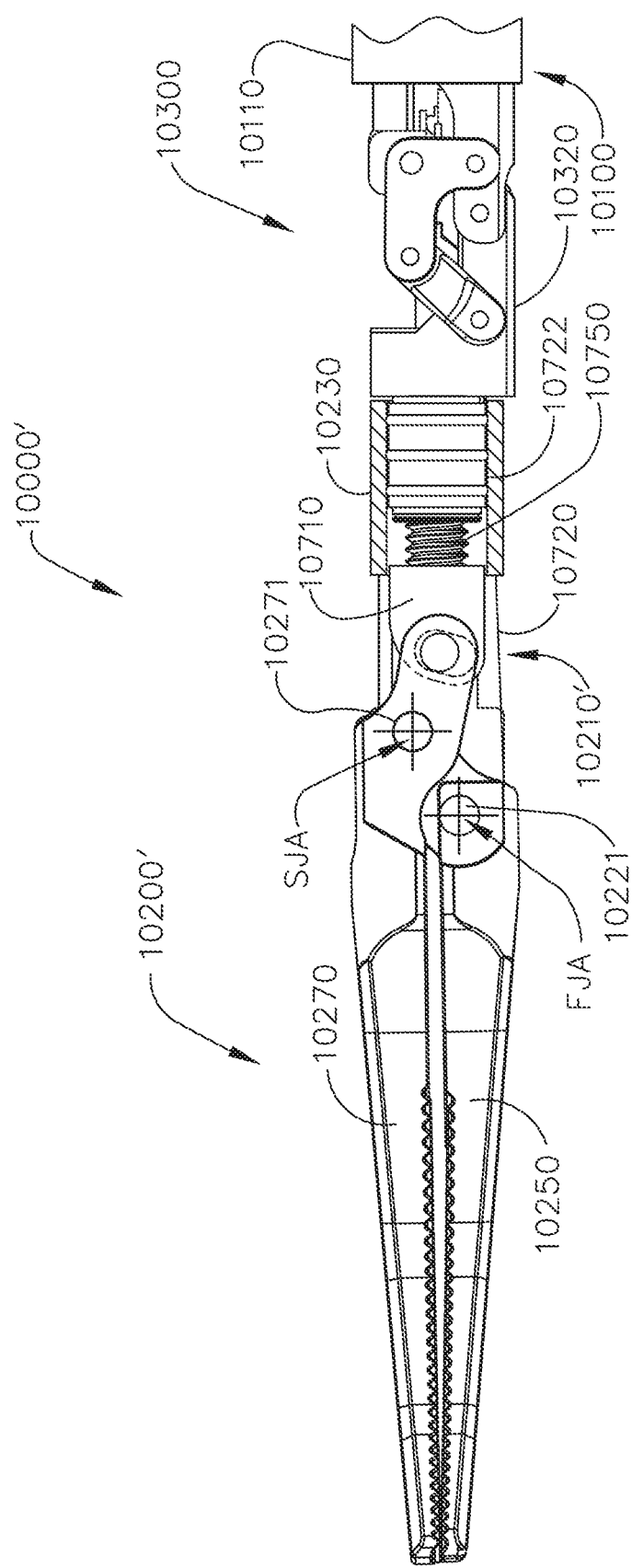
FIG. 47 is a side view of a portion of another surgical instrument with a surgical end effector thereof in an unarticulated position and jaws thereof in a closed position with portions thereof shown in phantom, in accordance with at least one aspect of the present disclosure.
Figure 48:
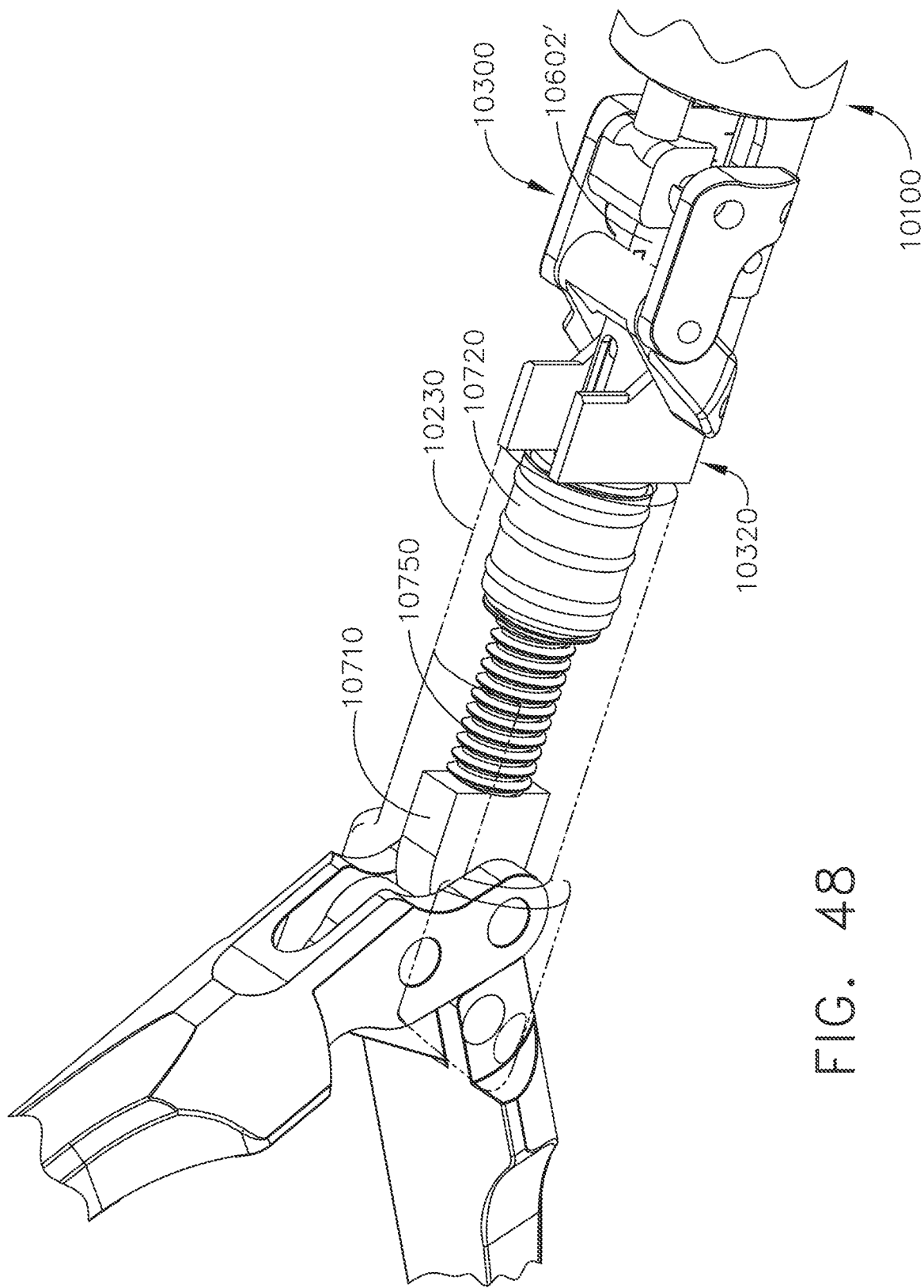
FIG. 48 is a partial perspective view of a portion of the surgical instrument of FIG. 47 with some elements thereof shown in phantom.
Figure 49:
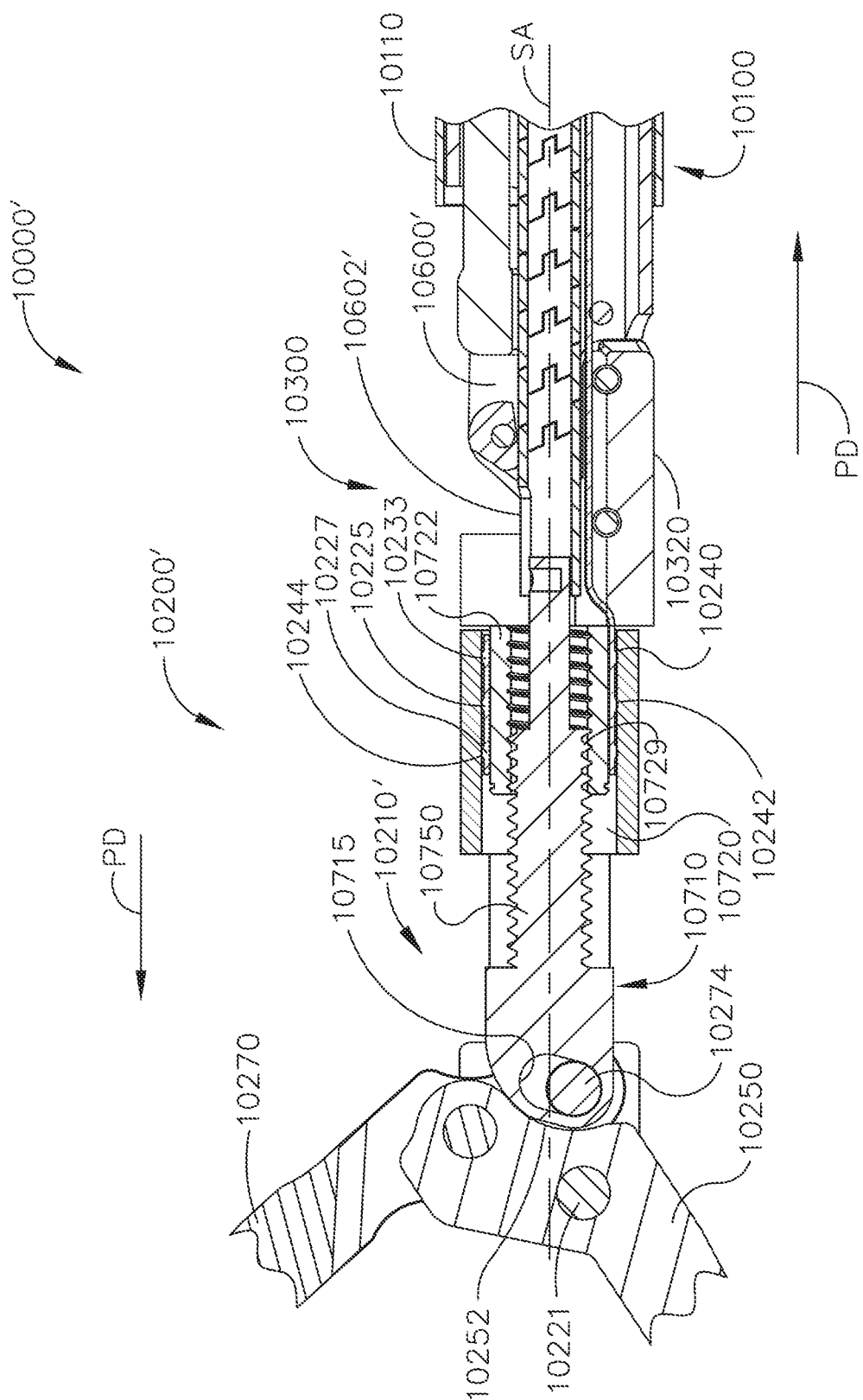
FIG. 49 is a cross-sectional side view of a portion of the surgical instrument of FIG. 47 with the jaws thereof in an open position.
Figure 50:
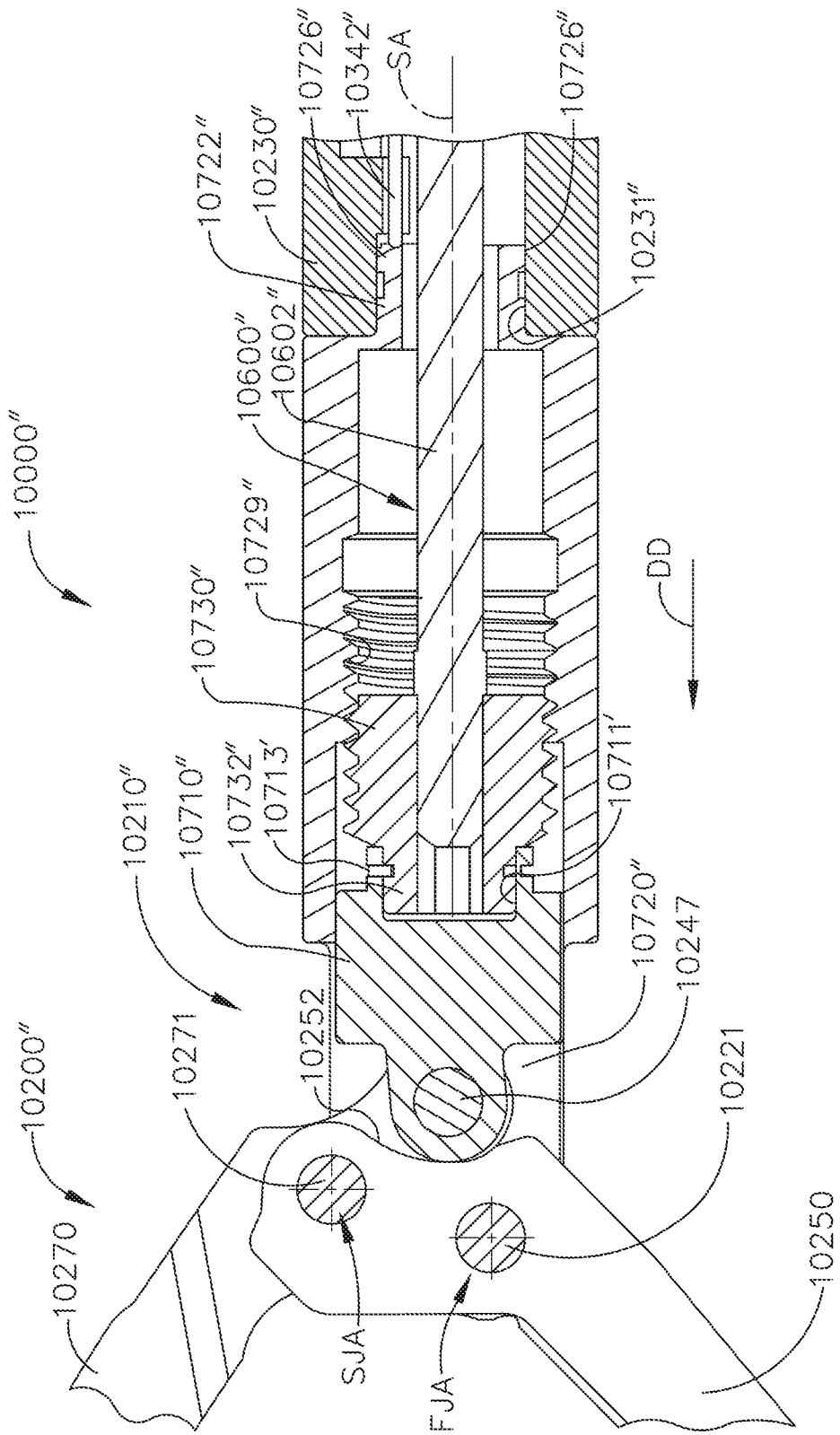
FIG. 50 is a partial cross-sectional view of another surgical instrument with the jaws thereof in an open position, in accordance with at least one aspect of the present disclosure.
Figure 51:
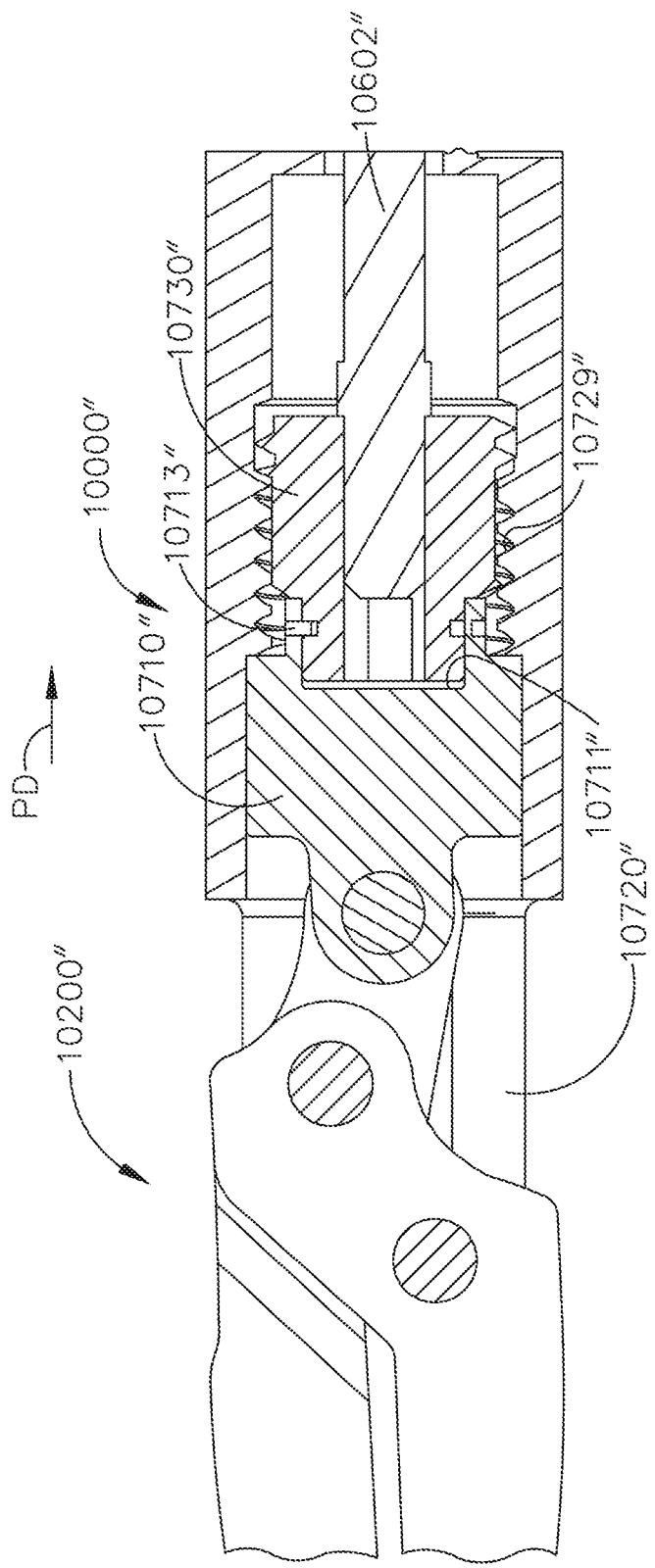
FIG. 51 is another partial cross-sectional view of the surgical instrument of FIG. 50 with the jaws thereof in a closed position.
Figure 52:
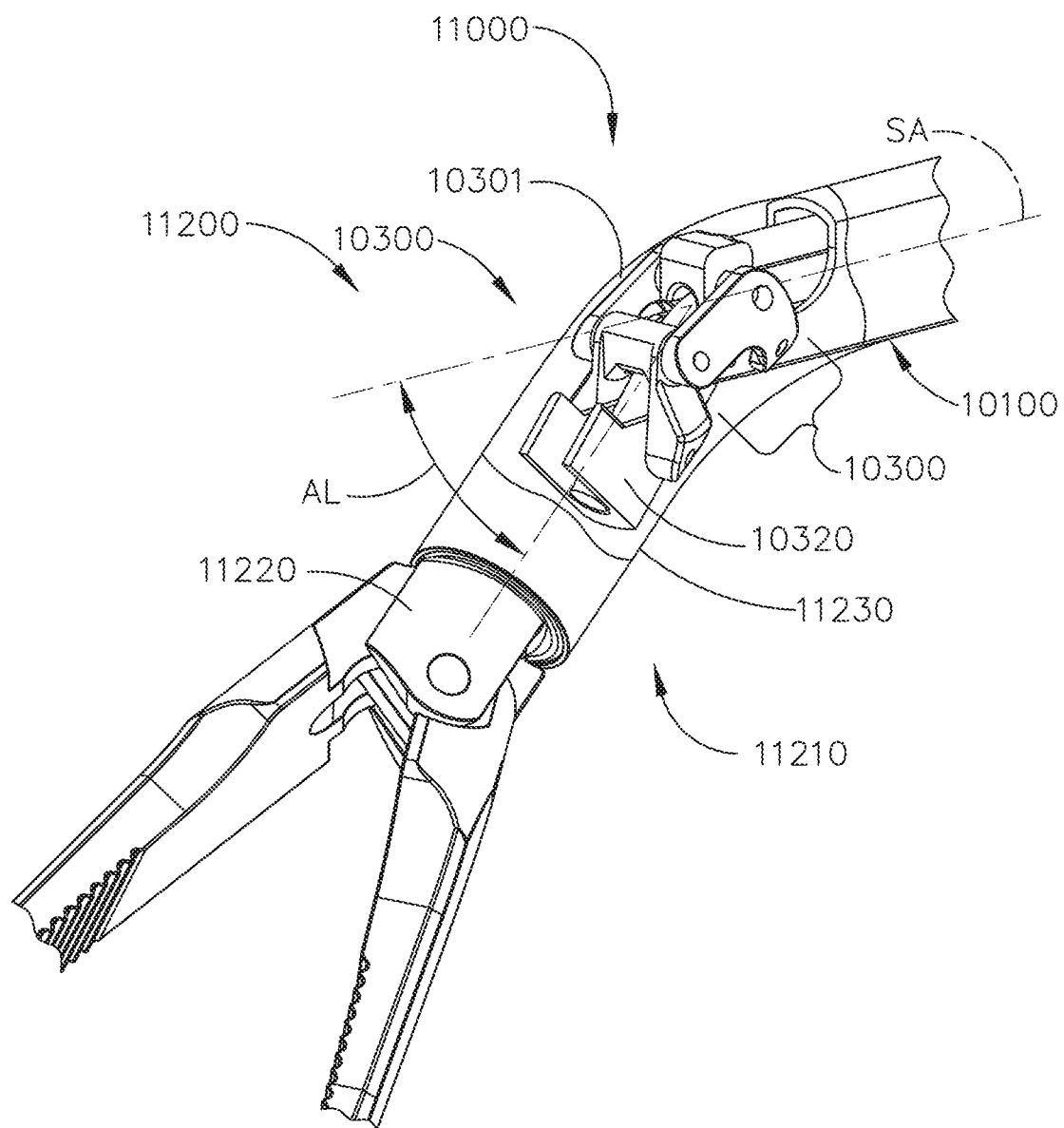
FIG. 52 is a perspective view of a portion of another articulatable surgical instrument with a surgical end effector thereof in an articulated position and jaws of the surgical end effector in an open position, in accordance with at least one aspect of the present disclosure.
Figure 53:
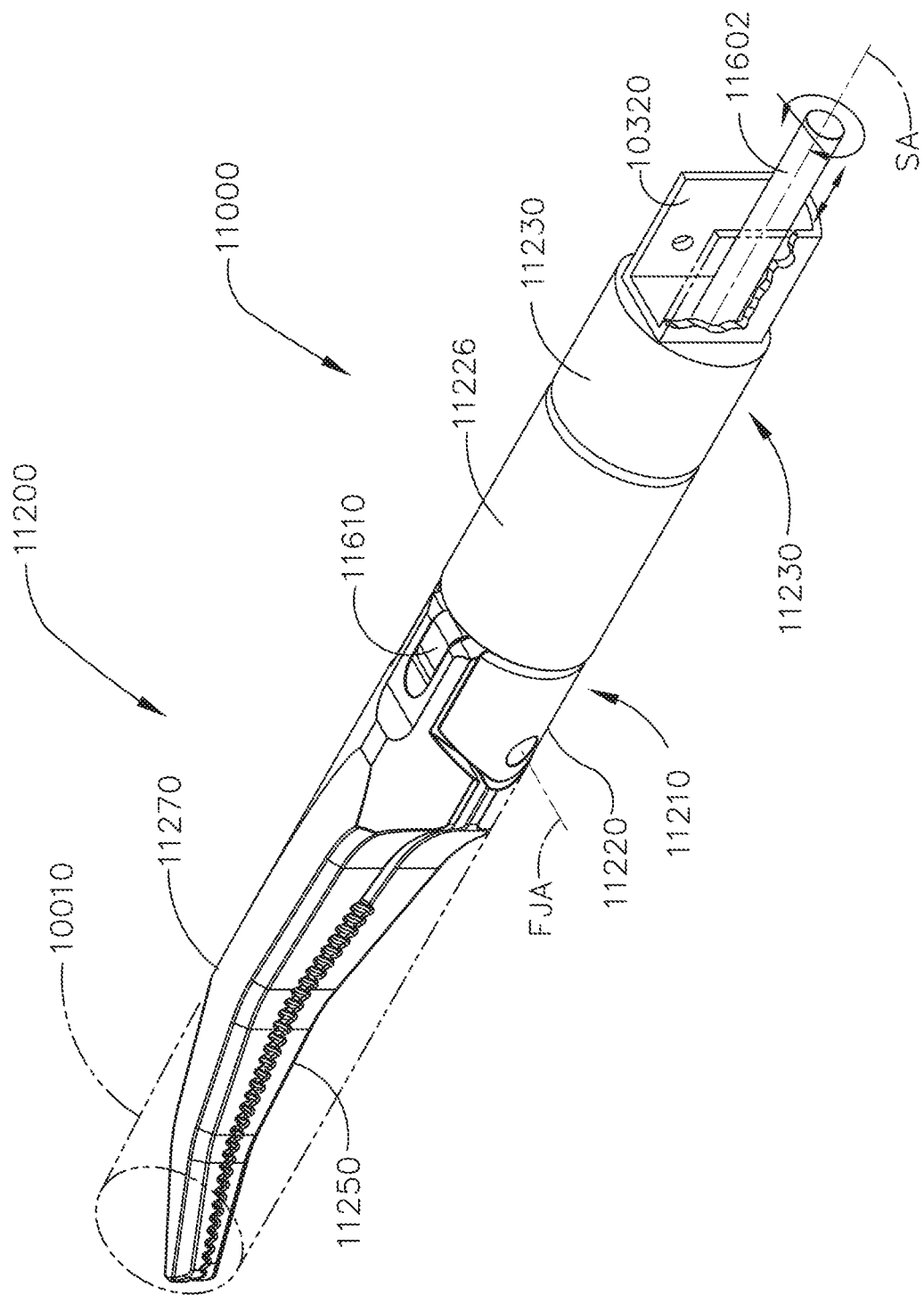
FIG. 53 is a perspective view of a portion of the surgical instrument of FIG. 52 with the surgical end effector thereof in an unarticulated position and the jaws thereof in a closed position.
Figure 150:
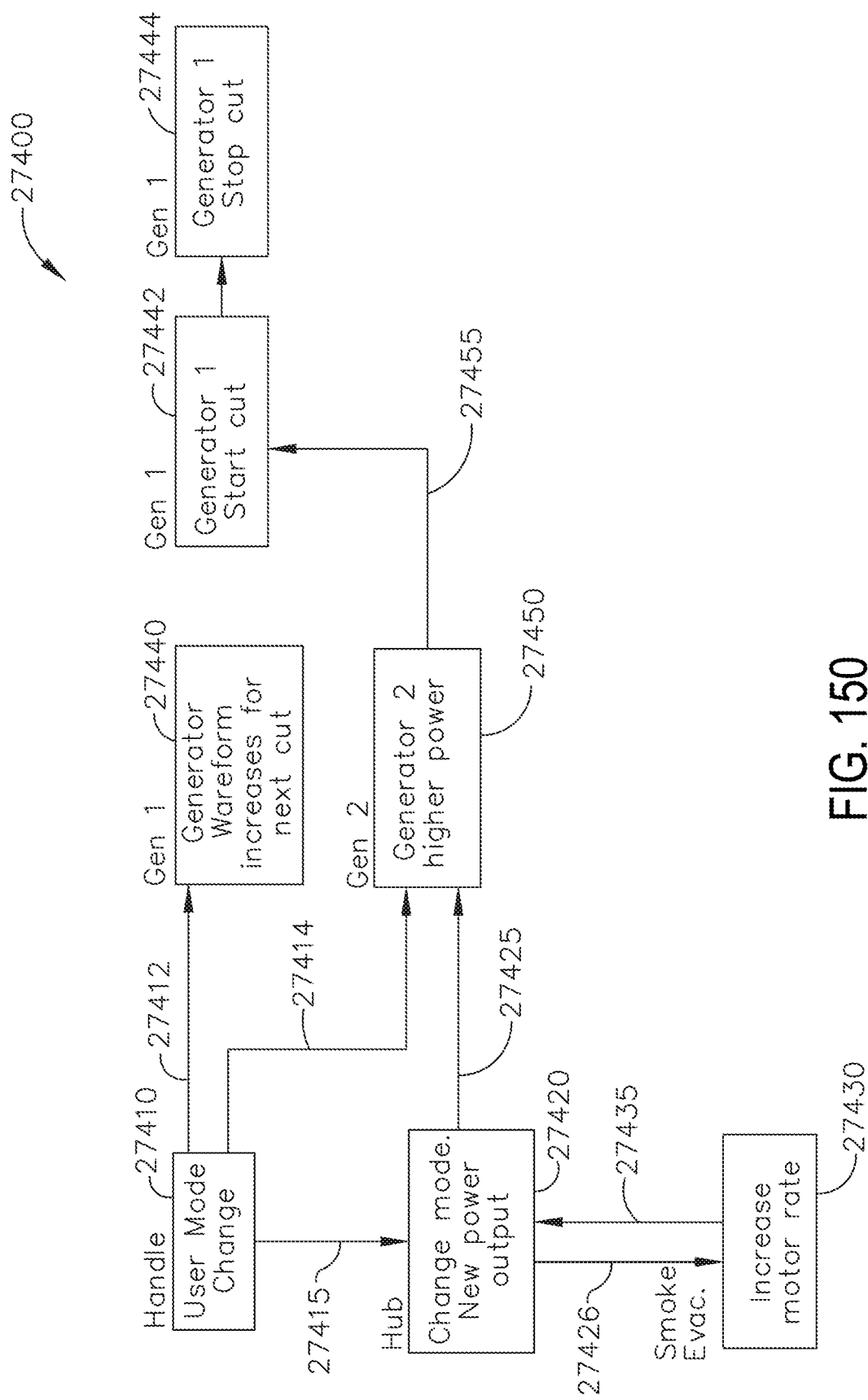
Figure 151:
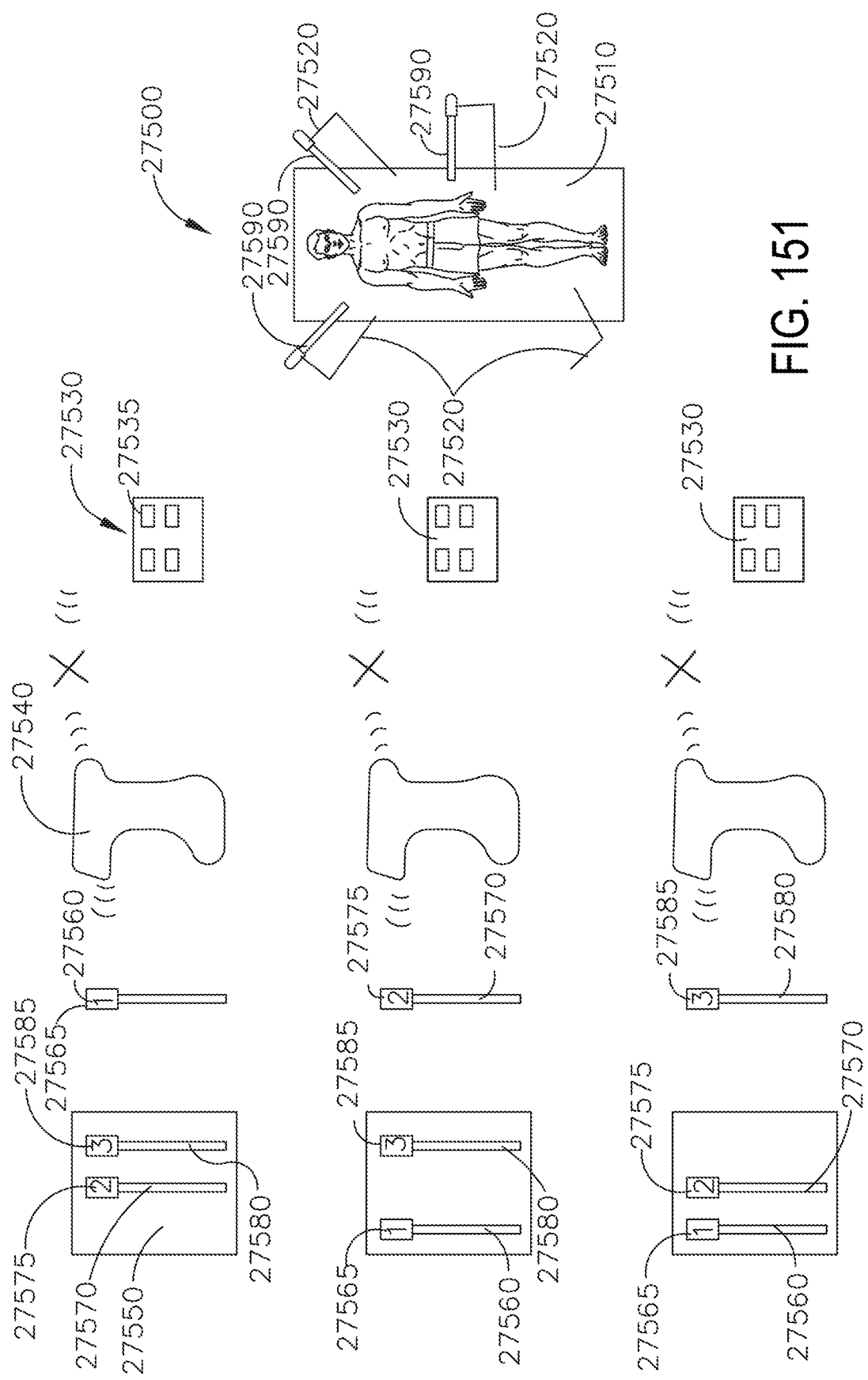
Figure 152:
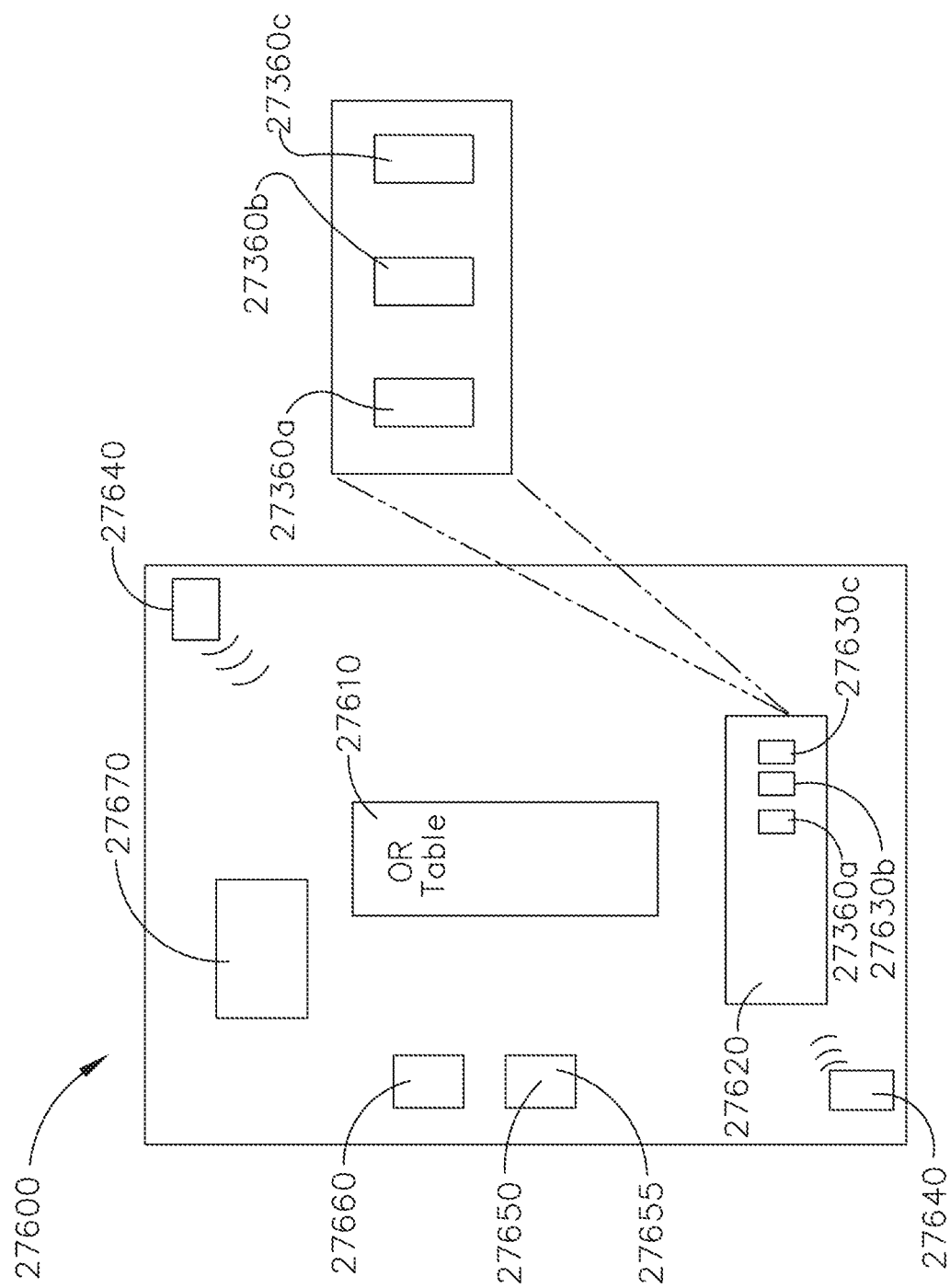
Figure 154:
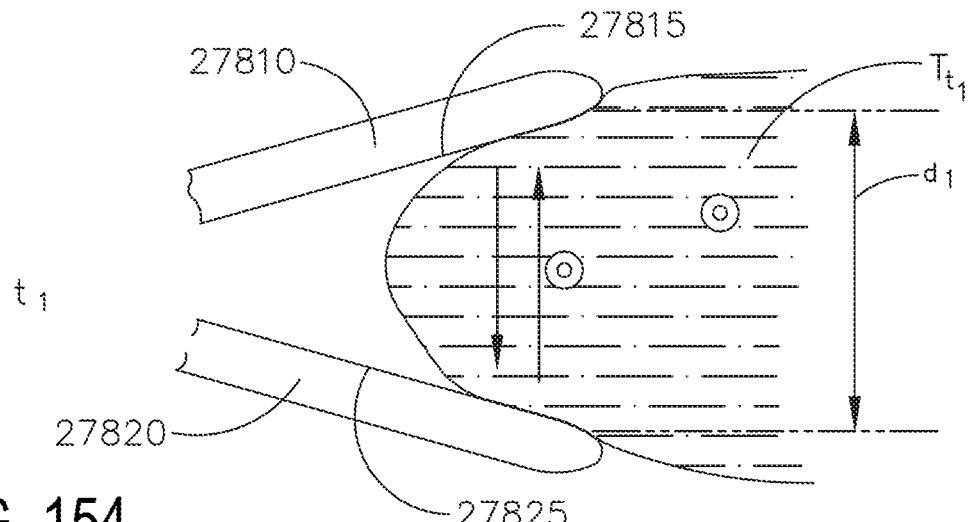
Figure 155:
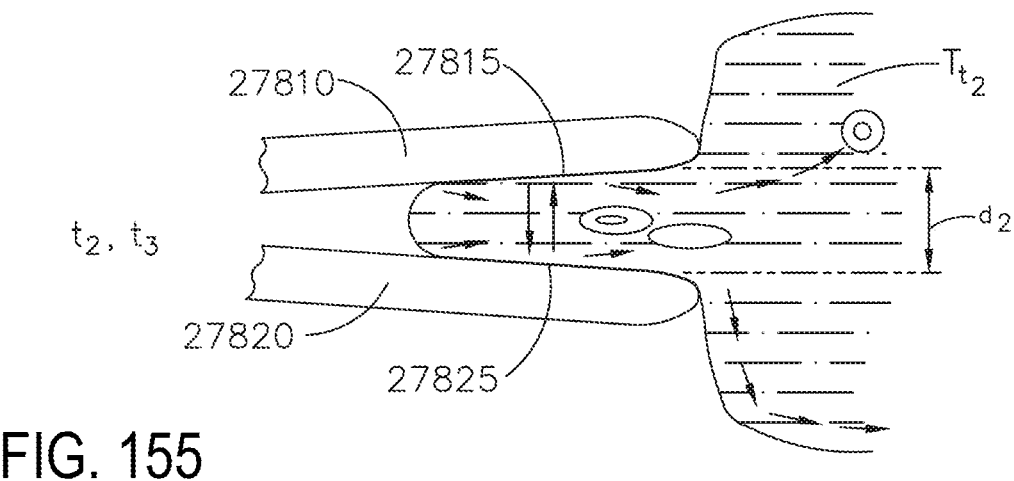
Figure 156:
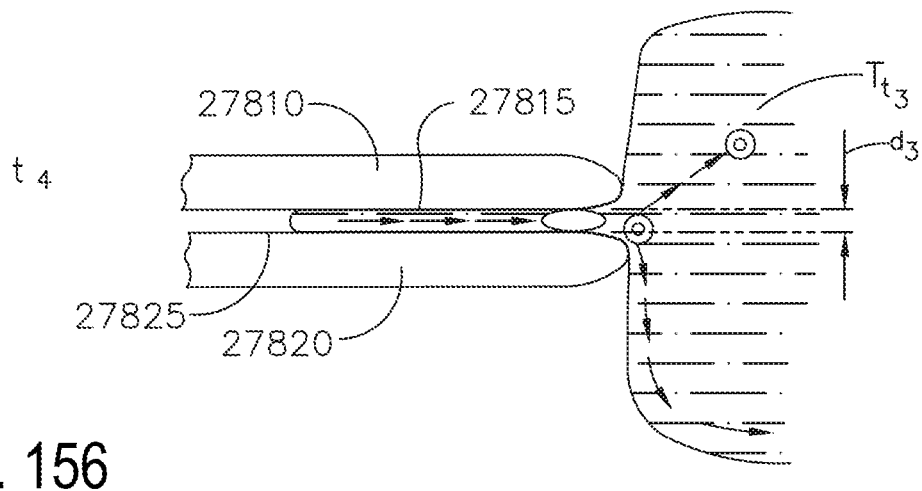
Figure 157:
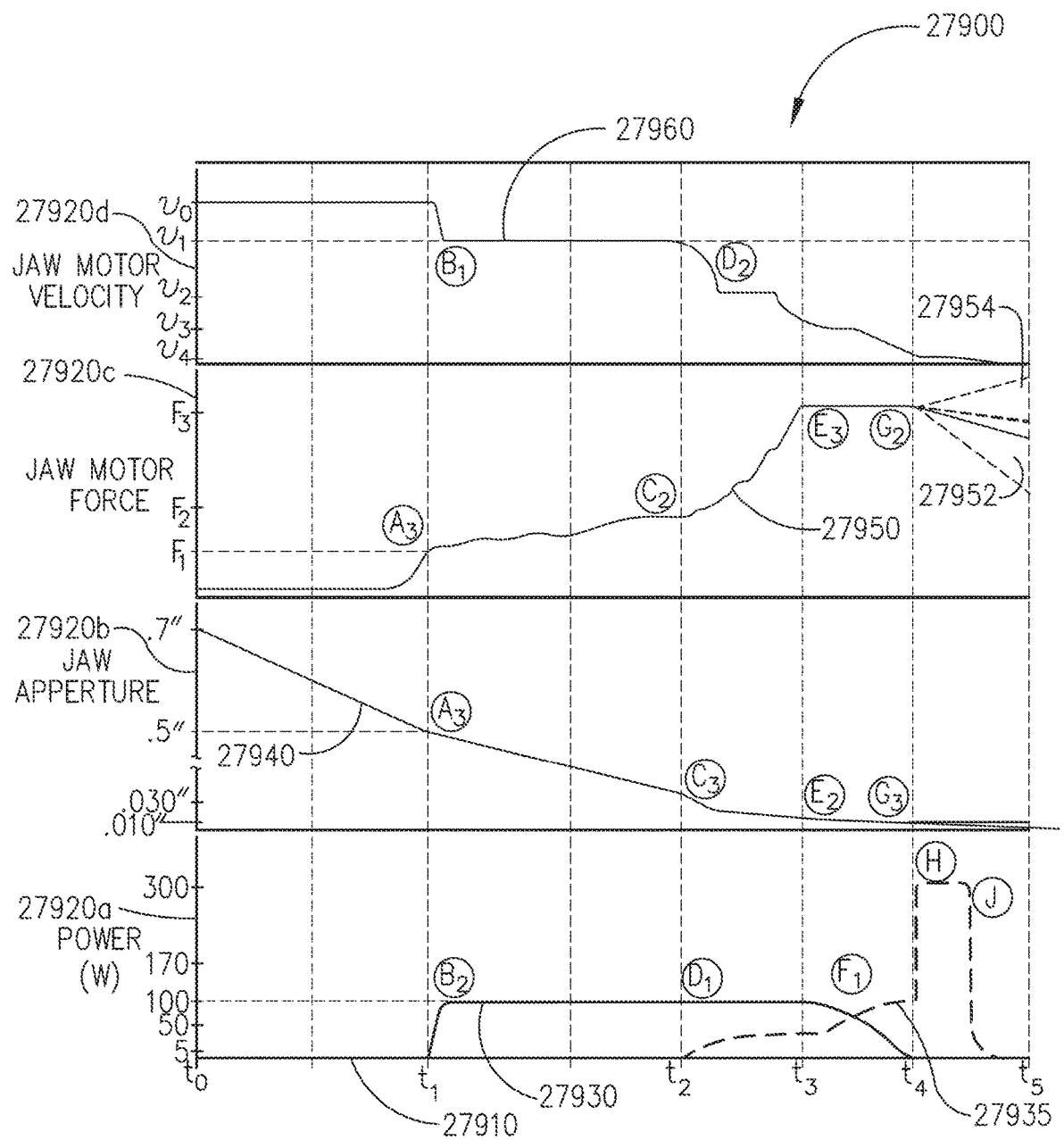
Figure 159:
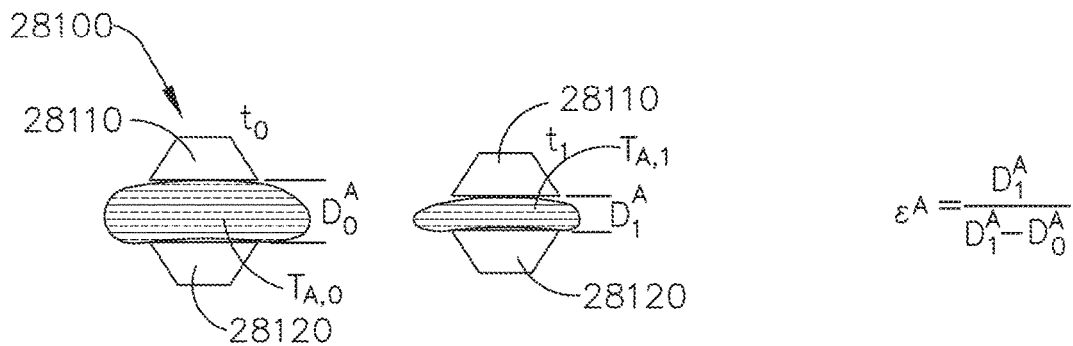
Figure 160:
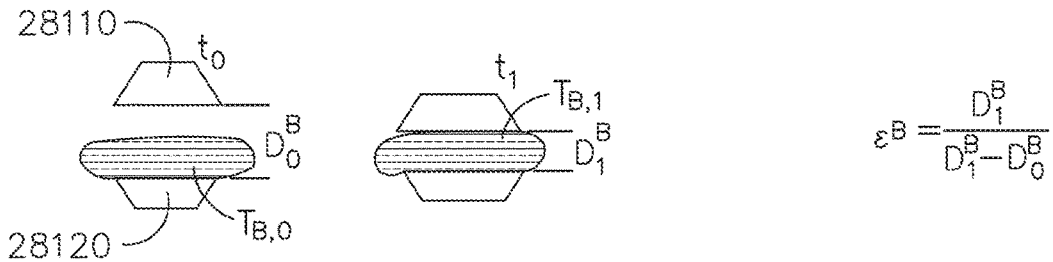
Figure 161:
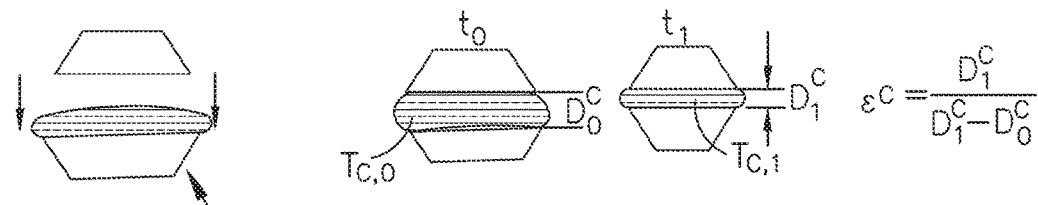
Figure 158:
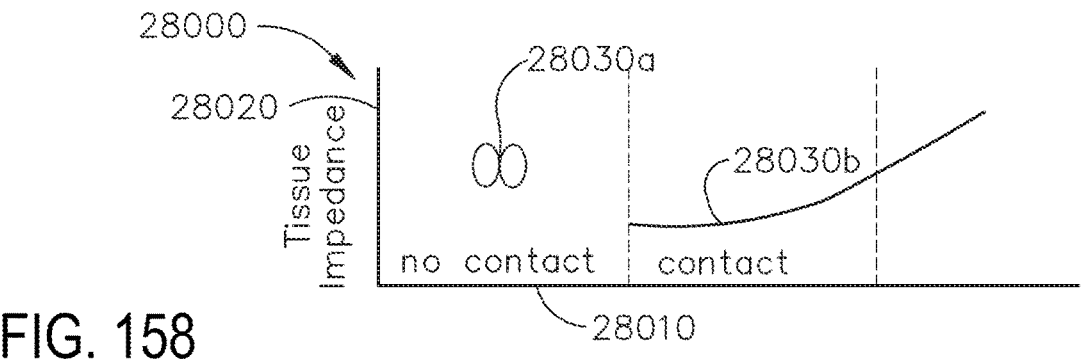
Figure 162:
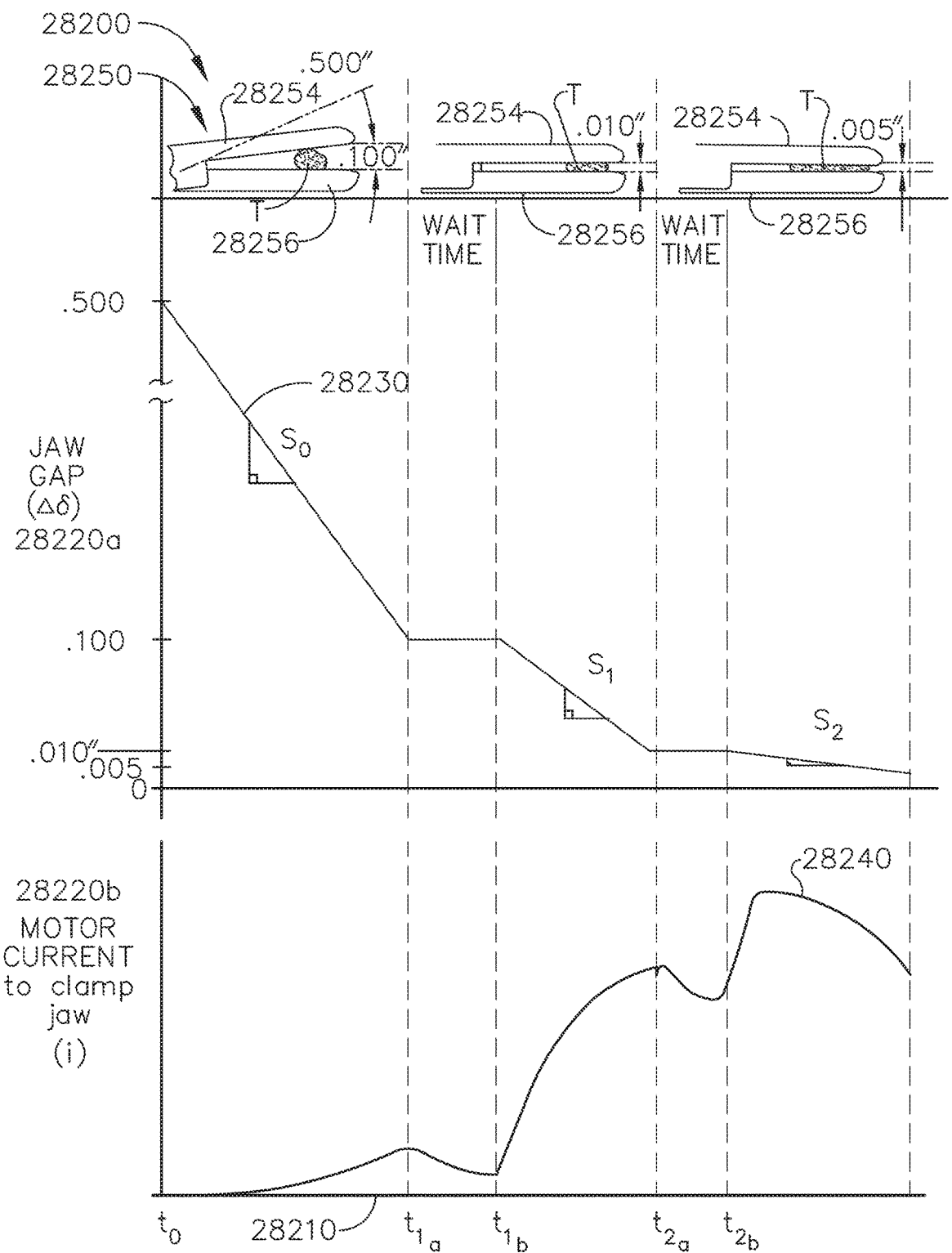
Figure 163:
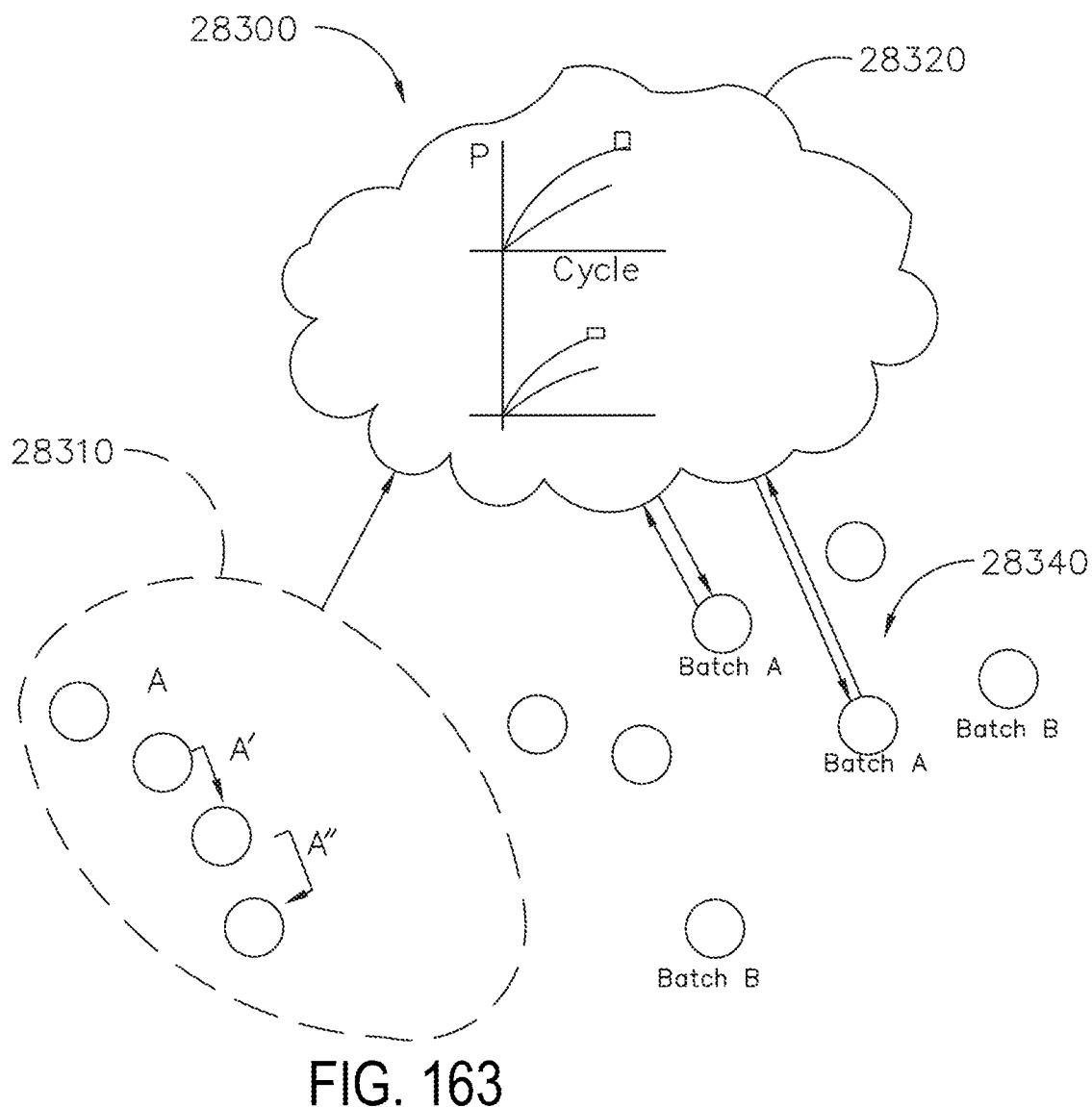
Figure 164:
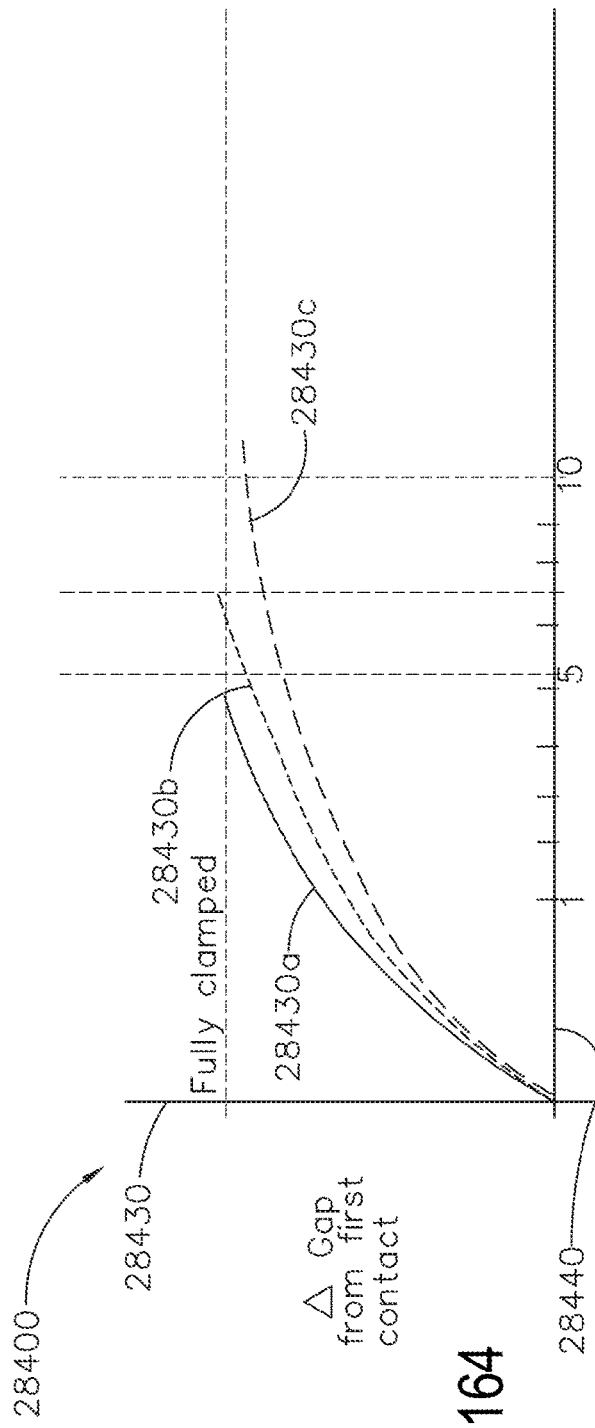
Figure 165:
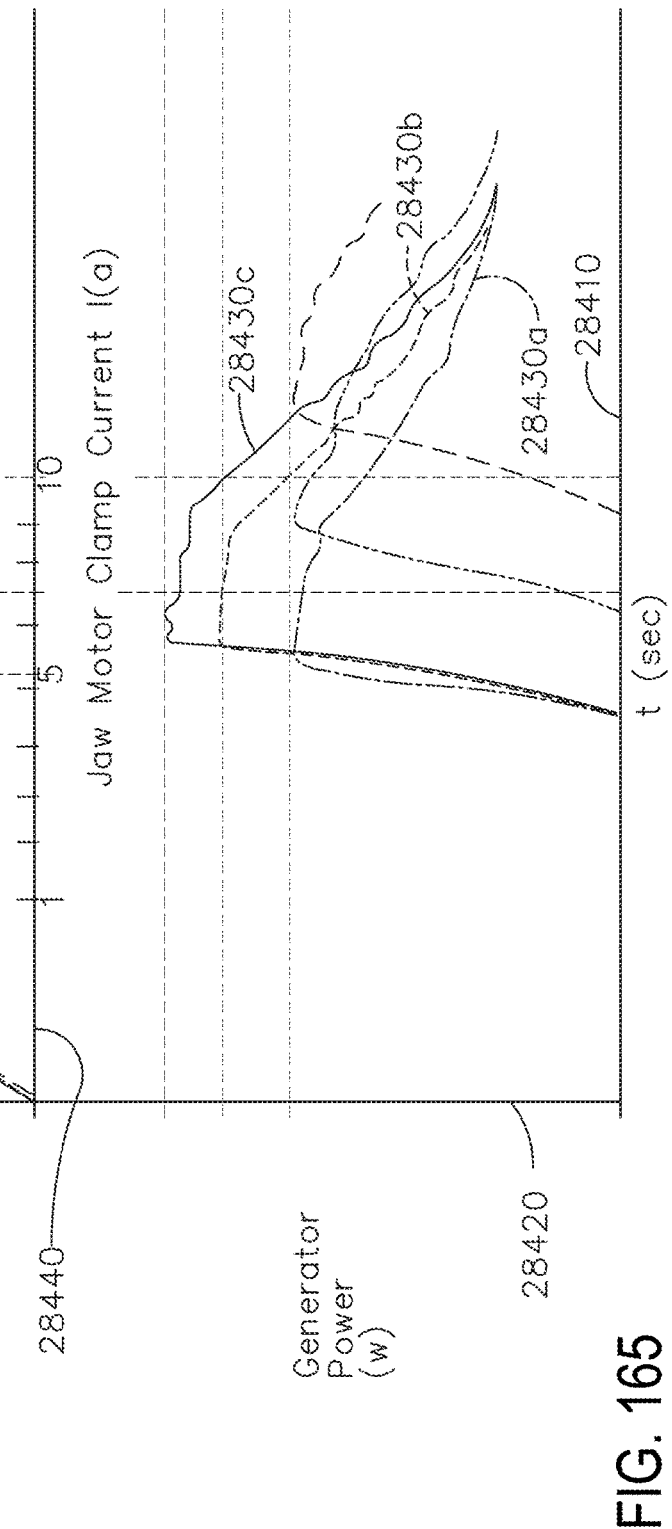
Figure 166:
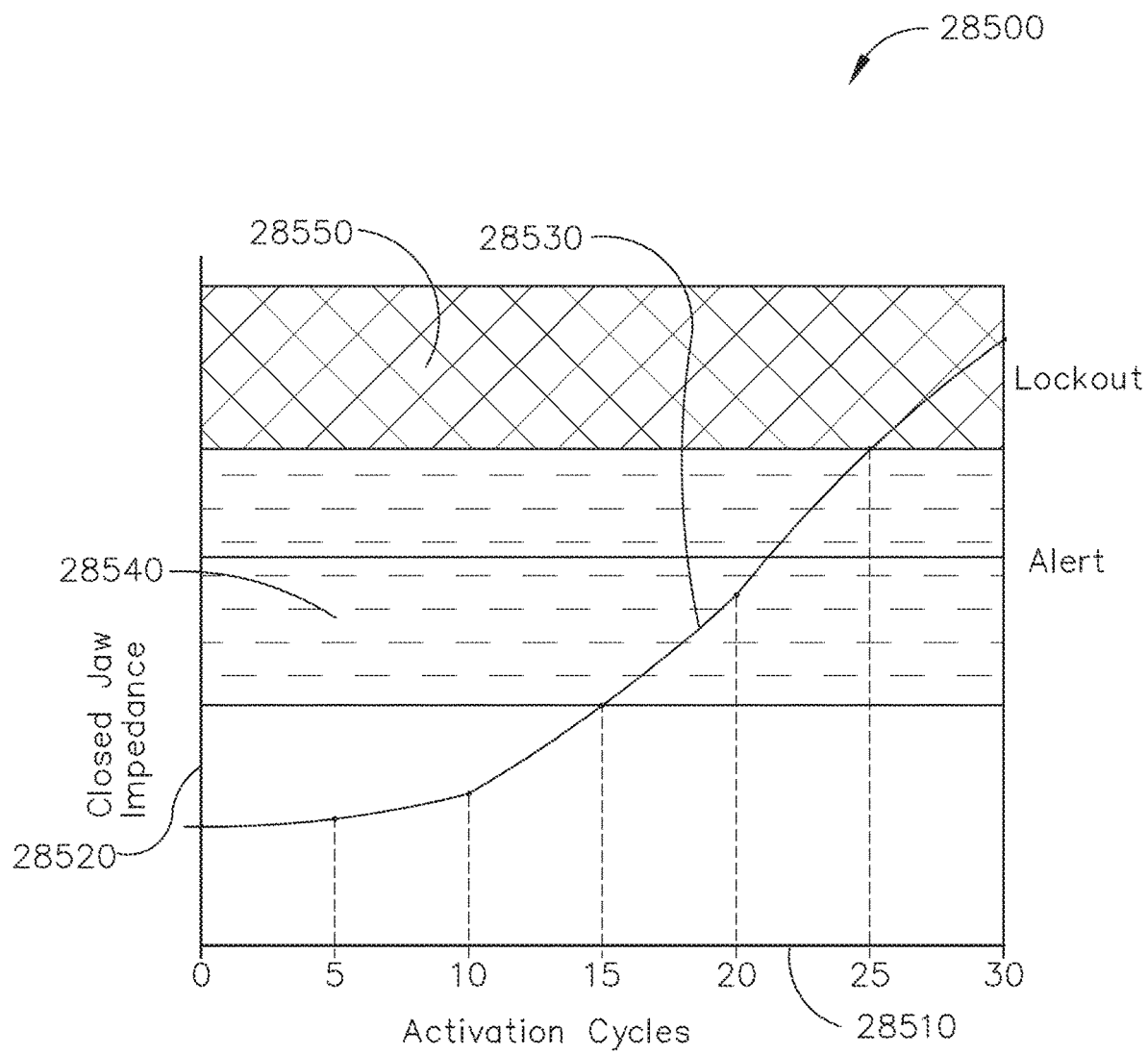
Figure 167:
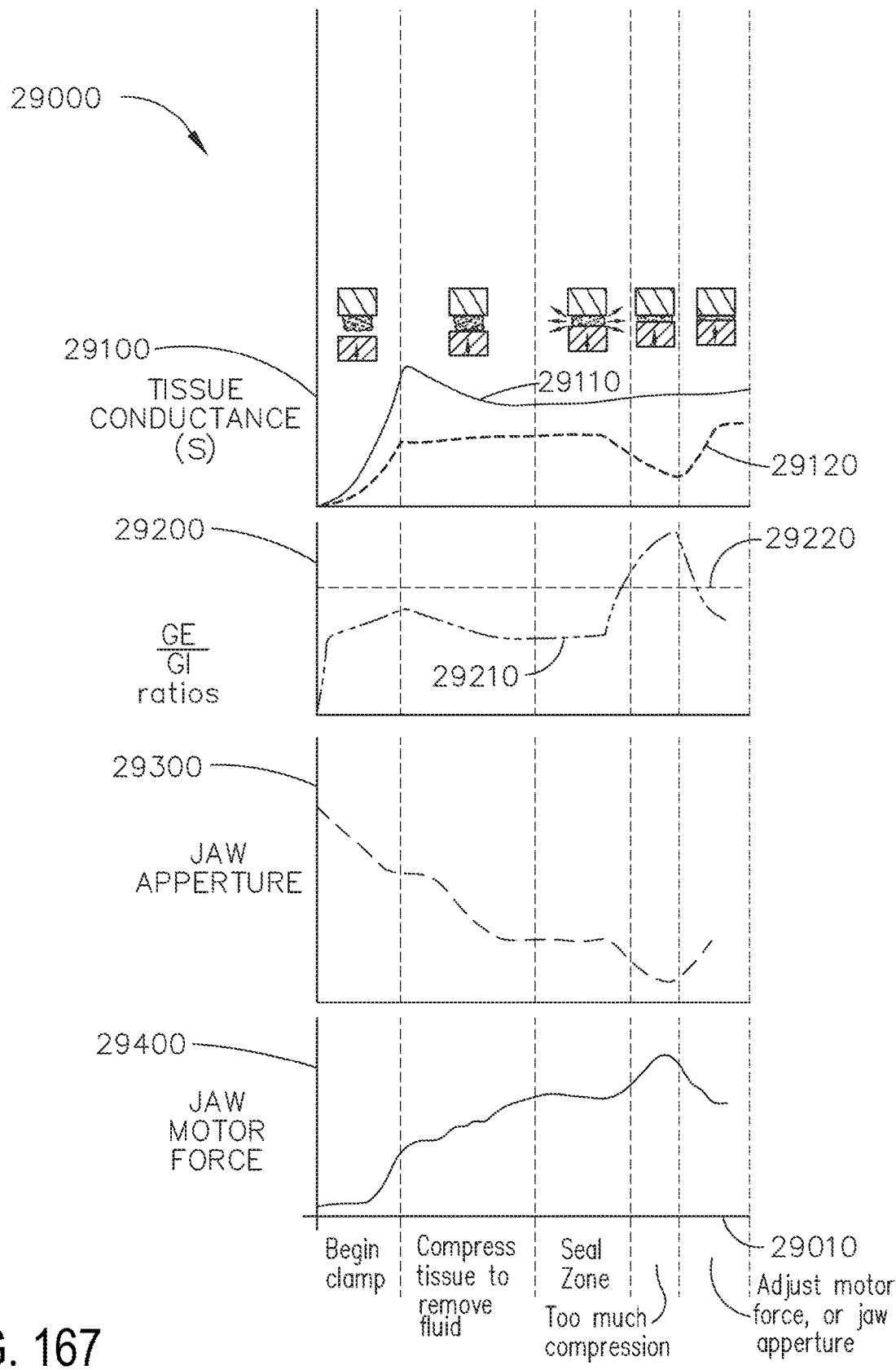
Figure 168:
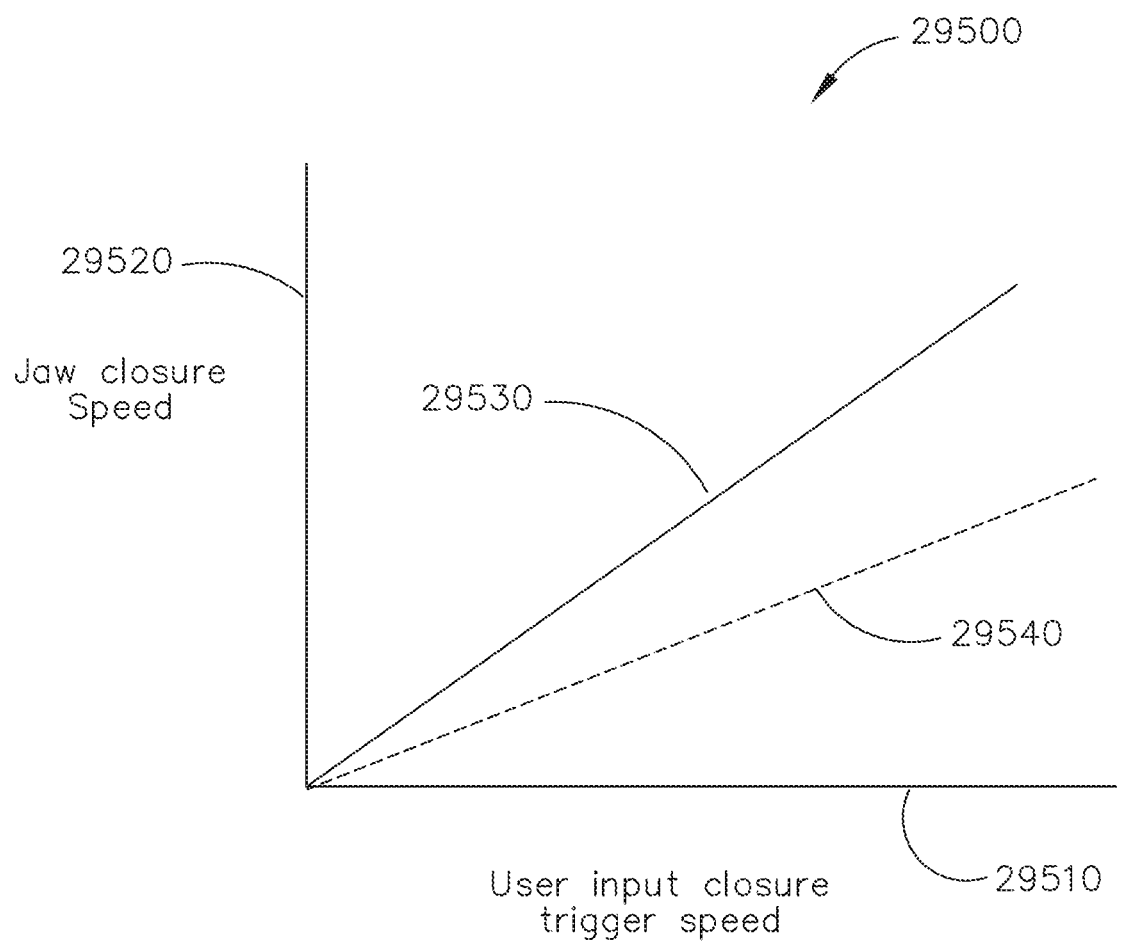
Figure 175:
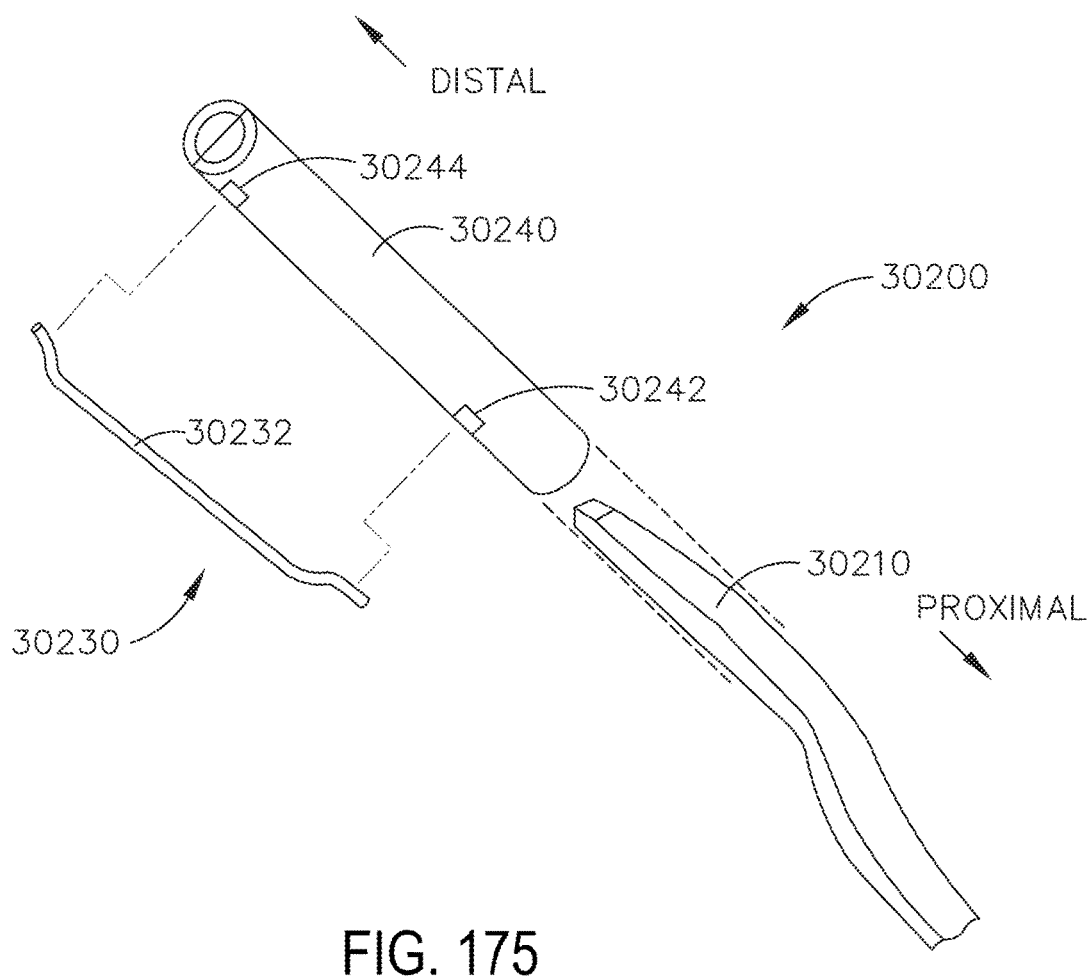
Figures 173, 174:
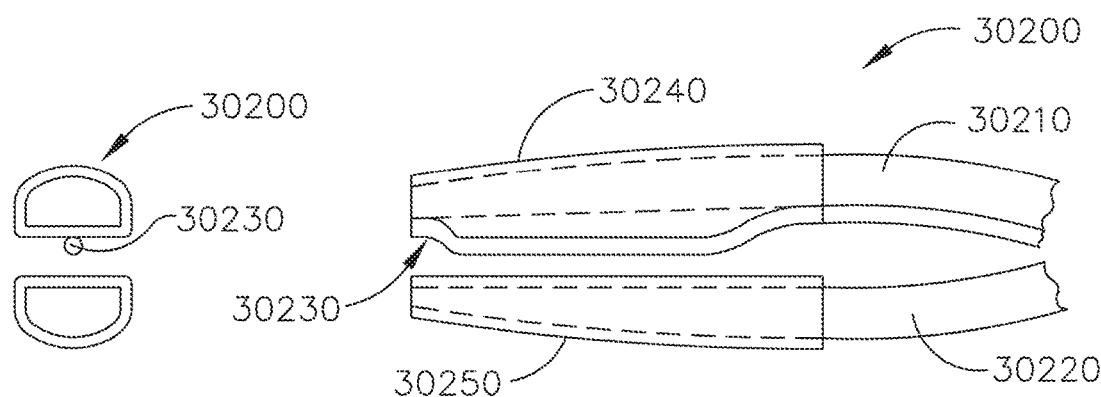
Figure 176:
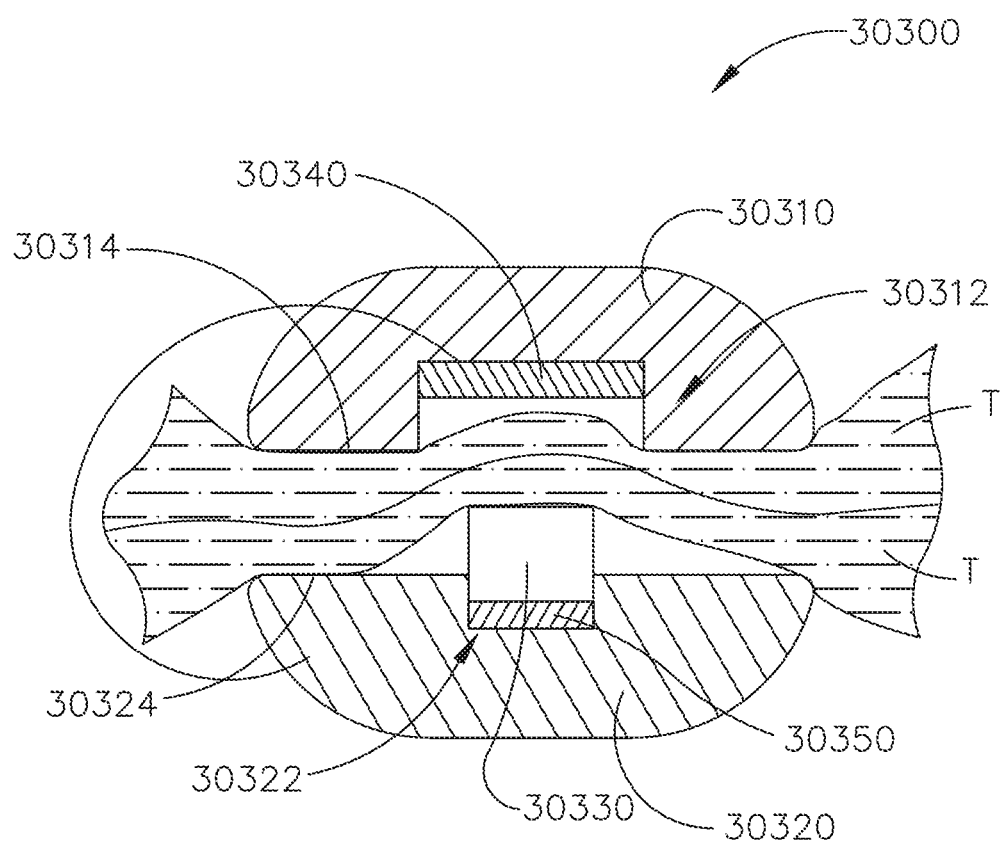
Figure 183:
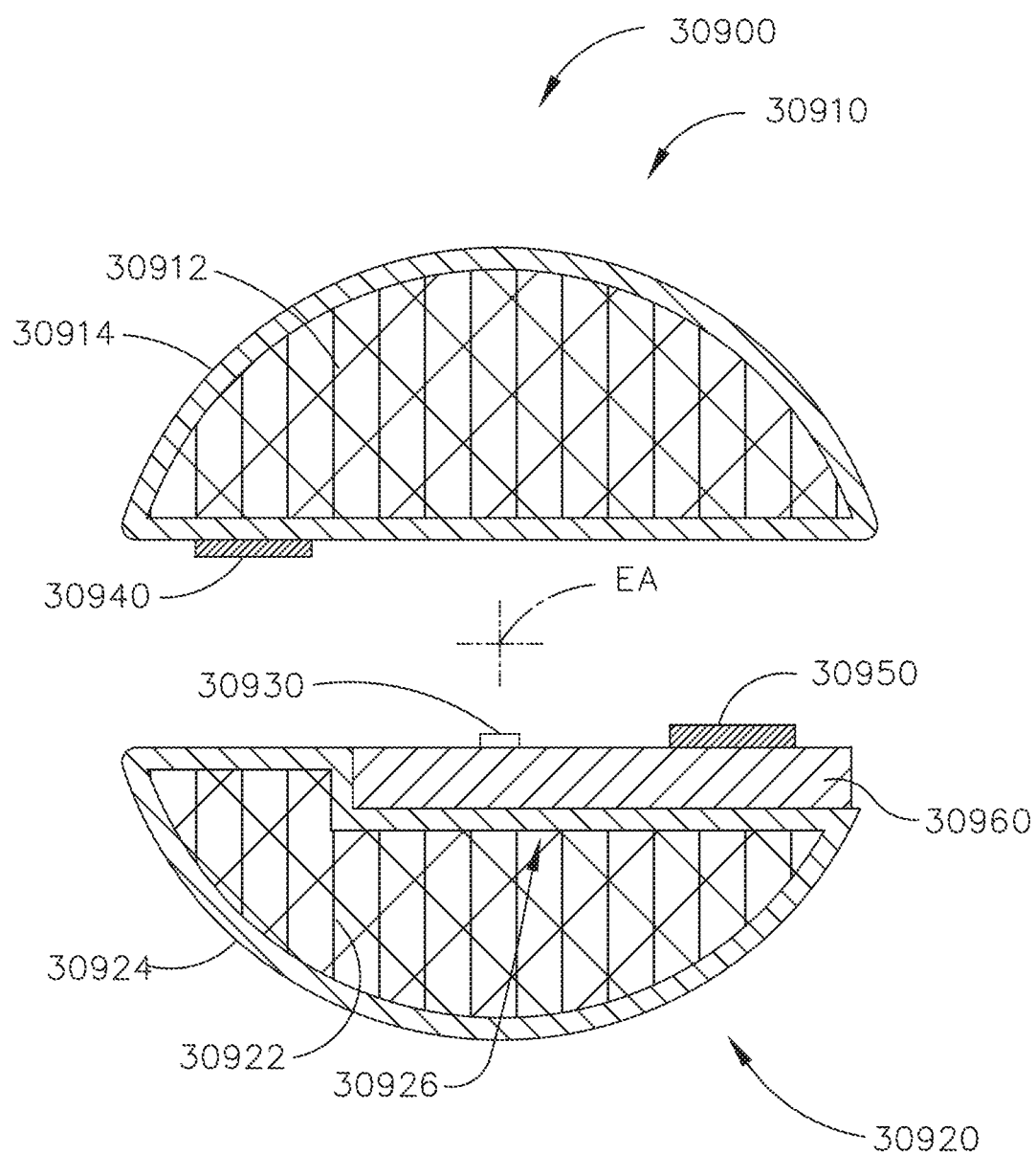
Figure 184:
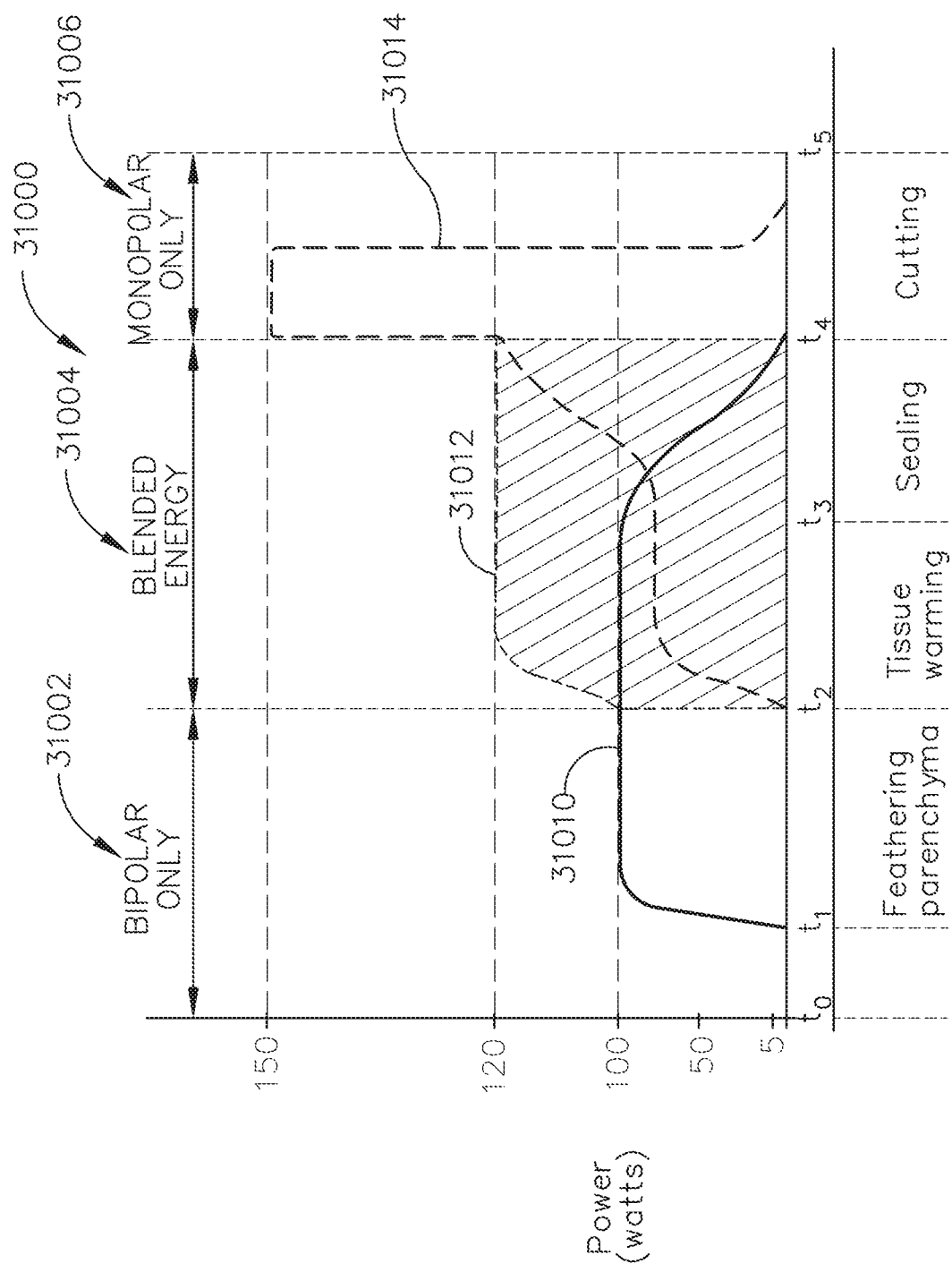
Figure 185:
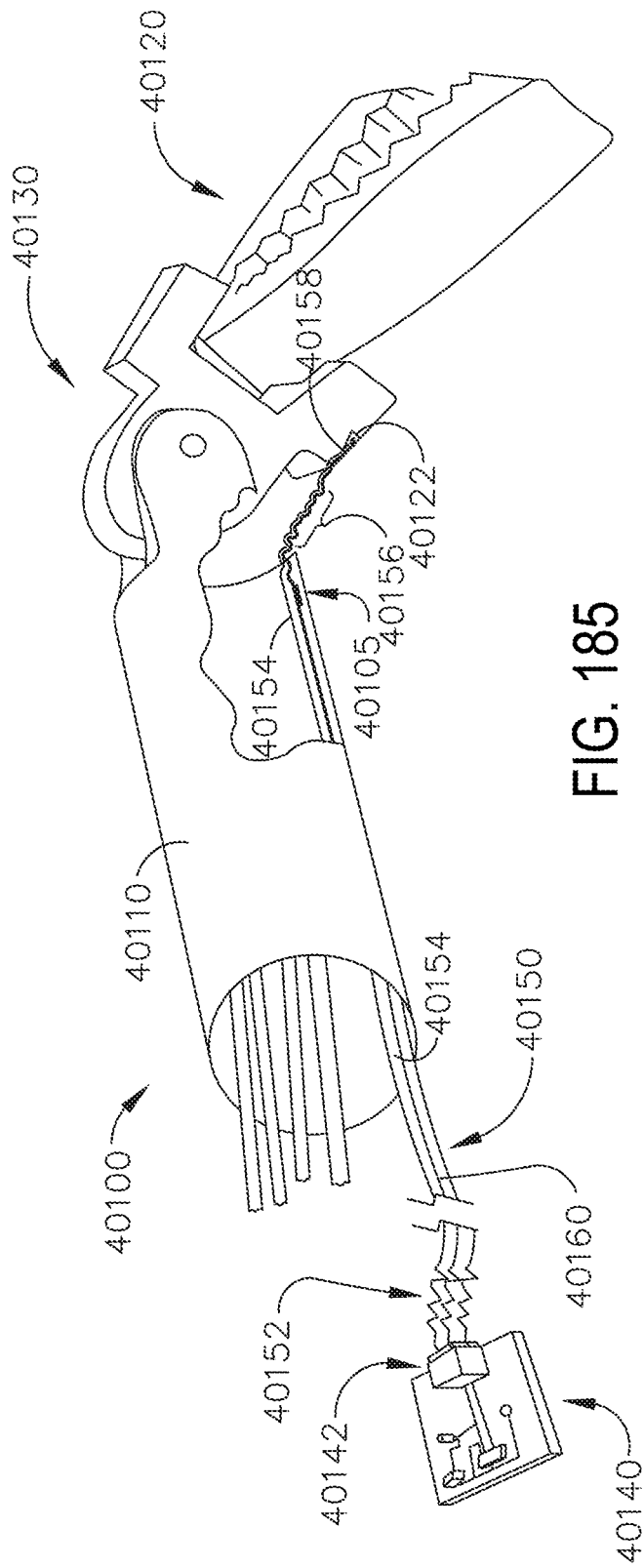
Figure 186:
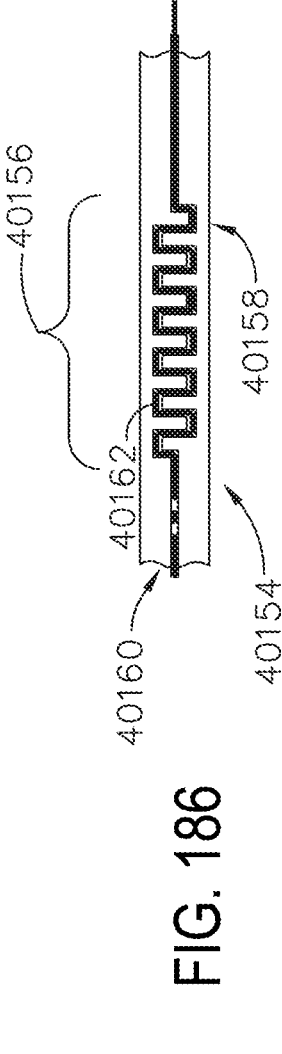
Figure 187:
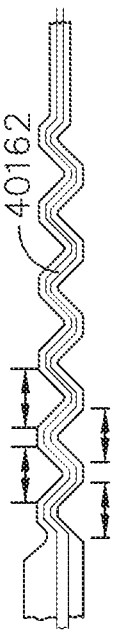
Figure 188:
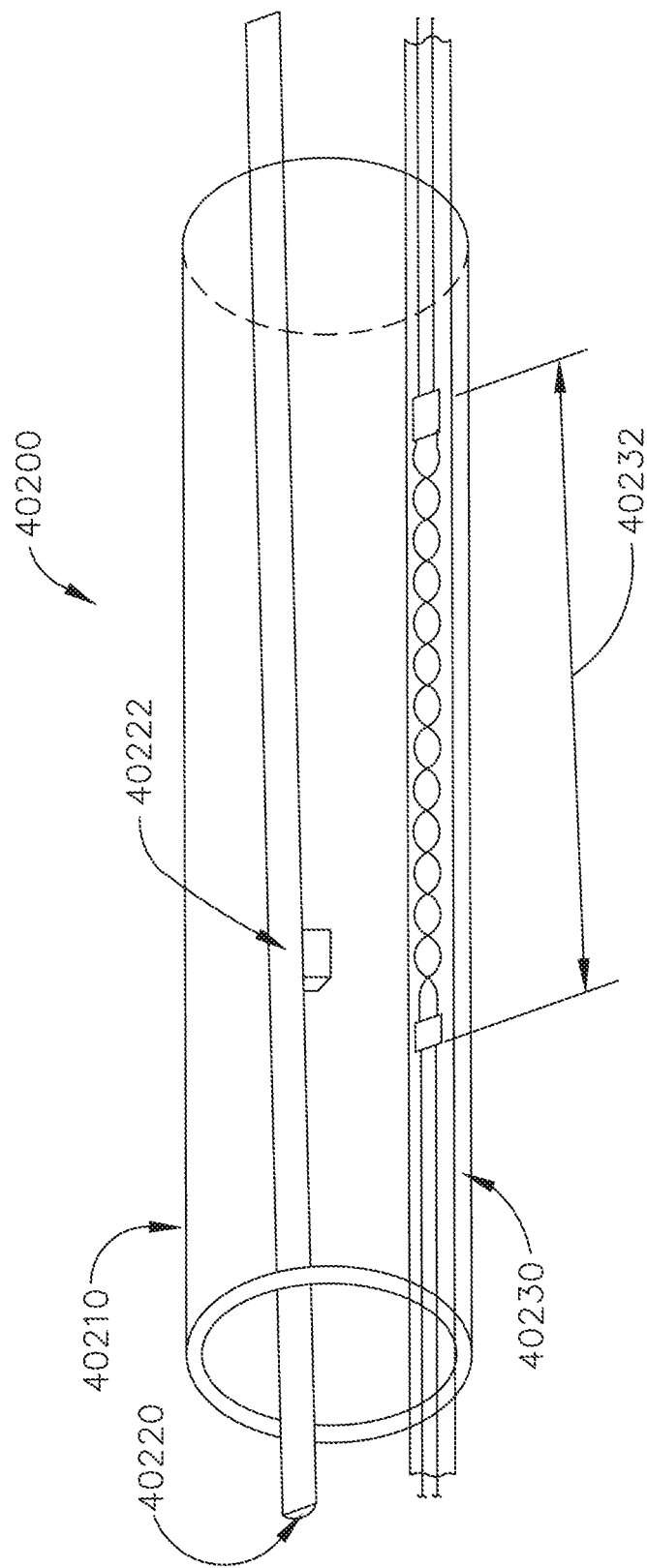
Figure 189:
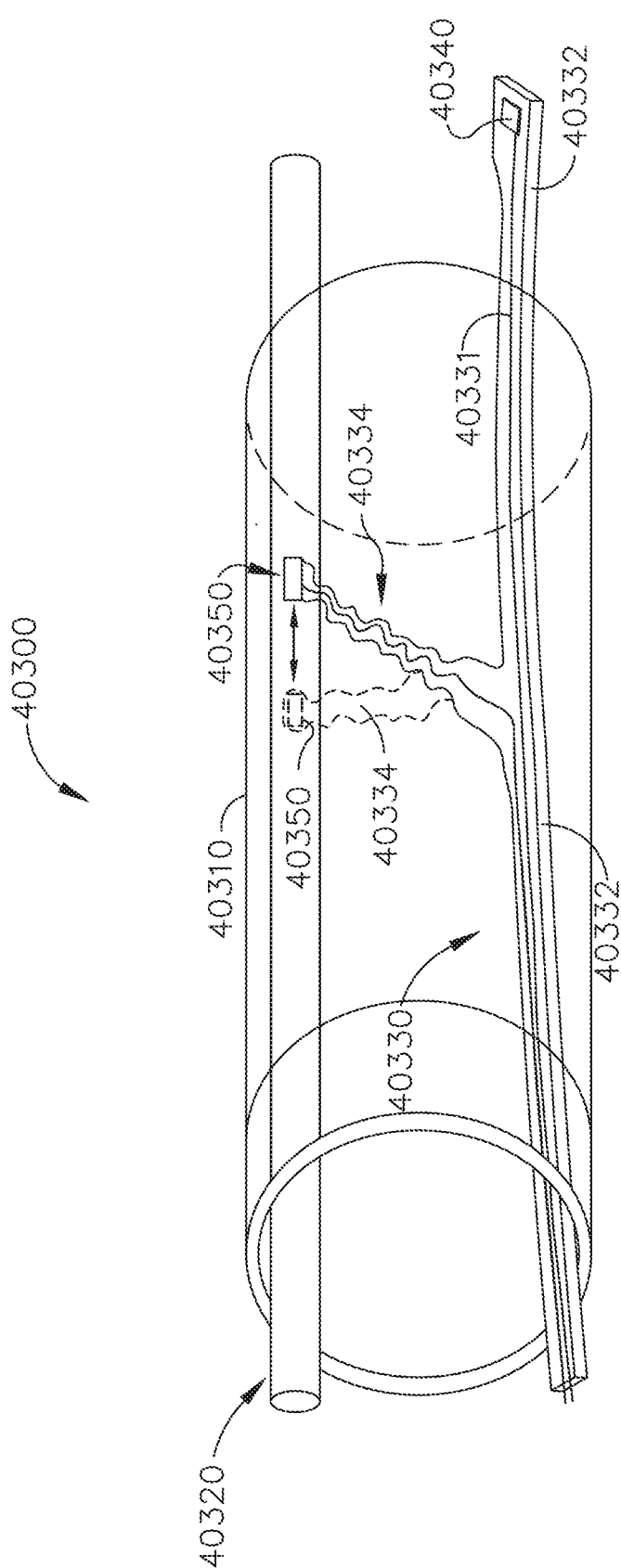
Figure 190:
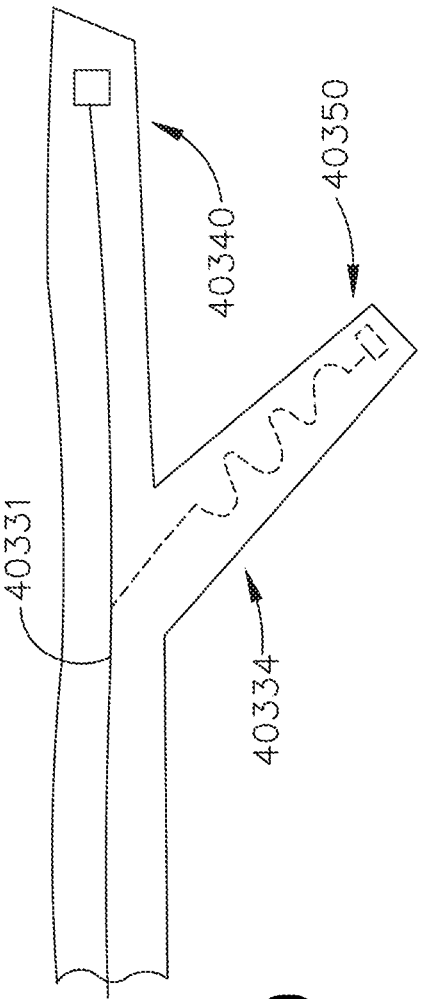
Figure 191:
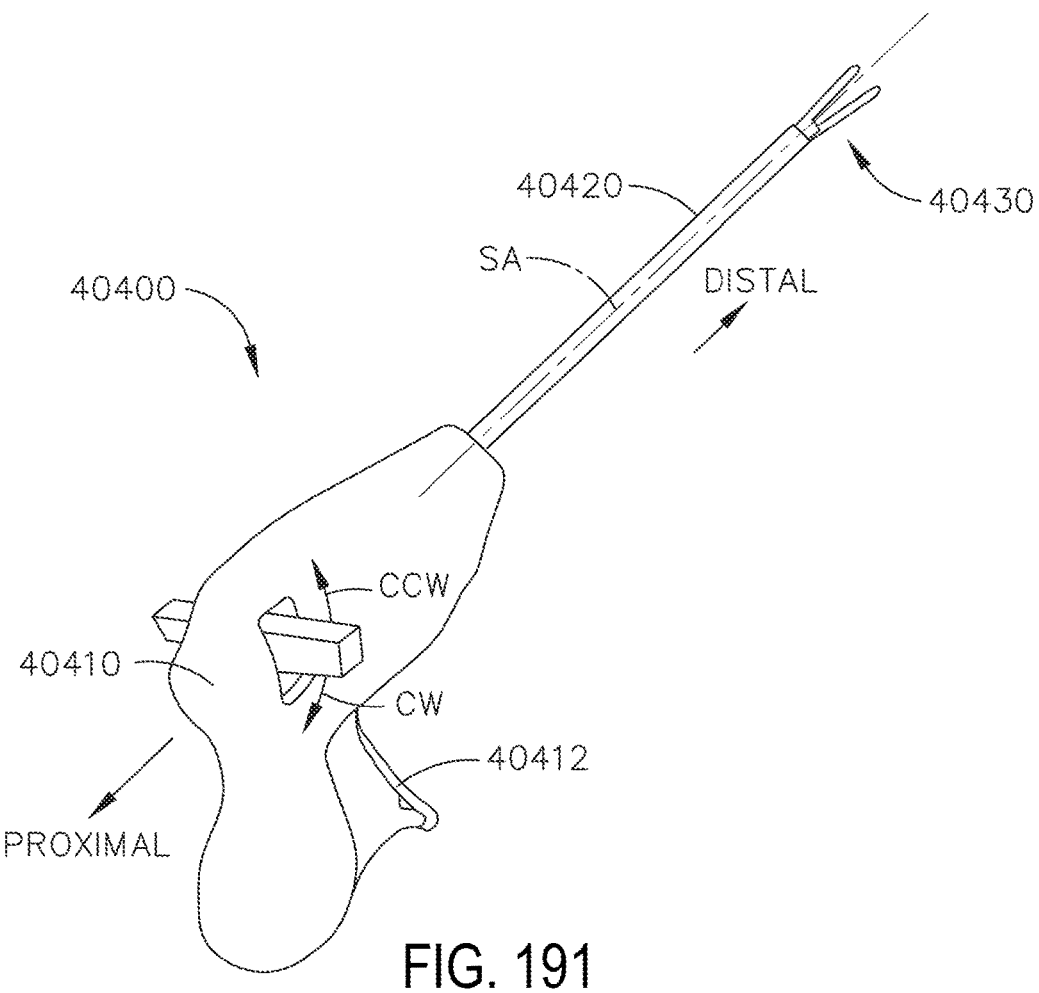
Figure 192:
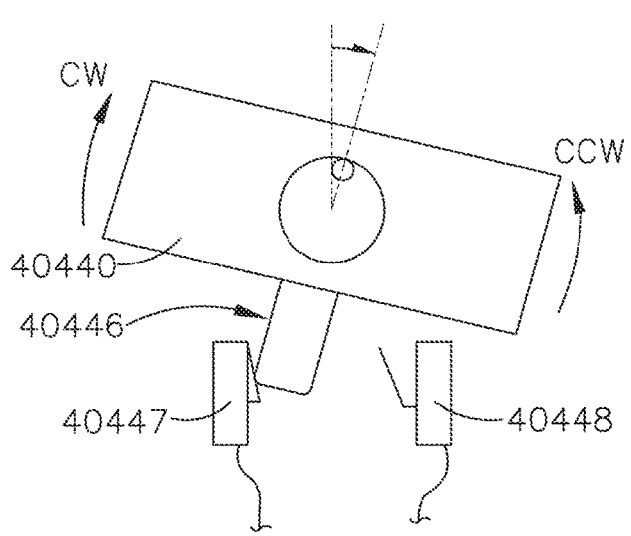
Figure 193:
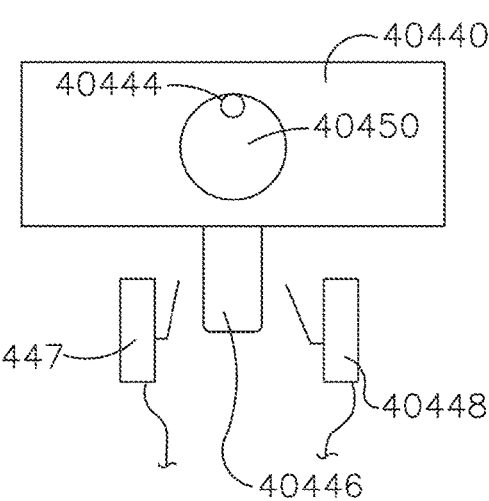
Figure 194:
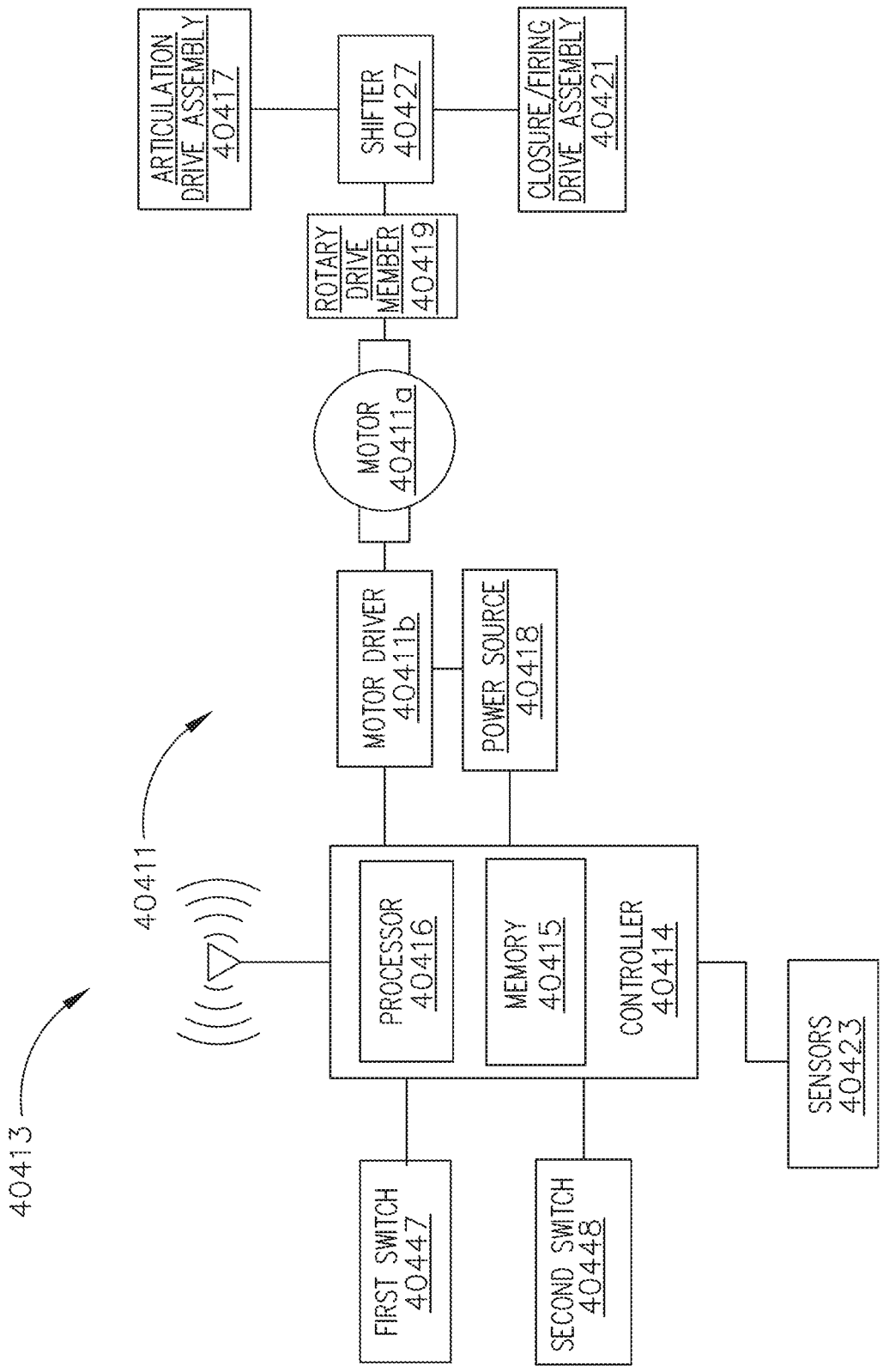
Figure 199:
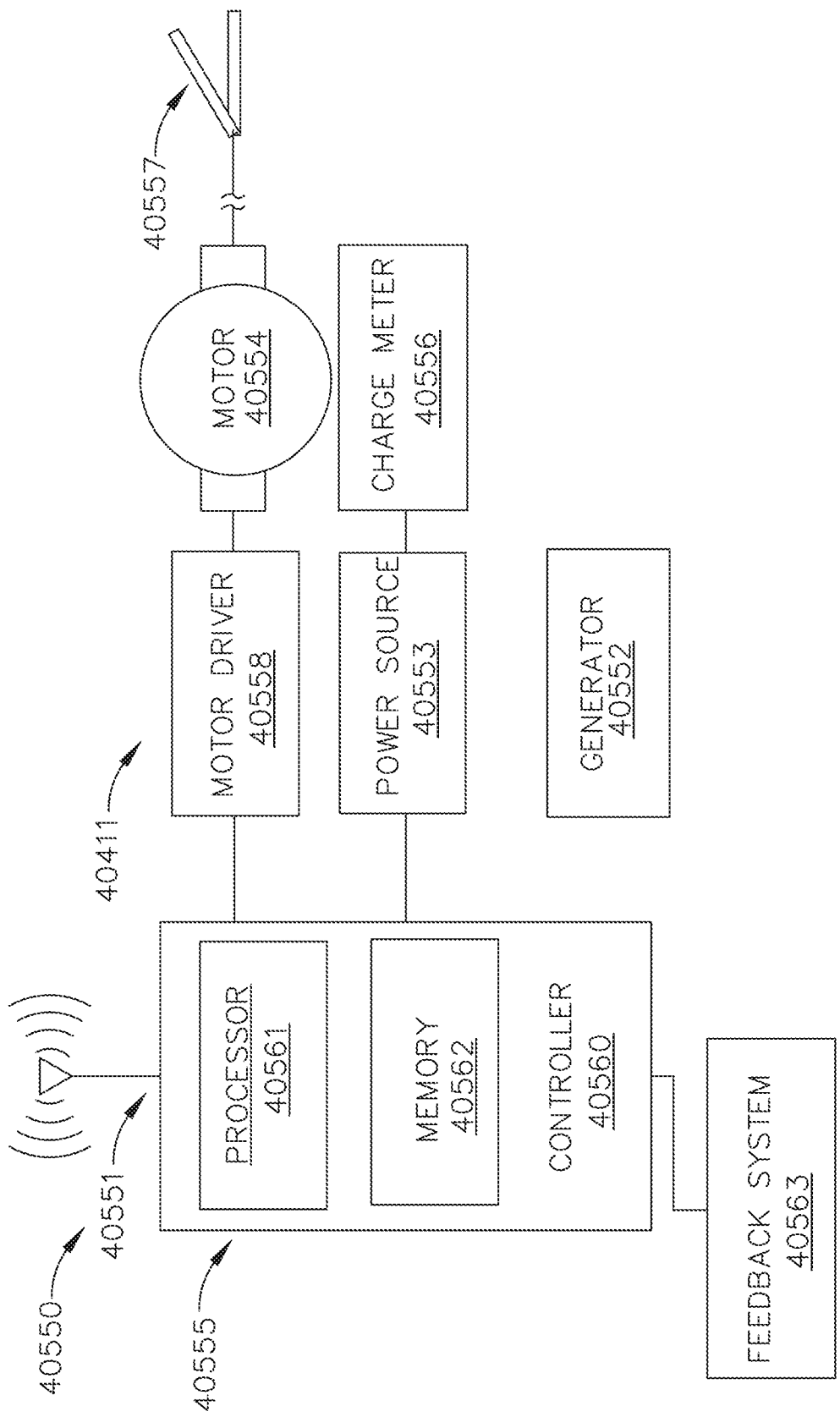
Figure 200:
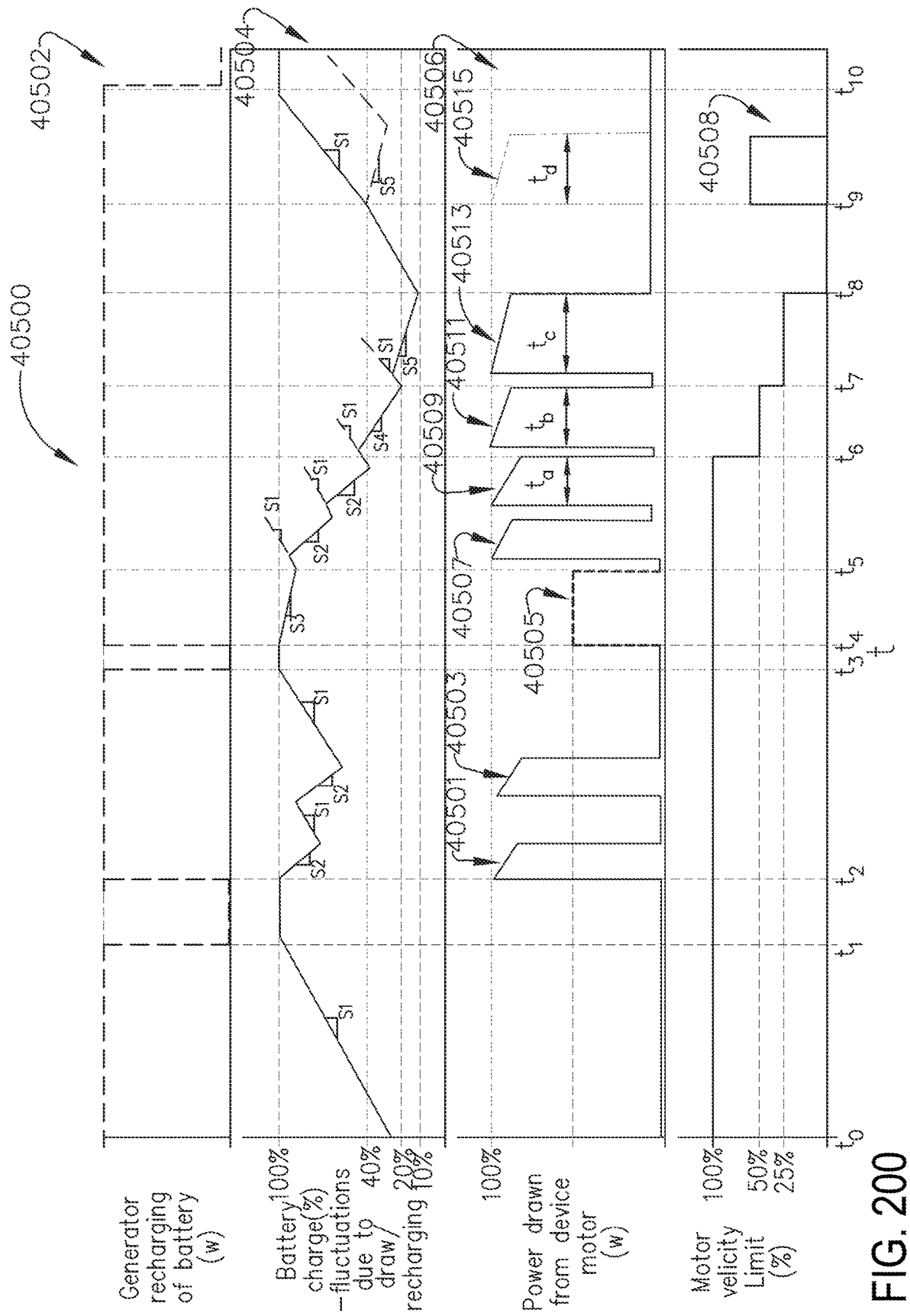
Figure 201:
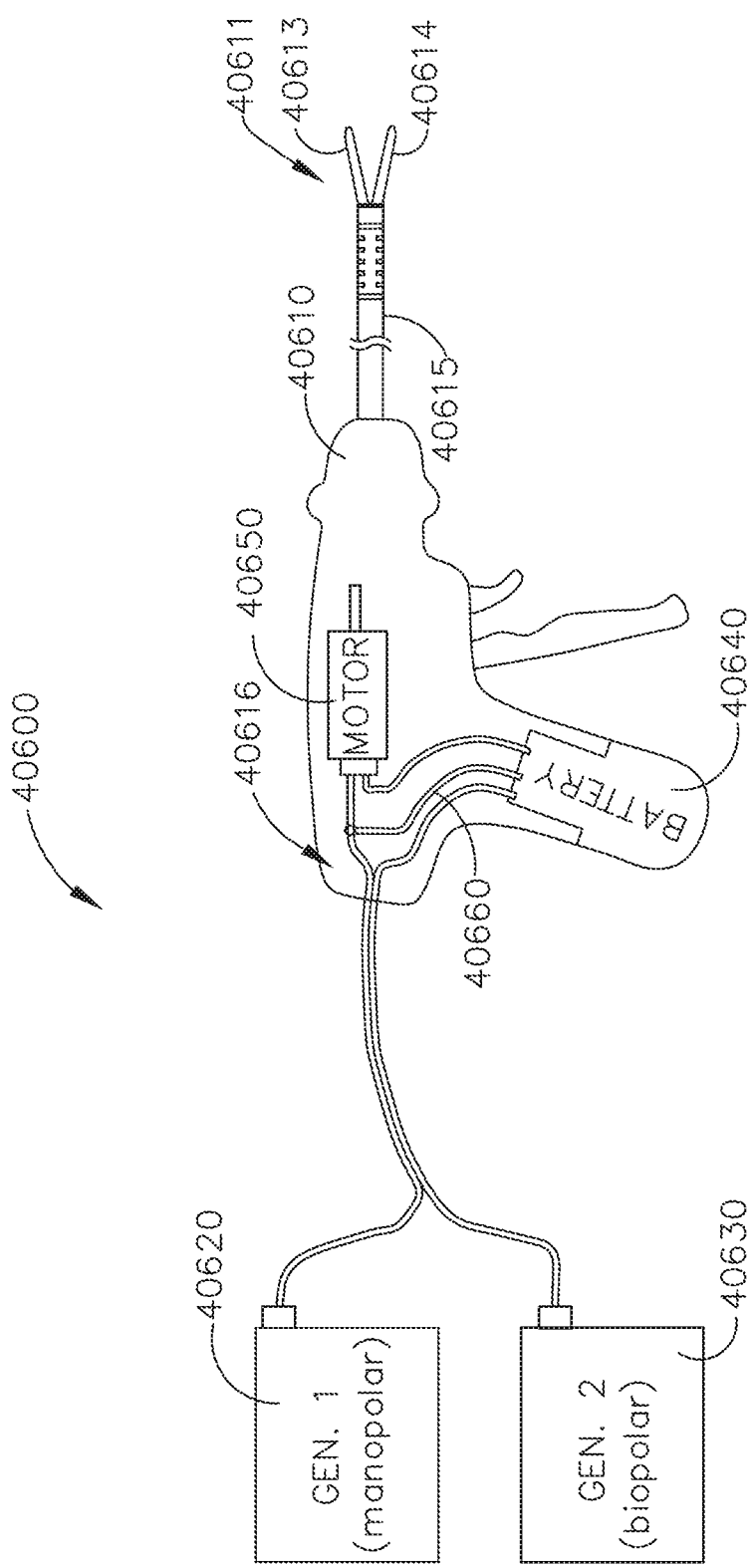
Figure 202:
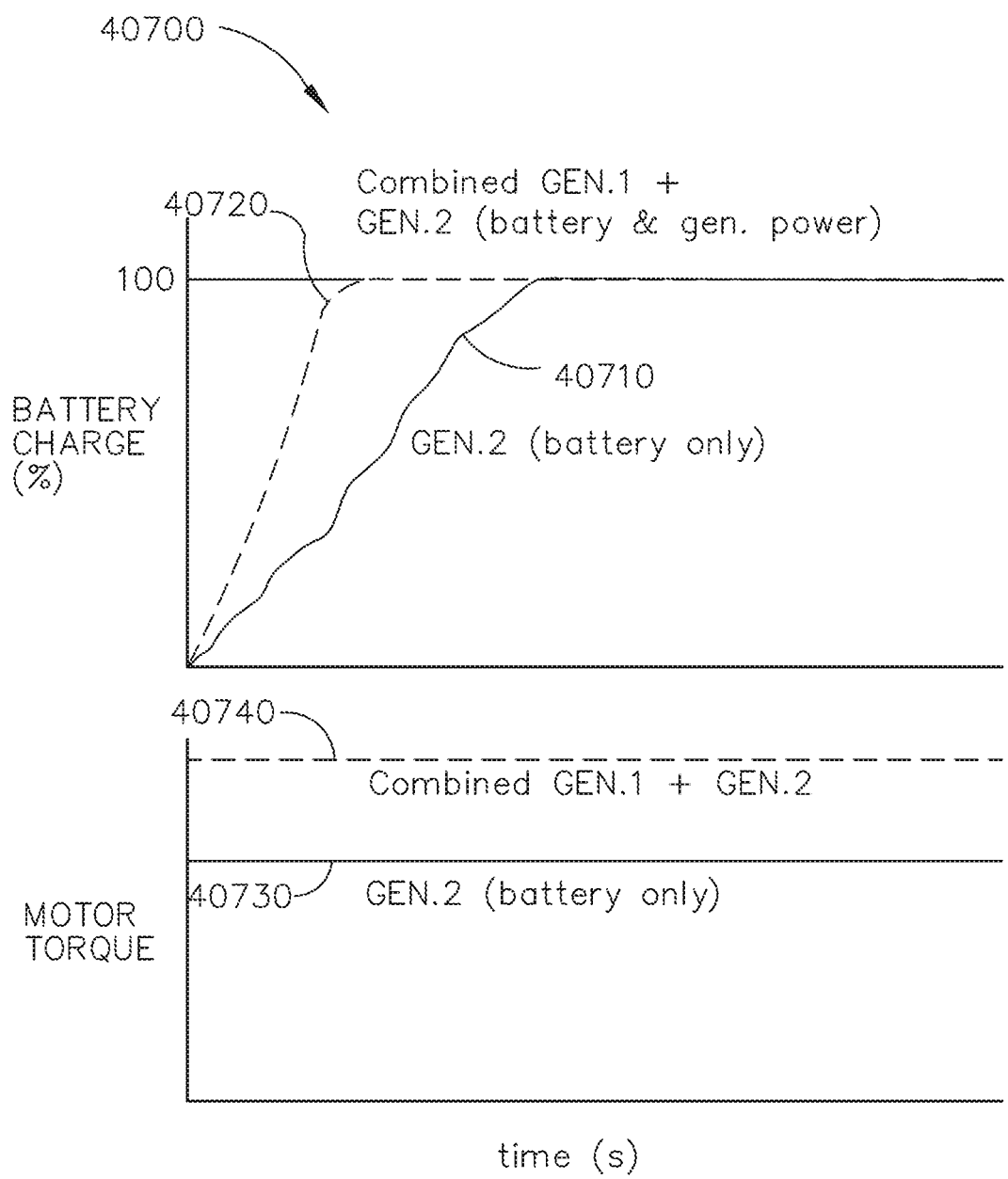

FIG. 150 is a schematic representation of the communication pathways with a surgical system, wherein the surgical system comprises a surgical hub, a smoke evacuation device, a surgical instrument, a first generator configured to power a first operation of the surgical instrument, and a second generator configured to power a second operation of the surgical instrument in accordance with at least one embodiment;

FIG. 151 is a schematic representation of a surgical system comprising a surgical hub and a plurality of robotic arms configured to receive tools thereon, wherein the surgical system comprises an authentication module configured to approve the tools for attachment to and/or use with the surgical system in accordance with at least one embodiment;

FIG. 152 is a schematic representation of a surgical system positioned within a treatment room in accordance with at least one embodiment;

FIG. 153 is a chart depicting various operational parameters and/or specifications of a surgical instrument at various stages of a surgical procedure in accordance with at least one embodiment;

FIG. 154 is an elevational view of the surgical instrument of FIG. 153 shown at a first time delivering bipolar energy to patient tissue;

FIG. 155 is an elevational view of the surgical instrument of FIG. 153 shown at a second time delivering bipolar and monopolar energies to patient tissue;

FIG. 156 is an elevational view of the surgical instrument of FIG. 153 shown at a fourth time delivering monopolar energy to patient tissue;

FIG. 157 is a graphical representation of various operational parameters and/or specifications of the surgical instrument of FIG. 153 at various stages of the surgical procedure;

FIG. 158 is a graphical representation of measured tissue impedance over a duration of a surgical procedure in accordance with at least one embodiment;

FIG. 159 is a schematic representing a strain calculation, wherein the applied strain is calculated using a gap defined between jaws of an end effector when the end effector is in an open configuration in accordance with at least one embodiment;

FIG. 160 is a schematic representing the strain calculation of FIG. 22, wherein the calculated applied strain overestimates an actual applied strain as the patient tissue is not in contact with positioned between the jaws of the end effector;

FIG. 161 is a schematic representing a tissue impedance calculation, wherein the tissue impedance is calculated using a gap defined between the jaws of the end effector when the jaws of the end effector contact the patient tissue positioned therebetween in accordance with at least one embodiment;

FIG. 162 is a graphical representation of a relationship between motor current and jaw gap over time in accordance with at least one embodiment;

FIG. 163 is a schematic representation of a network formed by surgical instruments and a cloud-based storage medium in accordance with at least one embodiment;

FIG. 164 is a graphical representation of a relationship between a change in jaw gap and jaw motor clamp current determined from the network of FIG. 163;

FIG. 165 is a graphical representation of a relationship between generator power over time determined from the network of FIG. 163;

FIG. 166 is a graphical representation of a relationship between activation cycles of a surgical instrument and a measured impedance when an end effector of the surgical instrument is in a closed configuration without patient tissue positioned therebetween in accordance with at least one embodiment;

FIG. 167 is a graphical representation of the relationships between tissue conductance, jaw aperture dimension, and jaw motor force during a jaw clamp stroke in accordance with at least one embodiment;

FIG. 168 is a graphical representation of a jaw closure speed based on a user input and the jaw closure speed based on the user input and a monitored parameter in accordance with at least one embodiment;

FIG. 169 is a side elevational view of an end effector for use with an electrosurgical instrument in accordance with at least one aspect of the present disclosure;

FIG. 170 is a side elevational view of the end effector of FIG. 169 in a closed configuration;

FIG. 171 is a plan view of one of the jaws of the end effector of FIG. 169;

FIG. 172 is a side elevational view of another one of the jaws of the end effector of FIG. 169;

FIG. 173 is a side elevational view of an end effector for use with an electrosurgical instrument in accordance with at least one aspect of the present disclosure;

FIG. 174 is an end view of the end effector of FIG. 173;

FIG. 175 is an exploded perspective view of one of the jaws of the end effector of FIG. 173;

FIG. 176 is a cross-sectional end view of an end effector for use with an electrosurgical instrument in accordance with at least one aspect of the present disclosure;

FIG. 177 is a cross-sectional end view of an end effector for use with an electrosurgical instrument in accordance with at least one aspect of the present disclosure;

FIG. 178 is a cross-sectional end view of an end effector for use with an electrosurgical instrument in accordance with at least one aspect of the present disclosure;

FIG. 179 is a cross-sectional end view of an end effector for use with an electrosurgical instrument in accordance with at least one aspect of the present disclosure;

FIG. 180 is a cross-sectional end view of an end effector for use with an electrosurgical instrument in accordance with at least one aspect of the present disclosure;

FIG. 181 is a cross sectional end view of an end effector for use with an electrosurgical instrument in accordance with at least one aspect of the present disclosure;

FIG. 182 is a cross-sectional end view of an end effector for use with an electrosurgical instrument in accordance with at least one aspect of the present disclosure;

FIG. 183 is a cross-sectional end view of an end effector for use with an electrosurgical instrument in accordance with at least one aspect of the present disclosure;

FIG. 184 is a graph illustrating a power scheme for coagulating and cutting a tissue treatment region in a treatment cycle applied by an end effector, in accordance with at least one aspect of the present disclosure;

FIG. 185 is a perspective view of a surgical instrument comprising a flexible wiring assembly in accordance with at least one aspect of the present disclosure;

FIG. 186 is a partial side elevational of the flexible wiring assembly of FIG. 185 in a relaxed configuration;

FIG. 187 is a partial side elevational view of the flexible wiring assembly of FIG. 185 in a stretched configuration;

FIG. 188 is a perspective view of a wiring harness and an inductive sensor for use with a surgical instrument in accordance with at least one aspect of the present disclosure;

FIG. 189 is a perspective view of a flexible wiring harness and an inductive sensor for use with a surgical instrument in accordance with at least one aspect of the present disclosure;

FIG. 190 is an enlarged view of portion of the flexible wiring harness of FIG. 189;

FIG. 191 is a perspective view of a surgical instrument comprising a manual toggle member in accordance with at least one aspect of the present disclosure;

FIG. 192 is an end cross-sectional view of the manual toggle of FIG. 191 illustrating the manual toggle member in a rotated position;

FIG. 193 is an end cross-sectional view of the manual toggle member of FIG. 192 in a centered position;

FIG. 194 is a schematic diagram of the surgical instrument of FIG. 191;

FIG. 195 is a perspective exploded view of the surgical instrument of FIG. 191 illustrating the manual toggle member and an elongate shaft;

FIG. 196 is a plan view of the elongate shaft of FIG. 195 illustrating the position of the elongate shaft when the manual rocker member is in a centered position;

FIG. 197 is a plan view of the elongate shaft of FIG. 195 illustrating the position of the elongate shaft when the manual toggle member is rotated counter clockwise;

FIG. 198 is a plan view of the elongate shaft of FIG. 195 illustrating the position of the elongate shaft when the manual toggle member is rotated clockwise;

FIG. 199 is a schematic diagram of a surgical system in accordance with at least one aspect of the present disclosure;

FIG. 200 is a graph of the battery recharge rate, battery charge percentage, power draw, and motor velocity of the surgical system of FIG. 199 over time;

FIG. 201 is a side view of a surgical system including a surgical instrument, a monopolar power generator, and a bipolar power generator in accordance with at least one aspect of the present disclosure; and FIG. 202 is a schematic of the battery charge percentage and motor torque of multiple surgical instrument systems over time in accordance with at least one aspect of the present disclosure.

DESCRIPTION

Applicant of the present application owns the following U.S. Patent Applications that are filed on May 28, 2020, and which are each herein incorporated by reference in their respective entireties:

U.S. patent application Serial No. 16/885,820, entitled ARTICULATABLE SURGICAL INSTRUMENT, now U.S. Pat. No. 11,696,776;

U.S. patent application Ser. No. 16/885,823, entitled SURGICAL INSTRUMENT WITH JAW ALIGNMENT FEATURES, now U.S. Pat. No. 11,707,318;

U.S. patent application Ser. No. 16/885,826, entitled SURGICAL INSTRUMENT WITH ROTATABLE AND ARTICULATABLE SURGICAL END EFFECTOR, now U.S. Pat. No. 11,684,412;

U.S. patent application Ser. No. 16/885,838, entitled ELECTROSURGICAL INSTRUMENT WITH ASYNCHRONOUS ENERGIZING ELECTRODES, now U.S. Patent Application Publication No. 2021/0196357;

U.S. patent application Ser. No. 16/885,851, entitled ELECTROSURGICAL INSTRUMENT WITH ELECTRODES BIASING SUPPORT, now U.S. Patent Application Publication No. 2021/0196358;

U.S. patent application Ser. No. 16/885,860, entitled ELECTROSURGICAL INSTRUMENT WITH FLEXIBLE WRING ASSEMBLIES, now U.S. Patent Application Publication No. 2021/0196349;

U.S. patent application Ser. No. 16/885,866, entitled ELECTROSURGICAL INSTRUMENT WITH VARIABLE CONTROL MECHANISMS, now U.S. Pat. No. 11,723,716;

U.S. patent application Ser. No. 16/885,870, entitled ELECTROSURGICAL SYSTEMS WITH INTEGRATED AND EXTERNAL POWER SOURCES, now U.S. Pat.No. 11,744,636;

U.S. patent application Ser. No. 16/885,873, entitled ELECTROSURGICAL INSTRUMENTS WITH ELECTRODES HAVING ENERGY FOCUSING FEATURES, now U.S. Patent Application Publication No. 2021/0196359;

U.S. patent application Ser. No. 16/885,879, entitled ELECTROSURGICAL INSTRUMENTS WITH ELECTRODES HAVING VARIABLE ENERGY DENSITIES, now U.S. Pat. No. 11,589,916;

U.S. patent application Ser. No. 16/885,881, entitled ELECTROSURGICAL INSTRUMENT WITH MONOPOLAR AND BIPOLAR ENERGY CAPABILITIES, now U.S. Patent Application Publication No. 2021/0196361;

U.S. patent application Ser. No. 16/885.888, entitled ELECTROSURGICAL END EFFECTORS WITH THERMALLY INSULATIVE AND THERMALLY CONDUCTIVE PORTIONS, now U.S. Patent Application Publication No. 2021/0196362;

U.S. patent application Ser. No. 16/885,893, entitled ELECTROSURGICAL INSTRUMENT WITH ELECTRODES OPERABLE IN BIPOLAR AND MONOPOLAR MODES, now U.S. Patent Application Publication No. 2021/0196363;

U.S. patent application Ser. No. 16/885,900, entitled ELECTROSURGICAL INSTRUMENT FOR DELIVERING BLENDED ENERGY MODALITIES TO TISSUE, now U.S. Patent Application Publication No. 2021/0196364;

U.S. patent application Ser. No. 16/885,917, entitled CONTROL PROGRAM ADAPTATION BASED ON DEVICE STATUS AND USER INPUT, now U.S. Pat. No. 11,759,251;

U.S. patent application Ser. No. 16/885,923, entitled CONTROL PROGRAM FOR MODULAR COMBINATION ENERGY DEVICE, now U.S. Pat. No. 11,786,294; and U.S. patent application Ser. No. 16/885,931, entitled SURGICAL SYSTEM COMMUNICATION PATHWAYS, now U.S. Pat. Application Publication No. 2021/0196344.

Applicant of the present application owns the following U.S. Provisional Patent Applications that were filed on Dec. 30, 2019, the disclosure of each of which is herein incorporated by reference in its entirety:

U.S. Provisional Patent Application Ser. No. 62/955,294, entitled USER INTERFACE FOR SURGICAL INSTRUMENT WITH COMBINATION ENERGY MODALITY END-EFFECTOR;

U.S. Provisional Patent Application Ser. No. 62/955,292, entitled COMBINATION ENERGY MODALITY END-EFFECTOR; and U.S. Provisional Patent Application Ser. No. 62/955,306, entitled SURGICAL INSTRUMENT SYSTEMS.

Applicant of the present application owns the following U.S. Patent Applications, the disclosure of each of which is herein incorporated by reference in its entirety:

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Patent Application Publication No. 2019/0201137;

U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;

U.S. patent application Ser. No. 16/209,490, titled METHOD FOR FACILITY DATA COLLECTION AND INTERPRETATION, now U.S. Patent Application Publication No. 2019/0206564;

U.S. patent application Ser. No. 16/209,491, titled METHOD FOR CIRCULAR STAPLER CONTROL ALGORITHM ADJUSTMENT BASED ON SITUATIONAL AWARENESS, now U.S. Patent Application Publication No. 2019/0200998;

U.S. patent application Ser. No. 16/562,123, titled METHOD FOR CONSTRUCTING AND USING A MODULAR SURGICAL ENERGY SYSTEM WITH MULTIPLE DEVICES;

U.S. patent application Ser. No. 16/562,135, titled METHOD FOR CONTROLLING AN ENERGY MODULE OUTPUT;

U.S. patent application Ser. No. 16/562,144, titled METHOD FOR CONTROLLING A MODULAR ENERGY SYSTEM USER INTERFACE; and U.S. patent application Ser. No. 16/562,125, titled METHOD FOR COMMUNICATING BETWEEN MODULES AND DEVICES IN A MODULAR SURGICAL SYSTEM.

Before explaining various aspects of an electrosurgical system in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Various aspects are directed to electrosurgical systems that include electrosurgical instruments powered by generators to effect tissue dissecting, cutting, and/or coagulation during surgical procedures. The electrosurgical instruments may be configured for use in open surgical procedures, but has applications in other types of surgery, such as laparoscopic, endoscopic, and robotic-assisted procedures.

As described below in greater detail, an electrosurgical instrument generally includes a shaft having a distally-mounted end effector (e.g., one or more electrodes). The end effector can be positioned against the tissue such that electrical current is introduced into the tissue. Electrosurgical instruments can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example.

Figure 1:
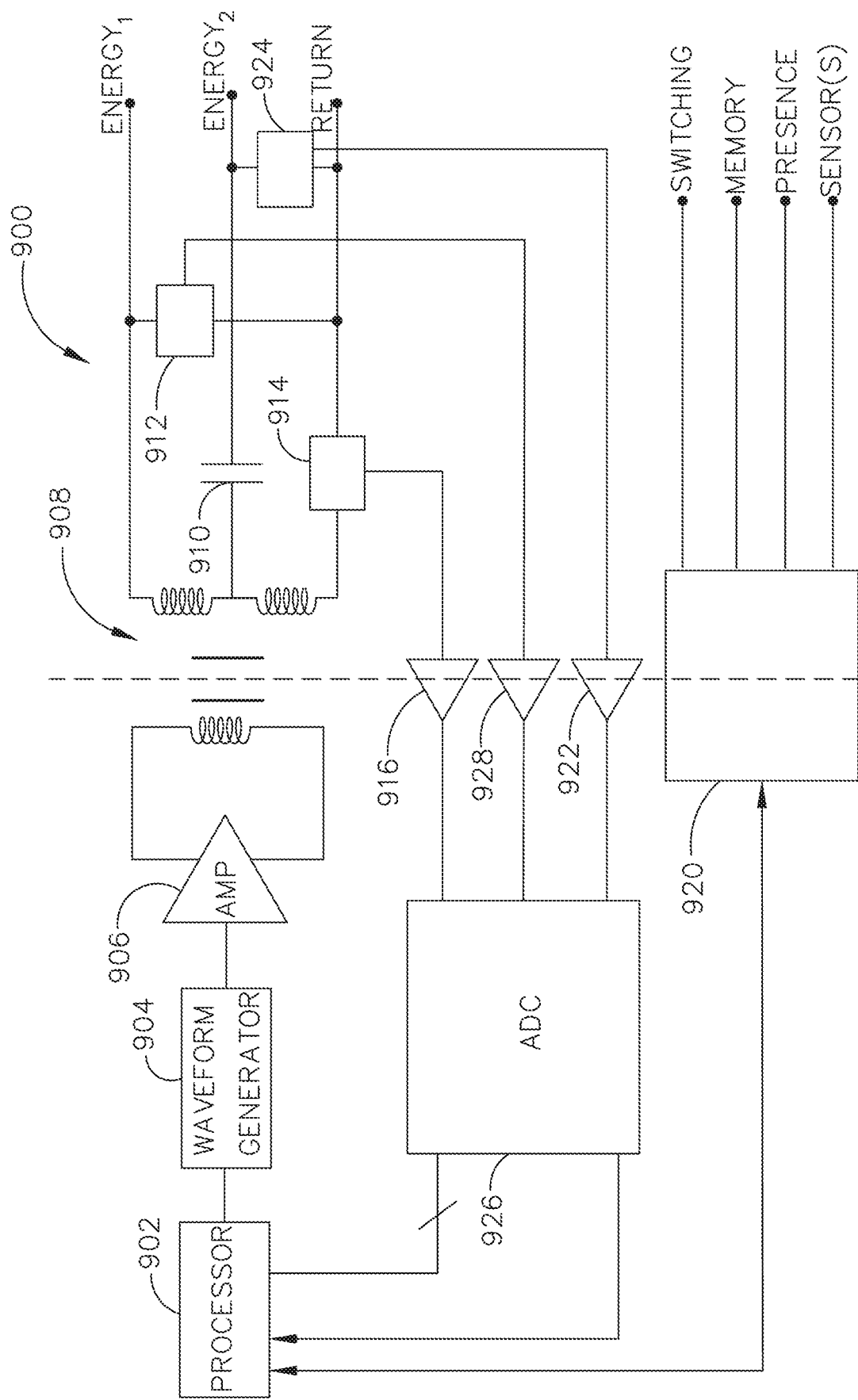
FIG. 1 illustrates an example of a generator for use with a surgical system, in accordance with at least one aspect of the present disclosure.

FIG. 1 illustrates an example of a generator 900 configured to deliver multiple energy modalities to a surgical instrument. The generator 900 provides RF and/or ultrasonic signals for delivering energy to a surgical instrument. The generator 900 comprises at least one generator output that can deliver multiple energy modalities (e.g., ultrasonic, bipolar or monopolar RF, irreversible and/or reversible electroporation, and/or microwave energy, among others) through a single port, and these signals can be delivered separately or simultaneously to an end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 906 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY$_1$ and RETURN. A second signal of a second energy modality is coupled across a capacitor 910 and is provided to the surgical instrument between the terminals labeled ENERGY$_2$ and RETURN. It will be appreciated that more than two energy modalities may be output and thus the subscript "n" may be used to designate that up to n ENERGY$_n$ terminals may be provided, where n is a positive integer greater than 1. It also will be appreciated that up to "n" return paths RETURN$_n$ may be provided without departing from the scope of the present disclosure.

A first voltage sensing circuit 912 is coupled across the terminals labeled ENERGY$_1$ and the RETURN path to measure the output voltage therebetween. A second voltage sensing circuit 924 is coupled across the terminals labeled ENERGY$_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 928, 922 and the output of the current sensing circuit 914 is provided to another isolation transformer 916. The outputs of the isolation transformers 916, 928, 922 on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY$_1$/RETURN or the second voltage sensing circuit 924 coupled across the terminals labeled ENERGY$_2$/RETURN by the output of the current sensing circuit 914 disposed in series with the RETURN leg of the secondary side of the power transformer 908. The outputs of the first and second voltage sensing circuits 912, 924 are provided to separate isolations transformers 928, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY$_1$ may be RF monopolar energy and the second energy modality ENERGY$_2$ may be RF bipolar energy. Nevertheless, in addition to bipolar and monopolar RF energy modalities, other energy modalities include ultrasonic energy, irreversible and/or reversible electroporation and/or microwave energy, among others. Also, although the example illustrated in FIG. 1 shows a single return path RETURN may be provided for two or more energy modalities, in other aspects, multiple return paths RETURN$_n$ may be provided for each energy modality ENERGY$_n$.

As shown in FIG. 1, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. In one example, a connection of RF bipolar electrodes to the generator 900 output would be preferably located between the output labeled ENERGY$_2$ and RETURN. In the case of monopolar output, the preferred connections would be active electrode (e.g., pencil or other probe) to the ENERGY$_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

Figure 2:
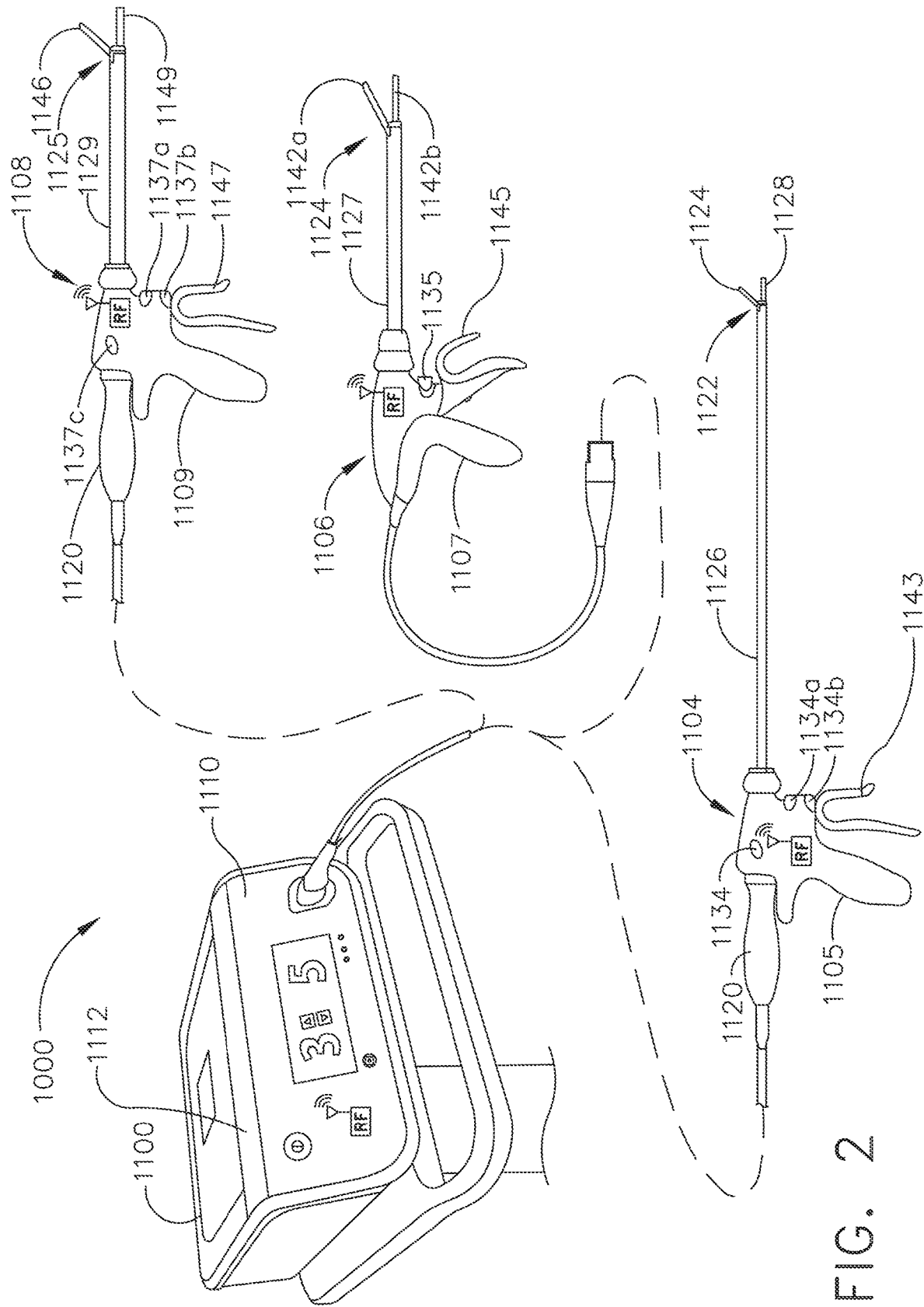
FIG. 2 illustrates one form of a surgical system comprising a generator and an electrosurgical instrument usable therewith, in accordance with at least one aspect of the present disclosure.

FIG. 2 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 2 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1137, 1134b, 1134c to energize and drive the ultrasonic blade 1128 or other function. The toggle buttons 1137, 1134*b*, 1134*c* can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1145, 1142*b* and return through an electrical conductor portion of the shaft 1127. The electrodes are coupled to and energized by a bipolar energy source within the generator 1100. The handpiece 1107 comprises a trigger 1145 to operate the clamp arms 1145, 1142*b* and an energy button 1135 to actuate an energy switch to energize the electrodes in the end effector 1124. The second surgical instrument 1106 can also be used with a return pad to deliver monopolar energy to tissue.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 11310, 1137*b*, 1137*c* to energize and drive the ultrasonic blade 1149 or other function. The toggle buttons 11310, 1137*b*, 1137*c* can be configured to energize the ultrasonic transducer 1120 with the generator 1100 and energize the ultrasonic blade 1149 with a bipolar energy source also contained within the generator 1100. Monopolar energy can be delivered to the tissue in combination with, or separately from, the bipolar energy.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 2, the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent application publication US-2017-0086914-A1, which is herein incorporated by reference in its entirety.

Figure 3:
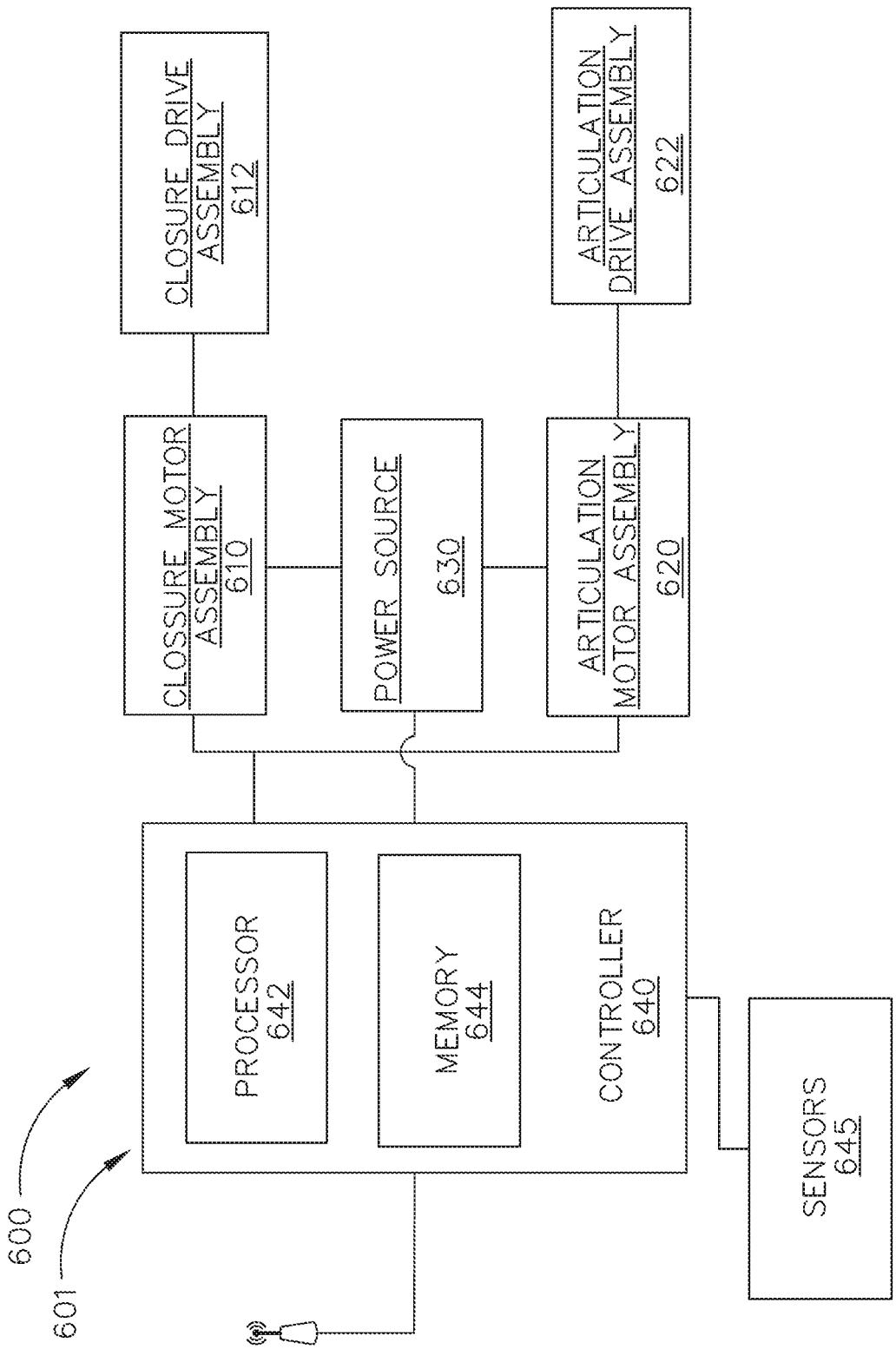
FIG. 3 illustrates a schematic diagram of a surgical instrument or tool, in accordance with at least one aspect of the present disclosure.
Figure 4:
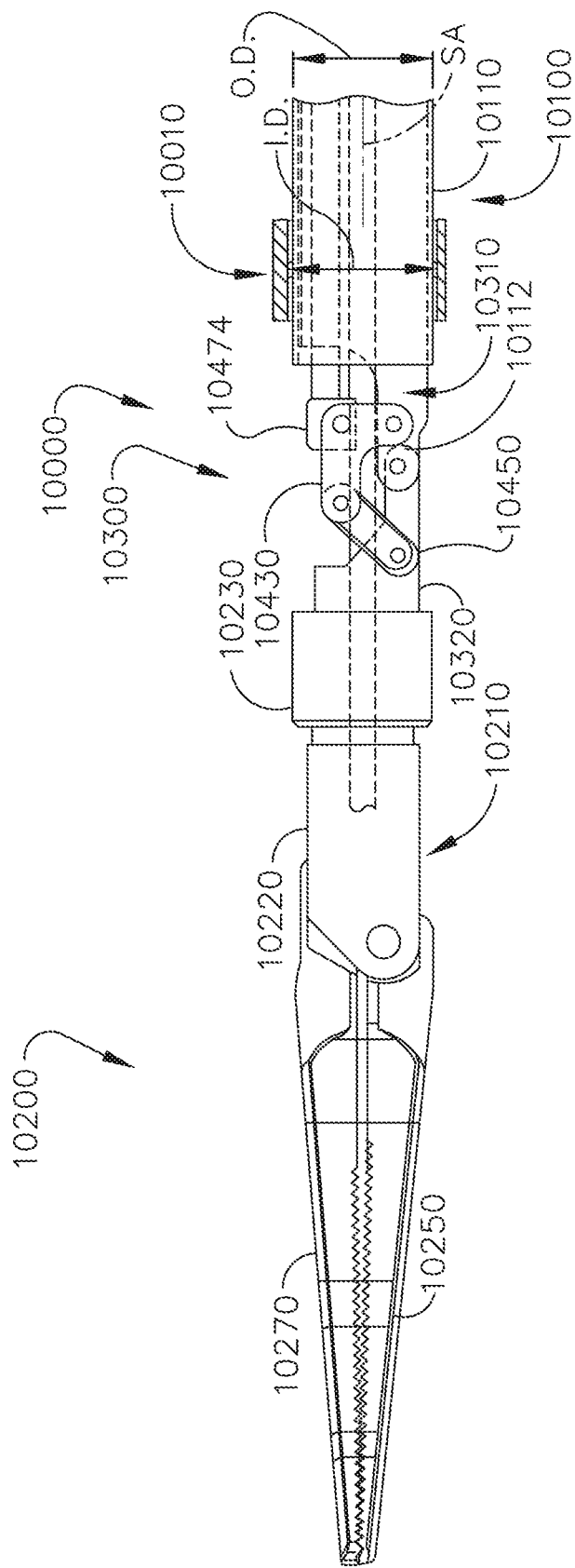
FIG. 4 is a side elevational view of a portion of a surgical instrument in an unarticulated position, in accordance with at least one aspect of the present disclosure.
Figure 5:
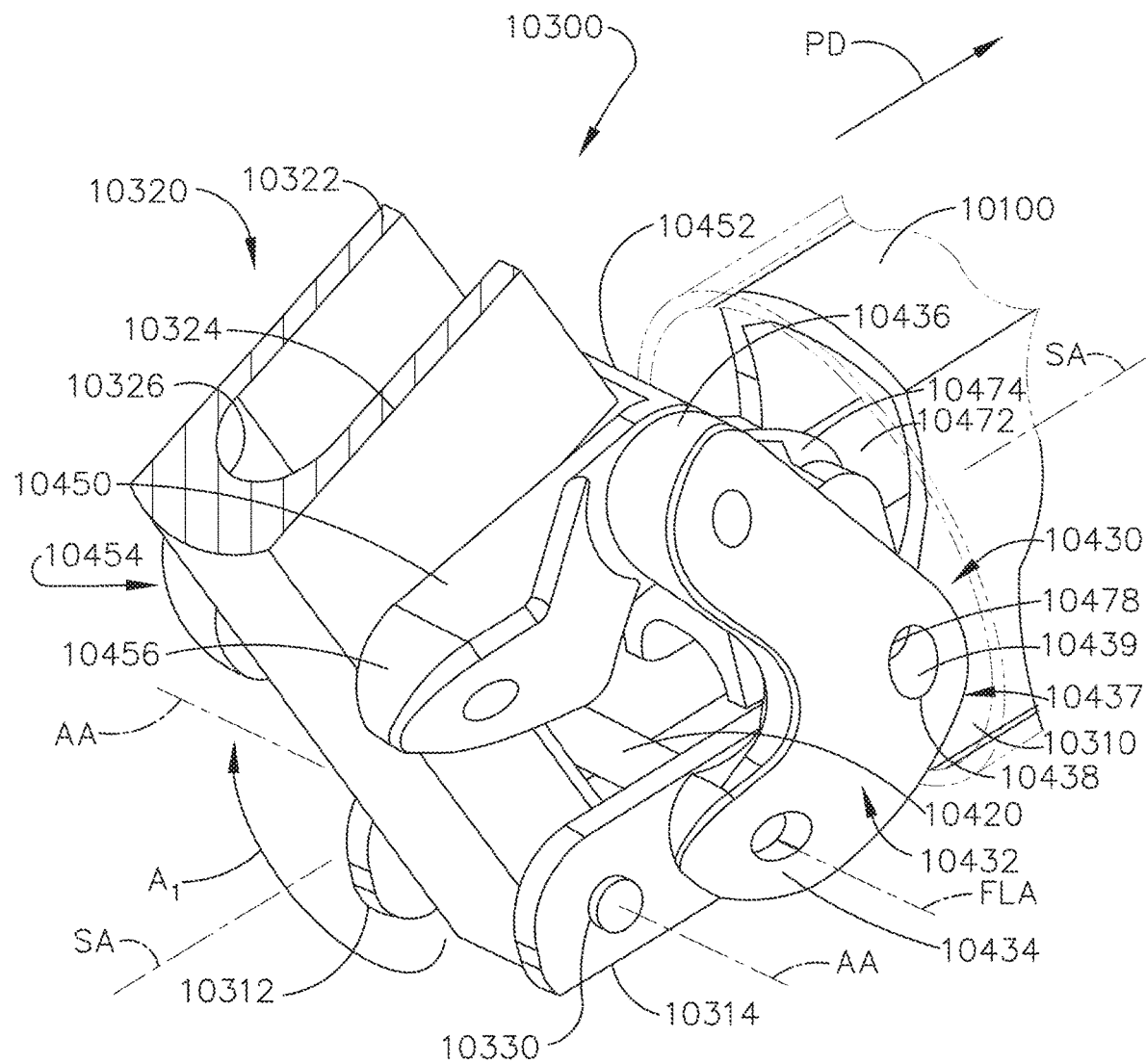
FIG. 5 is a perspective view of a portion of an articulation joint of the surgical instrument of FIG. 4 articulated in a first direction.
Figure 6:
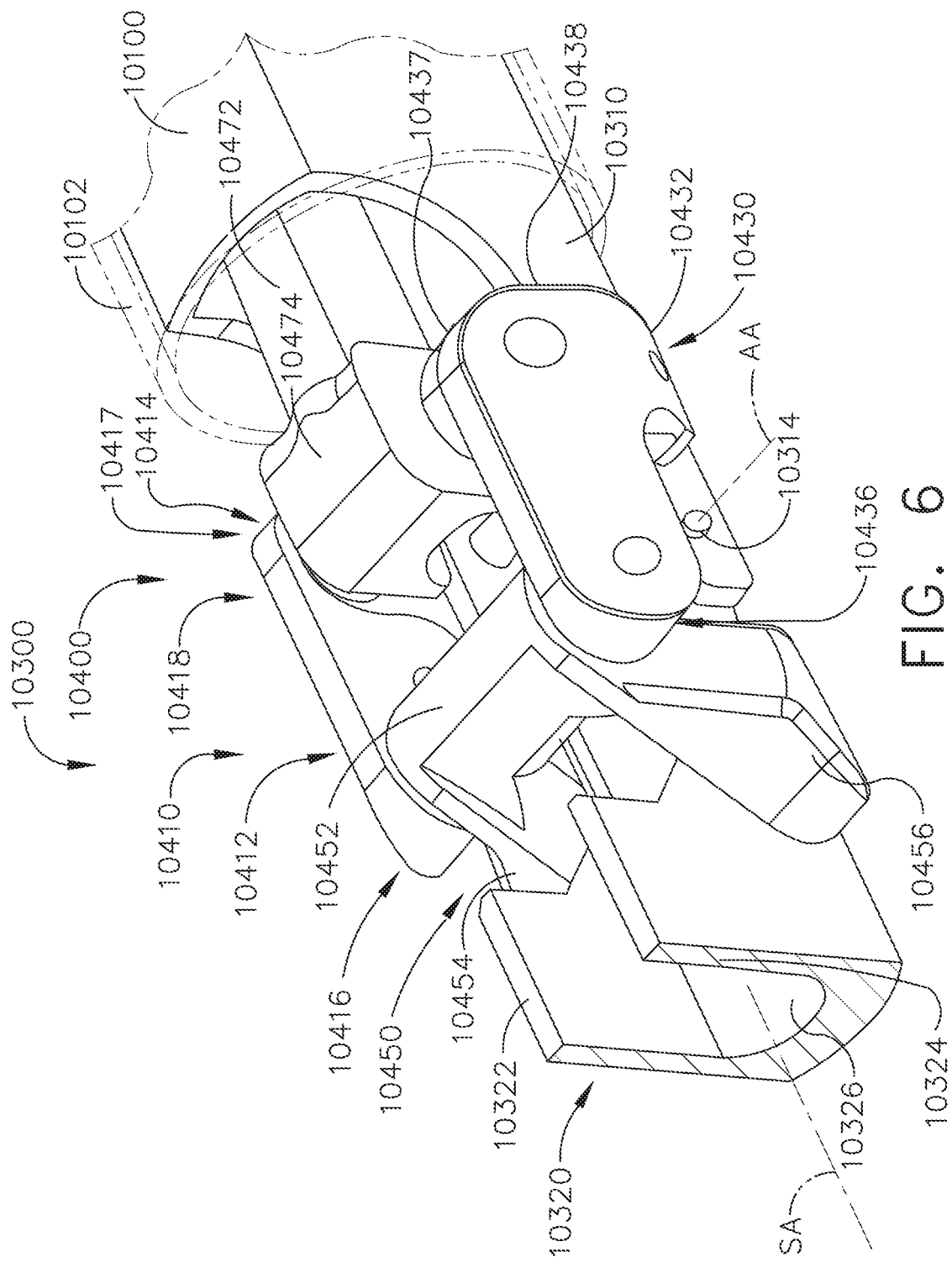
FIG. 6 is another perspective view of the articulation joint of FIG. 5 in an unarticulated position.
Figure 7:
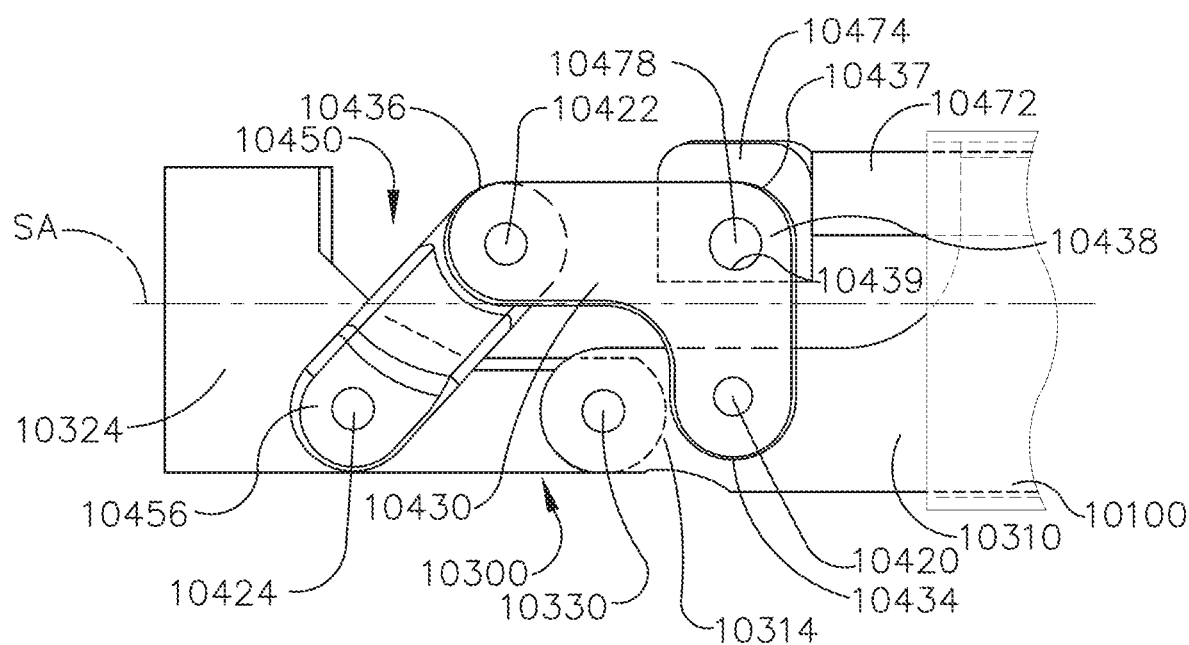
FIG. 7 is a side elevational view of the articulation joint of FIG. 6.
Figure 8:
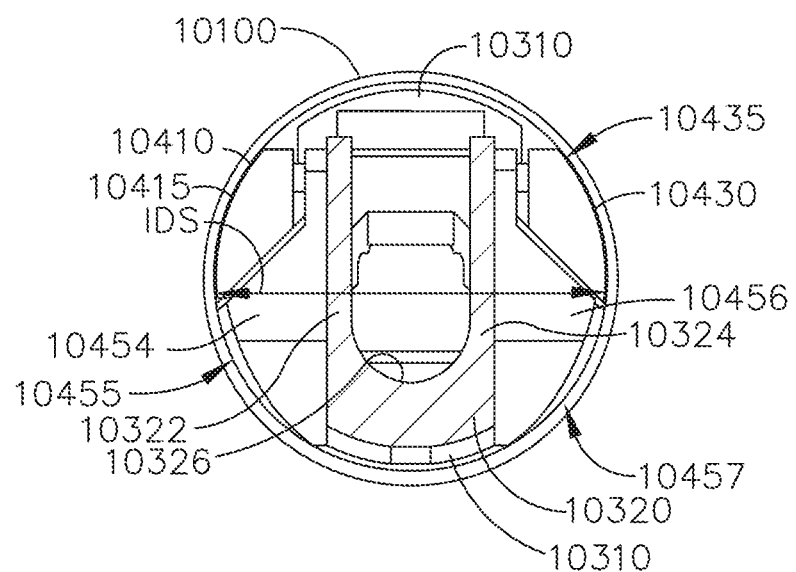
FIG. 8 is an end elevational view of the articulation joint of FIG. 7.
Figure 9:
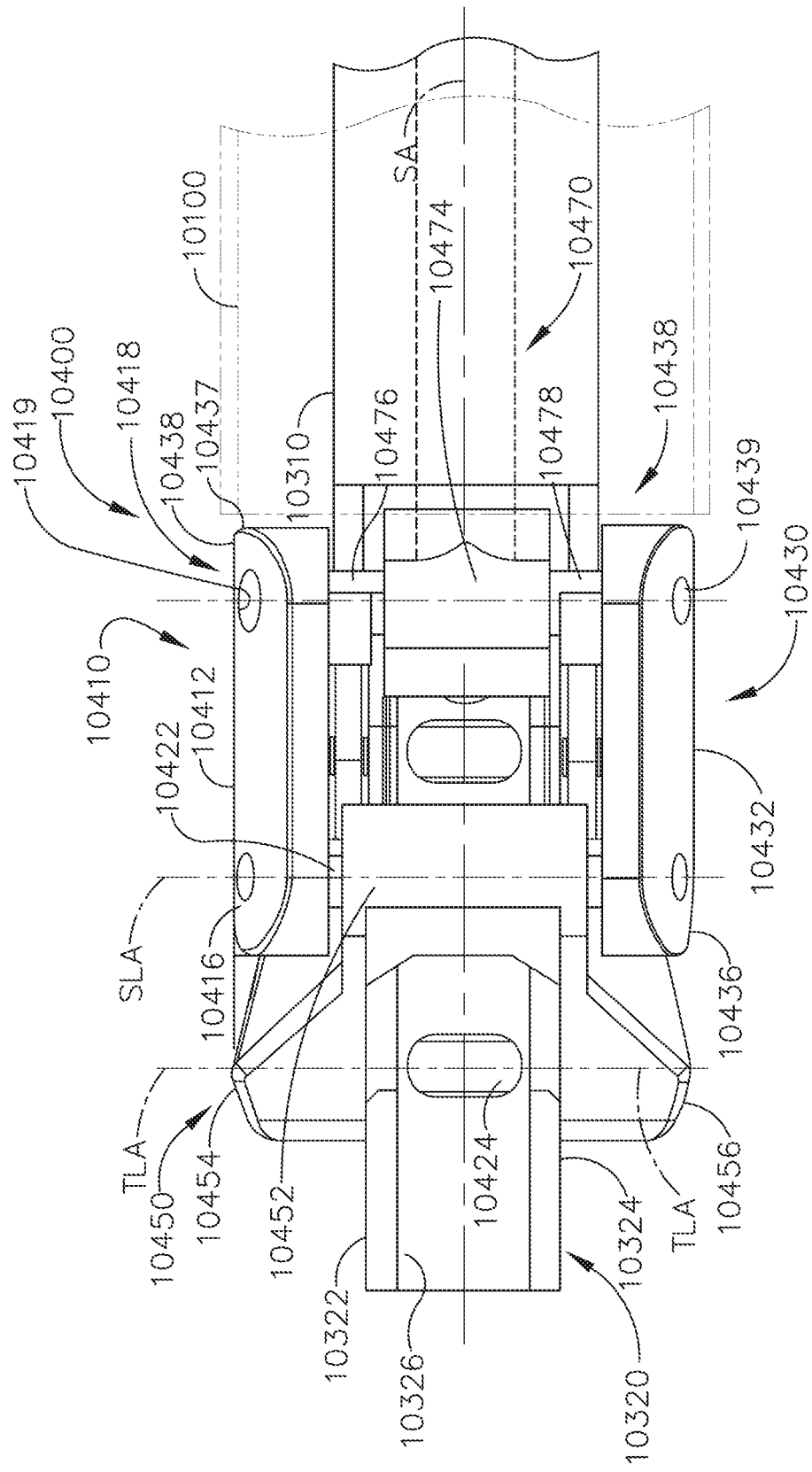
FIG. 9 is a top view of the articulation joint of FIG. 7.
Figure 10:
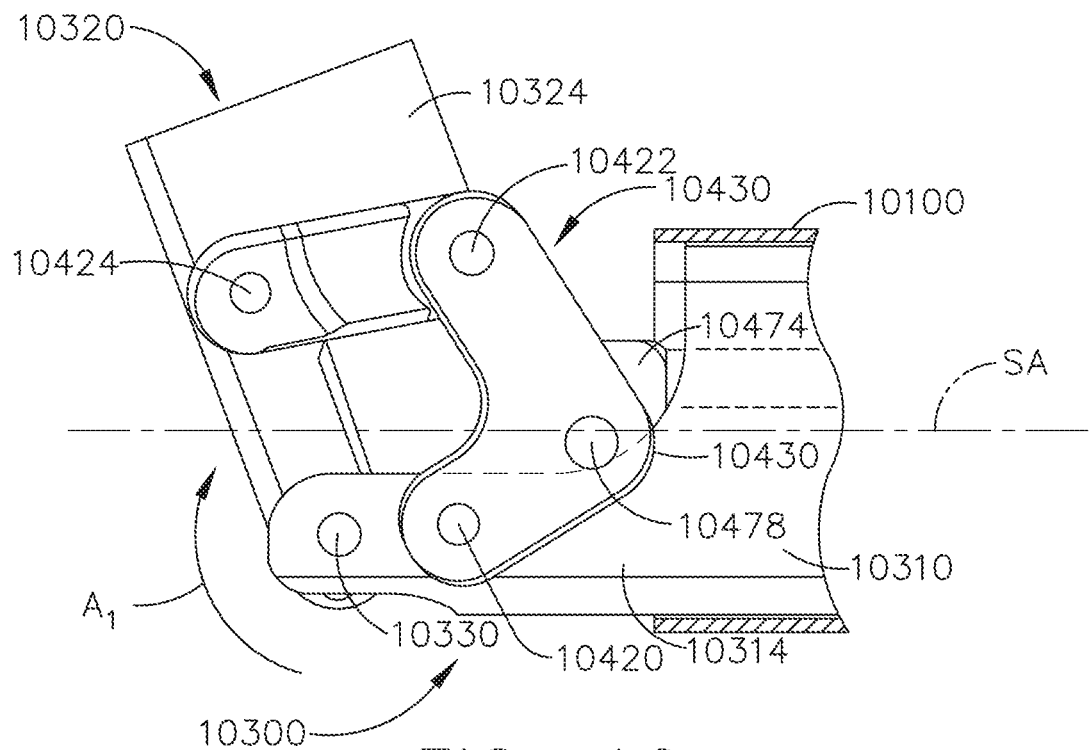
FIG. 10 is a side elevational view of the articulation joint of the surgical instrument of FIG. 4 articulated in a first direction.
Figure 11:
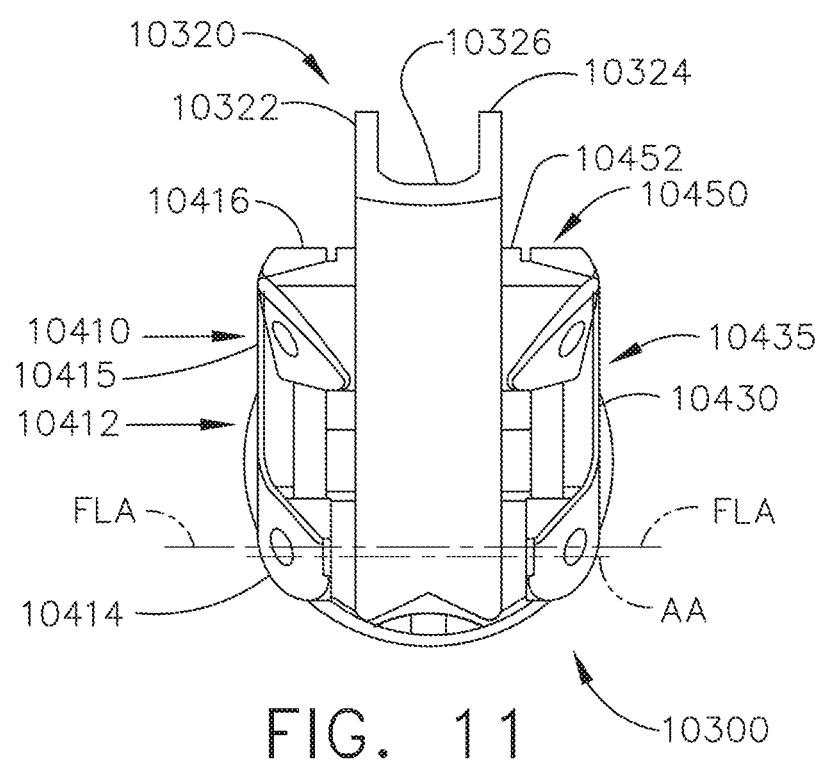
FIG. 11 is an end elevational view of the articulation joint of FIG. 10.
Figure 12:
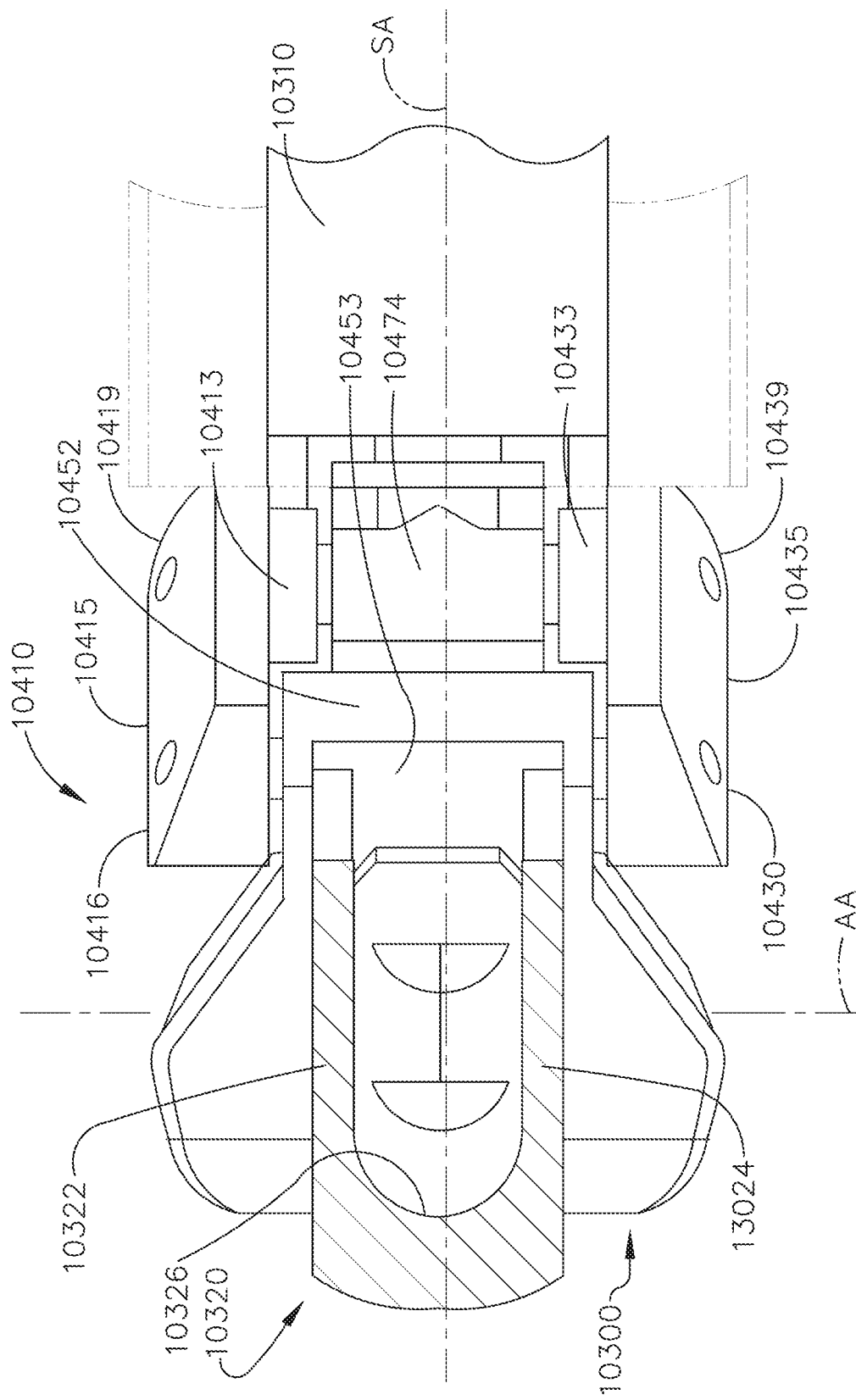
FIG. 12 is a top view of the articulation joint of FIG. 10.
Figure 13:
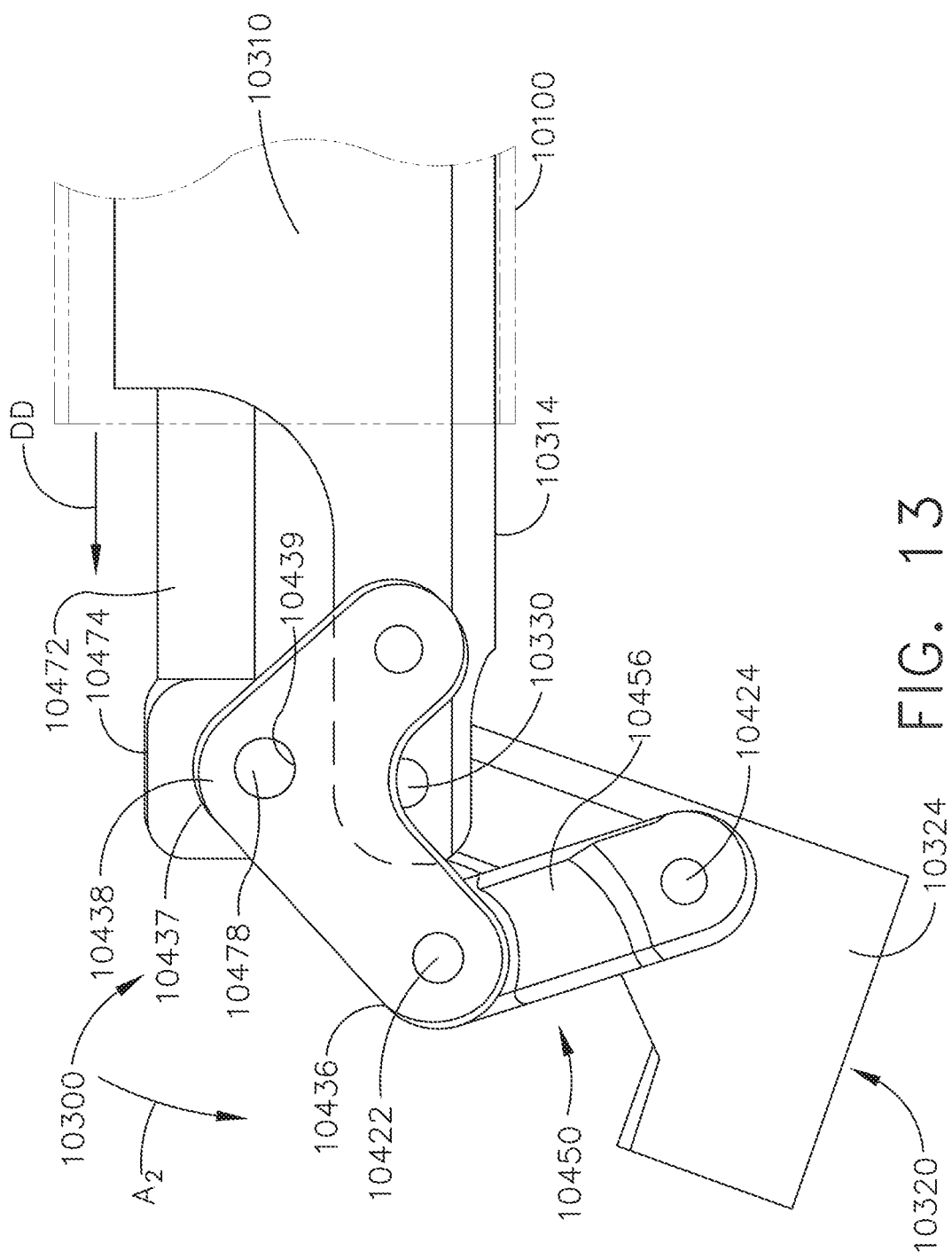
FIG. 13 is a side elevational view of the articulation joint of the surgical instrument of FIG. 4 articulated in a second direction.
Figure 15:
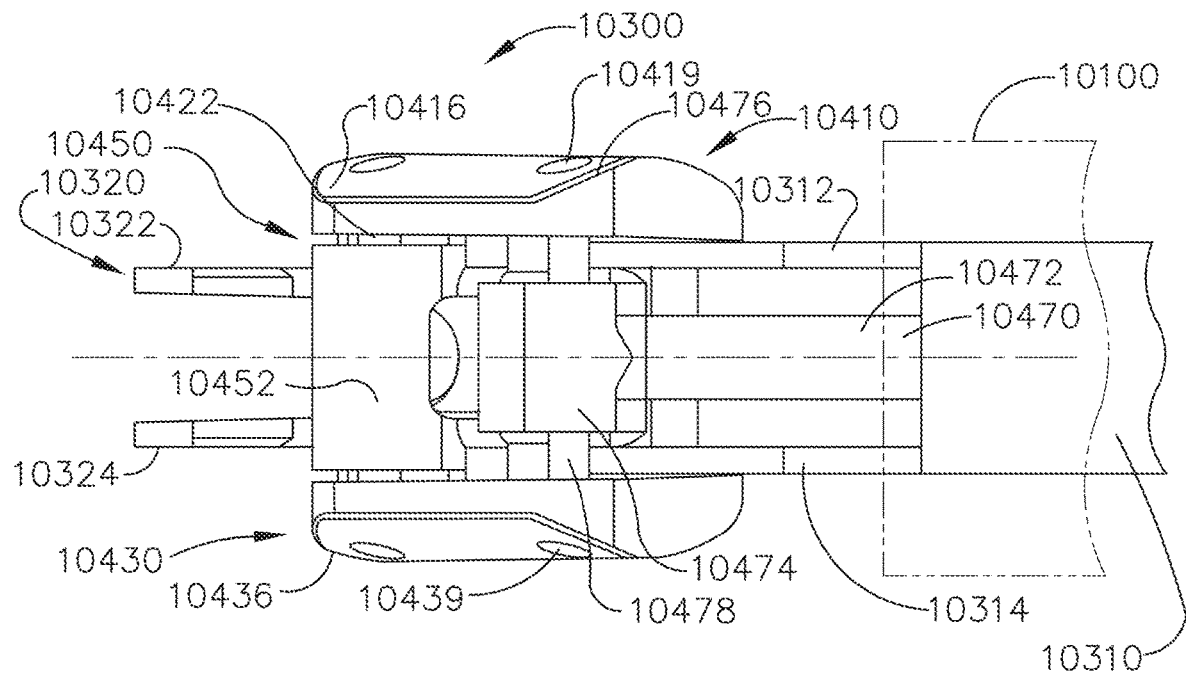
FIG. 15 is a top view of the articulation joint of FIG. 13.
Figure 14:
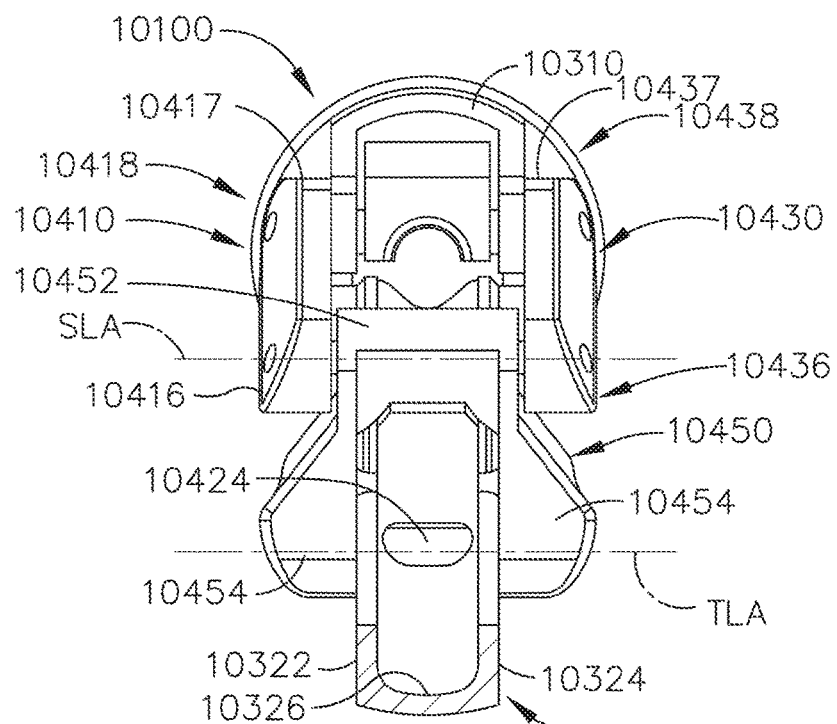
FIG. 14 is an end elevational view of the articulation joint of FIG. 13.
Figure 16:
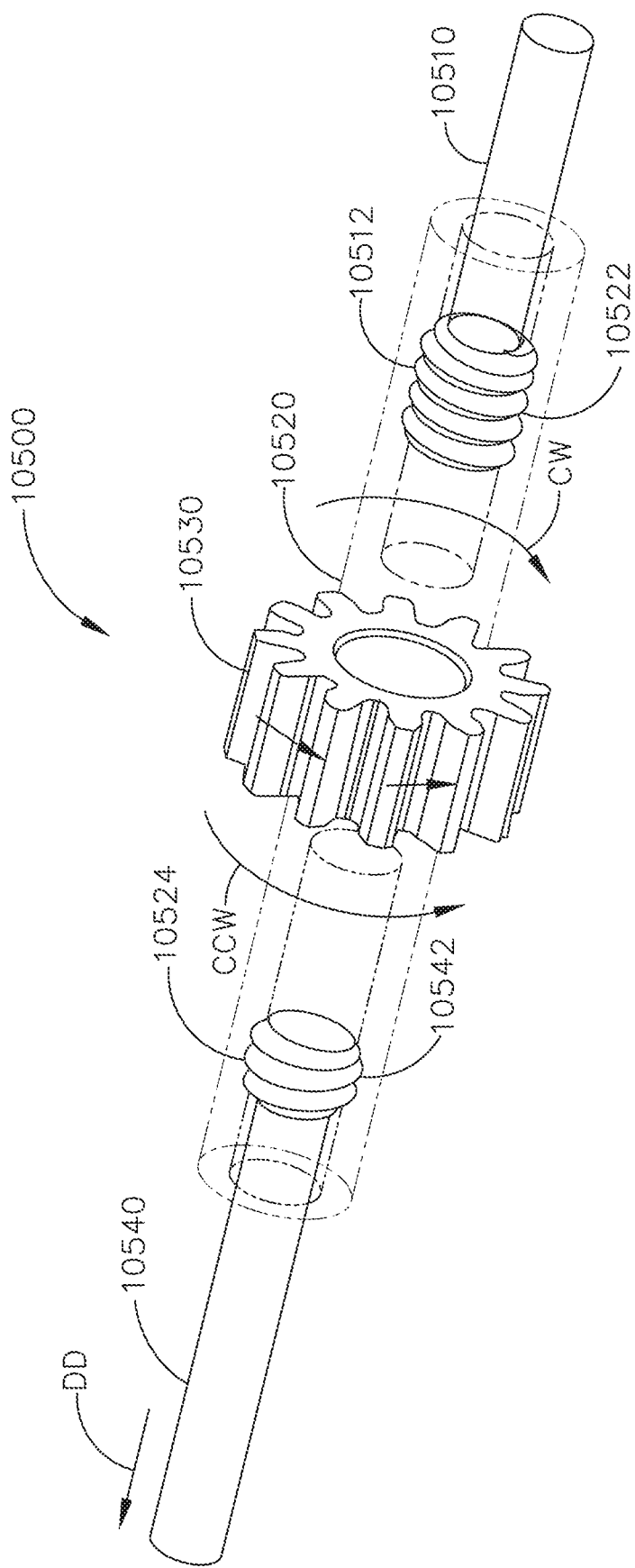
FIG. 16 is a perspective view of a portion of an axial drive system embodiment, in accordance with at least one aspect of the present disclosure.
Figure 18:
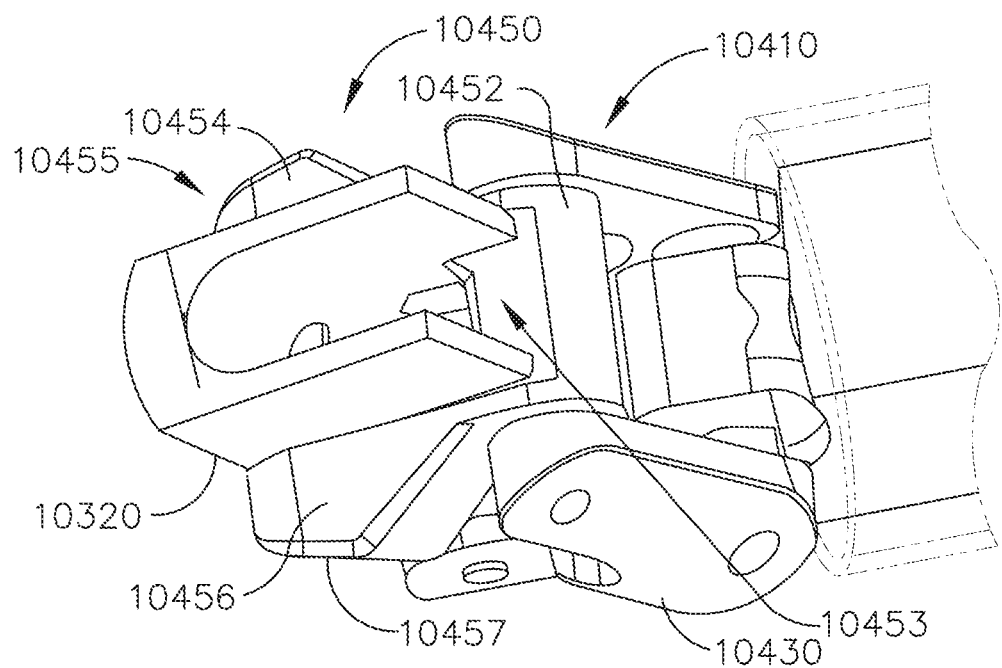
FIG. 18 is another perspective view of the articulation joint of FIG. 17.
Figure 17:
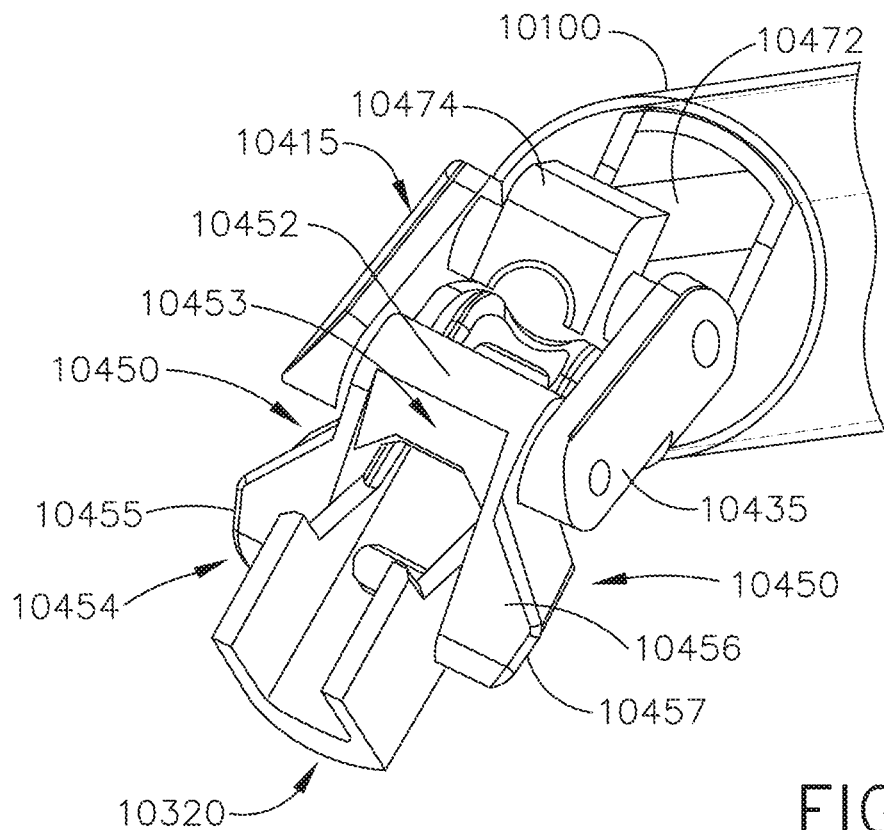
FIG. 17 is another perspective view of the articulation joint of the surgical instrument of FIG. 4.

FIG. 3 illustrates a schematic diagram of a surgical instrument or tool 600 comprising a plurality of motor assemblies that can be activated to perform various functions. In the illustrated example, a closure motor assembly 610 is operable to transition an end effector between an open configuration and a closed configuration, and an articulation motor assembly 620 is operable to articulate the end effector relative to a shaft assembly. In certain instances, the plurality of motors assemblies can be individually activated to cause firing, closure, and/or articulation motions in the end effector. The firing, closure, and/or articulation motions can be transmitted to the end effector through a shaft assembly, for example.

In certain instances, the closure motor assembly 610 includes a closure motor. The closure 603 may be operably coupled to a closure motor drive assembly 612 which can be configured to transmit closure motions, generated by the motor to the end effector, in particular to displace a closure member to close to transition the end effector to the closed configuration. The closure motions may cause the end effector to transition from an open configuration to a closed configuration to capture tissue, for example. The end effector may be transitioned to an open position by reversing the direction of the motor.

In certain instances, the articulation motor assembly 620 includes an articulation motor that be operably coupled to an articulation drive assembly 622 which can be configured to transmit articulation motions, generated by the motor to the end effector. In certain instances, the articulation motions may cause the end effector to articulate relative to the shaft, for example.

One or more of the motors of the surgical instrument 600 may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, the motor assemblies 610, 620 include one or more motor drivers that may comprise one or more H-Bridge FETs. The motor drivers may modulate the power transmitted from a power source 630 to a motor based on input from a microcontroller 640 (the "controller"), for example, of a control circuit 601. In certain instances, the microcontroller 640 can be employed to determine the current drawn by the motor, for example.

In certain instances, the microcontroller 640 may include a microprocessor 642 (the "processor") and one or more non-transitory computer-readable mediums or memory units 644 (the "memory"). In certain instances, the memory 644 may store various program instructions, which when executed may cause the processor 642 to perform a plurality of functions and/or calculations described herein. In certain instances, one or more of the memory units 644 may be coupled to the processor 642, for example. In various aspects, the microcontroller 640 may communicate over a wired or wireless channel, or combinations thereof.

In certain instances, the power source 630 can be employed to supply power to the microcontroller 640, for example. In certain instances, the power source 630 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 630. In certain instances, the power source 630 may be replaceable and/or rechargeable, for example.

In various instances, the processor 642 may control a motor driver to control the position, direction of rotation, and/or velocity of a motor of the assemblies 610, 620. In certain instances, the processor 642 can signal the motor driver to stop and/or disable the motor. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 642 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 642 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the surgical instrument 600. Accordingly, the present disclosure should not be limited in this context.

In certain instances, the memory 644 may include program instructions for controlling each of the motors of the surgical instrument 600. For example, the memory 644 may include program instructions for controlling the closure motor and the articulation motor. Such program instructions may cause the processor 642 to control the closure and articulation functions in accordance with inputs from algorithms or control programs of the surgical instrument 600.

In certain instances, one or more mechanisms and/or sensors such as, for example, sensors 645 can be employed to alert the processor 642 to the program instructions that should be used in a particular setting. For example, the sensors 645 may alert the processor 642 to use the program instructions associated with closing and articulating the end effector. In certain instances, the sensors 645 may comprise position sensors which can be employed to sense the position of a closure actuator, for example. Accordingly, the processor 642 may use the program instructions associated with closing the end effector to activate the motor of the closure drive assembly 620 if the processor 642 receives a signal from the sensors 630 indicative of actuation of the closure actuator.

In some examples, the motors may be brushless DC electric motors, and the respective motor drive signals may comprise a PWM signal provided to one or more stator windings of the motors. Also, in some examples, the motor drivers may be omitted and the control circuit 601 may generate the motor drive signals directly.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that position during the actuation of the end effector and completion of the surgical procedure. Such articulation joint arrangements must also be able to withstand external forces that are experienced by the end effector during use.

Various modes of one or more surgical devices are often used throughout a particular surgical procedure. Communication pathways extending between the surgical devices and a centralized surgical hub can promote efficiency and increase success of the surgical procedure, for example. In various instances, each surgical device within a surgical system comprises a display, wherein the display communicates a presence and/or an operating status of other surgical devices within the surgical system. The surgical hub can use the information received through the communication pathways to assess compatibility of the surgical devices for use with one another, assess compatibility of the surgical devices for use during a particular surgical procedure, and/or optimize operating parameters of the surgical devices. As described in greater detail herein, the operating parameters of the one or more surgical devices can be optimized based on patient demographics, a particular surgical procedure, and/or detected environmental conditions such as tissue thickness, for example.

FIGS. 95 and 96 illustrate an exploded view (FIG. 95) and a cross-sectional view (FIG. 96) of an end effector 1200 of an electrosurgical instrument (e.g. surgical instruments described in U.S. Pat. No. 11,696,776). For example, the end effector 1200 can be, actuated, articulated, and/or rotated with respect to a shaft assembly of a surgical instrument in a similar manner to end effectors described in U.S. Pat. No. 11,696,776. Additionally, the end effectors 1200 and other similar end effectors, which are described elsewhere herein, can be powered by one or more generators of a surgical system. Example surgical systems for use with the surgical instrument are described in U.S. application Ser. No. 16/562,123, filed Sep. 5, 2019, and titled METHOD FOR CONSTRUCTING AND USING A MODULAR SURGICAL ENERGY SYSTEM WITH MULTIPLE DEVICES, which is hereby incorporated herein in its entirety.

Referring to FIGS. 97-99, the end effector 1200 includes a first jaw 1250 and a second jaw 1270. At least one of the first jaw 1250 and the second jaw 1270 is pivotable toward and away from the other jaw to transition the end effector 1200 between an open configuration and a closed configuration. The jaws 1250, 1270 are configured to grasp tissue therebetween to apply at least one of a therapeutic energy and a non-therapeutic energy to the tissue. Energy delivery to the tissue grasped by the jaws 1250, 1270 of the end effector 1200 is achieved by electrodes 1252, 1272, 1274, which are configured to deliver the energy in a monopolar mode, bipolar mode, and/or a combination mode with alternating or blended bipolar and monopolar energies. The different energy modalities that can be delivered to the tissue by the end effector 1200 are described in greater detail elsewhere in the present disclosure.

In addition to the electrodes 1252, 1272, 1274, a patient return pad is employed with the application of monopolar energy. Furthermore, the bipolar and monopolar energies are delivered using electrically isolated generators. During use, the patient return pad can detect unexpected power crossover by monitoring power transmission to the return pad via one or more suitable sensors on the return pad. The unexpected power crossover can occur where the bipolar and monopolar energy modalities are used simultaneously. In at least one example, the bipolar mode uses a higher current (e.g. 2-3 amp) than the monopolar mode (e.g. 1 amp). In at least one example, the return pad includes a control circuit and at least one sensor (e.g. current sensor) coupled thereto. In use, the control circuit can receive an input indicative of an unexpected power crossover based on measurements of the at least one sensor. In response, the control circuit may employ a feedback system to issue an alert and/or pause application of one or both of the bipolar and monopolar energy modalities to tissue.

Further to the above, the jaws 1250, 1270 of the end effector 1200 comprise angular profiles where a plurality of angles are defined between discrete portions of each of the jaws 1250, 1270. For example, a first angle is defined by portions 1250a, 1250b (FIG. 95), and a second angle is defined by portions 1250b, 1250c of the first jaw 1250. Similarly, a first angle is defined by portions 1270a, 1270b, and a second angle is defined by portions 1270b, 1270c of the second jaw 1270. In various aspects, the discrete portions of the jaws 1250, 1270 are linear segments. Consecutive linear segments intersect at angles such as, for example, the first angle, or the second angle. The linear segments cooperate to form a generally angular profile of each of the jaws 1250, 1270. The angular profile is general bent away from a central axis.

In one example, the first angles and the second angles are the same, or at least substantially the same. In another example, the first angles and the second angles are different. In another example, the first angle and the second angle comprise values selected from a range of about 120° to about 175°. In yet another example, the first angle and the second angle comprise values selected from a range of about 130° to about 170°.

Furthermore, the portions 1250a, 1270a, which are proximal portions, are larger than the portions 1250b, 1270b, which are intermediate portions. Similarly, the intermediate portions 1250b, 1270b are larger than the portions 1250c, 1270c. In other examples, the distal portions can be larger than the intermediate and/or proximal portions. In other examples, the intermediate portions are larger than the proximal and/or distal portions.

Further to the above, the electrodes 1252, 1272, 1274 of the jaws 1250, 1270 comprise angular profiles that are similar to the angular profiles of the jaws 1250, 1270. In the example of FIGS. 95, 96, the electrodes 1252, 1272, 1274 include discrete segments 1252a, 1252b, 1252c, 1272a, 1272b, 1272c, 1274a, 1274b, 1274c, respectively, which define first and second angles at their respective intersections, as described above.

When in the closed configuration, the jaws 1250, 1270 cooperate to define a tip electrode 1260 formed of electrode portions 1261, 1262 at the distal ends of the jaws 1250, 1270, respectively. The tip electrode 1260 can be energized to deliver monopolar energy to tissue in contact therewith. Both of the electrode portions 1261, 1262 can be activated simultaneously to deliver the monopolar energy, as illustrated in FIG. 97 or, alternatively, only one of the electrode portions 1261, 1262 can be selectively activated to deliver the monopolar energy on one side of the distal tip electrode 1260, as illustrated in FIG. 101, for example.

The angular profiles of the jaws 1250, 1270 cause the tip electrode 1260 to be on one side of a plane extending laterally between the proximal portion 1252c and the proximal portion 1272c in the closed configuration. The angular profiles may also cause the intersections between portions 1252b, 1252c, portions, 1272b, 1272c, and portions 1274b, 1274c to be on the same side of the plane as the tip electrode 1260.

In at least one example, the jaws 1250, 1270 include conductive skeletons 1253, 1273, which can be comprised, or at least partially comprised, of a conductive material such as, for example, Titanium. The skeletons 1253, 1273 can be comprised of other conductive materials such as, for example, Aluminum. In at least one example, the skeletons 1253, 1273 are prepared by injection molding. In various examples, the skeletons 1253, 1273 are selectively coated/covered with an insulative material to prevent thermal conduction and electrical conduction in all but predefined thin energizable zones forming the electrodes 1252, 1272, 1274, 1260. The skeletons 1253, 1273 act as electrodes with electron focusing where the jaws 1250, 1270 have built-in isolation from one jaw to the other. The insulative material can be an insulative polymer such as, for example, PolyTetraFluoroEthylene (e.g. Teflon®). The energizable zones that are defined by the electrodes 1252, 1272 are on the inside of the jaws 1250, 1270, and are operable independently in a bipolar mode to deliver energy to tissue grasped between the jaws 1250, 1270. Meanwhile, the energizable zones that are defined by the electrode tip 1260 and the electrode 1274 are on the outside of the jaws 1250, 1270, and are operable to deliver energy to tissue adjacent an external surface of the end effector 1200 in a monopolar mode. Both of the jaws 1250, 1270 can be energized to deliver the energy in the monopolar mode.

In various aspects, the coating 1264 is a high temperature PolyTetraFluoroEthylene (e.g. Teflon®) coating that is selectively applied to a conductive skeleton yielding selective exposed metallic internal portions that define a three-dimensional geometric electron modulation (GEM) for a focused dissection and coagulation. In at least one example, the coating 1264 comprises a thickness of about 0.003 inches, about 0.0035 inches, or about 0.0025 inches. In various examples, the thickness of the coating 1264 can be any value selected from a range of about 0.002 inches to about 0.004 inches, a range of about 0.0025 inches to about 0.0035 inches, or a range of about 0.0027 inches to about 0.0033 inches. Other thicknesses for the coating 1263 that are capable of three-dimensional geometric electron modulation (GEM) are contemplated by the present disclosure.

The electrodes 1252, 1272, which cooperate to transmit bipolar energy through the tissue, are offset to prevent circuit shorting. As energy flows between the offset electrodes 1252, 1272, the tissue-grasped therebetween is heated generating a seal at the area between electrodes 1252, 1272. Meanwhile, regions of the jaws 1250, 1270 surrounding the electrodes 1252, 1272 provide non-conductive tissue contact surfaces owing to an insulative coating 1264 selectively deposited onto the jaws 1250, 1270 on such regions but not the electrodes 1252, 1272. Accordingly, the electrodes 1252, 1272 are defined by regions of the metallic jaws 1250, 1270, which remain exposed following application of the insulative coating 1264 to the jaws 1250, 1270. While the jaws 1250, 1270 are generally formed of electrically conductive material in this example, the non-conductive regions are defined by the electrically insulative coating 1264.

FIG. 97 illustrates an application of a bipolar energy mode to tissue grasped between the jaws 1250, 1270. In the bipolar energy mode, RF energy flows through the tissue along a path 1271 that is oblique relative to a curved plane (CL) extending centrally, and longitudinally bisecting, the jaws 1250, 1270 such that the electrodes 1252, 1272 are on opposite sides of the curved plane (CL). In other words, the region of tissue that actually receives bipolar RF energy will only be the tissue that is contacting and extending between the electrodes 1252, 1257. Thus, the tissue grasped by the jaws 1250, 1270 will not receive RF energy across the entire lateral width of jaws 1250, 1270. This configuration may thus minimize the thermal spread of heat caused by the application of bipolar RF energy to the tissue. Such minimization of thermal spread may in turn minimize potential collateral damage to tissue that is adjacent to the particular tissue region that the surgeon wishes to weld/seal/coagulate and/or cut.

In at least one example, a lateral gap is defined between the offset electrodes 1252, 1272 in a closed configuration without tissue therebetween. In at least one example, the lateral gap is defined between the offset electrodes 1252, 1272 in the closed configuration by any distance selected from a range of about 0.01 inch to about 0.025 inch, a range of about 0.015 inch to about 0.020 inch, or a range of about 0.016 inch to about 0.019 inch. In at least one example, the lateral gap is defined by a distance of about 0.017 inch.

In the example illustrated in FIGS. 95 and 96, the electrodes 1252, 1272, 1274 comprise gradually narrowing widths as each of the electrodes 1252, 1272, 1274 extends from a proximal end to a distal end. Consequently, the proximal segments 1252*a*, 1272*a*, 1274*a* comprise surface areas that are greater than the intermediate portions 1252*b*, 1272*b*, 1274*b*, respectively. Also, the intermediate segments 1252*b*, 1272*b*, 1274*b* comprise surfaces that are greater than the distal segments 1252*c*, 1272*c*, 1274*c*.

The angular and narrowing profiles of the jaws 1250, 1270 gives the end effector 1200 a bent finger-like shape or an angular hook shape in the closed configuration. This shape permits accurate delivery of energy to a small portion of the tissue using the tip electrode 1260 (FIG. 101) by orienting the end effector 1200 such that the electrode tip 1260 is pointed down toward the tissue. In such orientation, only the electrode tip 1260 is in contact with the tissue, which focuses the energy delivery to the tissue.

Furthermore, as illustrated in FIG. 99, the electrode 1274 extends on an outer surface on a peripheral side 1275 of the second jaw 1270, which affords it the ability effectively separate tissue in contact therewith while the end effector 1200 is in the closed configuration. To separate the tissue, the end effector 1200 is positioned, at least partially, on the peripheral side 1275 that includes the electrode 1274. Activation of the monopolar energy mode through the jaw 1270 cause monopolar energy to flow through the electrode 1274 into the tissue in contact therewith.

FIGS. 100-102 illustrate an end effector 1200' in use to deliver bipolar energy to tissue through electrodes 1252', 1272' (FIG. 100) in a bipolar energy mode of operation, to deliver monopolar energy to tissue through the electrode tip 1261 in a first monopolar mode of operation, and/or to deliver monopolar energy to tissue through the external electrode 1274 in a second monopolar mode of operation. The end effector 1200' is similar in many respects to the end effector 1200. Accordingly, various features of the end effector 1200' that are previously described with respect to the end effector 1200 are not repeated herein in the same level of detail for brevity.

The electrodes 1252', 1272' are different from the electrodes 1252", 1272" in that they define stepped, or uneven, tissue contacting surfaces 1257, 1277. Electrically conductive skeletons 1253', 1273' of the jaws 1250', 1270' include bulging, or protruding, portions that form the conductive tissue contacting surfaces of the electrodes 1252', 1272'. The coating 1264 partially wraps around the bulging, or protruding portions, that form the electrodes 1252', 1272', only leaving exposed the conductive tissue contacting surfaces of the electrodes 1252', 1272'. Accordingly, in the example illustrated in FIG. 100, each of the tissue-contacting surfaces 1257, 1277 includes a step comprising a conductive tissue-contacting surface positioned between two insulative tissue-contacting surfaces that gradually descend the step. Said another way, each of the tissue-contacting surfaces 1257, 1277 includes a first partially conductive tissue-contacting surface and a second insulative tissue-contacting surface stepped down with respect to the first partially conductive tissue-contacting surface. Methods for forming the electrodes 1252', 1272' are later described in connection with FIG. 103.

Furthermore, in a closed configuration without tissue therebetween, the offset electrodes 1252', 1272' overlap defining a gap between opposing insulative outer surfaces of the jaws 1250', 1270'. Accordingly, this configuration provides electrode surfaces that are both vertically offset from each other and laterally offset from each other when jaws 1250', 1270' are closed. In one example, the gap is about 0.01 inch to about 0.025 inch. In addition, while overlapping, the electrodes 1252', 1272' are spaced apart by a lateral gap. To prevent circuit shorting, the lateral gap is less than or equal to a predetermined threshold. In one example, the predetermined threshold is selected from a range of 0.006 inch to 0.008 inch. In one example, the predetermined threshold is about 0.006 inch.

Referring again to FIGS. 98, 101, the tip electrode 1260 is defined by uncoated electrode portions 1261, 1262 that are directly preceded by proximal coated portions that are circumferentially coated to allow for tip coagulation and otomy creation from either or both jaws 1250, 1270. In certain examples, the electrode portions 1261, 1262 are covered by spring-biased, or compliant, insulative housings that allow the electrode portions 1261, 1262 to be exposed only when the distal end of the end effector 1200 is pressed against the tissue to be treated.

Additionally, the segments 1274a, 1274b, 1274c define an angular profile extending along the peripheral side 1275 of the jaw 1270. The segments 1274a, 1274b, 1274c are defined by uncoated linear portions protruding from an angular body of the skeleton 1273 on the peripheral side 1275. The segments 1274a, 1274b, 1274c comprise outer surfaces that are flush with an outer surface of the coating 1264 defined on the peripheral side 1275. In various examples, a horizontal plane extends through the segments 1274a, 1274b, 1274c. The angular profile of the electrode 1274 is defined in the horizontal plane such that the electrode 1274 does not extend more than 45 degrees off a curvature centerline to prevent unintended lateral thermal damage while using the electrode 1274 to dissect or separate tissue.

FIG. 105 illustrates a jaw 6270 for use with an end effector (e.g. 1200) of an electrosurgical instrument (e.g. electrosurgical instrument 1106) to treat tissue using RF energy. Further, the jaw 6270 is electrically couplable to a generator (e.g. generator 1100), and is energizable by the generator to deliver a monopolar RF energy to the tissue and/or cooperate with another jaw of the end effector to deliver a bipolar RF energy to the tissue. In addition, the jaw 6270 is similar in many respects to the jaws 1250, 1270. For example, the jaw 6270 comprises an angular profile that is similar to the angular profile of the jaw 1270. In addition, the jaw 6270 presents a thermal mitigation improvement that can be applied to one or both of the jaws 1250, 1270.

In use, jaws of an end effector of an electrosurgical instrument are subjected to a thermal load that can interfere with the performance of their electrode(s). To minimize the thermal load interference without negatively affecting the electrode(s) tissue treatment capabilities, the jaw 6270 includes an electrically conductive skeleton 6273 that has a thermally insulative portion and a thermally conductive portion integral with the thermally insulative portion. The thermally conductive portion defines a heat sink and the thermally insulative portion resists heat transfer. In certain examples, the thermally insulative portion includes inner gaps, voids, or pockets that effectively isolate the thermal mass of the outer surfaces of the jaw 6270 that are directly in contact with the tissue without compromising the electrical conductivity of the jaw 6270.

In the illustrated example, the thermally conductive portion defines a conductive outer layer 6269 that surrounds, or at least partially surrounds, an inner conductive core. In at least one example, the inner conductive core comprises gap-setting members, which can be in the form of pillars, columns, and/or walls extending between opposite sides of the outer layer 6269 with gaps, voids, or pockets extending between the gap setting members.

In at least one example, the gap-setting members form honeycomb-like lattice structures 6267 to provide directional force capabilities as the jaws (i.e. the jaw 6270 and another jaw of the end effector) are transitioned into a closed configuration to grasp tissue therebetween (similar to the jaws 1250, 1270 of FIG. 97). The directional force can be accomplished by aligning the lattices 6267 in a direction that intersects the tissue-contacting surface of the jaw 6270 such that their honeycomb walls 6268 are positioned perpendicularly with respect to the tissue-contacting surface.

Alternatively, or additionally, the conductive inner core of jaw 6270 may include micro pockets of air, which could be more homogeneously distributed and shaped with no predefined organization relative to exterior shape of the jaw to create a more homogeneous stress-strain distribution within the jaw. In various aspects, the electrically conductive skeleton 6273 can be prepared by three-dimensional printing, and may include three dimensionally printed interior pockets that produce electrically conductive but proportionally thermally insulated cores.

Referring still to FIG. 105, the electrically conductive skeleton 6273 is connectable to an energy source (e.g. generator 1100), and comprises electrodes 6262, 6272, and 6274 that are defined on portions of the outer layer 6273 that are selectively not covered by the coating 1264. Accordingly, the jaw 6270 selective thermal and electrical conductivity that controls/focuses energy interaction with tissue through the electrodes 6272, 6274, while reducing thermal spread and thermal mass. The thermally insulated portions of the conductive skeleton 6273 limit the thermal load on the electrodes 6262, 6272, and 6274 during use.

Furthermore, the outer layer 6273 defines gripping features 6277 that extend on opposite sides of the electrode 6272, and are at least partially covered by the coating 1264. The gripping features 6277 improve the ability of the jaw 6270 to adhere to tissue, and resist tissue slippage with respect to the jaw 6270.

In the illustrated examples, the walls 6268 extend diagonally from a first lateral side of the jaw 6270 to a second lateral side of the jaw 6270. The walls 6268 intersect at structural nodes. In the illustrated example, intersecting walls 6268 define pockets 6271 that are covered from the top and/or bottom by the outer layer 6269. Various methods for manufacturing the jaw 6270 are described below.

Figure 104:
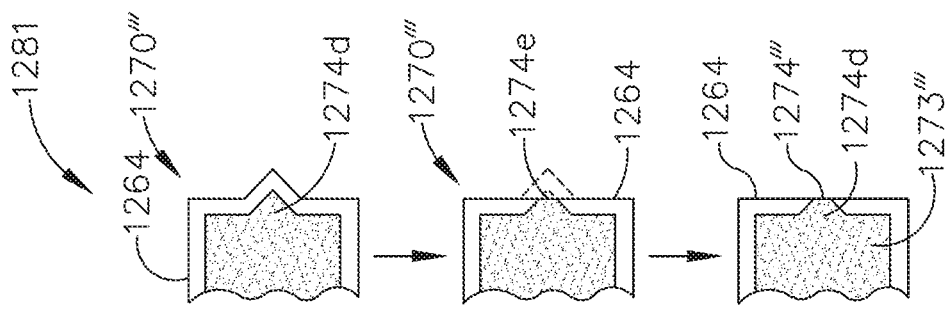
FIG. 104 illustrates a method of manufacturing a jaw of an end effector, in accordance with at least one aspect of the present disclosure.
Figure 103:
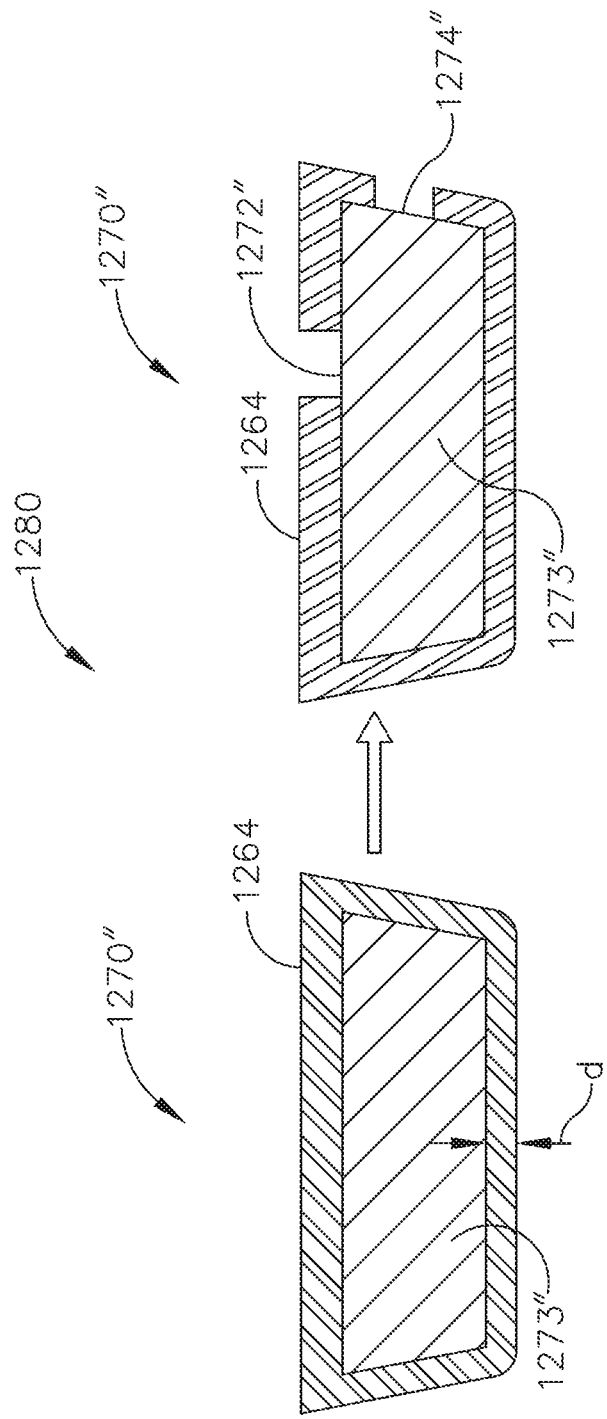
FIG. 103 illustrates a method of manufacturing a jaw of an end effector, in accordance with at least one aspect of the present disclosure.

FIGS. 103, 104 illustrate methods 1280, 1281 for manufacturing jaws 1273'', 1273'''. In various examples, one more of the jaws 1250, 1270, 1250', 1270' are manufactured in accordance with the methods 1280, 1281. The jaws 1273'', 1273''' are prepared by applying a coating 1264 (e.g. with a thickness d) to their entire external surfaces. Then, electrodes are defined by selectively removing portions of the coating 1264 from desired zones to expose the external surface of the skeletons 1273'', 1273''' at such zones. In at least one example, selective removal of the coating can be performed by etching (FIG. 103) or by partially cutting away (FIG. 104) tapered portions of the skeleton 1273''' along with their respective coating portions to form flush conductive and non-conductive surfaces. In the example illustrated FIG. 103, electrodes 1272'', 1274'' are formed by etching. In the example illustrated FIG. 104, an electrode 1274''' is formed from a raised narrow band or ridge 1274d extending alongside the skeleton 1273'''. A portion of the ridge 1274D and the coating 1264, directly covering the ridge 1274D, are cut away yielding an external surface of the electrode 1274''' that is flush with an external surface of the coating 1264.

Accordingly, a jaw 1270''' manufactured by the method 1281 includes a tapered electrode 1274''' that is comprised of narrow raised electrically conductive portion 1274e extending alongside the skeleton 1273''', which can help focus the energy delivered from the skeleton 1273''' to the tissue, wherein the portion 1274e has a conductive external surface that is flush with the coating 1264.

Figure 106:
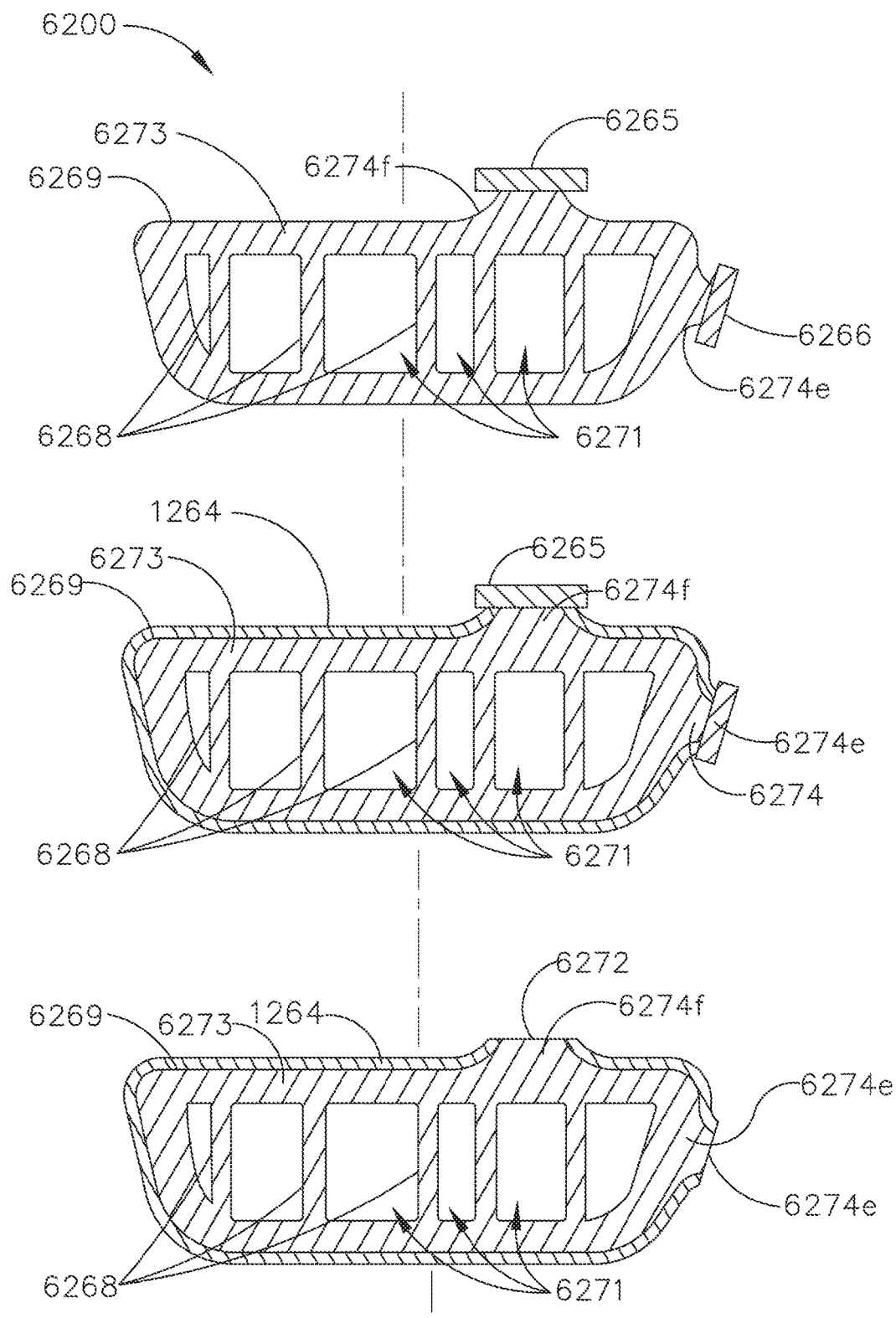
FIG. 106 illustrates steps of a process of manufacturing the jaw of FIG. 105.

In another manufacturing process 6200, the jaw 6270 can be prepared as depicted in FIG. 106. The electrically conductive skeleton 6273 is formed with narrow raised bands or ridges 6274e, 6274f that define the electrodes 6272, and 6274. In the illustrated example, the skeleton 6273 of the jaw 6270 includes ridges 6274e, 6274f, with flat, or at least substantially flat, outer surfaces that are configured to define the electrodes 6272, 6274. In at least one example, the skeleton 6273 is prepared by 3D printing. Masks 6265, 6266 are applied to the ridges 6274e, 6274f, and a coating 1264, which is similar to the coating 1264, is applied to the skeleton 6273. After coating, the masks 6265, 6266 are removed exposing outer surfaces of the electrodes 6272, 6274 that are flush with the outer surface of the coating 1264.

Referring to FIGS. 105 and 106, in various examples, the outer layer 6269 comprises gripping features 6277 extending laterally on one or both sides of each of the electrode 6272. The gripping features 6277 are covered by the coating 1264. In one example, the coating 1264 defines compressible features causing the gap between the jaws of an end effector to vary depending on clamping loads applied to the end effector 1200. In at least one example, the coating 1264 on the jaws yields at least a 0.010"-0.020" overlap of insulation along the centerline of the jaws. The coating 1264 could be applied directly over the gripping features 6277 and/or clamp induced jaw re-alignment features.

In various aspects, the coating 1264 may comprise coating materials such as Titanium Nitride, Diamond-Like coating (DLC), Chromium Nitride, Graphit iC™, etc. In at least one example, the DLC is comprised of an amorphous carbon-hydrogen network with graphite and diamond bondings between the carbon atoms. The DLC coating 1264 can form films with low friction and high hardness characteristics around the skeletons 1253, 1273 (FIG. 97). The DLC coating 1264 can be doped or undoped, and is generally in the form of amorphous carbon (a-C) or hydrogenated amorphous carbon (a-C:H) containing a large fraction of sp3 bonds. Various surface coating technologies can be utilized to form the DLC coating 1264 such as the surface coating technologies developed by Oerlikon Balzers. In at least one example, the DLC coating 1264 is generated using Plasma-assisted Chemical Vapor Deposition (PACVD).

Referring still to FIG. 106, in use, electrical energy flows from the electrically conductive skeleton 6269 to tissue through the electrode 6272. The coating 1264 prevents transfer of the electrical energy to the tissue from other regions of the outer layer 6269 that are covered with the coating 1264. As the surface of the electrode 6272 increases in temperature during a tissue treatment, the thermal energy transfer from the outer layer 6269 to the inner core of the skeleton 6273 is slowed down, or dampened, due to the gaps, voids, or pockets defined by the walls 6268 of the inner core.

Figure 107:
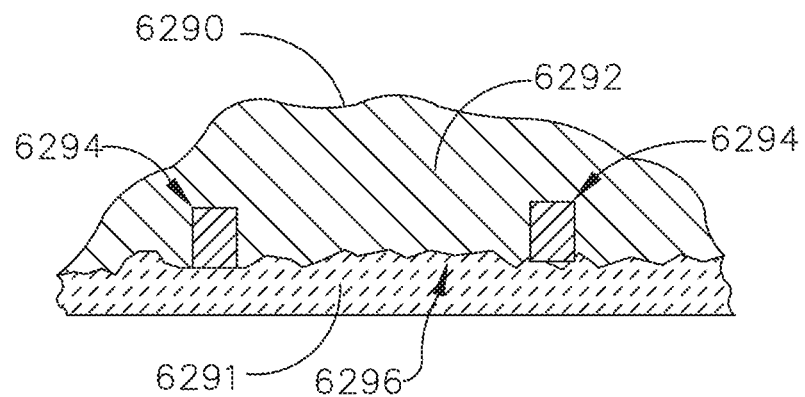
FIG. 107 illustrates steps of a process of manufacturing the jaw of FIG. 105.

FIG. 107 illustrates a skeleton 6290 manufactured for use with a jaw of an end effector of an electrosurgical instrument. One more of the skeletons 1253, 1273, 1253', 1273', 1273", 1273''' can comprise a material composition and/or can be manufactured in a similar manner to the skeleton 6290. In the illustrated example, the skeleton 6290 is comprised of at least two materials: an electrically conductive material such as, for example, Titanium, and a thermally insulative material such as, for example, a ceramic material (e.g. Ceramic Oxide). The Titanium and Ceramic Oxide combination yields jaw components with composite thermal, mechanical, and electrical properties.

In the illustrated example, the composite skeleton 6290 comprises a ceramic base 6291 formed by three-dimensional printing, for example. Additionally, the composite skeleton 6290 includes a titanium crown 6292 prepared separately from the ceramic base 6291 using, for example, three-dimensional printing. The base 6291 and the crown 6292 include complementing attachment features 6294. In the illustrated example, the base 6291 includes posts or projections that are received in corresponding apertures of the crown 6292. The attachment features 6294 also control shrinking. Additionally, or alternatively, contacting surfaces of the base 6291 and the crown 6292 include complementing surface irregularities 6296 specifically design for a mating engagement with one another. The surface irregularities 6296 also resist shrinking caused by the different material compositions of the base 6291 and the crown 6292. In various examples, the composite skeleton 6290 is selectively coated with an insulative coating 1264 leaving exposed certain portions of the crown 6292, which define electrodes, as described above in connection with the jaws 1250, 1270, for example.

Figure 19:
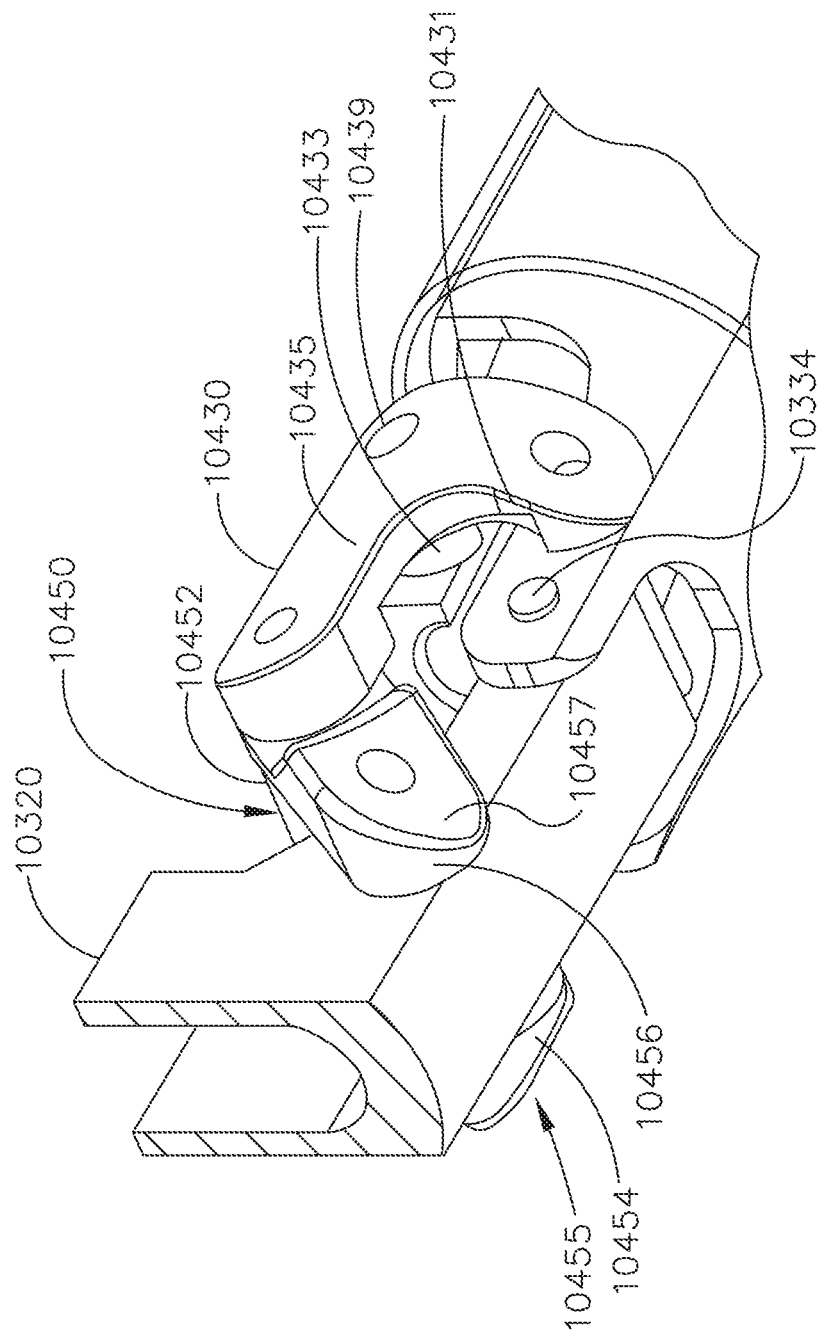
FIG. 19 is another perspective view of the articulation joint of FIG. 17 in an unarticulated position.
Figure 20:
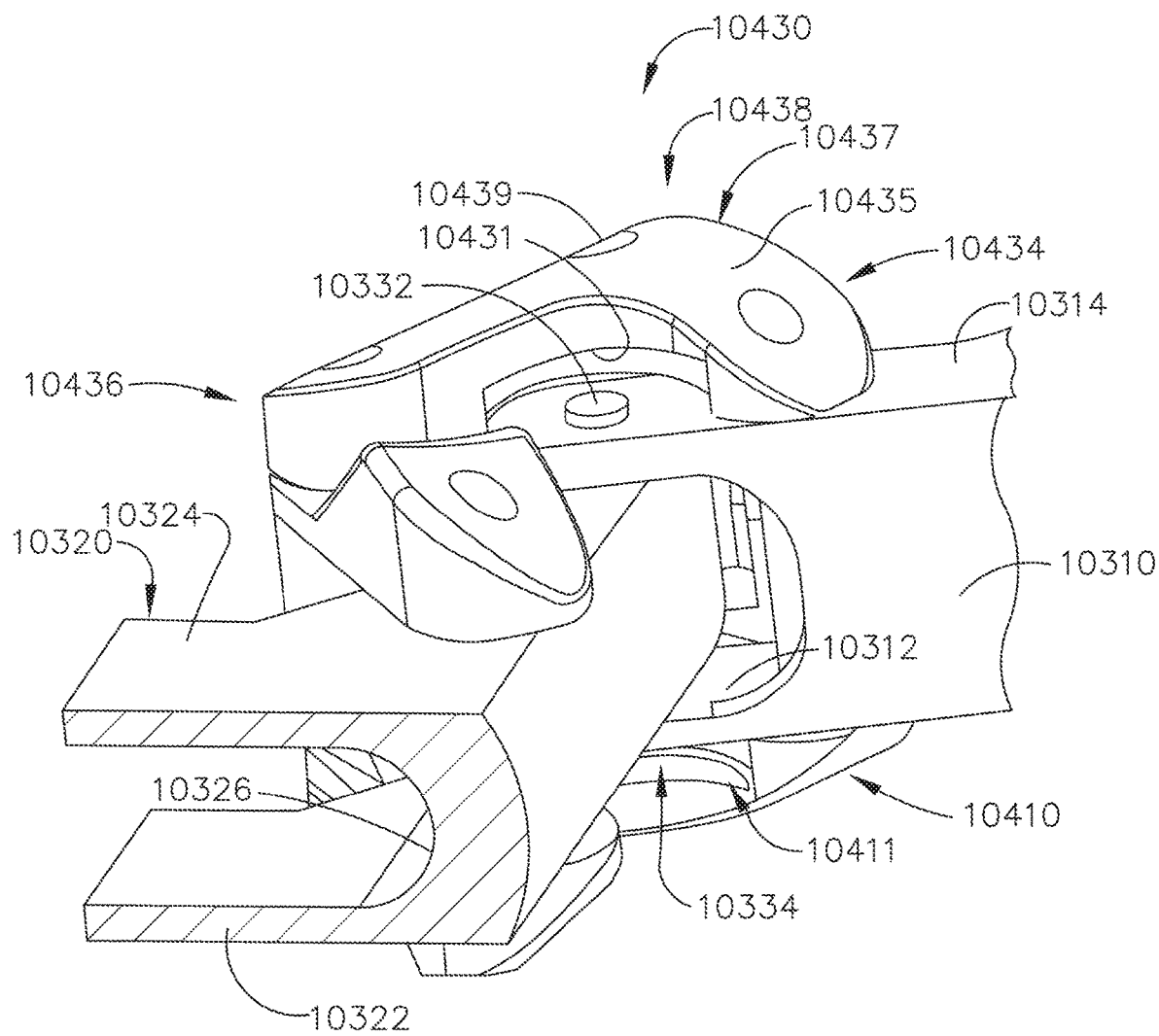
FIG. 20 is a bottom perspective view of the articulation joint of FIG. 4 articulated in a second direction.
Figure 21:
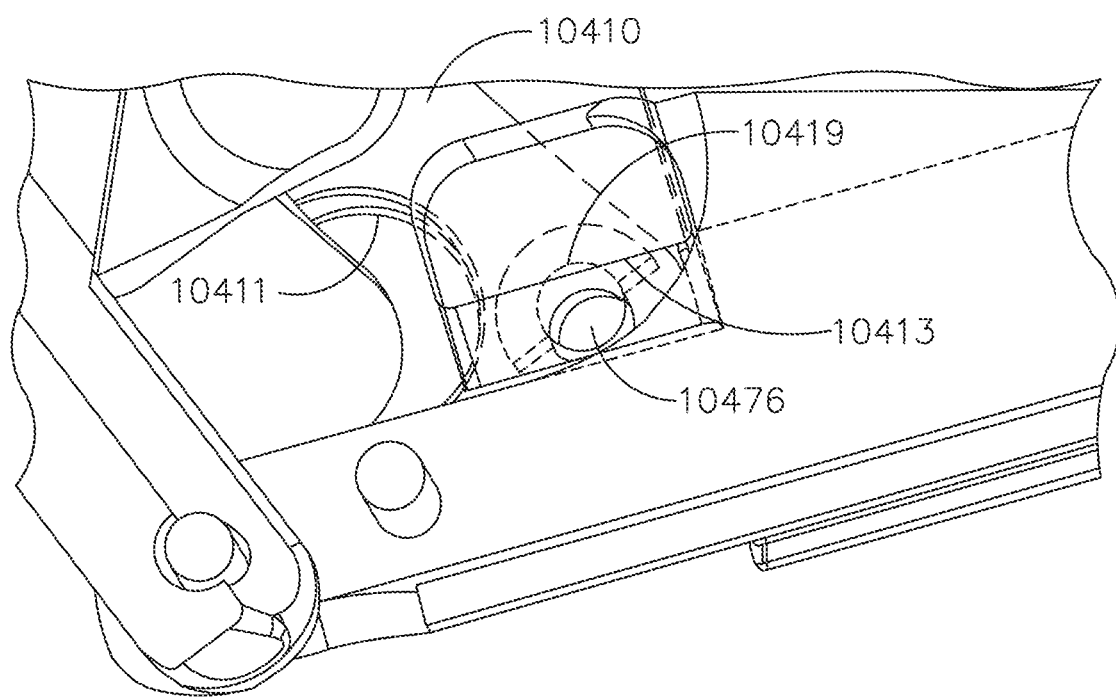
FIG. 21 is a partial cross-sectional view of the articulation joint of FIG. 4 articulated in a first direction.
Figure 108:
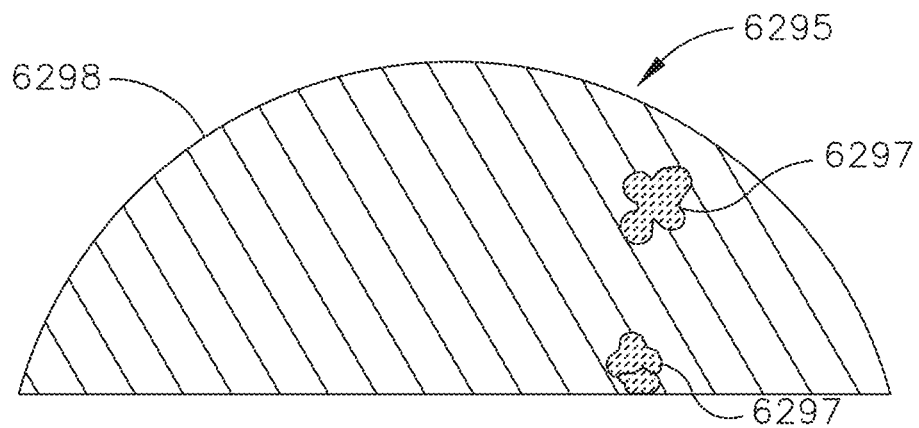
FIGS. 108-110 illustrates steps of a process of manufacturing the jaw of FIG. 105.
Figure 109:
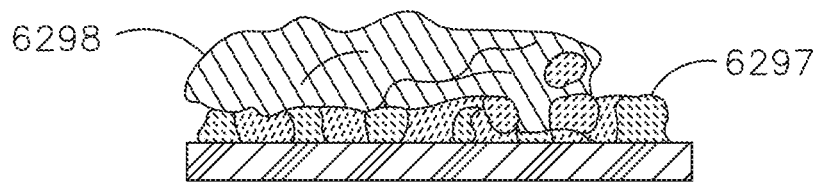
Figure 110:
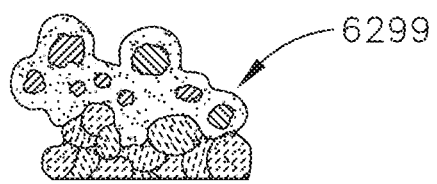

FIGS. 108 and 109 illustrate a manufacturing process for making a skeleton 6296 for use with a jaw of an end effector of an electrosurgical instrument. One more of the skeletons 1253, 1273, 1253', 1273', 1273", 1273''' can comprise a material composition and/or can be manufactured in a similar manner to the skeleton 6295. In the illustrated example, the composite skeleton 6295 is produced by injection molding utilizing a ceramic powder 6297 and a titanium powder 6298. The powders are fused together (FIG. 109) to form the titanium-ceramic composite 6299 (FIG. 19). In at least one example, a PolyTetraFluoroEthylene (e.g. Teflon®) coating can be selectively applied to the metallic regions of the composite skeleton 6295 for thermal insulation as well as electrical insulation.

FIGS. 111-113 illustrate a jaw 1290 for use with an end effector (e.g. 1200) of an electrosurgical instrument (e.g. electrosurgical instrument 1106) to treat tissue using RF energy. Further, the jaw 6270 is electrically couplable to a generator (e.g. generator 1100), and is energizable by the generator to deliver a monopolar RF energy to the tissue and/or cooperate with another jaw of the end effector to deliver a bipolar RF energy to the tissue. In addition, the jaw 1290 is similar in many respects to the jaws 1250, 1270. For example, the jaw 1290 comprises an angular profile that is similar to the angular or curved profile of the jaw 1270.

In addition, the jaw 1290 is similar to the jaw 6270 in that the jaw 1290 also presents a thermal mitigation improvement. Like the jaw 6270, the jaw 1290 includes a conductive skeleton 1293 that has a thermally insulative portion and a thermally conductive portion integral with, or attached to, the thermally insulative portion. The thermally conductive portion defines a heat sink and the thermally insulative portion resists heat transfer. In certain examples, the thermally insulative portion of the conductive skeleton 1293 comprises a conductive inner core 1297 with inner gaps, voids, or pockets that effectively isolate the thermal mass of the outer surface of the jaw 1290, which defines an electrode 1294 that is directly in contact with the tissue, without compromising the electrical conductivity of the jaw 1290. The thermally conductive portions define a conductive outer layer 1303 that surrounds, or at least partially surrounds, the conductive inner core 1297. In at least one example, the conductive inner core 1297 comprises gap-setting members 1299, which can be in the form of pillars, columns, and/or walls extending between opposite sides of the outer layer 1303 of the jaw 1290 with gaps, voids, or pockets extending between the gap setting members.

Alternatively, or additionally, the conductive inner core 1297 may include micro pockets of air, which could be homogeneously, or non-homogenously, distributed in the conductive inner core 1297. The pockets can comprise predefined, or random shapes, and can be dispersed at predetermined, or random, portions of the conductive inner core 1297. In at least one example, the pockets are dispersed in a manner that creates a more homogeneous stress-strain distribution within the jaw 1290. In various aspects, the skeleton 1293 can be prepared by three-dimensional printing, and may include three dimensionally printed interior pockets that produce electrically conductive but proportionally thermally insulated cores.

Accordingly, the jaw 1290 comprises selective thermal and electrical conductivity that controls/focuses the energy interaction with tissue, while reducing thermal spread and thermal mass. The thermally insulated portions of the conductive skeleton 1293 limit the thermal load on the electrodes of the jaw 1290 during use.

FIG. 113 illustrates an expanded portion of a tissue-contacting surface 1291 of the jaw 1290. In various aspects, the outer layer 1303 of the skeleton 1293 is selectively coated/covered with a first insulative layer 1264 comprising a first material such as, for example, DLC. In the illustrated example, the DLC coating causes the tissue-contacting surface 1291 to be electrically insulated except an intermediate area extending along a length of the tissue-contacting surface 1291, which defines the electrode 1294. In at least one example, the DLC coating extends around the skeleton 1293 covering the jaw 1290 up to perimeters defined on opposite sides 1294', 1294" of the electrode 1294. Conductive zones 1294a, 1294b, 1294c remain exposed, and alternate with insulative zones 1298 along a length of the electrode 1294. In various aspects, the insulative zones 1298 comprise a high temperature PolyTetraFluoroEthylene (e.g. Teflon®). Since the DLC coating is thermally conductive, only the portions of the tissue-contacting surface 1291 that comprise the insulative regions 1298 are thermally insulated. The portions of the issue-contacting surface 1291 that are covered with the DLC coating and the thin conductive energizable zones 1294a, 1294b, 1294c are thermally conductive. Further, only the thin conductive energizable zones 1294a, 1294b, 1294c are electrically conductive. The remaining portions of the tissue-contacting surface 1291, which are covered with either the DLC coating or the PolyTetraFluoroEthylene (e.g. Teflon®), are electrically insulated.

The conductive zones 1294a, 1294b, 1294c define energy concentration locations along the jaw 1290 based on the geometry of the zones 1294a, 1294b, 1294c. Further, the size, shape, and arrangement of the conductive zones 1294a, 1294b, 1294c and insulative zones 1298 causes coagulation energy transmitted through the electrode 1294 to be directed into the tissue in predefined treatment regions thereby preventing parasitic leaching of both the energy and heat from the treatment regions. Furthermore, the thermally insulative conductive inner core 1297 resists heat transfer to portions of the jaw 1290 that do not form treatment regions, which prevents inadvertent collateral thermal damage by incidental contact of tissue with non-treatment areas of the jaw 1290.

The electrode 1294 is selectively interrupted by the regions 1298. Selective application of the high temperature PolyTetraFluoroEthylene (e.g. Teflon®) coating to portions of the electrode 1294 yields selectively exposed metallic internal portions that define a three-dimensional geometric electron modulation (GEM) for a focused dissection and coagulation at the conductive zones 1294a, 1294b, 1294c of the electrode 1294. The regions 1298 are selectively deposited onto the electrode 1294, as illustrated in FIG. 113, yielding a treatment surface with alternating thermally and electrically conductive regions and thermally and electrically insulative regions surrounded by a thermally conductive but electrically insulative outer perimeter region defined by the DLC coating.

Referring to FIG. 113, the jaw 1290 comprises an angular profile where a plurality of angles are defined between discrete portions 1290a, 1290b, 1290c, 1290d of the jaw 1290. For example, a first angle ($\alpha 1$) is defined by portions 1290a, 1290b, a second angle ($\alpha 2$) is defined by portions 1290b, 1290c, and a third angle ($\alpha 3$) is defined by portions 1290c, 1290d of the first jaw 1250. In other examples, at least a portion of a jaw 1290 comprises a smooth curved profile with no angles. In various aspects, the discrete portions 1290a, 1290b, 1290c, 1290d of the jaw 1290 are linear segments. Consecutive linear segments intersect at angles such as, for example, the first angle ($\alpha 1$), or the second angle ($\alpha 2$), and the third angle ($\alpha 3$). The linear segments cooperate to form a generally curved profile of each of the jaw 1290.

In one example, the angles ($\alpha 1$, $\alpha 2$, $\alpha 3$) comprise the same, or at least substantially the same, values. In another example, at least two of the angles ($\alpha 1$, $\alpha 2$, $\alpha 3$) comprise different values. In another example, at least one of the angles ($\alpha 1$, $\alpha 2$, $\alpha 3$) comprises a value selected from a range of about 120° to about 175°. In yet another example, at least one of the angles ($\alpha 1$, $\alpha 2$, $\alpha 3$) comprises a value selected from a range of about 130° to about 170°.

Furthermore, due to the gradually narrowing profile of the jaw 1290, the portion 1290a, which is a proximal portion, is larger than the portion 1290b, which is an intermediate portion. Similarly, the intermediate portion 1290b is larger than the portion 1290d that defines a distal portion of the jaw 1290. In other examples, the distal portion can be larger than the intermediate and/or proximal portions. In other examples, the intermediate portion is larger than the proximal and/or distal portions. In addition, the electrode 1294 of the jaw 1290 comprises an angular profile that is similar to the angular profile of the jaw 1290.

Referring to FIG. 114, in certain aspects, a jaw 1300 includes a solid conductive skeleton 1301 that is partially surrounded by a DLC coating 1264. The exposed regions of the skeleton 1301 define one or more electrodes 1302. This arrangement yields a thermally conductive and electrically conductive portion of the jaw 1300, wherein the thermal energy is delivered indiscriminately, but the electrical energy is exclusively delivered through the one or more electrodes 1302.

Figure 117:
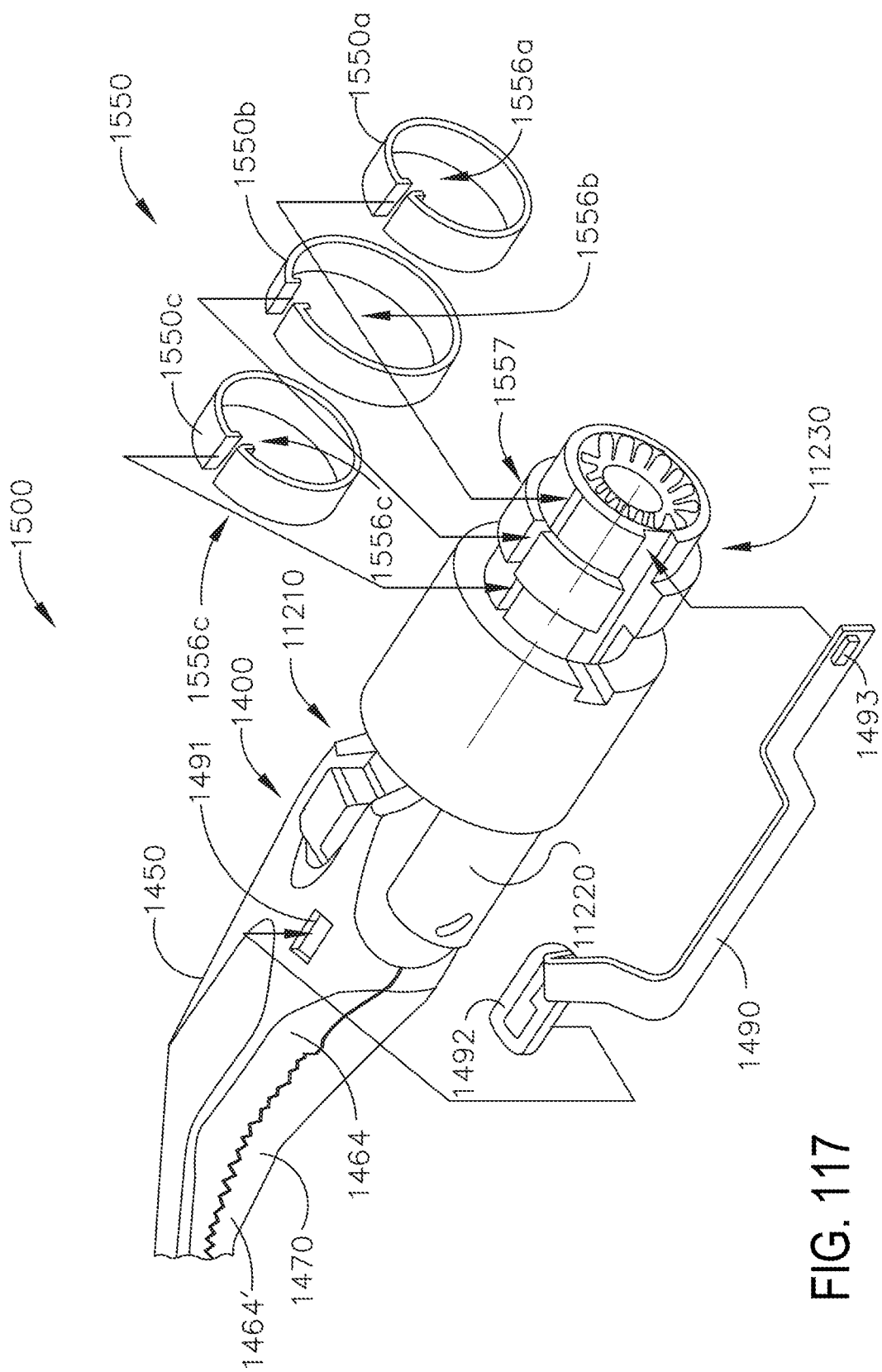
FIG. 117 illustrates a partial exploded view of an end effector of an electrosurgical instrument, in accordance with at least one aspect of the present disclosure.

Referring now to FIGS. 115-117, an electrosurgical instrument 1500 includes an end effector 1400 configured to deliver monopolar energy and/or bipolar energy to tissue grasped by the end effector 1400, as described in greater detail below. The end effector 1400 is similar in many respects to the end effector 1200. For example, the end effector 1400 includes a first jaw 1450 and a second jaw 1470. At least one of the first jaw 1450 and the second jaw 1470 is movable relative to the other jaw to transition the end effector 1400 from an open configuration to a closed configuration to grasp the tissue therebetween. The grasped tissue can then be sealed and/or cut using monopolar and bipolar energies. As described below in greater details, the end effector 1400 utilizes GEM to adjust energy densities at a tissue treatment interface of the jaws 1450, 1470 to effect a desired tissue treatment.

Like the jaws 1250, 1270, the jaws 1450, 1470 include generally angular profiles formed from linear portions that are angled with respect to one another, yielding a bent or finger-like shape, as illustrated in FIG. 117. Furthermore, the jaws 1450, 1470 include conductive skeletons 1452, 1472 that have narrowing angular bodies extending distally along the angular profile of the jaws 1450, 1470. The conductive skeletons 1452, 1472 can be comprised of a conductive material such as, for example, Titanium. In certain aspects, each of the conductive skeletons 1453, 1473 comprise a thermally insulative portion and a thermally conductive portion integral with the thermally insulative portion. The thermally conductive portion defines a heat sink and the thermally insulative portion resists heat transfer. In certain examples, the thermally insulative portions of the skeletons 1453, 1473 define inner cores comprising inner gaps, voids, or pockets that effectively isolate the thermal mass of the outer surfaces of the jaws 1452, 1472 that are directly in contact with the tissue without compromising the electrical conductivity of the jaws 1450, 1470.

The thermally conductive portions comprise conductive outer layers 1469, 1469' that surround, or at least partially surround, the inner conductive cores. In at least one example, the inner conductive cores comprise gap-setting members, which can be in the form of pillars, columns, and/or walls extending between opposite sides of the outer layers 1469, 1469' of each of the jaws 1250, 1270 with gaps, voids, or pockets extending between the gap setting members. In at least one example, the gap-setting members form honeycomb-like lattice structures 1467, 1467'.

Further to the above, the conductive skeletons 1453, 1473 include first conductive portions 1453a, 1473a extending distally along the angular profile of the jaws 1450, 1470 and second conductive portions 1453b, 1473b defining a tapered electrodes protruding from the first conductive portions 1453a, 1473a and extending distally along at least a portion of the gradually narrowing body of the skeletons 1453, 1473. In at least on example, the first conductive portions 1453a, 1473a are thicker than the second conductive portions 1453b, 1473b in a transverse cross-section (e.g. FIG. 116) of the gradually narrowing bodies of the skeletons 1453, 1473. In at least one example, the second conductive portions 1453b, 1473b are integral with, or permanently attached to, the first conductive portions 1453a, 1473a such that electrical energy flows from the first conductive portions 1453a, 1473a to the tissue only through the second conductive portions 1453b, 1473b. Electrically insulative layers 1464, 1464' are configured to completely electrically insulate the first conductive portions 1453a, 1473a but not the second conductive portions 1453b, 1473b. At least outer surfaces of the second conductive portions 1453b, 1473b, which define electrodes 1452, 1472, are not covered by the electrically insulative layers 1464, 1464'. In the illustrated example, the electrodes 1452, 1472 and the electrically insulative layers 1464, 1464' define flush tissue treatment surfaces.

As described above, the first conductive portions 1453a, 1473a are generally thicker than the second conductive portions 1453b, 1473b, and are wrapped with the electrically insulative layers 1464, 1464', which causes the second conductive portions 1453b, 1473b to become high energy density areas. In at least one example, the electrically insulative layers 1464, 1464' are comprised of high temperature PolyTetraFluoroEthylene (e.g. Teflon®) coatings, DLC coatings, and/or ceramic coatings for insulation and resistance to char sticking. In various examples, the thicker first conductive portion 1453a conducts more potential power with a smaller resistance to the tissue-contacting second conductive portion 1453b yielding the higher energy density at the electrode 1452.

In various aspects, the outer surfaces of the electrodes 1452, 1472 include consecutive linear segments that extend along angled tissue treatment surfaces of the jaws 1450, 1470. The linear segments intersect at predefined angles, and comprise widths that gradually narrow as the linear segments extend distally. In the example illustrated in FIG. 115, the electrode 1452 includes segments 1452a, 1452b, 1452c, 1452c, 1452d, and the electrode 1472 includes segments 1472a, 1472b, 1472c, 1472c, 1472d. The electrode 1452 of the jaw 1450 is illustrated by dashed lines on the jaw 1470 of FIG. 115 to show the lateral position of the electrode 1452 with respect to the electrode 1452 in a closed configuration of the end effector 1400. The electrodes 1452, 1472 are laterally offset from one another in the closed configuration. In a bipolar energy mode, the electrical energy supplied by the generator (e.g. generator 1100) flows from the first conductive portion 1453a to the electrode 1452 of the second conductive portion 1453b, and from the electrode 1452 to the tissue grasped between the jaws 1450, 1470. The bipolar energy then flows from the tissue to the electrode 1472 of the second conductive portion 1473b, and from the electrode 1472 to the first conductive portion 1473a.

In various aspects, as illustrated in FIGS. 115, 116, the second jaw 1470 further includes an electrode 1474 spaced apart from the skeleton 1473. In at least one example, the electrode 1474 is a monopolar electrode configured to deliver monopolar energy to the tissue grasped between the jaws 1450, 1470 in the closed configuration. A return pad can be placed under the patient, for example, to receive the monopolar energy from the patient. Like the electrode 1472, the electrode 1474 includes consecutive linear segments 1474a, 1474b, 1474c, 1474d that extend distally along the angular profile defined by the second jaw 1470 from an electrode proximal end to an electrode distal end. Further, the electrode 1474 is laterally offset from the electrodes 1472, 1452.

The electrode 1474 includes a base 1474e positioned in a cradle 1480 extending distally along the angular profile of the second jaw 1470 from a cradle proximal 1480a and to a cradle distal end 1480b. The cradle 1480 is centrally situated with respect to lateral edges 1470e, 1470f of the second jaw 1470. The electrode 1474 further comprises a tapered edge 1474f extending from the base 1474e beyond sidewalls of the cradle 1480. In addition, the cradle 1480 is partially embedded in a valley defined in an outer tissue-treatment surface of the narrowing curved body. The cradle 1480 is spaced apart from the gradually narrowing body of the skeleton 1473 by the electrically insulative coating 1464'. As illustrated in FIG. 115, the base 1480 comprises widths that gradually narrow as the base extends along the angular profile from a base proximal end 1480a to a base distal end 1480b.

In various examples, the cradle 1480 is comprised of a compliant substrate. In an uncompressed state, as illustrated in FIG. 116, the sidewalls of the cradle 1480 extend beyond a tissue treatment surface of the jaw 1472. When tissue is compressed between the jaws 1450, 1470, the compressed tissue applies a biasing force against the sidewalls of the cradle 1480 further exposing the tapered edge 1474f of the electrode 1474.

One or more of the jaws described by the present disclosure include stop members or gap-setting members, which are features extending outwardly from one or both of the tissue treatment surfaces of the jaws of an end effector. The stop members help maintain a separation or a predetermined gap between the jaws in a closed configuration with no tissue between the jaws. In at least one example, the sidewalls of the cradle 1480 define such stop members. In another example, the stop members can be in the form of insulative pillars or laterally extending spring-biased features that allow the gap between opposing jaws and the closed configuration to vary based on clamping loads.

Most electrosurgery generators use constant power modes. With constant power modes, the power output remains constant as impedance increases. In constant power modes, the voltage increases as the impedance increases. Increased voltage causes thermal damage to tissue. GEM focuses the energy output of the jaws 1250, 1270, for example, by controlling the size and shape of the electrodes 1252, 1272, 1274, 1260, 1294, 1472, 1452, 1474, as described above, and modulating the power level based on tissue impedance to create a low voltage plasma.

In certain instances, GEM maintains a constant minimum voltage required for cutting at the surgical site. The generator (e.g. 1100) modulates the power in order to maintain the voltage as close as possible to the minimum voltage required for cutting at the surgical site. In order to obtain an arc plasma and cut, current is pushed by voltage from gradually narrowing portions of the electrodes 1252, 1272, 1274, 1260, 1294, 1472, 1452, 1474, to the tissue. In certain examples, a minimum voltage of approximately 200 Volts is maintained. Cutting with greater than 200 Volts increases thermal damage and cutting with less than 200 Volts results in minimal arcing and drag in the tissue. Accordingly, the generator (e.g. 1100) modulates the power to ensure utilizing the minimum voltage possible that will still form an arc plasma and cut.

Referring primarily to FIG. 117, a surgical instrument 1500 includes the end effector 1400. The surgical instrument 1500 is similar in many respects to other surgical instruments described in U.S. Pat No. 11,696,776. Various actuation and articulation mechanisms described elsewhere in connection with such surgical instruments could be similarly utilized to articulate and/or actuate the surgical instrument 1500. For brevity, such mechanisms are not repeated herein.

The end effector 1400 comprises an end effector frame assembly 11210 that comprises a distal frame member 11220 that is rotatably supported in a proximal frame housing 11230. In the illustrated example, the distal frame member 11220 is rotatably attached to the proximal frame housing 11230 by an annular rib on the distal frame member 11220 that is received within an annular groove in the proximal frame housing 11230.

Electrical energy is transmitted to the electrodes 1452, 1472, 1474 of the end effector 1400 by one or more flex circuits extending distally through, or alongside, the distal frame member 11220. In the illustrated example, a flex circuit 1490 is fixedly attached to the first jaw 1450. More particularly, the flex circuit 1490 includes a distal portion 1492 that can be fixedly attached to an exposed portion 1491 of the first jaw 1450, which is not covered by the insulative layer 1464.

A slip ring assembly 1550 within the proximal frame housing 11230 allows free rotation of the end effector 1400 about a shaft of the surgical instrument 1500 without entanglement of the wires of the circuits transmitting electrical energy to the electrodes 1452, 1472, 1474. In the illustrated example, the flex circuit 1490 includes an electrical contact 1493 in movable engagement with a slip ring 1550a of the slip ring assembly 1550. Electrical energy is transmitted from the slip ring 1550a to the conductive skeleton 1453, and then to the electrode 1452, through the flex circuit 1490. Since the electrical contact 1493 is not fixedly attached to the slip ring 1550a, the rotation of the end effector 1400 about the shaft of the surgical instrument 1500 is permissible without losing the electrical connection between the electrical contact 1493 and the slip ring 1550a. Further, a similar electrical contact transmits the electrical energy to the slip ring 1550a.

In the example illustrated in FIG. 117, the slip ring 1550a is configured to transmit bipolar energy to the electrode 1452 of the jaw 1450. A slip ring 1550b cooperates with similar electrical contacts and the electrode 1472 to define a return path for the bipolar energy. In addition, a slip ring 1550c cooperates with similar electrical contacts and the electrode 1474 to provide a pathway for monopolar electrical energy into tissue. The bipolar and monopolar electrical energies can be delivered to the slip rings 1550a, 1550b through one or more electrical generators (e.g. generator 1100). The bipolar and monopolar electrical energies can be delivered simultaneously or separately, as described in greater detail elsewhere herein.

In various examples, the slip rings 1550a, 1550b, 1550c are integrated electrical slip rings with mechanical features 1556a, 1556b, 1556c configured to couple the slip rings 1550a, 1550b, 1550c to an insulative support structure 1557, or a conductive support structure coated with an insulative material, as illustrated in FIG. 117. Furthermore, the slip rings 1550a, 1550b, 1550c are sufficiently spaced apart to ensure that circuit shorting will not occur if a conductive fluid fills the space between the slip rings 1550a, 1550b, 1550c. In at least one example, a core flat stamped metallic shaft member includes a three dimensionally printed, or over-molded, nonconductive portion for supporting the slip ring assembly 1550.

Figure 118:
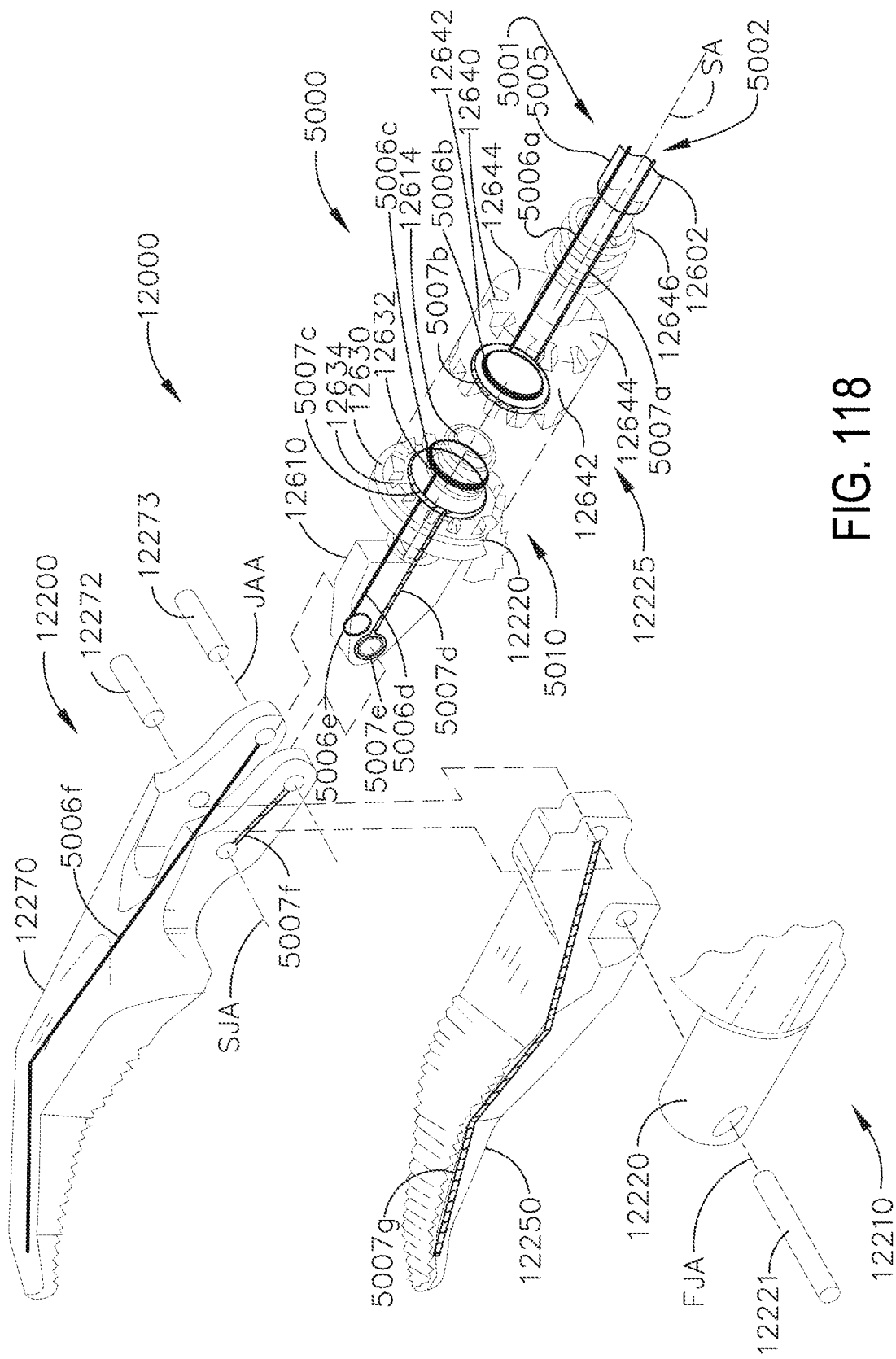
FIG. 118 illustrates an exploded perspective assembly view of a portion of an electrosurgical instrument including an electrical connection assembly, in accordance with at least one aspect of the present disclosure.

FIG. 118 illustrates a portion of an electrosurgical instrument 12000 that comprises a surgical end effector 12200 that may be coupled to a proximal shaft segment by an articulation joint in the various suitable manners. In certain instances, the surgical end effector 12200 comprises an end effector frame assembly 12210 that comprises a distal frame member 12220 that is rotatably supported in a proximal frame housing that is attached to the articulation joint.

The surgical end effector 12200 comprises a first jaw 12250 and a second jaw 12270. In the illustrated example, the first jaw 12250 is pivotally pinned to the distal frame member 12220 for selective pivotal travel relative thereto about a first jaw axis FJA defined by a first jaw pin 12221. The second jaw 12270 is pivotally pinned to the first jaw 12250 for selective pivotal travel relative to the first jaw 12250 about a second jaw axis SJA that is defined by a second jaw pin 12272. In the illustrated example, the surgical end effector 12200 employs an actuator yoke assembly 12610 that is pivotally coupled to the second jaw 12270 by a second jaw attachment pin 12273 for pivotal travel about a jaw actuation axis JAA that is proximal and parallel to the first jaw axis FJA and the second jaw axis SJA. The actuator yoke assembly 12610 comprises a proximal threaded drive shaft 12614 that is threadably received in a threaded bore 12632 in a distal lock plate 12630. The threaded drive shaft 12614 is mounted to the actuator yoke assembly 12610 for relative rotation therebetween. The distal lock plate 12630 is supported for rotational travel within the distal frame member 12220. Thus rotation of the distal lock plate 12630 will result in the axial travel of the actuator yoke assembly 12610.

In certain instances, the distal lock plate 12630 comprises a portion of an end effector locking system 12225. The end effector locking system 12225 further comprises a dual-acting rotary lock head 12640 that is attached to a rotary drive shaft 12602 of the various types disclosed herein. The lock head 12640 comprises a first plurality of radially arranged distal lock features 12642 that are adapted to lockingly engage a plurality of proximally-facing, radial grooves or recesses 12634 that are formed in the distal lock plate 12630. When the distal lock features 12642 are in locking engagement with the radial grooves 12634 in the distal lock plate 12630, rotation of the rotary lock head 12640 will cause the distal lock plate 12630 to rotate within the distal frame member 12220. Also in at least one example, the rotary lock head 12640 further comprises a second series of proximally-facing proximal lock features 12644 that are adapted to lockingly engage a corresponding series of lock grooves that are provided in the distal frame member 12220. A locking spring 12646 serves to bias the rotary lock head distally into locking engagement with the distal lock plate 12630. In various instances, the rotary lock head 12640 may be pulled proximally by an unlocking cable or other member in the manner described herein. In another arrangement, the rotary drive shaft 12602 may be configured to also move axially to move the rotary lock head 12640 axially within the distal frame member 12220. When the proximal lock features 12644 in the rotary lock head 12640 are in locking engagement with the series of lock grooves in the distal frame member 12220, rotation of the rotary drive shaft 12602 will result in rotation of the surgical end effector 12200 about the shaft axis SA.

In certain instances, the first and second jaws 12250, 12270 are opened and closed as follows. To open and close the jaws, as was discussed in detail above, the rotary lock head 12640 is in locking engagement with the distal lock plate 12630. Thereafter, rotation of the rotary drive shaft 12602 in a first direction will rotate the distal lock plate 12630 which will axially drive the actuator yoke assembly 12610 in the distal direction DD and move the first jaw 12250 and the second jaw 12270 toward an open position. Rotation of the rotary drive shaft 12602 in an opposite second direction will axially drive the actuator yoke assembly 12610 proximally and pull the jaws 12250, 12270 toward a closed position. To rotate the surgical end effector 12200 about the shaft axis SA, the locking cable or member is pulled proximally to cause the rotary lock head 12640 to disengage from the distal lock plate 12630 and engage the distal frame member 12220. Thereafter, when the rotary drive shaft 12602 is rotated in a desired direction, the distal frame member 12220 (and the surgical end effector 12200) will rotate about the shaft axis SA.

Figure 127:
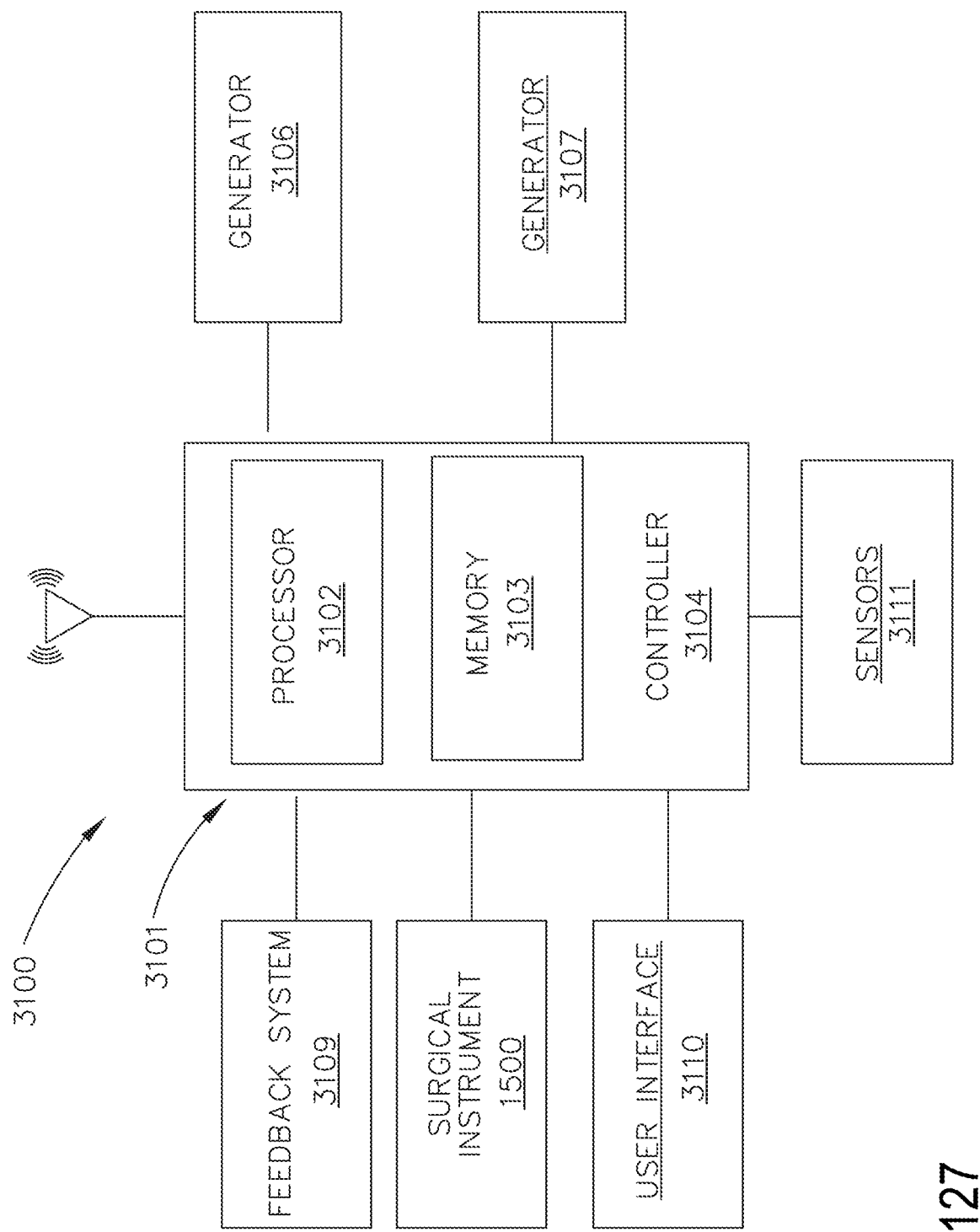
FIG. 127 is a schematic diagram of an electrosurgical system, in accordance with at least one aspect of the present disclosure.
Figure 129:
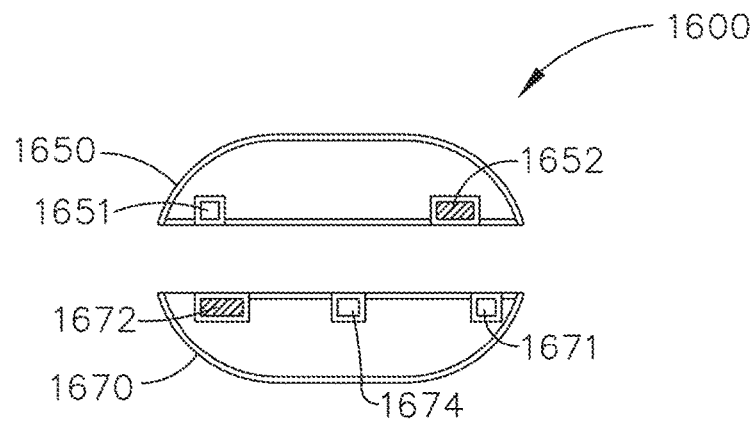
FIGS. 129-131 illustrate a tissue treatment cycle applied by an end effector to a tissue treatment region, in accordance with at least one aspect of the present disclosure.

FIG. 118 further illustrates an electrical connection assembly 5000 for electrically coupling the jaws 12250, 12270 to one or more power sources such as, for example, generators 3106, 3107 (FIG. 127). The electrical connection assembly 5000 defines two separate electrical pathways 5001, 5002 extending through the electrosurgical instrument 12000, as illustrated in FIG. 118. In a first configuration, the electrical pathways 5001, 5002 cooperate to deliver bipolar energy to the end effector 12200 where one of the electrical pathways 5001, 5002 acts as a return pathway. In addition, in a second configuration, the electrical pathways 5001, 5002 separately and/or simultaneously deliver monopolar energy 12200. Accordingly, in the second configuration, both of the electrical pathways 5001, 5002 can be used as supply pathways. Further, the electrical connection assembly 5000 can be utilized with other surgical instruments described elsewhere herein (e.g. the surgical instrument 1500) to electrically couple such surgical instruments with one or more power sources (e.g. generators 3106, 3107).

Figure 121:
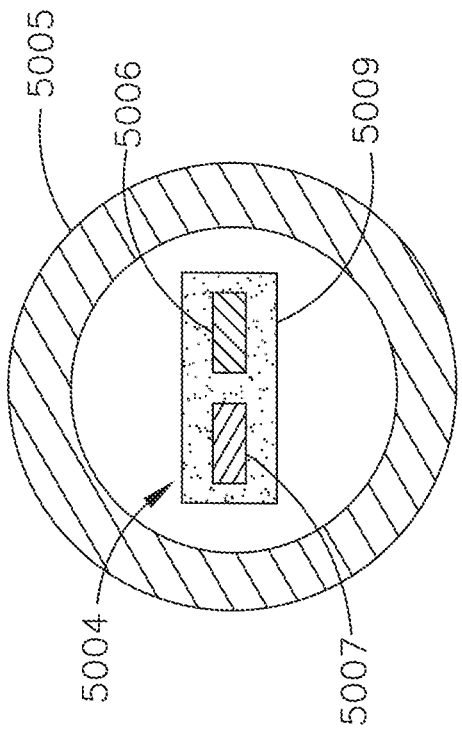
FIG. 121 illustrates a cross-sectional view of a flex circuit extending through a coil tube, in accordance with at least one aspect of the present disclosure.

In the illustrated example, the electrical pathways 5001, 5002 are implemented using a flex circuit 5004 extending, at least partially, through a coil tube 5005. As illustrated in FIG. 121, the flex circuit 5004 includes two separate conductive trace elements 5006, 5007 embedded in a PCB (printed circuit board) substrate 5009. In certain instances, a flex circuit 5004 could be attached to a core flat stamped metallic shaft member with a 3D printed or an over molded plastic casing to provide full shaft fill/support.

Figure 122:
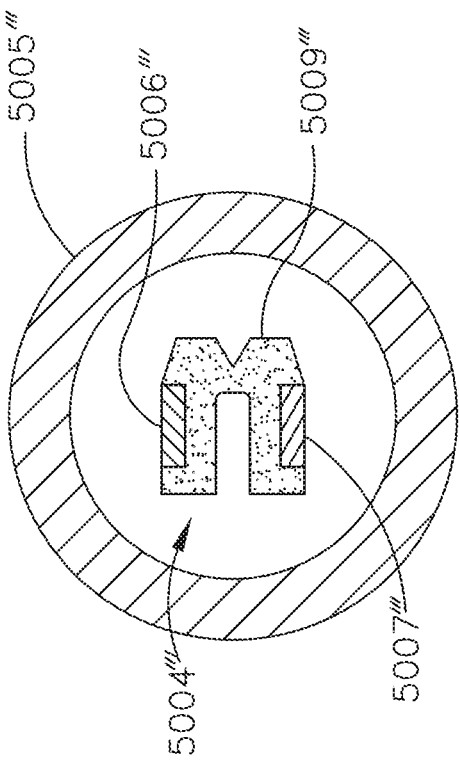
FIG. 122 illustrates a cross-sectional view of a flex circuit extending through a coil tube, in accordance with at least one aspect of the present disclosure.
Figure 123:
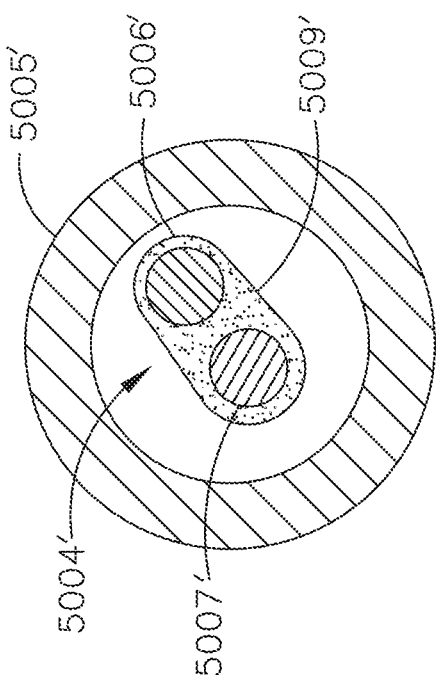
FIG. 123 illustrates a cross-sectional view of a flex circuit extending through a coil tube, in accordance with at least one aspect of the present disclosure.
Figure 124:
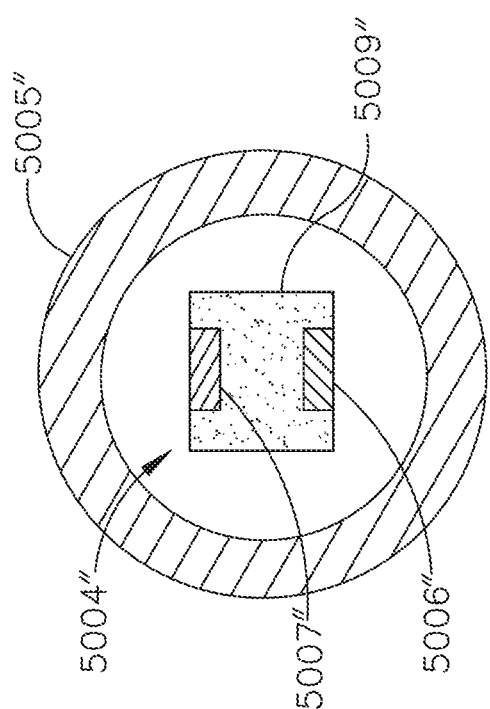
FIG. 124 illustrates a cross-sectional view of a flex circuit extending through a coil tube, in accordance with at least one aspect of the present disclosure.

In alternative examples, as illustrated in FIG. 123, a flex circuit 5004' extending through a coil tube 5005' can include conductive trace elements 5006', 5007' twisted in a PCB substrate 5009' in a helical profile resulting in a reduction of the overall size of the flex circuit 5004' and, in turn, a reduction in the inner/outer diameter of the coil tube 5005'. FIGS. 122 and 123 illustrate other examples of flex circuits 5004", 5004''' extending through coil tubes 5005", 5005''' and including conductive trace elements 5006", 5007" and 5006''', 5007''', respectively, which comprise alternative profiles for size reduction. For example, the flex circuit 5004''' comprises a folded profile while the flex circuit 5004" comprises trace elements 5006", 5007" on opposite sides of the PCB 5009".

Further to the above, the pathways 5001, 5002 are defined by trace portions 5006*a*-5006*g*, 5007*a*-5007*g*, respectively. The trace portions 5006*b*, 5006*c* and the trace portions 5007*b*, 5007*c* are in the form of rings that define a ring assembly 5010 which maintains electrical connections through the pathways 5001, 5002 while allowing rotation of the end effector 12200 relative to the shaft of the surgical instrument 12000. Further, trace portions 5006*e*, 5007*e* are disposed on opposite sides of the actuator yoke assembly 12610. In the illustrated example, the portions 5006*e*, 5007*e* are disposed around holes configured to receive the second jaw attachment pin 12273, as illustrated in FIG. 118. The trace portions 5006*e*, 5007*e* are configured to come into electrical contact with corresponding portions 5006*f*, 5007*f* disposed on the second jaw 12270. In addition, the trace portions 5007*f*, 5007*g* become electrically connected when the first jaw 12250 is assembled with the second jaw 12270.

Figure 120:
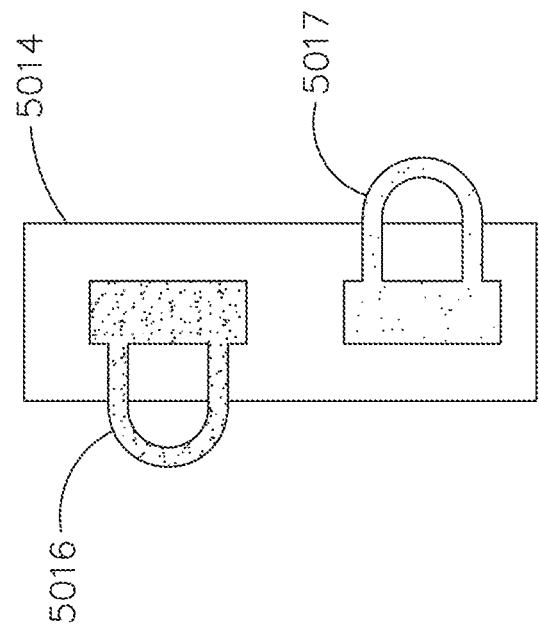
FIG. 120 illustrates a cross-sectional view of a flex circuit, in accordance with at least one aspect of the present disclosure.
Figure 119:
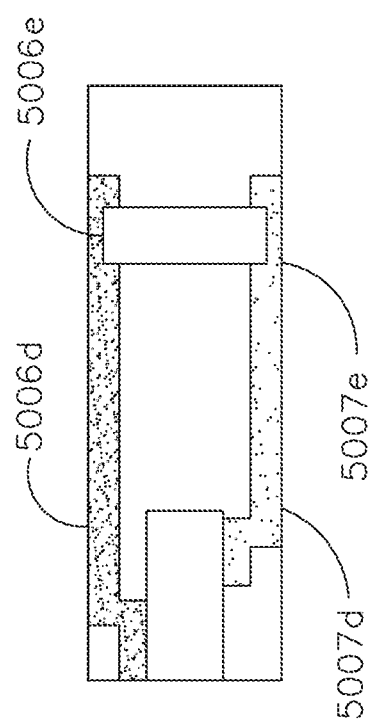
FIG. 119 illustrates a top view of electrical pathways defined in the surgical instrument portion of FIG. 118, in accordance with at least one aspect of the present disclosure.

Referring to FIG. 120, a flex circuit 5014 includes spring-biased trace elements 5016, 5017. The trace elements 5016, 5017 are configured to exert a biasing force against corresponding trace elements to ensure maintaining an electrical connection therewith particularly when corresponding trace portions are moving relative to one another. One or more of the trace portions of the pathways 5001, 5002 can be modified to include spring-biased trace elements in accordance with the flex circuit 5014.

Figure 125:
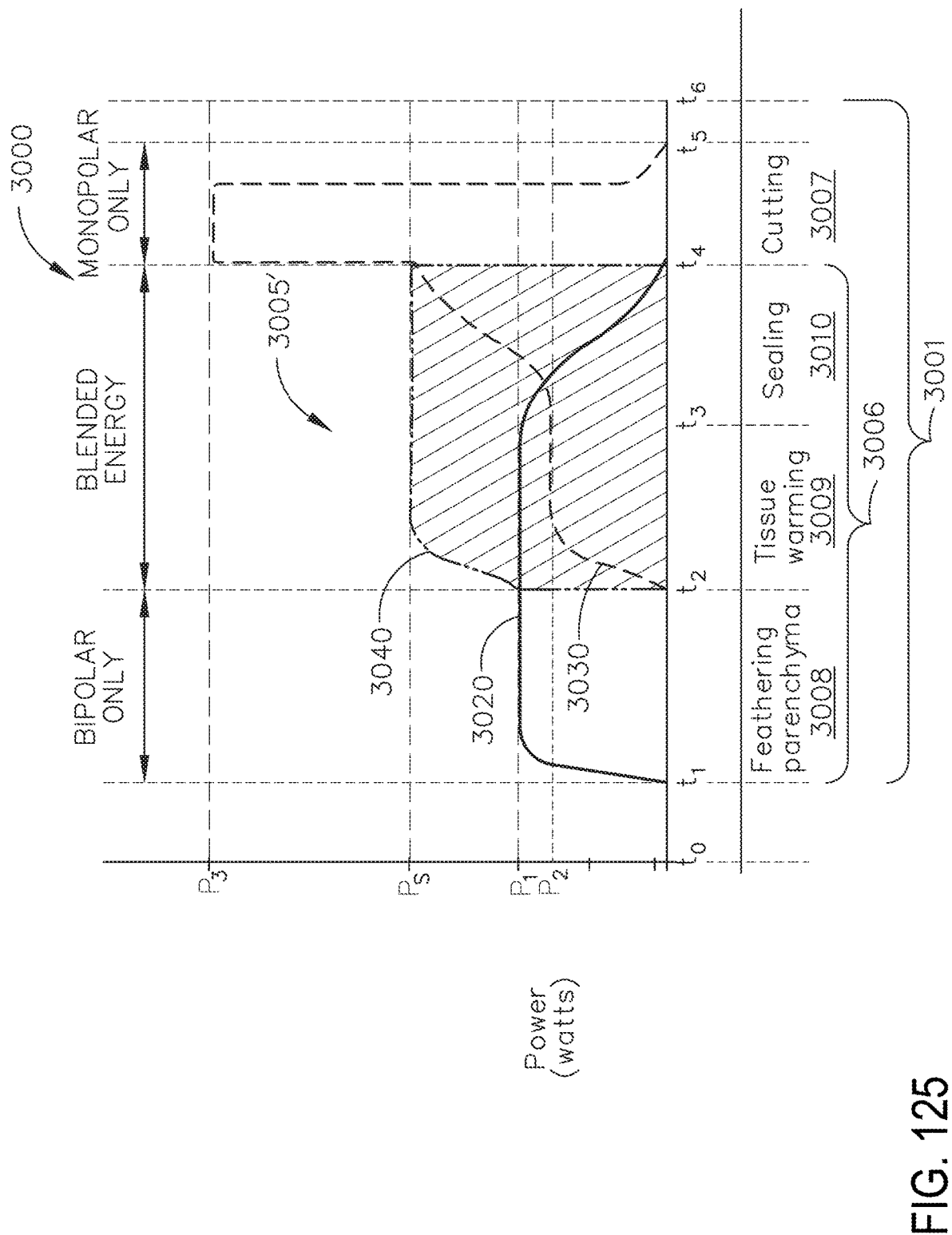
FIG. 125 is a graph illustrating a power scheme for coagulating and cutting a tissue treatment region in a treatment cycle applied by an end effector, in accordance with at least one aspect of the present disclosure.

Referring to FIG. 125, a graph 3000 illustrates a power scheme 3005' of a tissue treatment cycle 3001 applied by an end effector 1400, or any other suitable end effector of the present disclosure, to a tissue grasped by the end effector 1400. The tissue treatment cycle 3001 includes a tissue coagulation stage 3006 including a feathering segment 3008, a tissue-warming segment 3009, and a sealing segment 3010. The tissue treatment cycle 3001 further includes a tissue transection or cutting stage 3007.

FIG. 127 illustrates an electrosurgical system 3100 including a control circuit 3101 configured to execute the power scheme 3005'. In the illustrated example, the control circuit 3101 includes a controller 3104 with storage medium in the form of a memory 3103 and a processor 3102. The storage medium stores program instructions for executing the power scheme 3005'. The electrosurgical system 3100 includes a generator 3106 configured to supply monopolar energy to the end effector 1400, and a generator 3107 configured to supply bipolar energy to the end effector 1400, in accordance with the power scheme 3005'. In the illustrated example, control circuit 3101 is depicted separately from the surgical instrument 1500 and the generators 3106, 3107. In other examples, however, the control circuit 3101 can be integrated with the surgical instrument 1500, the generator 3106, or the generator 3107. In various aspects, the power scheme 3005' can be stored in the memory 3103 in the form of an algorism, equation, and/or look-up table, or any suitable other suitable format. The control circuit 3101 may cause the generators 3106, 3107 to supply monopolar and/or bipolar energies to the end effector 1400 in accordance with the power scheme 3005'.

In the illustrated example, the electrosurgical system 3100 further includes a feedback system 3109 in communication with the control circuit 3101. The feedback system 3109 can be a standalone system, or can be integrated with the surgical instrument 1500, for example. In various aspects, the feedback system 3109 can be employed by the control circuit 3101 to perform a predetermined function such as, for example, issuing an alert when one or more predetermined conditions are met. In certain instances, the feedback system 3109 may comprise one or more visual feedback systems such as display screens, backlights, and/or LEDs, for example. In certain instances, the feedback system 3109 may comprise one or more audio feedback systems such as speakers and/or buzzers, for example. In certain instances, the feedback system 3109 may comprise one or more haptic feedback systems, for example. In certain instances, the feedback system 3109 may comprise combinations of visual, audio, and/or haptic feedback systems, for example. Additionally, the electrosurgical system 3100 further includes a user interface 3110 in communication with the control circuit 3101. The user interface 3110 can be a standalone interface, or can be integrated with the surgical instrument 1500, for example.

The graph 3000 depicts power (W) on the y-axis and time on the x-axis. A bipolar energy curve 3020 spans the tissue coagulation stage 3005, and a monopolar energy curve 3030 starts in the tissue coagulation stage 3006 and terminates at the end of the tissue transection stage 3007. Accordingly, tissue treatment cycle 3001 is configured to apply a bipolar energy to the tissue throughout the tissue coagulation stage 3006, but not the tissue transection stage 3007, and apply a monopolar energy to the tissue in a portion of the coagulation stage 3006 and the transection stage 3007, as illustrated in FIG. 125.

In various aspects, a user input can be received by the control circuit 3101 from the user interface 3110. The user input causes the control circuit 3101 to initialize execution of the power scheme 3005' at time $t_1$. Alternatively, the initialization of the execution of the power scheme 3005' can be triggered automatically by sensor signals from one or more sensors 3111 in communication with the control circuit 3101. For example, the power scheme 3005' can be triggered automatically by the control circuit 3101 in response to a sensor signal indicative of a predetermined gap between the jaws 1450, 1470 of the end effector 1400.

During the feathering segment 3008, the control circuit 3101 causes generator 3107 to gradually increase the bipolar energy power supplied to the end effector 1400 to a predetermined power value P1 (e.g. 100 W), and to maintain the bipolar energy power at, or substantially at, the predetermined power value P1 throughout the remainder of the feathering segment 3008 and the tissue-warming segment 3009. The predetermined power value P1 can be stored in the memory 3103 and/or can be provided by a user through the user interface 3110. During the sealing segment 3010, the control circuit 3101 causes generator 3107 to gradually decrease the bipolar energy power. Bipolar energy application is terminated at the end of the sealing segment 3010 of the tissue coagulation stage 3006, and prior to the beginning of the cutting/transecting stage 3007.

Further to the above, at $t_2$, the control circuit 3101 causes generator 3107 to begin supplying monopolar energy power to the electrode 1474 of the end effector 1400, for example. The monopolar energy application to the tissue commences at the end of the feathering segment 3008 and the beginning of the tissue-warming segment 3009. The control circuit 3101 causes generator 3107 to gradually increase the monopolar energy power to a predetermined power level P2 (e.g. 75 W), and to maintain, or at least substantially maintain, the predetermined power level P2 for the remainder of the tissue-warming segment 3009 and a first portion of the sealing segment 3010. The predetermined power level P2 can also be stored in the memory 3103 and/or can be provided by a user through the user interface 3110.

During the sealing segment 3010 of the tissue coagulation stage 3006, the control circuit 3101 causes generator 3107 to gradually increase the monopolar energy power supplied to the end effector 1400. The beginning of the tissue transection stage 3007 is ushered by an inflection point in the monopolar energy curve 3030 where the previous gradual increase in monopolar energy, experienced during the sealing segment 3010, is followed by a step up to a predetermined maximum threshold power level P3 (e.g. 150 W) sufficient to transect the coagulated tissue.

At $t_4$, the control circuit 3101 causes generator 3107 to step up the monopolar energy power supplied to the end effector 1400 to the predetermined maximum threshold power level P3, and to maintain, or at least substantially maintain, predetermined maximum threshold power level P3 for a predetermined time period ($t_4$-$t_5$), or to the end of the tissue transection stage 3007. In the illustrated example, the monopolar energy power is terminated by the control circuit 3101 at t5. The tissue transection continues mechanically, as the jaws 1450, 1470 continue to apply pressure on the grasped tissue until the end of the issue transection stage 3007 at $t_6$. Alternatively, in other examples, the control circuit 3101 may cause the generator 3107 to continue supplying monopolar energy power to the end effector 1400 to the end of the tissue transection stage 3007.

Sensor readings of the sensors 3111 and/or a timer clock of the processor 3102 can be employed by the control circuit 3101 to determine when to cause the generator 3107 and/or the generator 3106 to begin, increase, decrease, and/or terminate energy supply to the end effector 1400, in accordance with a power scheme such as, for example, the power scheme 3005'. The control circuit 3101 may execute the power scheme 3005' by causing one or more timer clocks to count down from one or more predetermined time periods (e.g. $t_1$-$t_2$, $t_2$-$t_3$, $t_3$-$t_4$, $t_5$-$t_6$) that can be stored in the memory 3103, for example. Although the power scheme 3005' is time based, the control circuit 3101 may adjust predetermined time periods for any of the individual segments 3008, 3009, 3010 and/or the stages 3006, 3007 based on sensor readings received from one or more of the sensors 3111 such as, for example, a tissue impedance sensor.

The end effector 1400 is configured to deliver three different energy modalities to the grasped tissue. The first energy modality, which is applied to the tissue during the feathering segment 3008, includes bipolar energy but not monopolar energy. The second energy modality is a blended energy modality that includes a combination of monopolar energy and bipolar energy, and is applied to the tissue during the tissue warming stage 3009 and the tissue sealing stage 3010. Lastly, the third energy modality includes monopolar energy but not bipolar energy, and is applied to the tissue during the cutting stage 3007. In various aspects, the second energy modality comprises a power level that is the sum 3040 of the power levels of monopolar energy and bipolar energy. In at least one example, the power level of the second energy modality includes a maximum threshold Ps (e.g. 120 W).

In various aspects, the control circuit 3101 causes the monopolar energy and the bipolar energy to be delivered to the end effector 1400 from two different electrical generators 3106, 3107. In at least one example, energy from one of the generators 3106, 3107 can be detected using a return path of the other generator, or utilizing attached electrodes of the other generator to short to an unintended tissue interaction. Accordingly, a parasitic loss of energy through a return path that is not the intended can be detected by a generator connected to the return path. The inadvertent conductive path can be mitigated by effecting the voltage, power, waveform, or timing between uses.

Integrated sensors within the flex circuits of the surgical instrument 1500 can detect energizing/shorting of an electrode/conductive path when no potential should be present and the ability to prevent that conductive path once inadvertent use is sensed. Further, directional electronic gating elements that prevent cross talk from one generator down the source of the other generator can also be utilized.

One or more of the electrodes described by the present disclosure (e.g. electrodes 1452, 1472, 1474 in connection with the jaws 1450, 1470) may include a segmented pattern with segments that are linked together when the electrode is energized by a generator (e.g. generator 1100). However, when the electrode is not energized, the segments are separated to prevent circuit shorting across the electrode to other areas of the jaw.

In various aspects, thermal resistive electrode material are utilized with the end effector 1400. The material can be configured to inhibit electrical flow through electrodes that are at or above a predefined temperature level but continues to allow the energizing of other portions of the electrodes that are below the temperature threshold.

FIG. 128 illustrates a table representing an alternative power scheme 3005" that can be stored in the memory 3103, and can be executed by the processor 3102 in a similar manner to the power scheme 3005'. In executing the power scheme 3005", the control circuit 3101 relies on jaw aperture in addition to, or in lieu of, time in setting power values of the generators 3106, 3107. Accordingly, the power scheme 3005" is a jaw-aperture based power scheme.

In the illustrated example, jaw apertures $d_0$, $d_1$, $d_2$, $d_3$, $d_4$ from the power scheme 3005" correspond to the time values $t_1$, $t_2$, $t_3$, $t_4$ from the power scheme 3005'. Accordingly, the feathering segment corresponds to a jaw aperture from about $d_1$ to about $d_2$ (e.g. from about 0.700" to about 0.500"). In addition, the tissue-warming segment corresponds to a jaw aperture from about $d_2$ to about $d_3$ (e.g. from about 0.500" to about 0.300"). Further, the sealing segment corresponds to a jaw aperture from about $d_2$ to about $d_3$ (e.g. from about 0.030" to about 0.010"). Further, the tissue cutting stage corresponds to a jaw aperture from about $d_3$ to about $d_4$ (e.g. from about 0.010" to about 0.003").

Accordingly, the control circuit 3101 is configured to cause the generator 3106 to begin supplying bipolar energy power to the end effector 1400 when readings from one or more of the sensors 3111 corresponds to the predetermined jaw aperture d1, for example, thereby initializing the feathering segment. Likewise, the control circuit 3101 is configured to cause the generator 3106 to stop supplying bipolar energy power to the end effector 1400 when readings from one or more of the sensors 3111 corresponds to the predetermined jaw aperture d2, for example, thereby terminating the feathering segment. Likewise, the control circuit 3101 is configured to cause the generator 3107 to begin supplying monopolar energy power to the end effector 1400 when readings from one or more of the sensors 3111 corresponds to the predetermined jaw aperture d2, for example, thereby initializing the warming segment.

In the illustrated example, the jaw aperture is defined by the distance between two corresponding datum points on the jaws 1450, 1470. The corresponding datum points are in contact with one another when the jaws 1450, 1470 are in a closed configuration with no tissue therebetween. Alternatively, the jaw aperture can be defined by a distance between the jaws 1450, 1470 measured along a line intersecting the jaws 1450, 1470 and perpendicularly intersecting a longitudinal axis extending centrally through the end effector 1500. Alternatively, the jaw aperture can be defined by a distance between first and second parallel lines intersecting the jaws 1450, 1470, respectively. The distance is measured along a line extending perpendicularly to the first and second parallel lines, and extending through the intersection point between the first parallel line and the first jaw 1450, and through the intersection point between the second parallel line and the second jaw 1470.

Figure 126:
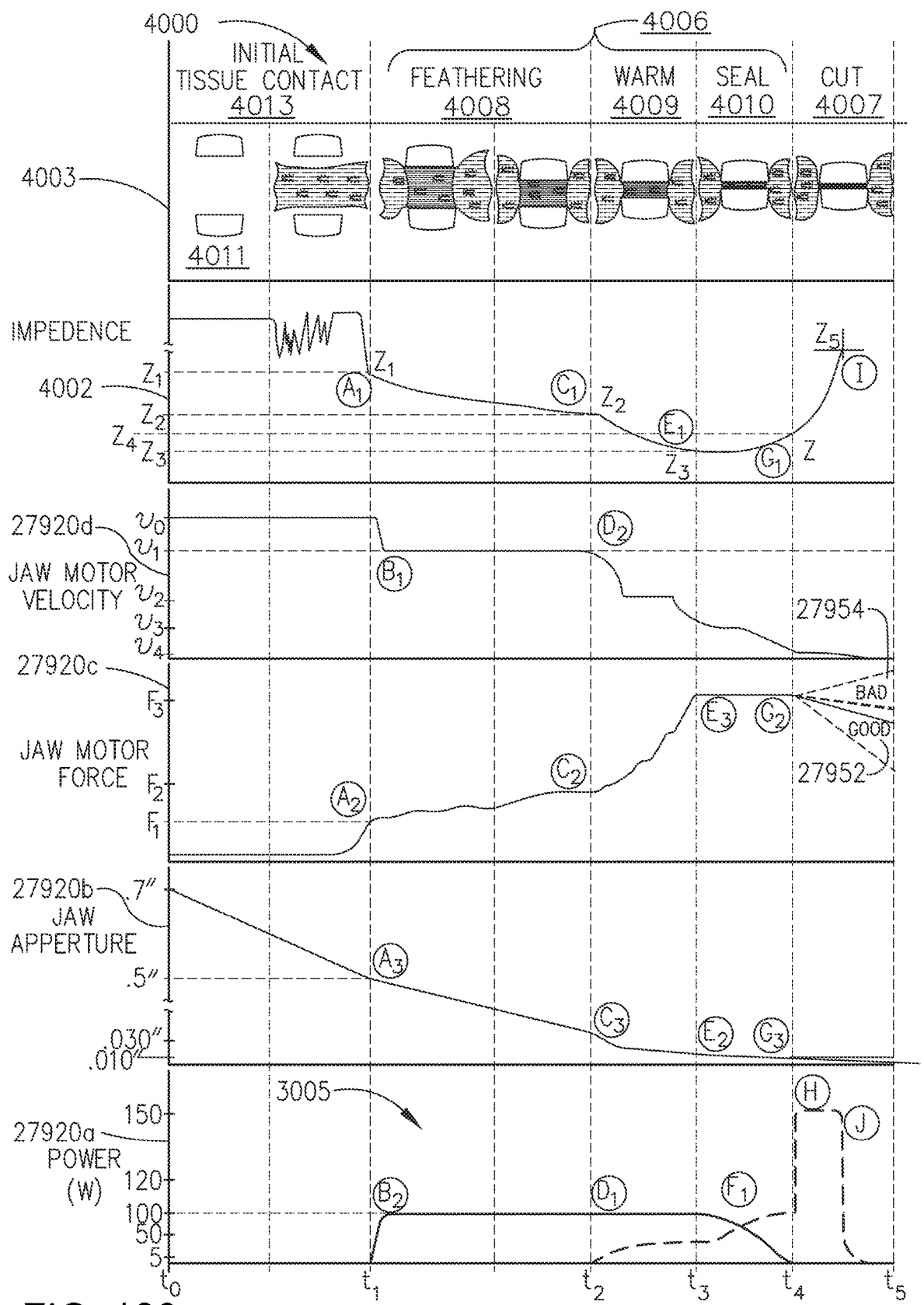
FIG. 126 is a graph illustrating a power scheme for coagulating and cutting a tissue treatment region in a treatment cycle applied by an end effector and a number of measured parameters of the end effector and the tissue, in accordance with at least one aspect of the present disclosure.

Referring to FIG. 126, in various examples, an electrosurgical system 3100 (FIG. 127) is configured to perform a tissue treatment cycle 4003 using a power scheme 3005. The tissue treatment cycle 4003 includes an initial tissue contacting stage 4013, a tissue coagulation stage 4006, and a tissue transection stage 4007. The tissue contacting stage 4013 include an open configuration segment 4011 where tissue is not between the jaws 1450 and 1470, and a proper orientation segment 4012 where the jaws 1450 and 1470 are properly positioned with respect to a desired tissue treatment region. The tissue coagulation stage 4006 includes a feathering segment 4008, a tissue-warming segment 4009, and the sealing segment 3010. The tissue transection stage 4007 includes a tissue-cutting segment. The tissue treatment cycle 4003 involves application of a bipolar energy and a monopolar energy separately and simultaneously to the tissue treatment region in accordance with a power scheme 3005. The tissue treatment cycle 4003 is similar in many respects to the tissue treatment cycle 3001, which are not repeated herein in the same level of detail for brevity.

FIG. 126 illustrates a graph 4000 that represents a power scheme 3005 similar in many respects to the power scheme 3005'. For example, the control circuit 3101 can execute the power scheme 3005, in a similar manner to the power scheme 3005', to deliver three different energy modalities to the tissue treatment region at three consecutive time periods of a tissue treatment cycle 4001. The first energy modality, which includes bipolar energy but not monopolar energy, is applied to the tissue treatment region from $t_1$ to $t_2$, in the feathering segment 4008. The second energy modality, which is a blended energy modality that includes a combination of monopolar energy and bipolar energy, is applied to the tissue treatment region from $t_2$ to $t_4$, in the tissue-warming segment 4009 and tissue-sealing segment. Lastly, the third energy modality, which includes monopolar energy but not bipolar energy 4010, is applied to the tissue from $t_0$ to $t_5$, in tissue transection stage 4007. Furthermore, the second energy modality comprises a power level that is the sum of the power levels of monopolar energy and bipolar energy. In at least one example, the power level of the second energy modality includes a maximum threshold (e.g. 120 W). In various aspects, the power scheme 3005 can be delivered to the end effector 1400 from two different electrical generators 3106, 3107. Additional aspects of the power scheme 3005 that are similar to aspects of the power scheme 3005' are not repeated herein in the same level of detail for brevity.

In various aspects, the control circuit 3101 causes the generators 3106, 3107 to adjust the bipolar and/or monopolar power levels of the power scheme 3005 applied to the tissue treatment region by the end effector 1400 based on one or more measured parameters including tissue impedance 4002, jaw motor velocity 27920d, jaw motor force 27920c, jaws aperture 27920b of the end effector 1400, and/or current draw of the motor effecting the end effector closure. FIG. 126 is a graph 4000 illustrating correlations between such measured parameters and the power scheme 3005 over time.

In various examples, the control circuit 3101 causes the generators 3106, 3107 to adjust the power levels of a power scheme (e.g. power schemes 3005, 3005') applied by the end effector 1400 to the tissue treatment region based on one or more parameters (e.g. tissue impedance 4002, jaw/closure motor velocity 27920d, jaw/closure motor force 27920c, jaws gap/aperture 27920b of the end effector 1400, and/or current draw of the motor) determined by one or more sensors 3111. For example, the control circuit 3101 may cause the generators 3106, 3107 to adjust the power levels based on the pressure within the jaws 1450, 1470.

In at least one example, the power levels are inversely proportional to the pressure within the jaws 1450, 1470. The control circuit 3101 may utilize such an inverse correlation to select the power levels based on the pressure values. In at least one example, current draw of the motor effecting the end effector closure is employed to determine the pressure values. Alternatively, the inverse correlation utilized by the control circuit 3101 can be directly based on the current draw as a proxy for the pressure. In various examples, the greater the compression applied by the jaws 1450, 1470 onto the tissue treatment region, the lower the power levels set by the control circuit 3101, which aids in minimizing sticking and inadvertent cutting of the tissue.

Graph 4000 provides several cues in the measured parameters of tissue impedance 4002, jaw/closure motor velocity 27920d, jaw/closure motor force 27920c, jaws gap/aperture 27920b of the end effector 1400, and/or current draw of the motor effecting the end effector closure, which can trigger an activation, an adjustment, and/or a termination of the bipolar energy and/or the monopolar energy application to tissue during the tissue treatment cycle 4003.

The control circuit 3101 may rely on one or more of such cues in executing and/or adjusting the default power scheme 3005 in the tissue treatment cycle 4003. In certain examples, the control circuit 3101 may rely on sensor readings of the one or more sensors 3111 to detect when one or more monitored parameters satisfy one or more predetermined conditions that can be stored in the memory 3103, for example. The one or more predetermined conditions can be reaching a predetermined threshold and/or detecting a meaningful increase and/or decrease in one or more of the monitored parameters. Satisfaction of the predetermined conditions, or the lack thereof, constitutes trigger/confirmation points for executing and/or adjusting portions of the default power scheme 3005 in the tissue treatment cycle 4003. The control circuit 3101 may rely exclusively on the cues in executing and/or adjusting a power scheme or, alternatively, use the cues to guide, or adjust, a timer clock of a time-based power scheme such as, for example, the power scheme 3005'.

For example, a sudden decrease ($A_1$) in tissue impedance to a predetermined threshold value ($Z_1$), occurring alone or coinciding with an increase ($A_2$) in jaw motor force to a predetermined threshold value ($F_1$) and/or a decrease ($A_3$) in jaw aperture to a predetermined threshold value (d1) (e.g. 0.5") may trigger the control circuit 3101 to begin the feathering segment 4008 of the tissue coagulation stage 4006 by activating the application of bipolar energy to the tissue treatment region. The control circuit 3101 may signal the generator 3106 to begin supplying bipolar power to the end effector 1400.

Furthermore, a decrease ($B_1$) in jaw motor velocity to a predetermined value (v1) following the activation of the bipolar energy triggers the control circuit 3101 to signal the generator 3106 to stabilize ($B_2$) the power level for bipolar energy at a constant, or at least substantially constant, value (e.g. 100 W).

In yet another example, the shifting from the feathering segment 4008 to the warming segment 4009 at $t_2$, which triggers an activation (D1) of the monopolar energy application to the tissue treatment region, coincides with an increase ($C_2$) in the jaw motor force to a predetermined threshold ($F_2$), a decrease ($C_3$) in the jaw aperture to a predetermined threshold (e.g. 0.03"), and/or a decrease (C1) in tissue impedance to a predetermined value $Z_2$. Satisfaction of one, or in certain instances two, or in certain instances all, of the conditions C1, C2, C3 causes the control circuit 3101 to cause the generator 3101 to begin application of monopolar energy to the tissue treatment region. In another example, satisfaction of one, or in certain instances two, or in certain instances all, of the conditions C1, C2, C3 at, or about, the time t2, triggers the application of monopolar energy to the tissue treatment region.

Activation of the monopolar energy by the generator 3107, in response to activation signals by the control circuit 3101, causes a blend ($D_1$) of the monopolar energy and bipolar energy to be delivered to the tissue treatment region, which causes a shift in the impedance curve characterized by a quicker decrease (E1) in impedance from $Z_2$ to $Z_3$ in comparison to a steady decrease (C1) prior to activation of the monopolar energy. In the illustrated example, the tissue impedance $Z_3$ defines a minimum impedance for the tissue treatment cycle 4003.

In the illustrated example, the control circuit 3101 determines that an acceptable seal is being achieved if ($E_1$) the minimum impedance value $Z_3$ coincides, or at least substantially coincides, with ($E_3$) a predetermined maximum jaw motor force threshold ($F_3$) and/or ($E_2$) a predetermined jaw aperture threshold range (e.g. 0.01"-0.003"). Satisfaction of one, or in certain instances two, or in certain instances all, of the conditions E1, E2, E3 signals the control circuit 3101 to shift from the warming segment 4009 to the sealing segment 4010.

Further to the above, beyond the minimum impedance value $Z_3$, the impedance level gradually increases to a threshold value Z4 corresponding to the end of the sealing segment 4010, at $t_4$. Satisfaction of the threshold value Z4 causes the control circuit 3101 to signal the generator 3107 to step up the monopolar power level to commence the tissue transection stage 4007, and signal the generator 3106 to terminate application of the bipolar energy application to the tissue treatment region.

In various examples, the control circuit 3101 can be configured to ($G_2$) verify that the jaw motor force is decreasing as ($G_1$) the impedance gradually increases from its minimum value $Z_3$, and/or ($G_3$) that the jaw aperture has decreased to a predetermined threshold (e.g. 0.01"-0.003"), prior to stepping up the power level of the monopolar energy to cut the tissue.

If, however, the jaw motor force continues to increase, the control circuit 3101 may pause application of the monopolar energy to the tissue treatment region for a predetermined time period to allow the jaw motor force to begin decreasing. Alternatively, the control circuit may signal the generator 3107 to deactivate the monopolar energy, and complete the seal using only the bipolar energy.

In certain instances, the control circuit 3101 may employ the feedback system 3109 to alert a user and/or provide instructions or recommendations to pause the application of the monopolar energy. In certain instances, the control circuit 3101 may instruct the user to utilize on a mechanical knife to transect the tissue.

In the illustrated example, the control circuit 3101 maintains (H) the stepped up monopolar power until a spike (I) is detected in tissue impedance. The control circuit 3101 may cause the generator 3107 to terminate (J) application of the monopolar energy to the tissue upon detection of the spike (I) in the impedance level to $Z_5$ following the gradual increase from $Z_3$ to $Z_4$. The spike indicates completion of the tissue treatment cycle 4003.

In various examples, the control circuit 3101 prevents the electrodes of the jaws 1450, 1470 from being energized before a suitable closure threshold is reached. The closure threshold can be based on a predetermined jaw aperture threshold and/or a predetermined jaw motor force threshold, for example, which can be stored in the memory 3103. In such examples, the control circuit 3101 may not act on user inputs through the user interface 3110 requesting of the treatment cycle 4003. In certain instances, the control circuit 3101 may respond by alerting the user through the feedback system 3109 that the suitable closure threshold has not been reached. The control circuit 3101 may also offer the user an override option.

Ultimately between time $t_4$ and $t_5$, monopolar energy is the only energy being delivered in order to cut the patient tissue. While the patient tissue is being cut, the force to clamp the jaws of the end effector may vary. In instances where the force to clamp the jaws decreases 27952 from its steady-state level maintained between time $t_3$ and $t_4$, an efficient and/or effective tissue cut is recognized by the surgical instrument and/or the surgical hub. In instances where the force to clamp the jaws increases 27954 from its steady-state level maintained between time $t_3$ and $t_4$, an inefficient and/or ineffective tissue cut is recognized by the surgical instrument and/or the surgical hub. In such instances, an error can be communicated to the user.

Figure 130:
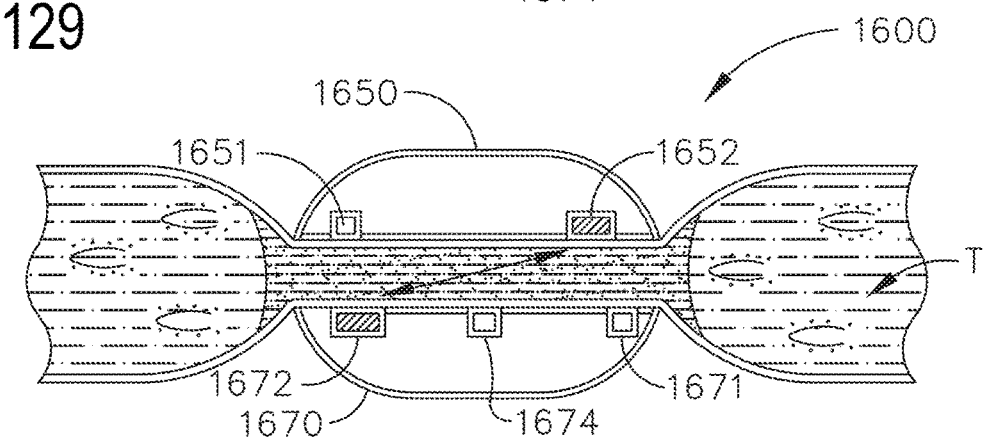
Figure 131:
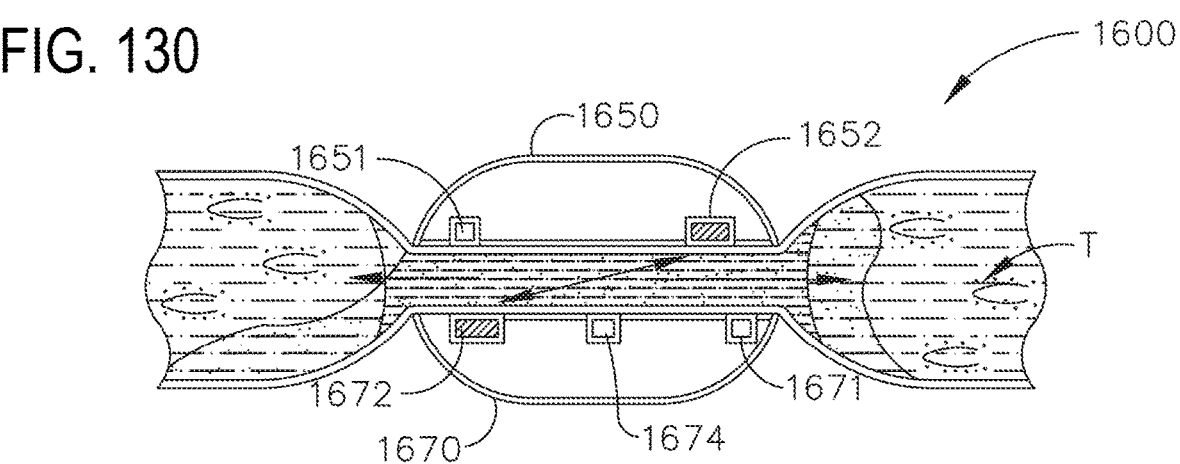
Figure 132:
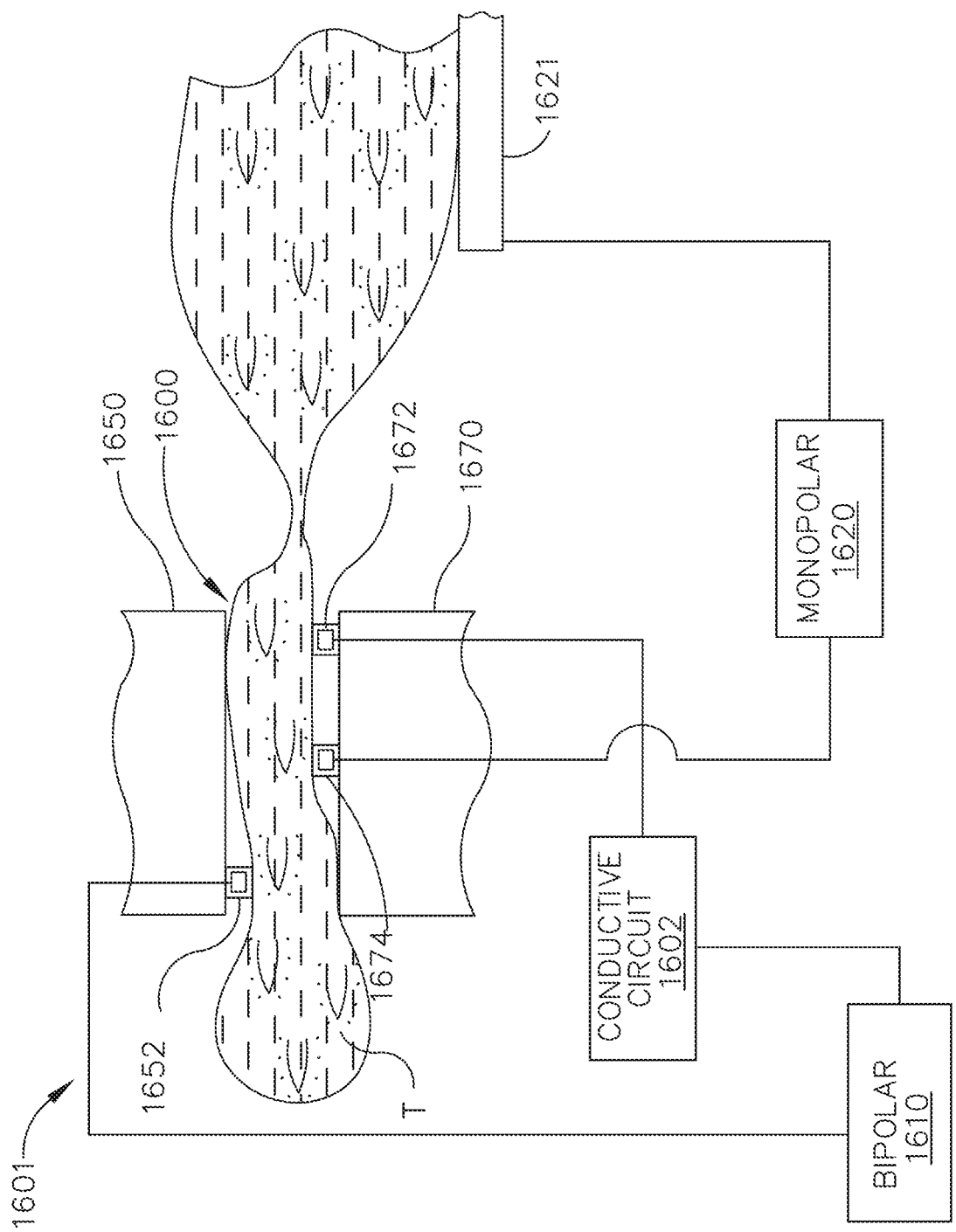
FIG. 132 illustrates an end effector applying therapeutic energy to a tissue grasped by the end effector, the therapeutic energy generated by a monopolar power source and a bipolar power source, in accordance with at least one aspect of the present disclosure.

Referring to FIGS. 129-133, a surgical instrument 1601 includes an end effector 1600 similar in many respects to the end effectors 1400, 1500, which are not repeated herein in the same level of detail for brevity. The end effector 1600 includes a first jaw 1650 and a second jaw 1670. At least one of the first jaw 1650 and the second jaw 1670 is movable to transition the end effector 1600 from an open configuration to a closed configuration to grasp tissue (T) between the first jaw 1650 and the second jaw 1670. Electrodes 1652, 1672 are configured to cooperate to deliver a bipolar energy to the tissue from a bipolar energy source 1610, as illustrated in FIG. 130. An electrode 1674 is configured to deliver a monopolar energy to the tissue from a monopolar energy source 1620. A return pad 1621 defines a return pathway for the monopolar energy. In at least one example, the monopolar energy and the bipolar energy are delivered to the tissue either simultaneously (FIG. 127), or in an alternating fashion, as illustrated in FIG. 127, to seal and/or cut the tissue, for example.

Figure 133:
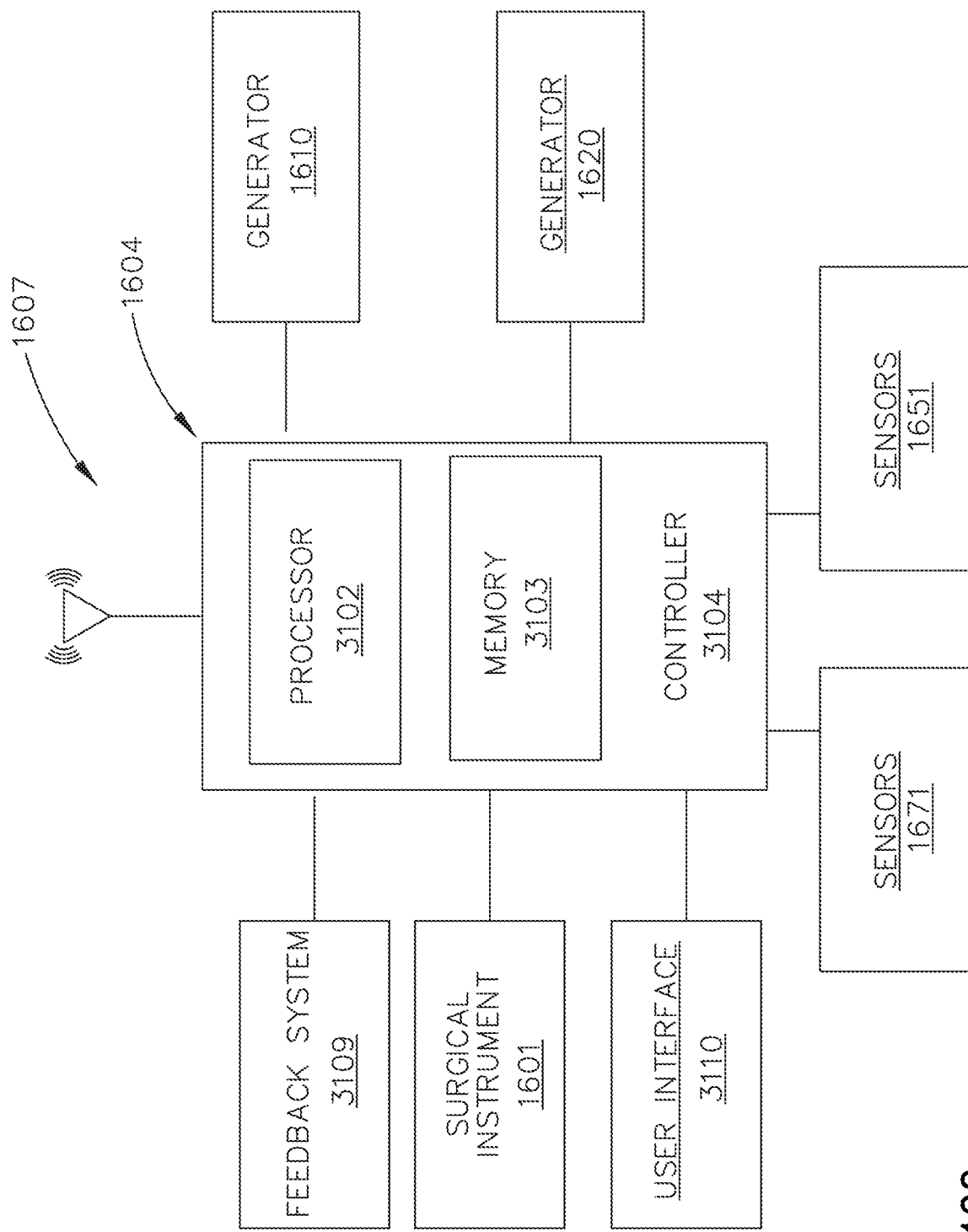
FIG. 133 illustrates a simplified schematic diagram of an electrosurgical system, in accordance with at least one aspect of the present disclosure.

FIG. 133 illustrates a simplified schematic diagram of an electrosurgical system 1607 includes a monopolar power source 1620 and bipolar power source 1610 connectable to an electrosurgical instrument 1601 that includes the end effector 1600. The electrosurgical system 1607 further includes a conductive circuit 1602 selectively transitionable between a connected configuration with the electrode 1672 and a disconnected configuration with the electrode 1672. The switching mechanism can be comprised of any suitable switch that can open and close the conductive circuit 1602, for example. In the connected configuration, the electrode 1672 is configured to cooperate with the electrode 1652 to deliver bipolar energy to the tissue, wherein the conductive circuit 1602 defines a return path for the bipolar energy after passing through the tissue. However, in the disconnected configuration, the electrode 1672 is isolated and therefore becomes an inert internally conductive and externally insulated structure on the jaw 1670. Accordingly, in the disconnected configuration the electrode 1652 is configured to deliver a monopolar energy to the tissue in addition to, or separate from, the monopolar energy delivered through the electrode 1674. In alternative examples, the electrode 1652, instead of the electrode 1672, can be transitionable between a connected configuration and a disconnected configuration with the conductive circuit 1602, allowing the electrode 1672 deliver monopolar energy to the tissue in addition to, or separate from, the monopolar energy delivered through the electrode 1674.

In various aspects, the electrosurgical instrument 1601 further includes a control circuit 1604 configured to adjust levels of the monopolar energy and the bipolar energy delivered to the tissue to minimize unintended thermal damage to surrounding tissue. The adjustments can be based on readings of at least one sensor such as, for example, a temperature sensor, an impedance sensor, and/or a current sensor. In the example illustrated in FIGS. 132 and 133, the control circuit 1604 is coupled to temperature sensors 1651, 1671 on the jaws 1650, 1670, respectively. The levels of the monopolar energy and the bipolar energy delivered to the tissue are adjusted by the control circuit 1604 based on temperature readings of the sensors 1651, 1671.

In the illustrated example, the control circuit 1604 includes a controller 3104 with a storage medium in the form of a memory 3103 and a processor 3102. The memory 3103 stores program instructions that, when executed by the processor 3102, cause the processor 3102 to adjust levels of the monopolar energy and the bipolar energy delivered to the tissue based on sensor readings received from one or more sensors such as, for example, the temperature sensors 1651, 1671. In various examples, as described in greater detail below, the control circuit 1604 may adjust a default power scheme 1701 based on readings from one or more sensors such as, for example, the temperature sensors 1651, 1671. The power scheme 1701 is similar in many respects to the power scheme 3005', which are not repeated herein in the same level of detail for brevity.

Figure 134:
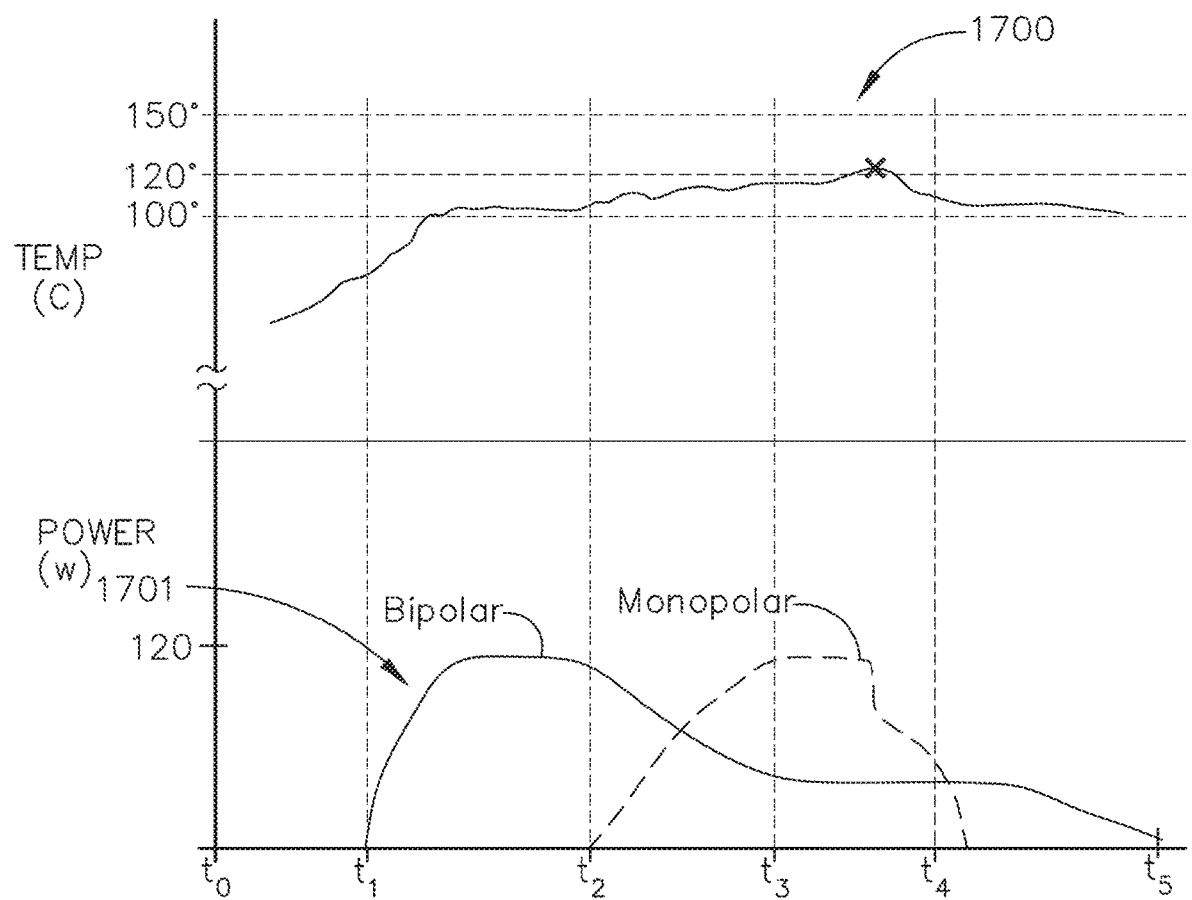
FIG. 134 is a graph illustrating a power scheme for coagulating and cutting a tissue treatment region in a treatment cycle applied by an end effector and corresponding temperature readings of the tissue treatment region, in accordance with at least one aspect of the present disclosure.

FIG. 134 illustrates a temperature-based adjustment of the power scheme 1701 for energy delivery to a tissue grasped by an end effector 1600. A graph 1700 depicts time on the x-axis, and power and temperature on the y-axis. In a tissue feathering segment ($t_1$-$t_2$), the control circuit 1604 causes the power level of the bipolar energy to gradually increase up to a predetermined threshold (e.g. 120 W), which causes the temperature of the tissue grasped by the end effector 1600 to gradually increase to a temperature within a predetermined range (e.g. 100° C.-120° C.). The power level of the bipolar energy is then maintained at the predetermined threshold as long as the tissue temperature remains within the predetermined range. In a tissue-warming segment ($t_2$-$t_3$), the control circuit 1604 activates the monopolar energy, and gradually decreases the power level of the bipolar energy, while gradually increasing the power level of the monopolar energy to maintain the tissue temperature within the predetermined range.

In the illustrated example, during a tissue-sealing segment ($t_3$-$t_4$), the control circuit 1604 detects that the tissue temperature has reached the upper limit of the predetermined range based on readings the temperature sensors 1651, 1671. The control circuit 1604 responds by stepping down the power level of the monopolar energy. In other examples, the reduction can be performed gradually. In certain examples, the reduction value, or a manner for determining the reduction value such as, for example, a table or an equation can be stored in the memory 3103. In certain examples, the reduction value can be a percentage of the present power level of the monopolar energy. In other examples, the reduction value can be based on a previous power level of the monopolar energy that corresponded to a tissue temperature within the predetermined range. In certain examples, the reduction can be performed in multiple steps that are temporally spaced apart. After each downward step, the control circuit 1604 allows a predetermined time period to pass before evaluating the tissue temperature.

In the illustrated example, the control circuit 1604 maintains the power level of the bipolar energy in accordance with the default power scheme 1701, but reduces the power level of the monopolar energy to maintain the temperature of the tissue within the predetermined range, while tissue sealing is completed. In other examples, the reduction in the power level of the monopolar energy is combined, or replaced, by a reduction in the power level of the bipolar energy.

Further to the above, an alert can be issued, through the feedback system 3109, to complete transection of the tissue using a mechanical knife, for example, instead of the monopolar energy to avoid unintended lateral thermal damage to surrounding tissue. In certain examples, the control circuit 1604 may temporarily pause the monopolar energy and/or the bipolar energy until the temperature of the tissue returns to a level within the predetermined temperature range. Monopolar energy can then be reactivated to perform a transection of the sealed tissue.

Figure 135:
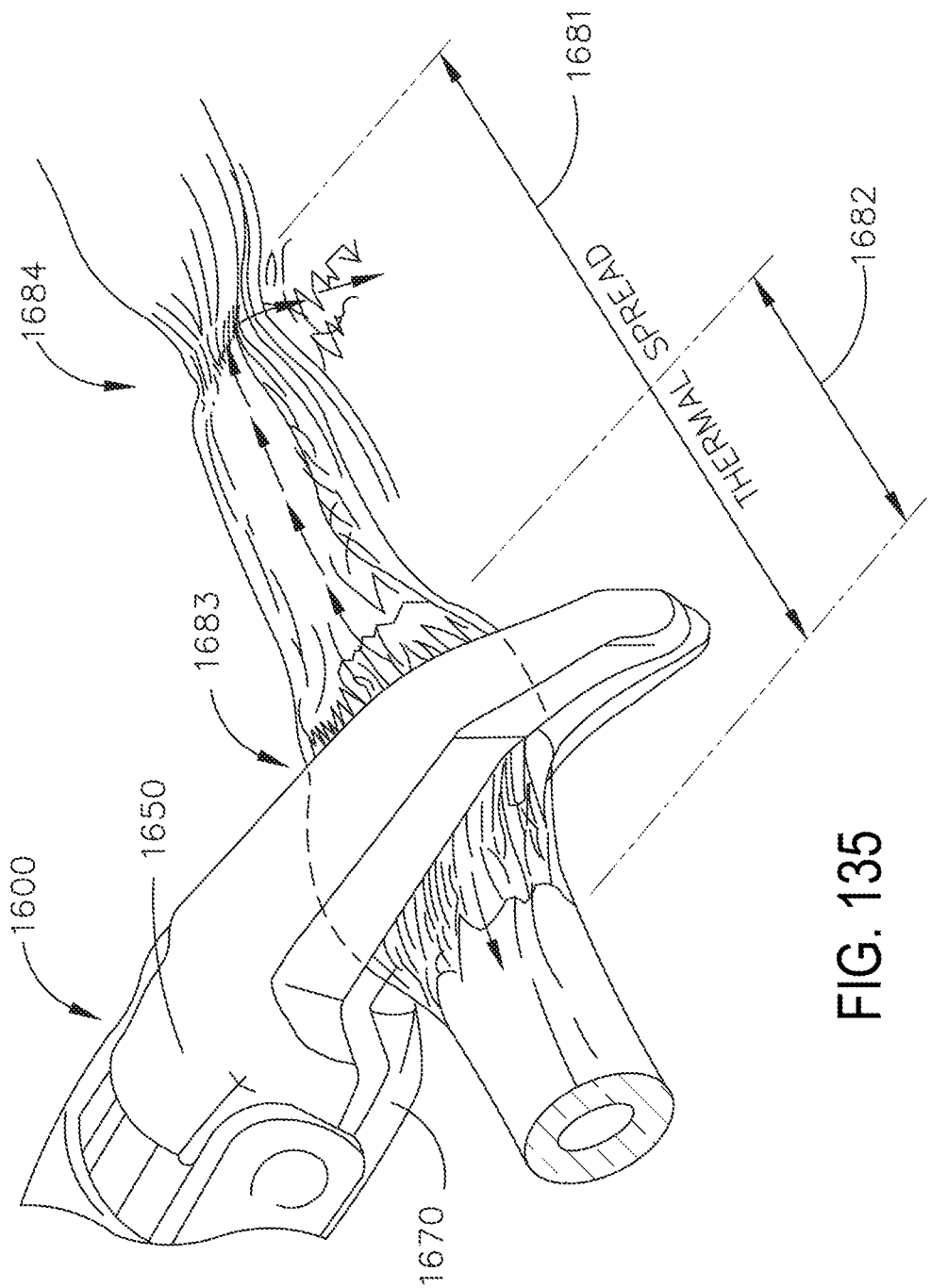
FIG. 135 illustrate an end effector treating an artery, in accordance with at least one aspect of the present disclosure.

Referring to FIG. 135, an end effector 1600 is applying monopolar energy to a tissue treatment region 1683 at a blood vessel such as, for example, an artery grasped by the end effector 1600. The monopolar energy flows from the end effector 1600 to the treatment region 1683, and eventually to a return pad (e.g. return pad 1621). Temperature of the tissue at the treatment region 1683 rises as monopolar energy is applied to the tissue. However, an actual thermal spread 1681 is greater than an expected thermal spread 1682, due to a constricted portion 1684 of the artery that inadvertently draws the monopolar energy, for example.

In various aspects, the control circuit 1604 monitors thermal effects at the treatment region 1683 resulting from application of the monopolar energy to the treatment region 1683. The control circuit 1604 can further detect a failure of the monitored thermal effects to comply with a predetermined correlation between the applied monopolar energy and thermal effects expected from application of the monopolar energy at the treatment region. In the illustrated example, the inadvertent energy draw at the constricted portion of the artery reduces the thermal effects at the treatment region, which is detected by the control circuit 1604.

In certain examples, the memory 3103 stores a predetermined correlation algorithm between monopolar energy level, as applied to a tissue treatment region grasped by the end effector 1600, and the thermal effects expected to result from application of the monopolar energy to the tissue treatment region. The correlation algorithm can be in the form of, for example, an array, lookup table, database, mathematical equation, or formula, etc. In at least one example, the stored correlation algorithm defines a correlation between power levels of the monopolar energy and expected temperatures. The control circuit 1604 can monitor the temperature of the tissue at the treatment region 1683 using the temperature sensors 1651, 1671, and can determine if a monitored temperature reading corresponds to an expected temperature reading at a certain power level.

The control circuit 1604 can be configured to take certain actions if a failure to comply with the stored correlation is detected. For example, the control circuit 1604 may alert a user of the failure. Additionally, or alternatively, the control circuit 1604 may reduce or pause delivery of the monopolar energy to the treatment region. In at least one example, the control circuit 1604 may adjust, or shift, from the monopolar energy to a bipolar energy application to the tissue treatment region to confirm the presence of a parasitic power draw. The control circuit 1604 may continue using bipolar energy at the treatment region if the parasitic power draw is confirmed. If, however, the control circuit 1604 refutes the presence of a parasitic power draw, the control circuit 1604 may reactivate, or re-increase, the monopolar power level. Changes to the monopolar and/or bipolar power levels can be achieved by the control circuit 1604 by signaling the monopolar power source 1620 and/or the bipolar power source 1610, for example.

Figure 136:
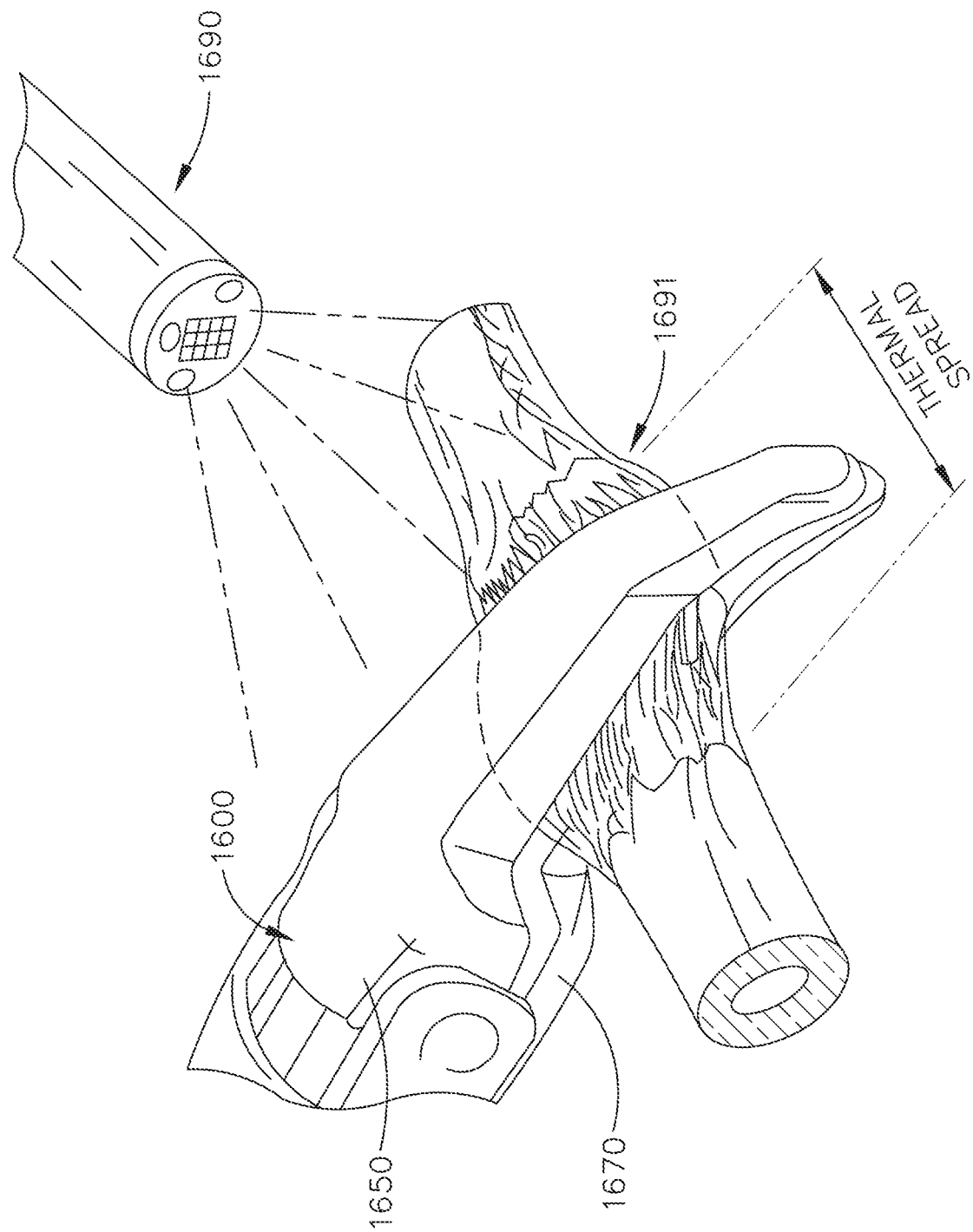
FIG. 136 illustrate an end effector treating an artery, in accordance with at least one aspect of the present disclosure.

In various aspects, one or more imaging devices such as, for example, a multi-spectral scope 1690 and/or an infrared imaging device can be utilized to monitor spectral tissue changes and/or the thermal effects at a tissue treatment region 1691, as illustrated in FIG. 136. Imaging data from the one or more imaging devices can be processed to estimate the temperature at the tissue treatment region 1691. For example, a user may direct the infrared imaging device at the treatment region 1691 as monopolar energy is being applied to the treatment region 1691 by the end effector of 1600. As the treatment region 1691 heats up, its infrared heat signature changes. Accordingly, changes in the heat signature correspond to changes in the temperature of the tissue at the treatment region 1691. Accordingly, the temperature of the tissue at the treatment region 1691 can be determined based on the heat signature captured by the one or more imaging devices. If the temperature estimated based on the heat signature at the treatment region 1691 associated with a certain part level is less than or equal to an expected temperature at the power level, the control circuit 1604 detects a discrepancy in the thermal effects at the treatment region 1691.

In other examples, the heat signature captured by the one or more imaging devices is not converted into an estimated temperature. Instead, it is directly compared heat signatures stored into the memory 3103 to assess whether a power level adjustment is needed.

In certain examples, the memory 3103 stores a predetermined a correlation algorithm between power levels of the monopolar energy, as applied to a tissue treatment region 1691 by the end effector 1600, and the heat signatures expected to result from application of the monopolar energy to the tissue treatment region. The correlation algorithm can be in the form of, for example, an array, lookup table, database, mathematical equation, or formula, etc. In at least one example, the stored correlation algorithm defines a correlation between power levels of the monopolar energy and expected heat signatures, or temperatures associated with the expected heat signatures.

Figure 137:
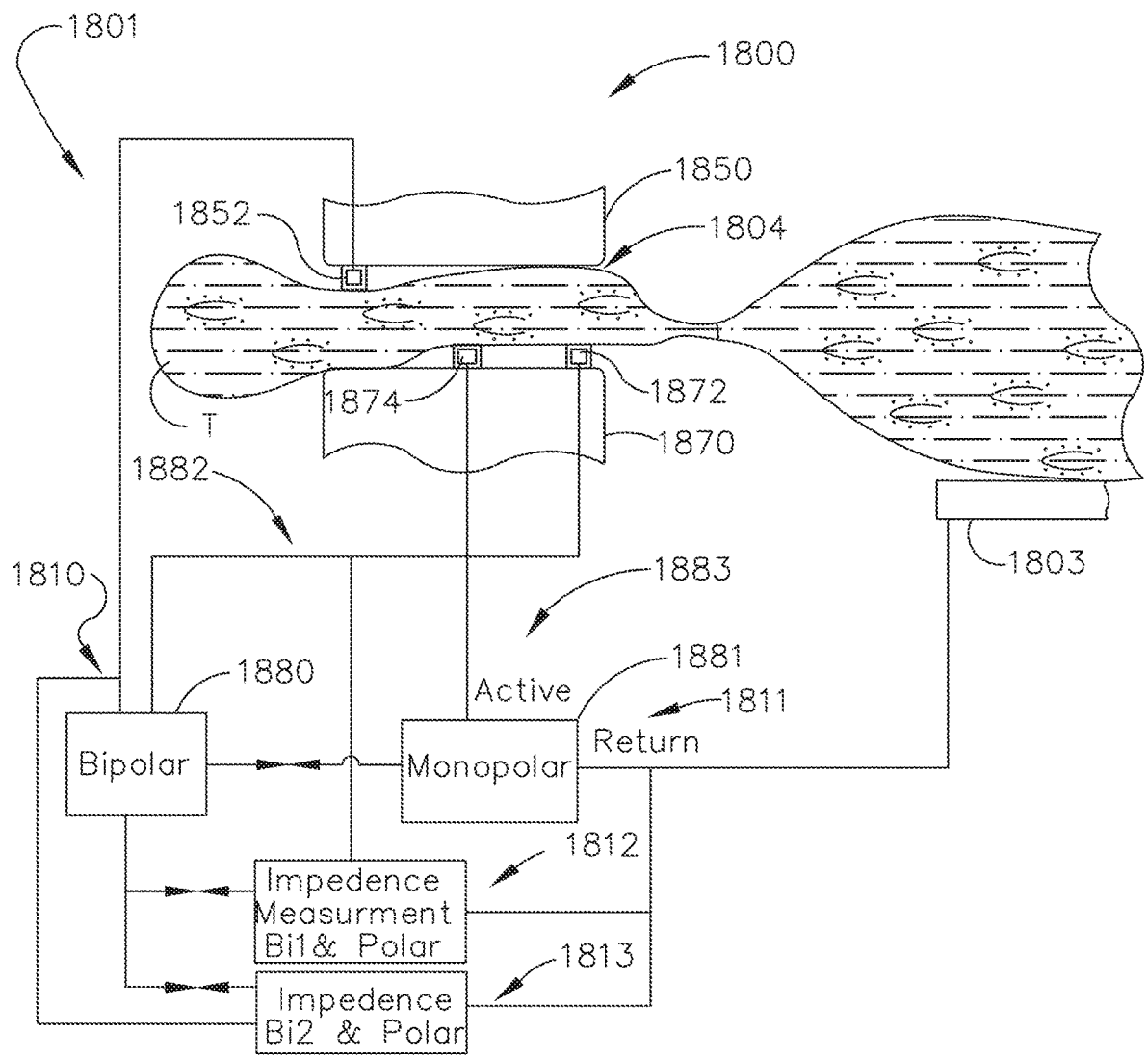
FIG. 137 illustrates an end effector applying therapeutic energy to a tissue grasped by the end effector, the therapeutic energy generated by a monopolar power source and a bipolar power source, in accordance with at least one aspect of the present disclosure.
Figure 138:
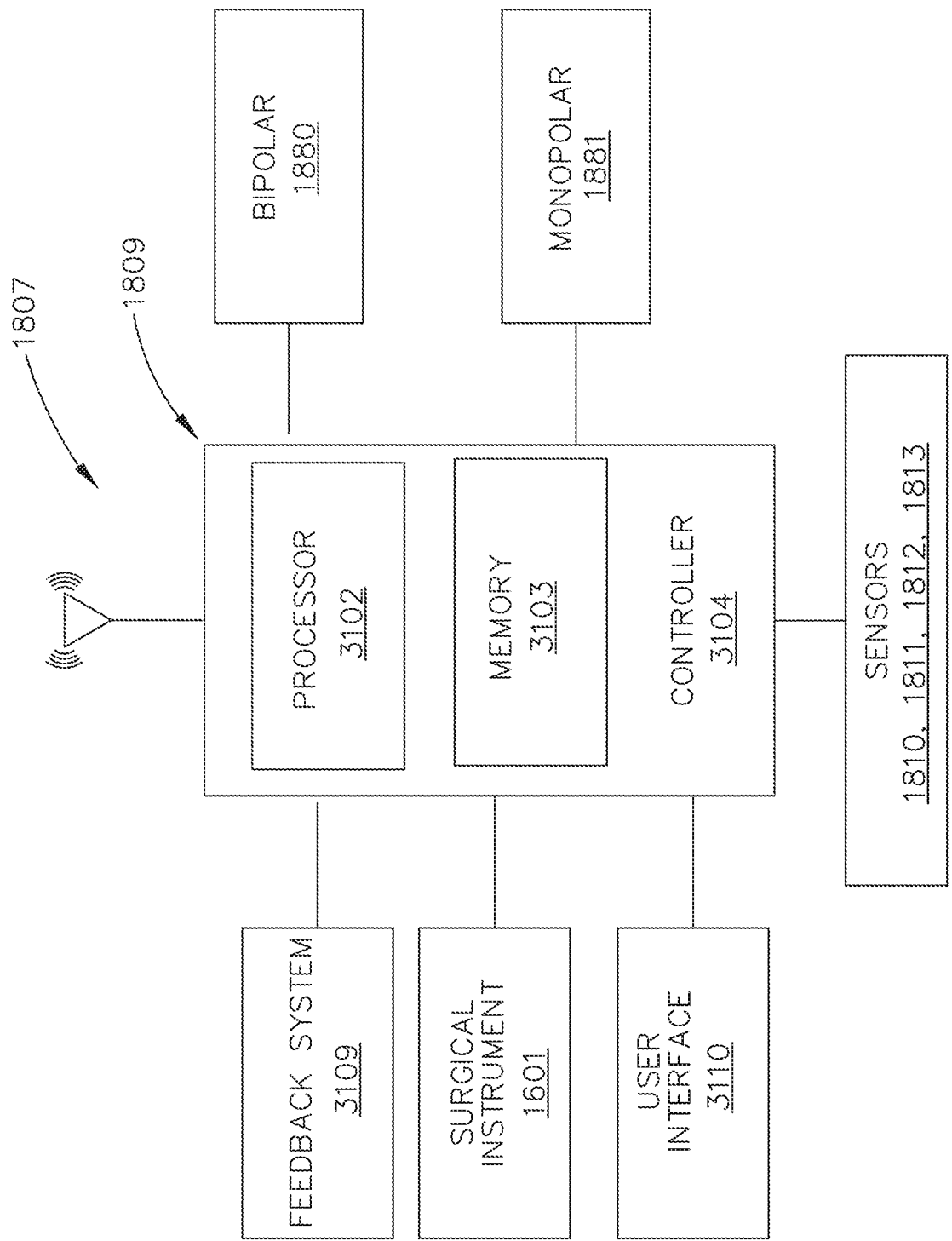
FIG. 138 illustrates a simplified schematic diagram of an electrosurgical system, in accordance with at least one aspect of the present disclosure.

Referring to FIGS. 137 and 138, an electrosurgical system includes an electrosurgical instrument 1801 that has an end effector 1800 similar to the end effectors 1400, 1500, 1600 in many respects, which are not repeated herein in the same level of detail for brevity. The end effector 1800 includes a first jaw 1850 and a second jaw 1870. At least one of the first jaw 1850 and the second jaw 1870 is movable to transition the end effector 1800 from an open configuration to a closed configuration to grasp tissue (T) between the first jaw 1850 and the second jaw 1870. Electrodes 1852, 1872 are configured to cooperate to deliver a bipolar energy to the tissue. An electrode 1874 is configured to deliver a monopolar energy to the tissue. In at least one example, the monopolar energy and the bipolar energy are delivered to the tissue either simultaneously, or in an alternating fashion, as illustrated in FIG. 125, to seal and/or cut the tissue, for example.

In the illustrated example, the bipolar energy and monopolar energy are generated by separate generators 1880, 1881, and are provided to the tissue by separate electrical circuits 1882, 1883 that connect the generator 1880 to the electrodes 1852, 1872, and the generator 1881 to the electrode 1874 and the return pad 1803, respectively. The power levels associated was the bipolar energy delivered to the tissue by the electrodes 1852, 1872 is set by the generator 1880, and the power levels associated with the monopolar energy delivered to the tissue by the electrode 1874 is set by the generator 1881, in accordance with the power scheme 3005', for example.

In use, as illustrated in FIG. 137, the end effector 1800 applies bipolar energy and/or monopolar energy to a tissue treatment region 1804 to seal and, in certain instances, transect the tissue. However, in certain instances, the energy is diverted from an intended target at the tissue treatment region 1804 causing an off-site thermal damage to surrounding tissue. To avoid, or at least reduce, such occurrences, the surgical instrument 1801 includes impedance sensors 1810, 1811, 1812, 1813, which are positioned between different electrodes and in different locations, as illustrated in FIG. 137, in order to detect off-site thermal damage.

In various aspects, the surgical system 1807 further includes a control circuit 1809 coupled to the impedance sensors 1810, 1811, 1812, 1813. The control circuit 1809 can detect an off-site, or an unintended, thermal damage based on one or more readings of the impedance sensors 1810, 1811, 1812, 1813. In response, the control circuit 1809 may alert a user to the off-site thermal damage, and instruct the user to pause energy delivery to the tissue treatment region 1804, or automatically pause the energy delivery, while maintaining the bipolar energy in accordance with a predetermined power scheme (e.g. power scheme 3005') to complete the tissue sealing. In certain instances, the control circuit 1809 may instruct the user to employ a mechanical knife to transect the tissue to avoid further off-site thermal damage.

Referring still to FIG. 137, the impedance sensor 1810 is configured to measure an impedance between the bipolar electrodes 1852, 1872. Further, the impedance sensor 1811 is configured to measure an impedance between the electrode 1874 and the return pad 1803. In addition, the impedance sensor 1812 is configured to measure an impedance between the electrode 1872 and the return pad 1803. In addition, the impedance sensor 1813 is configured to measure an impedance between the electrode 1852 and the return pad 1803. In other examples, additional impedance sensors are added inline between the monopolar and bipolar circuits 1882, 1883, which can be utilized to measure impedances at various locations to detect off-site thermal abnormalities with greater specificity as to the location and impedance path.

In various aspects, the off-site thermal damage occurs in tissue on one side (left/right) of the end effector 1800. The control circuit 1809 may detect the side on which the off-site thermal damage has occurred by comparing the readings of the impedance sensors 1810, 1811, 1812, 1813. In one example, a non-proportional change in the monopolar and bipolar impedance readings is indicative of an off-site thermal damage. On the contrary, if proportionality in the impedance readings is detected, the control circuit 1809 maintains that no off-site thermal damage has occurred. In one example, as described in greater detail below, the off-site thermal damage can be detected by the control circuit 1809 from a ratio of the bipolar to monopolar impedances.

Figure 139:
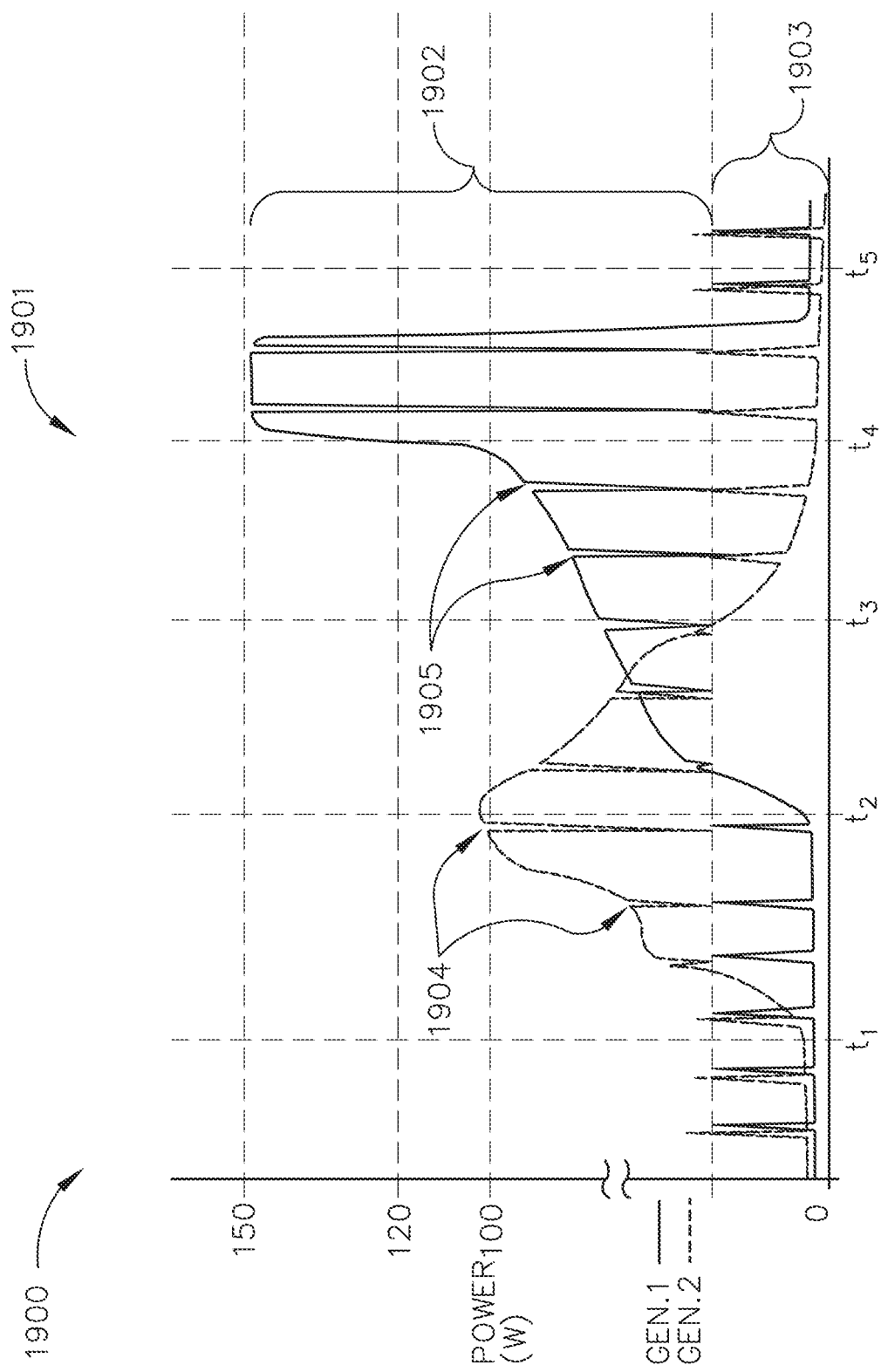
FIG. 139 is a graph illustrating a power scheme including a therapeutic portion for coagulating and cutting a tissue treatment range in a treatment cycle applied by an end effector, and non-therapeutic range, in accordance with at least one aspect of the present disclosure.

FIG. 139 illustrates a graph 1900 depicting time on the x-axis and power on the y-axis. The graph 1900 illustrates a power scheme 1901 similar in many respects to the power scheme 3005' illustrated in FIG. 125, which are not repeated in the same level of detail herein for brevity. A control circuit 3101 causes the power scheme 1901 to be applied by the generators 1880 (GEN. 2), 1881 (GEN. 1) to effect a tissue treatment cycle by the end effector 1800. The power scheme 1901 includes a therapeutic power component 1902 and a nontherapeutic, or sensing, power component 1903. The therapeutic power component 1902 defines monopolar and bipolar power levels similar to the monopolar and bipolar power levels described in connection with the power scheme 3005'. The sensing power component 1903 includes monopolar 1905 and bipolar 1904 sensing pings delivered at various points throughout the tissue treatment cycle performed by the end effector 1800. In at least one example, the sensing pings 1903, 1904 of the sensing power component are delivered at a predetermined current value (e.g. 10 mA) or a predetermined range. In at least one example, three different sensing pings are utilized to determine location/orientation of a potential off-site thermal damage.

The control circuit 3101 may determine whether energy is being diverted to a non-tissue therapy directed site during a tissue treatment cycle by causing the sensing pings 1903, 1904 to be delivered at predetermined time intervals. The control circuit 3101 may then assess return-path conductivity based on the delivered sensing pings. If it is determined that energy is being diverted from a target site, the control circuit 3101 can take one or more reactive measures. For example, the control circuit 3101 can adjust the power scheme 1901 to be applied by the generators 1880 (GEN. 2), 1881 (GEN. 1). The control circuit 3101 may pause bipolar and/or monopolar energy application to the target site. Further, the control circuit 3101 may issue an alert to a user through feedback system 3109, for example. If, however, determines that no energy diversion is detected, the control circuit 3101 continues execution of the power scheme 1901.

In various aspects, the control circuit 3101 assesses return-path conductivity by comparing a measured return-conductivity to a predetermined return-path conductivity stored in the memory 3103, for example. If the comparison indicates that the measured and predetermined return-path conductivities are different beyond a predetermined threshold, the control circuit 3101 concludes that energy is being diverted to a non-tissue therapy directed site, and performs one or more of the previously described reactive measures.

Figure 140:
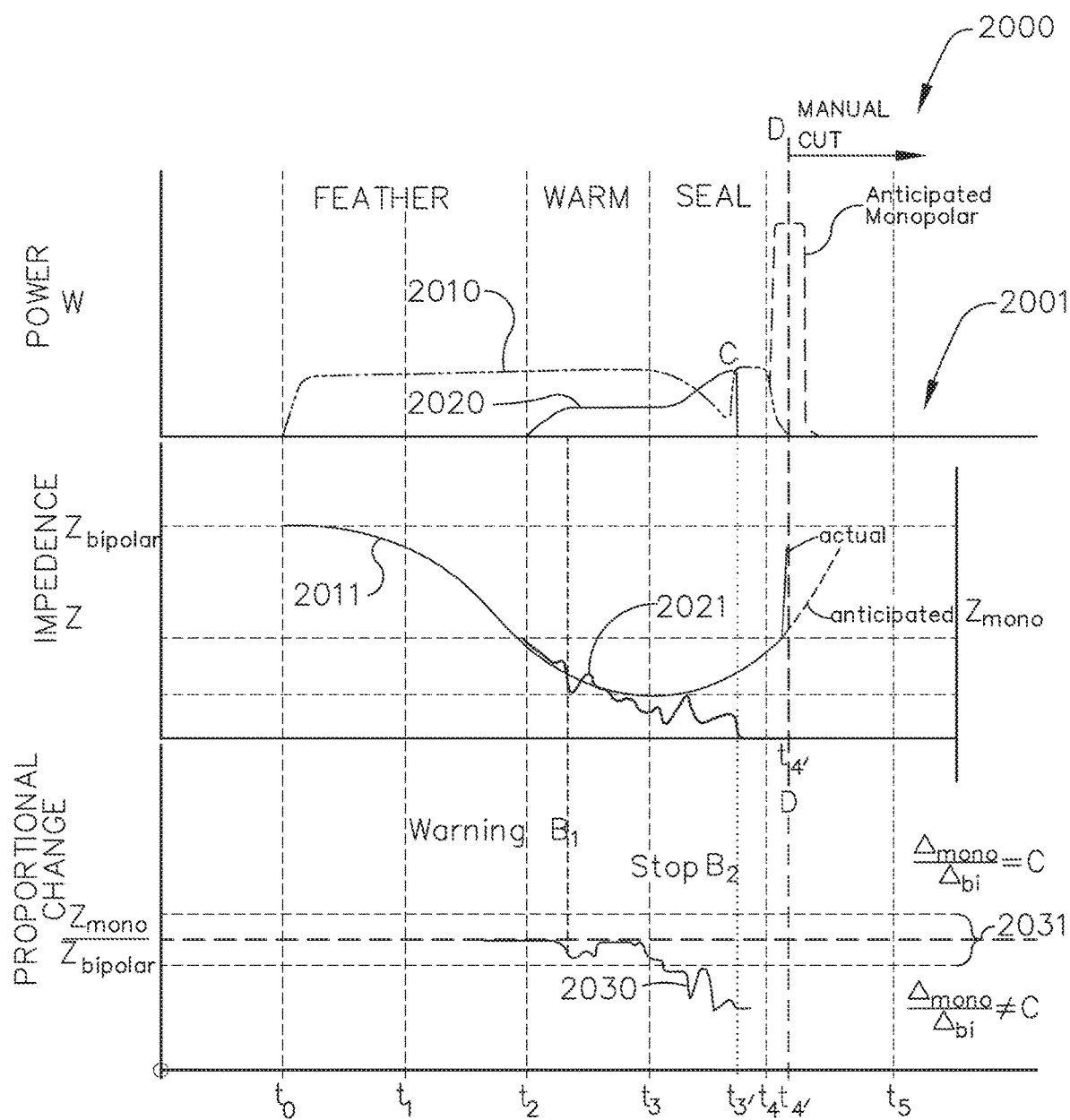
FIG. 140 is a graph illustrating a power scheme including for coagulating and cutting a tissue treatment range in a treatment cycle applied by an end effector, and corresponding monopolar and bipolar impedances and a ratio thereof, in accordance with at least one aspect of the present disclosure.

FIG. 140 is a graph 2000 illustrating a power scheme 2001 interrupted, at t3', due to a detected off-site thermal damage. The power scheme 2001 is similar in many respects to the power schemes illustrated in FIGS. 125, 139, which are not repeated herein in the same level of detail for brevity. The control circuit 1809 causes the generators 1880 (curve line 2010), 1881 (curve line 2020) to apply the power scheme 2001 to effect a tissue treatment cycle by the end effector 1800, for example. In addition to the power scheme 2001, the graph 2000 further depicts bipolar impedance 2011 ($Z_{bipolar}$), monopolar impedance 2021 ($Z_{monopolar}$), and a ratio 2030 ($Z_{monopolar}/Z_{bipolar}$) of the monopolar impedance to the bipolar impedance on the y-axis. During normal operation, while the monopolar energy and the bipolar energy are being applied to the tissue simultaneously, values of the bipolar impedance 2011 ($Z_{bipolar}$) and monopolar impedance 2021 ($Z_{monopolar}$) remain proportional, or at least substantially proportional. It follows that a constant, or at least substantially constant, impedance ratio 2030 ($Z_{monopolar}/Z_{bipolar}$) of the monopolar impedance 2021 to the bipolar impedance 2011 is maintained within a predetermined range 2031 during normal operation.

In various aspects, the control circuit 1809 monitors the impedance ratio 2030 to assess whether the monopolar energy is diverting to non-tissue therapy directed site. The diversion changes the proportionality of the detected values of the bipolar impedance 2011 ($Z_{bipolar}$) and monopolar impedance 2021 ($Z_{monopolar}$), which changes the impedance ratio 2030. A change in the impedance ratio 2030 within the predetermined range 2031 may cause the control circuit 1908 to issue a warning. If, however, the change extends to, or below, a lower threshold of the predetermined range 2031 the control circuit 1908 may take additional reactive measures.

In the illustrated example, the impedance ratio 2030 ($Z_{monopolar}/Z_{bipolar}$) remains constant, or at least substantially constant, for an initial part of treatment cycle that involves a blended monopolar and bipolar energy application to the tissue. At B1, however, a discrepancy occurs where the monopolar impedance ($Z_{monopolar}$) drops unexpectedly, or un-proportionally with, the bipolar impedance ($Z_{bipolar}$) indicating a potential off-site thermal damage. In at least one example, the control circuit 1809 monitors changes in the ratio of ratio ($Z_{monopolar}/Z_{bipolar}$) of the monopolar impedance to the bipolar impedance, and detects an off-site thermal damage if the changes persist for a predetermined amount of time, and/or change in value to, or below, a lower threshold of the predetermined range 2031. At B1, since the detected the impedance ratio 2030 is still within the predetermined range 2031, the control circuit 3101 only issues a warning through the feedback system 3109 that an off-site thermal damage has been detected, and continues to monitor the impedance ratio 2030.

At t3', the control circuit 3101 further detects that the impedance ratio 2030 has changed to a value at, or below, a lower threshold of the predetermined range 2031. In response, the control circuit 3101 may issue another warning and, optionally, may instruct the user to pause energy delivery to the tissue, or automatically pause the energy delivery, at B2, while maintaining or adjusting the power level of the bipolar energy to complete the tissue sealing without monopolar energy. In certain examples, the control circuit 1809 further instructs the user to employ a mechanical knife (t4') to transect the tissue to avoid further off-site thermal damage. In the illustrated example, the control circuit 1809 further causes the generator 1880 to adjust its power level to complete the tissue sealing without monopolar energy, and increases the time period allotted for the tissue sealing segment from time t4 to time t4'. In other words, the control circuit 1809 increases the bipolar energy delivery to the tissue to compensate for the loss of monopolar energy by increasing the bipolar power level and its delivery time.

Figure 141:
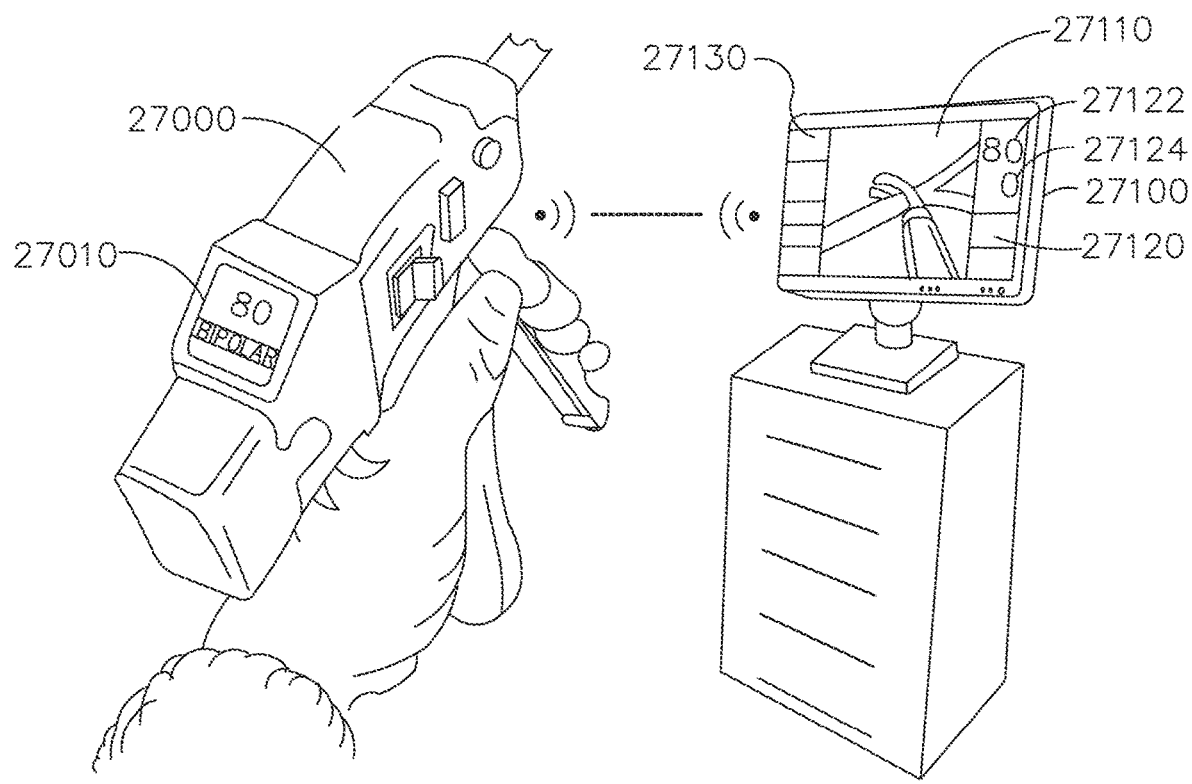
FIG. 141 is a perspective view of a surgical system comprising a surgical instrument and a display monitor, wherein the surgical instrument comprises a display screen in accordance with at least one embodiment.

A divided display system is shown in FIGS. 141-146 The divided display communicates various generator and/or surgical device parameters between a display 27010 of a handheld surgical instrument 27000 and a primary monitor display 27100. FIG. 141 depicts an example of the display 27010 of the handheld surgical instrument 27000. In various instances, the display 27010 includes a touch-sensitive graphical user interface capable of receiving user inputs. The display 27010 comprises various settings and/or modes that allow a user to customize the information and/or images shown on the display 27010 at any given time.

The surgical instrument 27000 is in communication with the main display monitor 27100. The main display monitor 27100 comprises a larger screen than the display 27010 of the surgical instrument 27000. In various instances, the main display monitor 27100 displays the same information and/or images as the display 27010 of the surgical instrument 27000. In other instances, the main display monitor 27100 displays different information and/or images than the display 27010 of the surgical instrument 27000. In various instances, the main display monitor 27100 includes a touch-sensitive graphical user interface capable of receiving user inputs. Similar to the display 27010 of the surgical instrument 27000, the main display monitor 27100 comprises various settings and/or modes that allow a user to customize the information and/or images shown on the main display monitor 27100 at any given time. As described in greater detail herein, a selected mode on the main display monitor 27100 can change the mode of the display 27010 on the surgical instrument 27000 and vice versa. Stated another way, the main display monitor 27100 and the surgical instrument display 27010 co-operate together to communicate the selected operational parameters most effectively to a user.

The depicted handheld surgical instrument 27000 comprises a combination electrosurgical functionality, wherein the surgical instrument 27000 includes an end effector comprising a first jaw and a second jaw. The first jaw and the second jaw comprise electrodes disposed thereon. The electrosurgical instrument 27000 comprises one or more power generators configured to supply power to the electrodes to energize the electrodes. More specifically, energy delivery to patient tissue supported between the first jaw and the second jaw is achieved by energizing the electrodes which are configured to deliver energy in a monopolar mode, bipolar mode, and/or a combination mode. The combination mode is configured to deliver alternating or blended bipolar and monopolar energies. In at least one embodiment, the at least one power generator comprises a battery, a rechargeable battery, a disposable battery, and/or combinations thereof. Various details regarding the operation of the first and second generators is described in greater detail in U.S. patent application Ser. No. 16/562,123, titled METHOD FOR CONSTRUCTING AND USING A MODULAR SURGICAL ENERGY SYSTEM WITH MULTIPLE DEVICES, and filed on Sep. 5, 2019, which is hereby incorporated by reference in its entirety.

The display 27010 of the surgical instrument 27000 and the main display monitor 27100 comprise divided displays to communicate numerous operational parameters to a user. The divided displays are configured to be selectively segmentable. Stated another way, a user is able to select which operational parameters to display and/or where to display the selected operational parameters. Such customization minimizes distraction by eliminating unwanted and/or unnecessary information while allowing the user to efficiently observe the information needed and/or desired to control the surgical instrument 27000 and/or to perform the surgical procedure. The display 27010 of the surgical instrument 27000 comprises a first portion 27012, wherein the power level of a particular mode is displayed. The display 27010 of the surgical instrument 27000 further comprises a second portion 27014, wherein the mode that the surgical instrument 27000 is in and/or the type of energy being delivered by the surgical instrument 27000 is identified, or otherwise communicated.

Similarly, the main display monitor 27100 comprises a segmented display; however, in various instances, the images displayed on the display monitor 27100 can be overlaid onto one another. A central portion 27110 of the main display monitor 27100 streams a live feed and/or still images of a surgical site to the procedure room. The live feed and/or images of the surgical site are captured through an appropriately positioned camera, such as an endoscope. A menu selection portion 27130 of the main display monitor 27100 prompts and/or otherwise allows a user to select which mode the main display monitor 27100 is in and/or what information a user wishes to see on the main display monitor 27100. A device status portion 27120 of the main display monitor 27100 communicates information similar to the first portion 27012 of the surgical instrument display 27010. In various instances, the device status portion 27120 is further divided into multiple sections. For example, a first portion 27122 is configured to communicate an operating parameter reflective of a bipolar mode. Such an operating parameter can be specific and/or generic. A specific operating parameter can reflect the power level of the bipolar mode, for example. A general operating parameter can indicate whether the bipolar mode is active or inactive, for example. A second portion 27124 is configured to communicate an operating parameter reflective of a monopolar mode. Such an operating parameter can be specific and/or generic. A specific operating parameter can reflect the power level of the monopolar mode, for example. A general operating parameter can indicate whether the monopolar mode is active or inactive, for example. A third portion 27126 is configured to communicate an operating parameter reflective of a smoke evacuation system. Such an operating parameter can be specific and/or generic. A specific operating parameter can reflect the power level of the smoke evacuation system, for example. A general operating parameter can indicate whether the smoke evacuation system is active or inactive, for example.

Referring now to FIGS. 142-146, the display 27010 of the surgical instrument 27000 is shown alongside a corresponding display on the main display monitor 27100. As described in greater detail herein, as a user changes a power level on the handheld surgical instrument 27000, such a power level change is reflected on the main display monitor 27100. For example, as shown in FIG. 142, a generator operating the bipolar mode is currently operating at a power level of 80 watts as indicated in the device status portion 27120 of the main display monitor 27100 and the first and second portions 27012, 27014 of the surgical instrument display 27010. More specifically, the first portion 27012 of the surgical instrument display 27010 represents the output of a generator while the second portion 27014 of the surgical instrument display 27010 represents the mode and/or type of energy. Similarly, the device status portion 27120 of the main display monitor 27100 indicates that a generator is operating the bipolar energy mode at a power level of 80 watts and a generator is operating the monopolar energy mode at a power level of zero watts. Upon receiving a command to increase the power output of the generator operating the bipolar mode to 100 watts, the surgical instrument display 27010 and the main display monitor 27100 change accordingly as shown in FIG. 143. More specifically, the first portion 27012 of the surgical instrument display 27010 now represents the power level of 100 watts, and the device status portion 27120 of the main display monitor 27100 now indicates that the generator is operating the bipolar mode at a power level of 100 watts. The main display monitor 27100 continues to indicate that the monopolar energy mode is operating at a power level of zero watts; however, the main display monitor 27100 also indicates that the smoke detection system has been activated to 20% 27126 due to the detection of smoke within the surgical site and/or the increased power level of the surgical instrument.

FIGS. 144-146 depict the display 27010 of the surgical instrument 27000 and the corresponding main display monitor 27100 when a combination of both bipolar and monopolar energies are being delivered to patient tissue. FIG. 144 shows the first portion 27012' of the surgical instrument display 27010 in a total power mode. As shown on the main display monitor 27100, the bipolar energy mode 27122 is operating at a power level of 60 watts and the monopolar energy model 27124 is operating at a power level of 60 watts. However, a combined and/or total power level of 120 watts is represented on the first portion 27012' of the surgical instrument display 27010. The main display monitor 27100 also indicates that the smoke detection system has been activated to 50% 27126 due to the detection of smoke within the surgical site and/or the increased power level of the surgical instrument. As shown in FIG. 145, the user may wish to see the individual power levels of the bipolar mode and the monopolar mode on the first portion 27012" of the surgical instrument display 27010 and the total power level on the device status portion 27122' of the main display monitor 27100. Stated another way, the information shown on the displays in FIG. 145 are reversed from the displays shown in FIG. 144. The main display monitor 27100 further indicates that the smoke detection system has been activated to 73% 27126 due to the detection of smoke within the surgical site and/or the change of power levels of the bipolar and/or monopolar modes. The pair of displays shown in FIG. 146 are similar in many respects to the pair of displays shown in FIG. 145; however, the user has selected to remove the indication of the operating level of the smoke detection system from the main display monitor 27100.

As discussed in greater detail herein, the surgical instrument display 27010 and/or the main display monitor 27100 can comprise touch-sensitive graphical user interfaces. In various instances, the surgical instrument display 27010 is used to control what is being displayed on the surgical instrument display 27010 versus what is being displayed on the main display monitor 27100. In other instances, the main display monitor 27100 is used to control what is being displayed on the surgical instrument display 27010 versus what is being displayed on the main display monitor 27100. In various instances, each display is configured to control what is displayed on its own display. In various instances, each display within a surgical system is configured to cooperatively control what is displayed on other displays within the surgical system.

In various instances, a surgical system comprises an electrosurgical device and a smoke evacuation system. As discussed in greater detail herein, the electrosurgical device is configured to deliver energy to patient tissue supported between the jaws of an end effector by energizing electrodes. The electrodes are configured to deliver energy in a monopolar mode, bipolar mode, and/or a combination mode with alternating or blended bipolar and monopolar energies. In various instances, a first generator is configured to control the bipolar energy modality and a second generator is configured to control the monopolar energy modality. A third generator is configured to control the smoke evacuation system. Various details regarding the operation of the first and second generators is described in greater detail in U.S. patent application Ser. No. 16/562,123, titled METHOD FOR CONSTRUCTING AND USING A MODULAR SURGICAL ENERGY SYSTEM WITH MULTIPLE DEVICES, and filed on Sep. 5, 2019, which is hereby incorporated by reference in its entirety.

Figure 147:
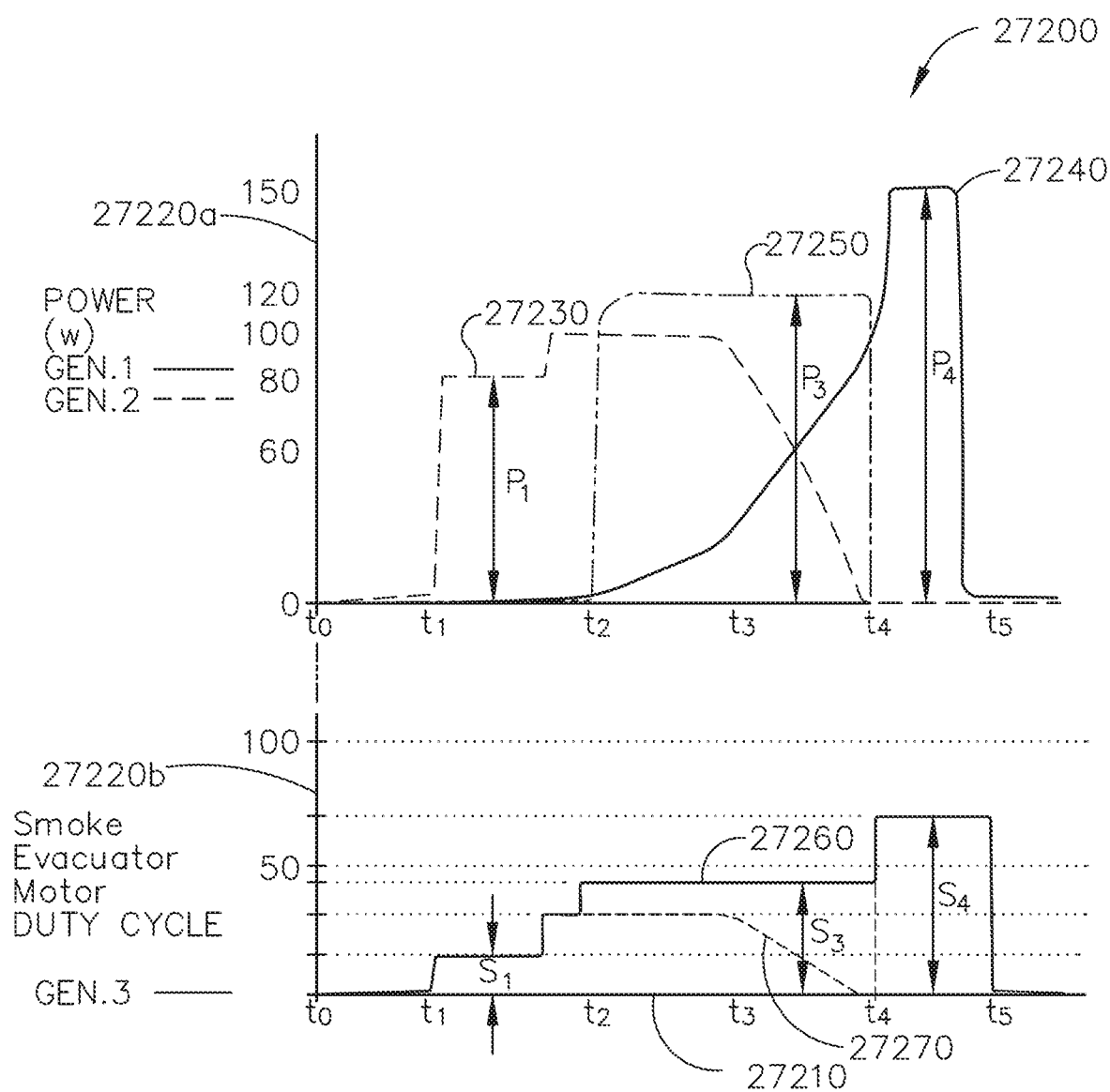
FIG. 147 is a graphical depiction of the relationship between the total effective energy delivered by one or more generators of a surgical system and a duty cycle of a motor from a smoke evacuator in accordance with at least one embodiment.

FIG. 147 is a graphical representation 27200 depicting the proportional relationship between a duty cycle of the smoke evacuation system and the total effective energy delivered to patient tissue. Time 27210 is represented along the x-axis while power (W) 27220*a* and duty cycle of the smoke evacuation system (%) 27220*b* are represented along the y-axis. The total effective energy is represented in three facets: (1) bipolar therapy 27230; (2) monopolar therapy 27240; and (3) combined energy 27250. The percentage of the smoke evacuator duty cycle is represented in two facets: (1) in response to the combined energy 27260; and (2) in response to only the bipolar therapy 27270. For example, at time $t_0$, power is not being delivered to the patient tissue and the smoke evacuation system is inactive. At time $t_1$, bipolar therapy 27230 is delivered at a first power level $P_1$. At time $t_1$, bipolar therapy 27230 is the only energy delivered to the patient tissue. As the power increased to $P_1$ during the time period of $t_0$ to $t_1$, the smoke evacuation system activated. At time $t_1$, a first percentage $S_1$ of the smoke evacuation duty cycle is utilized.

At time $t_2$, the power level of the bipolar therapy 27230 increased and monopolar therapy 27240 has begun to be delivered. At time $t_3$, the bipolar therapy 27230 decreased while the monopolar therapy 27240 increased. Overall, the combined energy 27250 has remained substantially the same from $t_2$ to $t_3$. At time $t_3$, the combined energy 27250 is delivered at a third power level $P_3$, which is higher than the first power level $P_1$ delivered at time $t_1$. As the power increased to $P_3$ during the time period of $t_1$ to $t_3$, the percentage of the smoke evacuation system duty cycle also increased. At time $t_3$, a third percentage $S_3$ of the smoke evacuation duty cycle is utilized. The third percentage $S_3$ is greater than the first percentage $S_1$. At time $t_4$, delivery of the bipolar therapy 27230 has ceased and the only energy delivered to the patient tissue is through monopolar therapy 27240. Notably, at time $t_4$, the monopolar therapy 27240 delivers energy to the patient tissue at the highest level $P_4$ of monopolar therapy delivered during the entire surgical procedure. Thus, as the delivered energy $P_4$ at time $t_4$ is greater than the delivered energy $P_3$ at time $t_3$, the percentage of the smoke evacuation duty cycle also increased. At time $t_4$, a fourth percentage $S_4$ of the smoke evacuation duty cycle is utilized. The fourth percentage S4 is greater than the third percentage $S_3$ and the first percentage $S_1$.

The graphical representation of FIG. 147 shows bipolar energy 27230 being delivered at varying levels throughout different time points of a surgical procedure. Such time points can correspond to a tissue sealing cycle in which the surgical hub commands the smoke evacuation system to increase or decrease its operating level in response to the current bipolar power level. After the tissue sealing cycle is complete, monopolar energy can be applied for a defined period of time in order to cut the patient tissue. As patient tissue is being cut, the surgical hub can command the smoke evacuation system to increase its operating level based on the increase in energy being applied to cut the tissue as such an increase in applied energy typically corresponds to an increase in smoke from burning tissue, for example. During the particular surgical procedure, the surgical hub is aware of pre-defined time points at which the energy delivery and power levels change. The pre-defined time points can vary based on the type of particular surgical procedure to be performed, for example. The pre-defined time points can vary based on patient demographics identified to the surgical hub, for example. Any detected change in the type of energy being applied and/or the level of energy being applied can trigger responses of different components of the surgical system.

Figure 148:
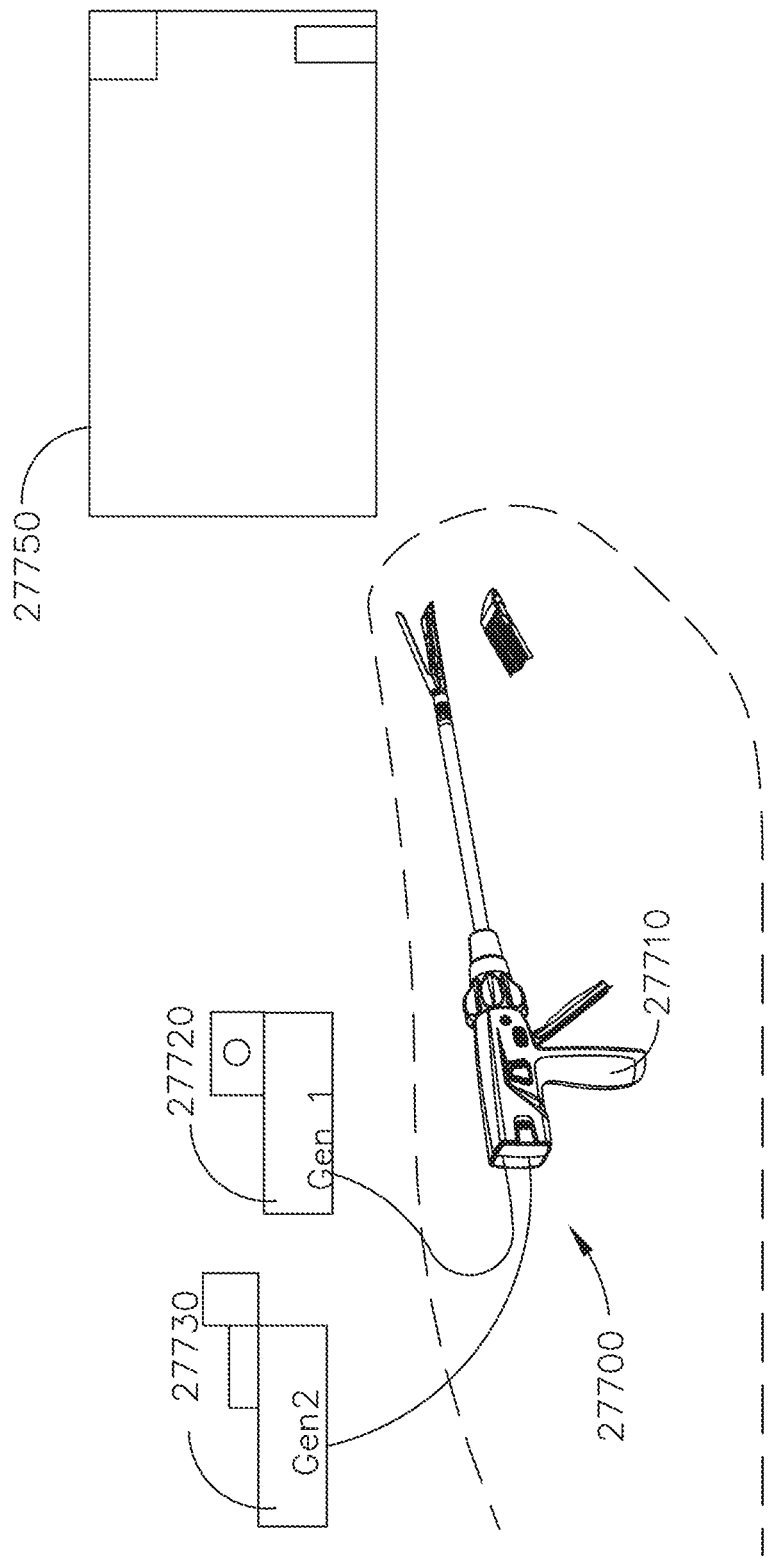
FIG. 148 is a schematic representation of a surgical system comprising a surgical hub, a combination electrosurgical instrument powered by a plurality of generators, a smoke evacuation system, and a display in accordance with at least one embodiment.

Similar to the surgical system described with respect to FIG. 147, a surgical system 27700 depicted in FIG. 148 comprises an electrosurgical instrument 27710 in communication with a surgical hub. The electrosurgical instrument 27710 is configured to deliver energy to patient tissue supported between the jaws of an end effector by electrodes which are configured to deliver energy in a monopolar mode, bipolar mode, and/or a combination mode. The electrosurgical instrument 27710 is configured to apply alternating or blended bipolar and monopolar energies to the patient tissue when in the combination mode. The surgical system 27700 further comprises a first generator 27720 configured to control the monopolar energy modality and a second generator 27730 configured to control the bipolar energy modality. A display screen 27750 is positioned in a location within a procedure room that is within a field of vision of a user. In various instances, the electrosurgical instrument 27710 comprises a display positioned thereon. As the second generator 27730 causes bipolar energy to be delivered to patient tissue, the instrument display and/or the display screen 27750 within the procedure room indicates the level of power being applied. In various instances, a level of smoke evacuation by the smoke evacuation system is indicated on the display(s), wherein the level of smoke evacuation is based on the level of power and/or type of energy being applied. As discussed in greater detail herein, when the first generator 27720 causes monopolar energy to be delivered to patient tissue and/or the second generator 27730 causes a reduced amount of bipolar energy to be delivered to patient tissue, the display(s) are configured to update the displayed, or otherwise communicated, operational parameters. As the levels of power change during the surgical procedure, such changes are communicated to the surgical hub. In response, the surgical hub is configured to automatically, or without an external prompt, alter the level of smoke evacuation to compensate for the changes in the level of energy and/or type of energy being applied to patient tissue.

At least one of the instrument display and the display screen 27750 comprise a touch-sensitive graphical user interface which is configured to receive a user input. The user is able to select what information is displayed, where the selected information is displayed on a particular display, and/or which display within the surgical system displays the desired information. In various instances, the surgical system 27700 further comprises one or more cameras positioned within the procedure room. The one or more cameras are configured to monitor movements of the user and/or the devices of the surgical system. The one or more cameras can communicate any detected movement to the surgical hub, wherein the surgical hub recognizes that the detected movement corresponds to a pre-determined command. For example, a camera can detect when a user waves an arm. A memory within the surgical hub correlates arm waving with the user's desire to clear the display of all operational parameters, so that all that remains on the display is a live feed and/or images of the surgical site. Exemplary commands that can be associated with a specific user and/or instrument movement include adjusting a position of the display(s), adjusting the view of the display(s), adjusting the information presented on the display(s), adjusting the location of the displayed information on a particular display, adjusting the size of the displayed information, controlling power levels of the generator(s), and/or controlling operational parameters of various surgical instruments of the surgical system.

Figure 149:
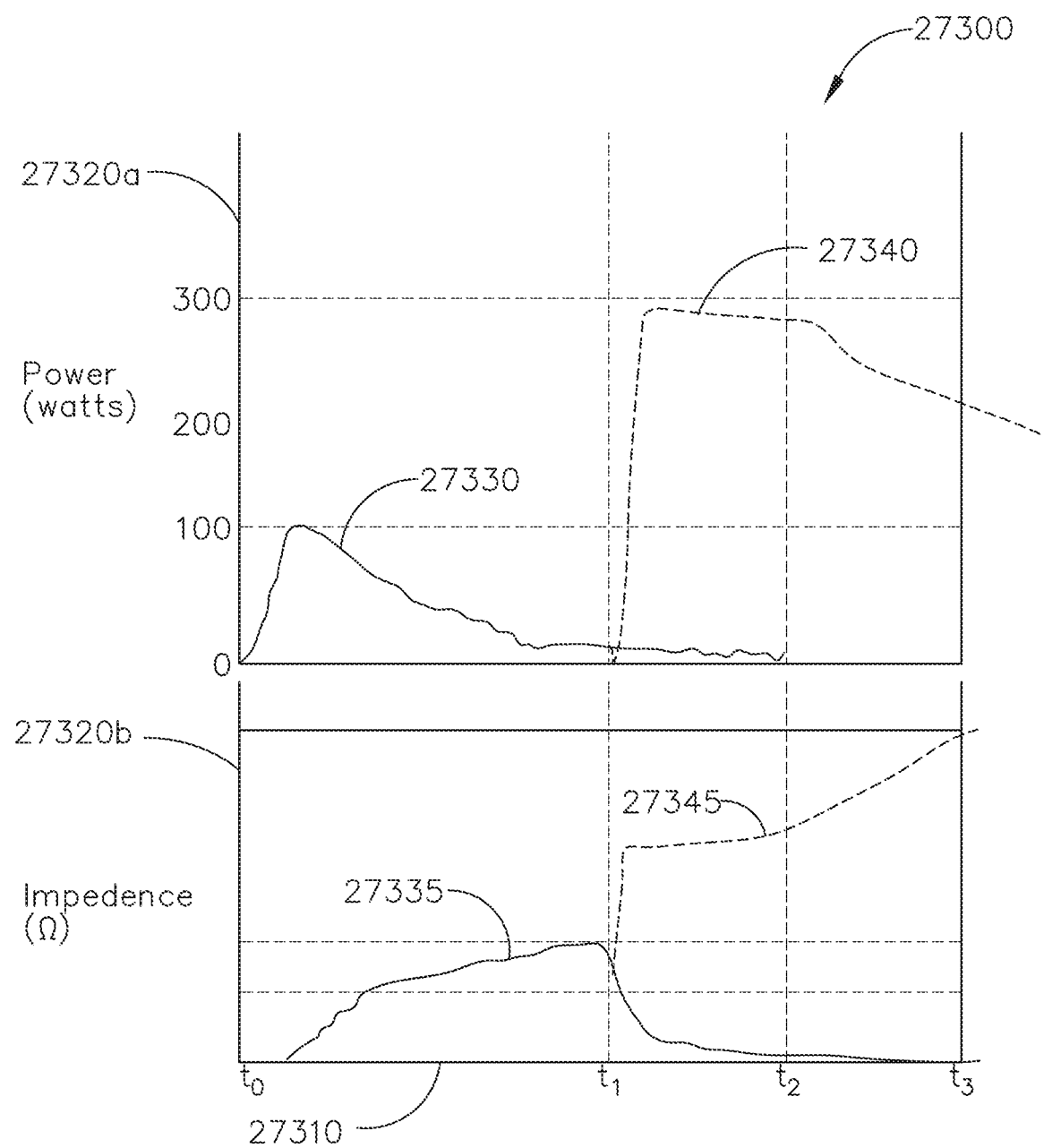
FIG. 149 is a graphical depiction of the relationship between the power supplied by one or more generators of a surgical system over time and the impedance of treated tissue over time in accordance with at least one embodiment.

As discussed with respect to the surgical system 27700, the electrosurgical instrument 27710 comprises a combination electrical modality. A monopolar modality of the electrosurgical instrument is operated by the first generator 27720, while a bipolar modality is operated by a second generator 27730. Monopolar energy is delivered to patient tissue to make an incision, or otherwise cut the treated tissue. Prior to cutting the patient tissue, bipolar energy is delivered to the tissue in order to seal and/or cauterize the target tissue. A graphical representation 27300 of the power level (wattage) of the first generator and the second generators 27320a with respect to time (t) 27310 is shown in FIG. 149. The power level is represented in two facets: (1) of the first generator 27340; and (2) of the second generator 27330. The graphical representation 27300 further depicts the relationship of tissue impedance (Ω) 27320b with respect to time (t) 27310. The tissue impedance is represented in two facets (1) in response to the monopolar energy delivered 27345; and (2) in response to the bipolar energy delivered 27335.

As the power level of the second generator 27330 increases from zero, bipolar energy is delivered to patient tissue. The impedance of the patient tissue increases in response to the application of bipolar energy 27335. Notably, the impedance of the patient tissue continues to increase for an amount of time even after the power level of the second generator 27330 begins to decrease. Stated another way, the impedance of the tissue sealed by the bipolar energy 27335 eventually decreases after the power level of the second generator 27330 is reduced absent the delivery of monopolar energy to cut the patient tissue; however, the impedance of the tissue in such instances does not necessarily immediately decrease. At time $t_1$, the power level of the first generator 27340 increases, thereby cutting the tissue through delivery of monopolar energy to the patient tissue. The impedance of the patient tissue also increases in response to the application of monopolar energy 27345. Notably, the impedance of the patient tissue exponentially grows as the tissue is cut and the power level of the first generator 27340 decreases.

FIG. 150 depicts an algorithm 27400 for controlling various components of a surgical system. The surgical system comprises a surgical instrument configured to perform an intended surgical function. In various instances, the surgical instrument is handheld and comprises a handle. A user is configured to operate various modes of the surgical instrument through an input element on the handle. As described in greater detail herein, the surgical instrument comprises a first generator configured to power a monopolar modality and a second generator configured to power a bipolar modality. The surgical system further comprises a smoke evacuation system configured to remove smoke and/or other unwanted particulates from a surgical site. The surgical instrument and/or the smoke evacuation system are in signal communication with a surgical hub, wherein the surgical hub is configured to orchestrate the appropriate response(s) of the components of the surgical system in response to a user input on the surgical instrument, the smoke evacuation system, and/or another component within the surgical system.

As shown in FIG. 150, a control algorithm 27400 begins when a user changes a mode 27410 of the surgical instrument. For example, the user may wish to increase the power level of the first generator to cut patient tissue. In another example, the user may wish for the surgical instrument to seal and/or cut patient tissue. In any event, the surgical instrument then communicates 27412, 27414 the user input to the first generator and the second generator, respectively. The surgical instrument further communicates 27415 the user input to the surgical hub. After the surgical hub is informed 27420 of the desired increase in monopolar energy, the surgical hub is configured to command the second generator 27425 to supply and/or administer an appropriate power level. Upon receiving the communication 27412 from the surgical instrument, the first generator increases a waveform 27440 in preparation for cutting patient tissue. Upon receiving the communication 27414 from the surgical instrument and the command 27425 from the surgical hub, the second generator increases the power level associated with the bipolar modality 27450 in preparation for sealing the patient tissue after the cut is performed. The second generator can then communicate 27455 its readiness to the first generator. The first generator is then able to start cutting the patient tissue 27442. Stated another way, the surgical hub prevents a monopolar electrode from being energized until the bipolar electrode has been energized to prevent cutting of tissue that has not been cauterized and/or sealed. The surgical hub is further configured to command 27426 the smoke evacuation system to increase a motor rate in response to an increase in power levels of the first and second generators. After the smoke evacuation system increases its motor rate 27430, the smoke evacuation system is configured to maintain a line of communication with the surgical hub, the surgical instrument, and/or the first and second generators throughout the duration of the surgical procedure. For example, the smoke evacuation system is configured to continuously communicate a current motor rate 27435 to the surgical hub. In such instances, the smoke evacuation system sends its current motor rate to the surgical hub every minute, or every two minutes; however, the smoke evacuation system is able to communicate its current motor rate at any suitable frequency. Upon the surgical instrument completing the desired tissue cut, the user can once again provide an input on the instrument handle to reduce the power level of the first generator and/or end the control algorithm 27400. In various instances, the control algorithm 27400 is configured to automatically reduce the power level of the first generator after a pre-determined period of time that corresponds to a completion a tissue cut. Utilizing the control algorithm 27400, the surgical hub is able to orchestrate the operating parameters of the components of the surgical system to facilitate an efficient and/or effective surgical procedure, for example.

Numerous surgical devices, tools, and/or replaceable components are often used during a particular surgical procedure. Various systems are disclosed herein that serve to, among other things, streamline the devices and/or components that are stocked within a procedure room for use during a particular procedure, minimize operator error, and/or minimize delays during surgical procedures. The systems described herein increase the efficiency of surgical procedures using, among other things, artificial intelligence and machine learning developed over the course of one or more surgical procedures.

Various components of an exemplary surgical system 27500 are shown in FIG. 151. During a particular surgical procedure, a patient rests on an operating table, or any suitable procedure surface 27510. In various instances, the particular procedure is performed at least in part using a surgical robot. The surgical robot comprises one or more robot arms 27520. Each robot arm 27520 is configured to receive a tool component 27590. The tool components 27590 are configured to cooperate with one another to perform and/or assist the clinician in performing the particular surgical procedure. The tool components may comprise, for example, a surgical stapling and/or tissue cutting tool component, a tissue grasping tool component, and/or an electrosurgical tool component. The tool components may comprise other distinguishing characteristics such as, for example, size, manufacturer, date of manufacture, number of previous uses, and/or expiration date.

The surgical system 27500 further comprises a surgical hub 27530. Various surgical hubs are described in described in U.S. patent application Ser. No. 16/209,395, titled METHOD OF HUB COMMUNICATION, and filed on Dec. 4, 2018, which is hereby incorporated by reference in its entirety. The surgical hub 27530 comprises a memory 27535 that stores various suitable, or otherwise appropriate, combinations of tool components 27590 to be used during the particular procedure. Stated another way, the memory 27535 of the surgical hub 27530 comprises a stored information bank which can be used to indicate which tool components 27590 are appropriate for utilization during a selected procedure.

Prior to performing a desired surgical procedure, a clinician can notify, or otherwise communicate, details relating to the desired surgical procedure and/or the patient to the surgical hub 27530. Such details can include, for example, an identity of the surgical procedure, an identity of the clinician performing the surgical procedure, and/or a biometric profile of the patient, for example. The surgical hub 27530 is then configured to utilize one or more of the communicated details to evaluate and/or determine which tool components 27950 are necessary and/or appropriate to perform the desired surgical procedure. In various instances, the surgical hub 27530 is configured to assess which modes of each tool components 27950 are appropriate for performing the desired surgical procedure on the particular patient.

As shown in FIG. 151, four robot arms 27250 surround, or are otherwise attached to, the operating table 27510. Three tool components 27590 are connected to three corresponding robot arms 27250, leaving one robot arm free to receive an additional tool component. A plurality of unique tool components 27560, 27570, 27580 are shown stored on a moving stand 27550 within the procedure room. As discussed above, the type and/or functionality of the tool components 27560, 27570, 27580 can be different. In such instances, the surgical hub 27530 evaluates the available tool components 27560, 27570, 27580 and identifies an appropriate tool component for attachment to the surgical robot. An appropriate tool component is identified based on one or more factors such as, which tool-type and/or function is still needed by the surgical robot and/or which tool component completes a pre-determined pairing of tool components that is associated with the desired surgical procedure, for example. In various instances, the surgical robot comprises a memory storing pre-determined tool component pairings based on a particular surgical procedure and/or a particular patient demographic, for example. In such instances, the surgical robot is able to identify an appropriate tool component for attachment to the surgical robot based on the identity of the tool components already attached.

In other instances, the tool components 27560, 27570, 27580 comprise the same type and/or functionality; however, the tool components 27560, 27570, 27580 comprise at least one other distinguishing characteristic such as, for example, a difference in size, manufacturer, expiration date, and/or number of previous uses. The surgical hub 27530 evaluates a profile of each available tool component 27560, 27570, 27580 and identifies an appropriate tool component based on which characteristics are compatible with the profiles of the other selected and/or attached tool components 27590.

As shown in FIG. 151 each tool component 27560, 27570, 27580 comprises a QR code 27565, 27575, 27585 positioned at any suitable location thereon, wherein each QR code contains a profile of information representative of the tool component to which the QR code is coupled. A user scans and/or reads the QR codes 27565, 27575, 27585 using any appropriate scanning tool 27540. The scanning tool 27540 then communicates the QR code and/or the information contained within the QR code to the surgical hub 27530. In instances where the QR code itself is communicated by the scanning tool 27540 to the surgical hub 27530, a processor of the surgical hub 27530 is configured to decrypt the profile of information contained by the received QR code. While the depicted embodiment comprises QR codes, the tool components can comprise any suitable memory device such as a barcode, an RFID tag, and/or a memory chip, for example.

The surgical hub 27530 is configured to alert a user when a tool component is not acceptable and/or desirable for use during the surgical procedure. Such an alert can be communicated through various forms of feedback, including, for example, haptic, acoustic, and/or visual feedback. In at least one instance, the feedback comprises audio feedback, and the surgical system 27500 can comprise a speaker which emits a sound, such as a beep, for example, when an error is detected. In certain instances, the feedback comprises visual feedback and the tool components can each comprise a light emitting diode (LED), for example, which flashes when an error is detected. In certain instances, the visual feedback can be communicated to a user through an alert presented on a display monitor within a field of vision of the clinician. In various instances, the feedback comprises haptic feedback and a component of the surgical system 27500 can comprise an electric motor comprising an eccentric element which vibrates when an error is detected. The alert can be specific or generic. For example, the alert can specifically state that the QR code on the tool component is unable to be detected, or the alert can specifically state that the QR code comprises information representative of an incompatible and/or defective tool component.

For example, a user attempts to attach a first tool component 27560 to the available robot arm 27590 of the surgical robot. Prior to attaching the first tool component 27560 to the robot arm 27590, the scanning tool 27540 scans the QR code 27565 displayed on the first tool component 27560. The scanning tool 27540 communicates the QR code 27565 and/or the information contained within the QR code 27565 to the surgical hub 27530. The surgical hub 27530 compares the information contained within the QR code 27565 to a stored list of acceptable tool components associated with the particular surgical procedure and/or a stored list of acceptable tool components compatible with the tool components that are currently attached to the surgical robot. In this instance, the surgical hub 27530 fails to recognize and/or locate the first tool component 27560 within its memory 27535. Thus, the first tool component 27560 is not recommended and/or appropriate for use with the surgical robot. As discussed above, the surgical hub 27530 is configured to alert the clinician of the incompatibility of the first tool component 27560 with the surgical robot and/or the particular surgical procedure. In various instances, the surgical system 27500 can prevent the first tool component 27560 from being attached thereto through a mechanical and/or electrical lockout, for example. Such an attachment lockout prevents a clinician from missing and/or simply ignoring the alert issued by the surgical system 27500. Stated another way, the attachment lockout requires the clinician to take affirmative steps in overriding the error communicated by the surgical system 27500. In such instances, an override can be activated to allow the clinician to override any system lockout and utilize operational functions of the first tool component 27560. In various instances, an override is unavailable in order to prevent a clinician from utilizing the functionality of the first tool component 27560 while the first tool component 27560 is recognized as incompatible for use with the surgical robot.

Similarly, a user attempts to attach a second tool component 27570 to the available robot arm 27590 of the surgical robot. Prior to attaching the second tool component 27570 to the robot arm 27590, the scanning tool 27540 scans the QR code 27575 displayed on the second tool component 27570. The scanning tool 27540 communicates the QR code 27575 and/or the information contained within the QR code 27575 to the surgical hub 27530. The surgical hub 27530 compares the information contained within the QR code 27575 to a stored list of acceptable tool components associated with the particular surgical procedure and/or a stored list of acceptable tool components compatible with the tool components that are currently attached to the surgical robot. In this instance, the surgical hub 27530 fails to recognize and/or locate the second tool component 27570 within its memory 27535. Thus, the second tool component 27570 is not recommended and/or appropriate for use with the surgical robot. As discussed above, the surgical hub 27530 is configured to alert the clinician of the incompatibility of the second tool component 27570 with the surgical robot and/or the particular surgical procedure. In various instances, the surgical system 27500 can prevent the second tool component 27570 from being attached thereto. Such an attachment lockout prevents a clinician from missing and/or simply ignoring the alert issued by the surgical system 27500. Stated another way, the attachment lockout requires the clinician to take affirmative steps in overriding the error communicated by the surgical system 27500. In such instances, an override can be activated to allow the clinician to override any system lockout and utilize operational functions of the second tool component 27570. In various instances, an override is unavailable in order to prevent a clinician from utilizing the functionality of the second tool component 27570 while the second tool component 27570 is recognized as incompatible for use with the surgical robot.

A user attempts to attach a third tool component 27580 to the available robot arm 27590 of the surgical robot. Prior to attaching the third tool component 27580 to the robot arm 27590, the scanning tool 27540 scans the QR code 27585 displayed on the third tool component 27580. The scanning tool 27540 communicates the QR code 27585 and/or the information contained within the QR code 27585 to the surgical hub 27530. The surgical hub 27530 compares the information contained within the QR code 27585 to a stored list of acceptable tool components associated with the particular surgical procedure and/or a stored list of acceptable tool components compatible with the tool components that are currently attached to the surgical robot. In this instance, the surgical hub 27530 successfully recognizes and/or locates the third tool component 27580 within its memory 27535. The third tool component 27580 is then determined to be appropriate for use with the surgical robot during the particular surgical procedure and/or with the other attached tool components. In various instances, the surgical hub 27530 is configured to alert the clinician of the compatibility of the third tool component 27580 with the surgical robot. In other instances, the surgical system 27500 simply does not prevent the attachment of the third tool component 27580 to the available robot arm 27590.

In various instances, the memory 27535 of the surgical hub 27530 is configured to store the QR codes associated with each tool component used during a particular surgical procedure. The surgical hub 27530 can then analyze the collected information to form observations and/or conclusions regarding factors such as, for example, the efficiency and/or the effectiveness of a particular tool component and/or a plurality of tool components during a surgical procedure. The observations and/or conclusions can then be used by the surgical hub 27530 in selecting and/or recommending which tool components to utilize during future surgical procedures.

FIG. 152 depicts a surgical system 27600 comprising one or more cameras configured to assist a clinician in performing an efficient and/or successful surgical procedure. Similar to the surgical system 27500, the surgical system 27600 comprises an operating table 27610, or any suitable procedure surface. The surgical system 27600 further comprises a surgical hub 27650, and a device tower 27660. Various surgical hubs are described in described in U.S. patent application Ser. No. 16/209,395, titled METHOD OF HUB COMMUNICATION, and filed on Dec. 4, 2018, which is hereby incorporated by reference in its entirety.

The surgical system 27600 further comprises a camera system including one or more cameras 27640 positioned at various locations throughout the procedure room. In the depicted embodiment, two cameras 27640 are positioned in opposing corners of the procedure room; however, the cameras 27640 can be positioned and/or oriented in any suitable location that allows the cameras 27640 to cooperatively capture the procedure room in an unimpeded manner. An artificial intelligence protocol detects and/or identifies various devices, equipment and/or personnel and their corresponding locations and/or orientations within the procedure room.

The cameras 27640 of the camera system are in communication with the surgical hub 27650. Stated another way, the live feeds of the cameras 27640 can be transmitted to the surgical hub 27650 for processing and analysis. Through analysis of the footage collected by the cameras 27640, the surgical hub 27650 is able to maintain a real-time inventory of the devices, equipment, and/or personnel within the procedure room and/or monitor and/or control the interactions between the detected devices, equipment and/or personnel. Using the images and/or data collected by the camera system, the surgical hub 27650 is configured to be informed regarding the identities of the detected devices, alert a clinician regarding compatibility concerns about the detected devices, and/or control various components of the surgical system 27600 based on the presence and/or operation of the detected devices. The surgical hub 27650 is configured to compare any detected devices to determine compatibility between the devices and/or during the particular surgical procedure, facilitate the cooperation of two devices that are intended to work together, and/or facilitate the cooperation of two devices that build off of one another's sensed and/or controlled operations.

As shown in FIG. 152, an anesthesia cart 27670 and a preparation table 27620 are positioned within a procedure room. The preparation table 27620 is configured to support various surgical tools and/or devices in a manner that makes them easily accessible for use during a surgical procedure. Such surgical tools and/or devices can include replaceable staple cartridges of varying sizes or shaft assemblies comprising end effectors of varying sizes and/or functionalities, for example. In the depicted embodiment, the preparation table 27620 supports a first device 27630*a*, a second device 27630*b*, and a third device 27630*c*.

The cameras 27640 are configured to detect identifying information regarding the devices, equipment, and/or personnel located within the procedure room. For example, the cameras 27640 can capture a serial number printed on a visible portion of each device 27630*a*, 27630*b*, 27630*c*, such as on a packaging of the devices, for example. In various instances, the packaging comprises a QR code printed thereon which contains information regarding a device contained therein. The QR code is captured by the cameras 27640 and communicated to the surgical hub 27650 for analysis and identification of the staple cartridge.

Such an identification system can be useful, for example, during a surgical procedure in which a surgical stapling instrument comprising an end effector, wherein a 60 mm staple cartridge is configured to be seated within the end effector. The cameras 27640 within the procedure room are configured to capture the presence of a surgical stapling instrument in the form of a live video feed and/or a still image, for example. The cameras 27640 then communicate the captured image(s) to the surgical hub 27650. The surgical hub 27650 is configured to identify the surgical stapling instrument based on the image(s) received from the cameras 27640. In instances where the surgical hub 27650 is aware of the surgical procedure to be performed, the surgical hub 27650 can alert the clinician as to whether or not the identified surgical stapling instrument is appropriate. For example, knowing that a 45 mm staple cartridge is associated with a particular surgical procedure, the surgical hub 27650 can alert the clinician that the detected surgical stapling instrument is inappropriate, as the end effector of the detected surgical stapling instrument is configured to receive a 60 mm staple cartridge.

The surgical hub 27650 comprises a memory 27655 that stores the technical requirements and/or specifications associated with various devices therein. For example, the memory 27655 of the surgical hub 27650 recognizes that the surgical stapling instrument described above is configured to receive a 60 mm staple cartridge. In various instances, the memory 27655 can also recognize a particular brand of 60 mm staple cartridges compatible with the surgical stapling instrument. In various instances, the cameras 27640 can capture the presence of replaceable staple cartridges in the form of a live video feed and/or a still image, for example. The cameras 27640 then communicate the captured image(s) to the surgical hub 27650. The surgical hub 27650 is configured to identify a characteristic of the replaceable staple cartridge based on the image(s) received from the cameras 27640. Such characteristics include, for example, a size, a brand, and/or a manufacturing lot. As discussed in greater detail herein, the alert can be specific or generic. In instances where the cameras 27640 capture the presence of packaging containing a replaceable 45 mm staple cartridge, the surgical hub 27650 is configured to alert the clinician that an incompatible staple cartridge has been mistakenly stocked within the room. Such an alert can prevent surgical instrument malfunction, injury to the patient, and/or valuable time loss during the surgical procedure, for example.

As discussed above, the camera system is configured to facilitate the surgical hub 27650 in coordinating the devices detected within the procedure room. In various instances, a combination energy device and a smoke evacuation system are detected by the camera system. The combination energy device is configured to apply bipolar energy and monopolar energy to patient tissue. As the camera system and/or the surgical hub 27650 detects an activation of the combination energy device, the presence of the combination energy device at a position near the patient, and/or the presence of smoke in the procedure room, the surgical hub 27650 is configured to direct a generator to enable the smoke evacuation system, for example.

A surgical instrument can utilize a measurable, or otherwise detectable, characteristic of an end effector to confirm a particular stage of the surgical procedure and/or to control various operational parameters of the surgical instrument. Such a characteristic can include, for example, a distance between the jaws of the end effector. A memory of the surgical instrument and/or the surgical hub comprises stored information that associates a particular jaw gap distance with a particular stage of a surgical procedure. For example, when the distance between the jaws is measured between 0.030 inches and 0.500 inches, the surgical instrument and/or the surgical hub confirms that the end effector is delivering bipolar energy to patient tissue. In other instances, when the distance between the jaws is measured between 0.030 inches and 0.500 inches, the surgical instrument and/or the surgical hub activates a generator, thereby initiating the delivery of bipolar energy to the patient tissue. Stated another way, a detection of a characteristic of the surgical instrument and/or contacted patient tissue can be used by the surgical instrument and/or the surgical hub in order to confirm and/or adapt the operation of the surgical instrument.

FIG. 153 comprises a chart depicting various operational parameters and/or specifications of a surgical instrument that correspond to various stages of a surgical procedure. Similar to the surgical instruments described in greater detail herein, the surgical instrument 27000 depicted in FIGS. 154-156 comprises a combination electrosurgical functionality, wherein the surgical instrument includes an end effector comprising a first jaw 27810 and a second jaw 27820. At least one of the first jaw 27810 and the second jaw 27820 are movable with respect to one another, and the end effector is configurable between an open configuration and a closed configuration. The first jaw 27810 comprises a first tissue-supporting and/or tissue-contacting surface 27815, and the second jaw 27820 comprises a second tissue-supporting and/or tissue-contacting surface 27825. The first jaw 27810 and the second jaw 27810 comprise electrodes disposed thereon. The electrosurgical instrument 27000 comprises one or more power generators configured to supply power to the electrodes to energize the electrodes. More specifically, energy delivery to patient tissue supported between the first jaw and the second jaw is achieved by the electrodes which are configured to deliver energy in a monopolar mode, bipolar mode, and/or a combination mode. Alternating or blended bipolar and monopolar energies are configured to be delivered in the combination mode. In at least one embodiment, the at least one power generator comprises a battery, a rechargeable battery, a disposable battery, and/or combinations thereof.

The end effector 27800 is used to perform various end effector functions during the surgical procedure. At an original time $t_0$, the end effector 27800 is not in contact with the patient tissue $T_{r0}$. Thus, the electrodes of the end effector 27800 are not delivering any energy. At the original time $t_0$, the patient tissue $T_{r0}$ is in a relaxed, uncompressed state. The end effector 27800 is shown in the open configuration. In the open configuration, a distance do spans anywhere from 0.500 inches to 0.700 inches between the first tissue-supporting surface 27815 and the second tissue-supporting surface 27825. Stated another way, the tissue-supporting surfaces 27815, 27825 are separated a maximum distance do of 0.500 inches to 0.700 inches from one another when the end effector 27800 is in the open configuration.

At a first time $t_1$, the jaws 27810, 27820 of the end effector 27800 are brought into contact with the patient tissue $T_{r1}$. At least a portion of the patient tissue $T_{r1}$ is positioned in between the jaws 27810, 27820 of the end effector 27800 as the end effector 27800 moves from the open configuration toward the closed configuration. As the jaws 27810, 27820 are moved toward the closed configuration, the tissue $T_{11}$ is compressed therebetween. At time $t_1$, the end effector 27800 is configured to deliver bipolar energy to the patient tissue $T_{11}$. The application of bipolar energy allows the end effector 27800 to feather through parenchymal cells, for example. The end effector 27800 is in a partially closed configuration at time $T_1$. A first distance $d_1$ spans anywhere from 0.030 inches to 0.500 inches between the first tissue-supporting surface 27815 and the second tissue-supporting surface 27825 at time $t_1$. Stated another way, the tissue-supporting surfaces 27815, 27825 are separated a maximum first distance $d_1$ of 0.030 inches to 0.500 inches when the end effector is delivering bipolar energy to the patient tissue $T_{r1}$ at time $t_1$. A detailed depiction of the jaws 27810, 27820 of the end effector 27800 delivering bipolar energy to the patient tissue $T_{r1}$ at a first time $t_1$ is shown in FIG. 154.

At a second time $t_2$, the jaws 27810, 27820 of the end effector 27800 maintain contact with the patient tissue $T_{r2}$. At least a portion of the patient tissue $T_{r2}$ is positioned in between the jaws 27810, 27820 of the end effector 27800. At time $t_2$, the end effector 27800 is configured to deliver a combination of bipolar and monopolar energies to the patient tissue $T_{r2}$. The application of bipolar energy and monopolar energy allows the end effector 27800 to warm the patient tissue $T_{r2}$. The end effector 27800 is in a partially closed configuration at time $t_2$; however, the end effector 27800 is closer to a fully-closed configuration at time $t_2$ than the end effector 27800 at time $t_1$. More specifically, a second distance $d_2$ spans anywhere from 0.010 inches to 0.030 inches between the first tissue-supporting surface 27815 and the second tissue-supporting surface 27825 at time $t_2$. Stated another way, the tissue-supporting surfaces 27815, 27825 are separated a maximum second distance $d_2$ of 0.010 inches to 0.030 inches when the end effector is delivering bipolar and monopolar energies to the patient tissue $T_{12}$ at time $t_2$. A detailed depiction of the jaws 27810, 27820 of the end effector 27800 delivering bipolar and monopolar energies to the patient tissue $T_{r2}$ at a second time $t_2$ is shown in FIG. 155.

At a third time $t_3$, the jaws 27810, 27820 of the end effector 27800 maintain contact with the patient tissue $T_{r3}$. At least a portion of the patient tissue $T_{r3}$ is positioned in between the jaws 27810, 27820 of the end effector 27800. At time $t_3$, the end effector 27800 is configured to continue delivering a combination of bipolar and monopolar energies to the patient tissue $T_{r3}$. The continued application of bipolar energy and monopolar energy allows the end effector 27800 to seal the patient tissue $T_{r3}$. The end effector 27800 is in a partially closed and/or fully-closed configuration at time $t_3$. Stated another way, the end effector 27800 is in the fully-closed configuration and/or closer to the fully-closed configuration at time $t_3$ than the end effector 27800 at time $t_2$. More specifically, a third distance $d_3$ spans anywhere from 0.003 inches to 0.010 inches between the first tissue-supporting surface 27815 and the second tissue-supporting surface 27825 at time $t_3$. Stated another way, the tissue-supporting surfaces 27815, 27825 are separated a maximum third distance $d_3$ of 0.003 inches to 0.100 inches when the end effector is delivering bipolar and monopolar energies to the patient tissue $T_{13}$ at time $t_3$. A detailed depiction of the jaws 27810, 27820 of the end effector 27800 delivering bipolar and monopolar energies to the patient tissue at a third time $t_3$ is also shown in FIG. 155.

At a fourth time $t_4$, the jaws 27810, 27820 of the end effector 27800 maintain contact with the patient tissue $T_{r4}$. At least a portion of the patient tissue $T_{r4}$ is positioned in between the jaws 27810, 27820 of the end effector 27800 as the end effector 27800. At time $t_4$, the end effector 27800 is configured to deliver monopolar energy to the patient tissue $T_{r4}$. The application of monopolar energy allows the end effector 27800 to cut through the patient tissue M. The end effector 27800 is in a partially closed and/or fully-closed configuration at time $t_4$. Stated another way, the end effector 27800 is in the fully-closed configuration and/or closer to the fully-closed configuration at time $t_4$ than the end effector 27800 at time $t_2$. More specifically, a fourth distance $d_4$ spans anywhere from 0.003 inches to 0.010 inches between the first tissue-supporting surface 27815 and the second tissue-supporting surface 27825 at time $t_4$. Stated another way, the tissue-supporting surfaces 27815, 27825 are separated a maximum fourth distance $d_4$ of 0.003 inches to 0.010 inches when the end effector is delivering monopolar energy to the patient tissue $T_{r4}$ at time $t_4$. A detailed depiction of the jaws 27810, 27820 of the end effector 27800 delivering monopolar energy to the patient tissue $T_{r4}$ at a fourth time $t_4$ is shown in FIG. 156.

The graph 27900 shown in FIG. 157 illustrates the relationships between various operational parameters and/or specifications of the surgical instrument of FIGS. 153-156 with respect to time. The surgical instrument and/or the surgical hub can utilize the depicted relationships to confirm proper functionality of the surgical instrument during the surgical procedure and/or to operate and/or adjust various functionalities of the surgical instrument in response to one or more measured parameters. The graph illustrates (1) the change 27930 in the power (W) 27920a of a generator controlling a bipolar modality of the surgical instrument time 27910; (2) the change 27935 in the power (W) 27920a of a generator controlling a monopolar modality of the surgical instrument over time 27910; (3) the change 27940 in the distance between the jaws of the end effector 27920b over time 27910; (4) the change 27950 in the force of the jaw motor (F) 27920c over time 27910; and (5) the change 27960 in the velocity of the jaw motor (V) 27920d over time 27910.

At time $t_0$, the electrodes of the end effector are not delivering energy to patient tissue, and the end effector is not yet in contact with patient tissue. The distance 27920b between the jaws of the end effector is at a maximum at time $t_0$ due to the end effector being in the open configuration. The force to clamp 27950 the jaws is minimal from time $t_0$ to time $t_1$ as the end effector experiences little to no resistance from patient tissue when moving from the open configuration toward the closed configuration. The jaws of the end effector continue to close around patient tissue from time $t_1$ to time $t_2$, over which time period the end effector begins to deliver bipolar energy 27930. The distance between the jaws of the end effector is less at time $t_1$ than at time $t_0$. From time $t_1$ to time $t_2$, the jaw motor velocity 27960 begins to slow down as the force to clamp 27950 the jaws of the end effector begins to increase.

As described with respect to FIGS. 153-166, a combination of monopolar energy 27935 and bipolar energy 27930 is delivered to patient tissue from time $t_2$ to time $t_3$. The jaws of the end effector continue to close around patient tissue during this time period. The distance between the jaws of the end effector is less at time $t_2$ than at time $t_1$. The particular distance between the jaws of the end effector at time $t_2$ indicates to the surgical instrument and/or the surgical hub that a tissue-warming phase of the surgical procedure has been reached and that a combination of monopolar and bipolar energies should be and/or is being delivered to the patient tissue. From time $t_2$ to time $t_3$, the jaw motor velocity continues to decrease and is less than the jaw motor velocity at $t_1$. The force required to clamp the jaws suddenly increases between time $t_2$ and time $t_3$, thereby confirming to the surgical instrument and/or the surgical hub that a combination of monopolar and bipolar energies is being delivered to the patient tissue.

Monopolar and bipolar energies continue to be delivered to the patient tissue, and the patient tissue is sealed from time $t_3$ to time $t_4$. As the end effector reaches its fully-closed configuration at time $t_3$, the force to clamp the jaws also reaches a maximum; however, the force to clamp the jaws remains stable between time $t_3$ and time $t_4$. The power level of the generator delivering monopolar energy increases between time $t_3$ and time $t_4$, while the power level of the generator delivering bipolar energy decreases between time $t_3$ and time $t_4$. Ultimately between time $t_4$ and $t_5$, monopolar energy is the only energy being delivered in order to cut the patient tissue. While the patient tissue is being cut, the force to clamp the jaws of the end effector may vary. In instances where the force to clamp the jaws decreases 27952 from its steady-state level maintained between time $t_3$ and $t_4$, an efficient and/or effective tissue cut is recognized by the surgical instrument and/or the surgical hub. In instances where the force to clamp the jaws increases 27954 from its steady-state level maintained between time $t_3$ and $t_4$, an inefficient and/or ineffective tissue cut is recognized by the surgical instrument and/or the surgical hub. In such instances, an error can be communicated to the user.

In various instances, the clamping operation of the jaws of the end effector can be adjusted based on a detected characteristic of contacted patient tissue. In various instances, the detected characteristic comprises tissue thickness and/or tissue type. For example, operations such as a range of gap distances between the jaws during a jaw closure stroke, a load threshold value, a rate of jaw closure, current limits applied during the jaw closure stroke, and/or a wait time between the jaw closure stroke and delivery of energy can be adjusted based on the detected thickness of patient tissue. In various instances, the detected characteristic of the contacted patient tissue can be used to adjust tissue weld parameters. More specifically, the detected characteristic can be used to adjust a multi-frequency sweep of impedance sensing, a balance and/or sequence of energy modality, an energy delivery level, an impedance shutoff level, and/or a wait time between energy level adjustments, for example.

As discussed in greater detail above, a surgical instrument and/or a surgical hub can utilize measured tissue characteristics to control and/or adjust an operational parameter of the surgical instrument. For example, tissue impedance can be detected as patient tissue is positioned between the jaws of an end effector. The detection of tissue impedance alerts the surgical instrument and/or the surgical hub that the jaws of the end effector are in contact with and/or near patient tissue. Referring now to FIG. 158, a graph 28000 illustrates the tissue impedance 28020 calculated over time 28010. When the jaws of the end effector are not in contact with patient tissue, the tissue impedance 28030a is infinite. As the jaws of the end effector are clamped around the patient tissue positioned therebetween, the patient tissue comes into contact with both jaws. In such instances, the tissue impedance 28030b is measureable. The ability to measure tissue impedance indicates to the surgical instrument and/or the surgical hub that patient tissue is appropriately positioned between the jaws of the end effector. The surgical instrument and/or the surgical hub can then initiate an operation, such as applying bipolar and/or monopolar energies to the patient tissue, for example.

In various instances, the surgical instrument and/or the surgical hub can utilize the magnitude of the detected tissue impedance to determine a phase of the surgical procedure. For example, as shown in FIG. 158, the tissue impedance 28030b is measured at a first level upon initial contact between the jaws of the end effector and the patient tissue. The surgical instrument can then begin to deliver bipolar energy to the patient tissue. Upon the detected tissue impedance 28030b increasing to and/or above a first pre-determined level, the surgical instrument begins to deliver a combination of bipolar and monopolar energies to the patient tissue to warm the patient tissue and/or to form a seal. As the detected tissue impedance 28030b continues to increase, the tissue impedance 28030b reaches and/or exceeds a second pre-determined level, at which point the surgical instrument ceases delivery of the bipolar energy while continuing to deliver monopolar energy to cut the patient tissue. Ultimately, the tissue impedance reaches an infinite level as the patient tissue is no longer positioned between the jaws of the end effector upon completion of the cut. In such instances, the surgical instrument and/or the surgical hub can cease delivery of the monopolar energy.

In various instances, strain can be a metric used to adjust operational parameters of the surgical instrument such as the clamping mechanism, for example. However, contact between the jaws of an end effector and patient tissue is desirable for an accurate estimation of compressive strain. As discussed in greater detail in reference to FIG. 158, a surgical instrument and/or a surgical hub can determine that contact exists between the jaws of the end effector and patient tissue by detected tissue impedance. FIG. 159 illustrates an end effector 28100 comprising a first jaw 28110 and a second jaw 28120, wherein the end effector is in an open configuration. A gap $D_0^A$ is defined between the first jaw 28110 and the second jaw 28120 in the open configuration. The jaws 28110, 28120 of the end effector 28100 are configured to receive patient tissue therebetween. At an initial time $t_0$, patient tissue $T_{A,0}$ is positioned in between the first jaw 28110 and the second jaw 28120. Notably, the patient tissue $T_{A,0}$ is in contact with both the first jaw 28110 and the second jaw 28120. Stated another way, a thickness of the patient tissue $T_{A,0}$ is greater than or equal to the gap $D_0^A$. As at least one of the first jaw 28110 and the second jaw 28120 move toward one another, the patient tissue compresses and the gap $D_1^A$ defined between the first jaw 28110 and the second jaw 28120 is reduced. The patient tissue $T_{A,1}$ is shown compressed between the first jaw 28110 and the second jaw 28120 at time $t_1$. The compressive strain can be calculated using the equation shown in FIG. 159. Because the patient tissue $T_{A,0}$ was in contact with the jaws 28110, 28120 of the end effector 28100 at time $t_0$, the applied strain is calculated accurately.

FIG. 160 illustrates the end effector 28100 of FIG. 159 in the open configuration. A gap $D_0^B$ is defined between the first jaw 28110 and the second jaw 28120 in the open configuration. The jaws 28110, 28120 of the end effector 28100 are configured to receive patient tissue therebetween. At an initial time $t_0$, patient tissue $T_{B,0}$ is positioned in between the first jaw 28110 and the second jaw 28120. However, unlike the patient tissue $T_{A,0}$ the patient tissue $T_{B,0}$ is not in contact with both the first jaw 28110 and the second jaw 28120. Stated another way, a thickness of the patient tissue $T_{B,0}$ is less than or equal to the gap $D_0^B$. As at least one of the first jaw 28110 and the second jaw 28120 move toward one another, the gap $D_1^B$ defined between the first jaw 28110 and the second jaw 28120 is reduced. The patient tissue $T_{B,1}$ is shown compressed between and/or in contact with the first jaw 28110 and the second jaw 28120 at time $t_1$. The compressive strain can be calculated using the equation shown in FIG. 160; however, the calculated compressive strain will be overestimated as the patient tissue $T_{B,0}$ was not in contact with the jaws 28110, 28120 of the end effector 28100 at time $t_0$.

As described above, calculating compressive strain by utilizing the gap defined between the first jaw and the second jaw of the end effector when the end effector is in the open configuration only leads to an accurate calculation when the patient tissue is in contact with both jaws of the end effector at an initial time $t_0$. Therefore, using the standard gap defined between the first jaw and the second jaw of the end effector when the end effector is in the open configuration is not desirable. Instead, the gap defined between the first jaw and the second jaw of the end effector when patient tissue initially contacts both jaws should be used when calculating compressive strain. An end effector is shown in the open configuration 28150 in FIG. 161. Notably, the patient tissue is not in contact with both end effector jaws 28110, 28120. Thus, no dimensions and/or specifications of the end effector in this configuration 28150 should be used in calculating compressive strain. As at least one of the first jaw 28110 and the second jaw 28120 continue to move toward one another, a gap $D_0^C$ is defined between the first jaw 28110 and the second jaw 28120. At an initial time $t_0$, patient tissue $T_{C,0}$ is positioned in between the first jaw 28110 and the second jaw 28120. Notably, the patient tissue $T_{C,0}$ is now in contact with both the first jaw 28110 and the second jaw 28120. Stated another way, a thickness of the patient tissue $T_{C,0}$ is greater than or equal to the gap $D_0^C$. As at least one of the first jaw 28110 and the second jaw 28120 continue to move toward one another, the patient tissue compresses and the gap $D_1^C$ defined between the first jaw 28110 and the second jaw 28120 is reduced. The patient tissue $T_{C,1}$ is shown compressed between the first jaw 28110 and the second jaw 28120 at time $t_1$. The compressive strain can be calculated using the equation shown in FIG. 161. As the patient tissue $T_{C,0}$ was in contact with the jaws 28110, 28120 of the end effector 28100 at time $t_0$ and the gap $D_0^C$ defined between the first jaw 28110 and the second jaw 28120 at the point of initial tissue contact was realized, the applied strain is calculated accurately.

A motor control program of a combination electrosurgical instrument can utilize detected tissue stability as an input. The surgical instrument can detect compression rate and/or can measure the creep of the patient tissue compressed between end effector jaws to determine tissue stability. The control program can be modified to adjust wait times between end effector functions, define when to make an additional tissue stability determination, and/or adjust the rate of jaw clamping based on the determined tissue stability.

As shown in FIG. 162, an end effector 28250 comprises a first jaw 28254 and a second jaw 28256, wherein at least one of the first jaw 28254 and the second jaw 28256 is configured to move toward one another, wherein patient tissue T is configured to be positioned therebetween. FIG. 162 provides a schematic representation of the various positions of the first jaw 28254 and the second jaw 28256 with respect to patient tissue T during a jaw clamping stroke. The gap 28220*a* defined between the jaws of the end effector and the motor current 28220*b* required to clamp the jaws of the end effector vary over time 28210 due, at least in part, to tissue stability measurement. An initial slope $S_0$ corresponds to the jaw gap 28230 change between when the jaws are fully open to the point at which an initial contact is made between the jaws and the patient tissue T. The resulting motor current 28240 remains low while no tissue contact is present up until the end effector jaws contact the patient tissue T. The surgical system is configured to monitor the current 28220*b* over time 28210 to identify when the current slop flattens—i.e., when the tissue stabilizes. When the current slope flattens, the surgical system is configured to take the difference between the peak current at the time at which the end effector made initial contact with the tissue and the point at which the current flattens out. Stated another way, the jaws are able to continue clamping the tissue positioned therebetween when a wait time expires, wherein the wait time is defined by the time it takes for the tissue compression to stabilize. The creep of the motor current drives the next stage of motor current and velocity to the desired jaw gap, or level of tissue compression. The measurement of creep is repeated to drive next stages of motor current and velocity until the final jaw cap, or level of tissue compression, is achieved.

In addition to sensing parameters associated with the jaw clamping stroke, the surgical system can monitor additional functions to adjust and/or refine operational parameters of the surgical instrument. For example, the surgical system can monitor an orientation of the surgical instrument with respect to the user and/or the patient, the impedance of tissue positioned between the jaws of the end effector to determine tissue position and/or tissue composition, the level of grounding to the patient, and/or leakage current. Leakage current can be monitored to determine secondary leakage from other devices and/or to create parasitic generated energy outputs through capacitive coupling.

In various instances, a surgical instrument is configured to modify instrument and/or generator settings and/or control programs using local unsupervised machine learning. In such instances, the surgical instrument may update and/or adjust local functional behaviors based on a summarization and/or aggregation of data from various surgical procedures performed with the same surgical instrument. Such functional behaviors can be adjusted based on previous uses and/or preferences of a particular user and/or hospital. In such instances, a control program of the surgical instrument recognizes the same user and automatically modifies a default program with the preferences of the identified user. The surgical instrument is able to be updated by receiving regional and/or global updates and/or improvements of digitally enabled control programs and/or displayed information through interaction with a non-local server.

In various instances, a surgical instrument is configured to modify instrument and/or generator settings and/or control programs using global aggregation of instrument operational parameters and/or surgical procedure outcomes. A global surgical system is configured to collect data regarding related and/or contributing instrument parameters such as, for example, outcomes, complications, co-morbities, cost of surgical instrument, instrument utilization, procedure duration, procedure data, and/or patient data. The global surgical system is further configured to collect data regarding generator operation data such as, for example, impedance curves, power levels, energy modalities, event annotation, and/or adverse incidents. The global surgical system is further configured to collect data regarding intelligent device operation parameters such as, for example, clamp time, tissue pressure, wait times, number of uses, time of the patient on the operating table, battery levels, motor current, and/or actuation strokes. The global surgical system is configured to adapt default control programs and/or update existing control programs based on the detected operational parameters. In this way, each surgical instrument within the global surgical system is able to perform the most effective and/or efficient surgical procedures as possible.

FIG. 163 illustrates a network 28300 of surgical instruments 28310 that communicate with a cloud-based storage medium 28320. The cloud-based storage medium 28320 is configured to receive data relating to operational parameters from the surgical instrument 28310 that was collected over numerous surgical procedures. The data is used by the cloud-based storage medium 28320 to optimize control programs to achieve efficient and/or desirable results. The cloud-based storage medium 28320 is further configured to analyze all of the collected data in random batches 28340. The results of the analysis from the random batches 28340 can further be used in re-defining a control program. For example, the data collected within Batch A might be representative of significantly different wear profiles. A conclusion might then be able to be made from this data that suggests that instruments that adjust power rather than clamp current degrade faster, for example. The cloud-based storage medium 28320 is configured to communicate this finding and/or conclusion with the surgical instrument. The surgical instrument could then maximize the life of the instrument by adjusting clamp current instead of power and/or the surgical system could alert a clinician of this finding.

FIG. 163 illustrates a network 28300 of surgical instruments 28310 that communicate with a cloud-based storage medium 28320. The cloud-based storage medium 28320 is configured to receive data relating to operational parameters from the surgical instrument 28310 that was collected over numerous surgical procedures. The data is used by the cloud-based storage medium 28320 to optimize control programs to achieve efficient and/or desirable results. The cloud-based storage medium 28320 is further configured to analyze all of the collected data in random batches 28340. The results of the analysis from the random batches 28340 can further be used in re-defining a control program. For example, the data collected within Batch A might be representative of significantly different wear profiles. A conclusion might then be able to be made from this data that suggests that instruments that adjust power rather than clamp current degrade faster, for example. The cloud-based storage medium 28320 is configured to communicate this finding and/or conclusion with the surgical instrument. The surgical instrument could then maximize the life of the instrument by adjusting clamp current instead of power and/or the surgical system could alert a clinician of this finding.

The information gathered from the network 28300 of surgical instruments 28310 by the cloud-based storage medium 28320 is presented in graphical form in FIGS. 164 and 165. More specifically, a relationship between the gap 28430 defined between the jaws of the end effector from the point of initial tissue contact changes over time during a surgical procedure as a function of jaw motor clamp current 28440 is shown in FIG. 164. The number of times that a particular end effector has reached a fully-clamped state during the jaw clamping stroke impacts the amount of force needed to clamp the same thickness tissue. For example, the jaws of the end effector are able to clamp to a greater degree with less current for instruments fully-clamped 1-10 times 28430*a* than instruments fully-clamped 10-15 times 28430*b*. Furthermore, the jaws of the end effector are able to clamp to a greater degree with less current for instruments fully-clamped 10-15 times 28430*b* than instruments fully-clamped 16-20 times 28430*c*. Ultimately, more force, and therefore current, is needed to clamp the same thickness tissue to the same fully-clamped gap as the surgical instrument continues to be used. A control program can be modified using the collected information from the surgical instruments 28310 and the cloud-based storage medium 28320 to perform a more efficient and/or time-effective jaw clamping stroke.

The current required to clamp the same thickness tissue by achieving the same fully-clamped gap between the jaws of the end effector is used to set a motor current threshold for a generator. As shown in FIG. 165, the motor current threshold is lower for an end effector that has reached a fully-clamped state less than ten times, as less current is required to achieve the fully-clamped state. Thus, a control program sets a lower threshold generator power of newer end effectors than the threshold generator power of older end effectors. If the same generator power was used in an older end effector than what is used in a newer end effector, the tissue may not be sufficiently clamped and/or compressed between the jaws of the end effector. If the same generator power was used in a newer end effector that what is used in an older end effector, the tissue and/or the instrument may be damaged as the tissue may be over-compressed by the jaws of the end effector.

In various instances, a surgical system comprises modular components. For example, the surgical system comprises a surgical robot comprising robot arms, wherein the robot arms are configured to receive tools of different capabilities thereon. A control program of the surgical system is modified based on the modular attachments, such as the type of tools connected to the surgical robot arms, for example. In other instances, the surgical system comprises a handheld surgical instrument configured to receive different and/or replaceable end effectors thereon. Prior to performing an intended surgical function, the handheld surgical instrument is configured to identify the attached end effector and modify a control program based on the determined identity of the end effector.

The surgical system is configured to identify the attached modular component using adaptive and/or intelligent interrogation techniques. In various instances, the surgical system uses a combination of electrical interrogations in combination with a mechanical actuation interrogation to determine the capacities and/or the capabilities of an attached component. Responses to interrogations can be recorded and/or compared to information stored within a memory of the surgical system to establish baseline operational parameters associated with the identified modular attachment. In various instances, the established baseline parameters are stored within the memory of the surgical system to be used when the same or a similar modular attachment is identified in the future.

In various instances, an electrical interrogation signal is sent from a handle of a surgical instrument to an attached modular component, wherein the electrical interrogation signal is sent in an effort to determine an identity, an operational parameter, and/or a status of the attached modular component. The attached modular component is configured to send a response signal with the identifying information. In various instances, no response is received to the interrogation signal and/or the response signal comprises unidentifiable information. In such instances, a surgical instrument can perform a default function in order to assess the capabilities of the attached modular component. The default function is defined by conservative operational parameters. Stated another way, the default operational parameters used during a performance of the default function are defined to a particular level so as to avoid damage to the surgical instrument and/or the attached modular component, injury to the patient, and/or injury to the user. The surgical instrument is configured to utilize results of the default function in order to set an operating program specific to the attached modular component.

For example, a surgical instrument can perform a tissue cutting stroke, wherein a cutting member traverses through an attached end effector from a proximal position toward a distal position. In instances where the surgical instrument is unable to identify the attached end effector, the surgical instrument is configured to perform the tissue cutting stroke using the default operational parameters. Utilizing a position of the cutting member within the end effector at the end of the tissue cutting stroke, the surgical instrument can determine a length of the tissue cutting stroke associated and/or appropriate for completion with the attached end effector. The surgical instrument is configured to record the distalmost position of the cutting member in order to set additional operational parameters associated with the attached end effector. Such additional operational parameters include, for example, a speed of the cutting element during the tissue cutting stroke and/or the length of the end effector.

The default function can also be used to determine a current state and/or status of the attached modular component. For example, the default function can be performed to determine if the attached end effector is articulated and/or to what degree the attached end effector is articulated. The surgical instrument is then configured to adjust a control program accordingly. A length of the cutting stroke changes as the end effector is articulated across a range of articulation angles. Stated another way, the length of the cutting stroke is different when the end effector is in articulated state as compared to when the end effector is in an unarticulated state. The surgical instrument is configured to update a control program to perform cutting strokes spanning the length associated with the last detected full stroke. The surgical instrument is further configured to use the length of the last completed cutting stroke to determine if the full length of the cutting stroke is accomplished and/or completed with the current control program when the end effector is unarticulated compared to when the end effector is articulated.

In various instances, the surgical system can perform an intelligent assessment of a characteristic of the attached component. Such a characteristic includes, for example, tissue pad wear, degree of attachment usage, and/or operating condition of the attachment. Stated another way, the surgical system is configured to assess the functionality and/or condition of the attached component. Upon detecting the characteristic of the attached modular component, a control program used to operate the surgical system is adjusted accordingly.

A surgical instrument comprises one or more tissue pads positioned on the jaws of an end effector. It is generally well known that tissue pads tend to degrade and wear over time due to frictional engagement with a blade when no tissue is present therebetween, for example. The surgical instrument is configured to determine a degree of tissue pad wear by analyzing the remaining tissue pad thickness and/or stiffness, for example. Utilizing the determined status of the tissue pad(s), the surgical instrument adjusts a control program accordingly. For example, the control program can alter an applied pressure and/or a power level of the surgical instrument based on the determined status of the tissue pad(s). In various instances, the power level of the surgical instrument can be automatically reduced by a processor of the surgical instrument in response to a detected thickness of the tissue pad(s) that is less than a threshold thickness.

A surgical instrument comprises a combination electrosurgical functionality, wherein the surgical instrument includes an end effector comprising a first jaw and a second jaw. At least one of the first jaw and the second jaw is configured to move toward one another to transition the end effector between an open configuration and a closed configuration. The first jaw and the second jaw comprise electrodes disposed thereon. The electrosurgical instrument comprises one or more power generators configured to supply power to the electrodes to energize the electrodes. The surgical instrument can assess a degree of charring and/or tissue contamination on one or more of the end effector jaws by measuring an impedance when the end effector is in the closed configuration without any patient tissue positioned therebetween. A pre-determined impedance can be stored within a memory of the surgical instrument, wherein if the impedance exceeds the pre-determined threshold, the jaws comprise an undesirable level of char and/or tissue contamination thereon. As discussed in greater detail herein, an alert can be issued to a user upon detection of an undesirable level of char. In various instances, an operational parameter can automatically be adjusted by a processor of the surgical instrument and/or a surgical hub in response to the detected closed jaw impedance. Such operational parameters include power level, applied pressure level, and/or advanced tissue cutting parameters, for example.

As shown in FIG. 166, a graphical representation 28500 illustrates a relationship 28530 between the measured impedance 28250 and a number of activation cycles 28510. A baseline impedance is measured and recorded within the memory prior to any energy activation (n=0 activations). As discussed above, the impedance is measured when the end effector of the surgical instrument is in the closed configuration and no patient tissue is positioned therebetween. The surgical instrument and/or a surgical hub prompts a user to transition the end effector into the closed configuration for the closed jaw impedance to be measured. Such prompts can be delivered at pre-defined activation intervals, such as n=5, 10, 15, etc., for example. As char and/or tissue contamination accumulate on the jaws of the end effector, impedance increases. At and/or above a first pre-determined level 28540, the surgical instrument and/or the surgical hub is configured to alert the user of such char accumulation and advise the user to clean the end effector. At and/or above a second pre-determined level 28550, the surgical instrument and/or the surgical hub can prevent the user from using various operational functions of the surgical instrument until the end effector is cleaned. The operational lockout can be removed upon cleaning of the end effector, assuming that the measured impedance has reduced to an acceptable level.

As discussed above, the surgical hub and/or the surgical instrument is configured to alert a user when a pre-determined impedance is met and/or exceeded. Such an alert can be communicated through various forms of feedback, including, for example, haptic, acoustic, and/or visual feedback. In at least one instance, the feedback comprises audio feedback, and the surgical instrument can comprise a speaker which emits a sound, such as a beep, for example, when an error is detected. In certain instances, the feedback comprises visual feedback and the surgical instrument can comprise a light emitting diode (LED), for example, which flashes when an error is detected. In certain instances, the visual feedback can be communicated to a user through an alert presented on a display monitor within a field of vision of the user. In various instances, the feedback comprises haptic feedback, and the surgical instrument can comprise an electric motor comprising an eccentric element which vibrates when an error is detected. The alert can be specific or generic. For example, the alert can specifically state that the closed jaw impedance exceeded a pre-determined level, or the alert can specifically state the measured impedance.

In various instances, the surgical instrument and/or the surgical hub is configured to detect parameters such as integral shaft stretch, damage, and/or tolerance stack up to compensate for functional parameter operations of motorized actuators. The surgical instrument is configured to alert a user when a detected parameter of the attached end effector and/or shaft is close to being and/or is outside of desirable operating ranges specific to the attached component. In addition to alerting the user, in various instances, operation of the surgical instrument is prevented when it has been detected that the surgical instrument is incapable of operating within a pre-defined envelope of adjustment. The surgical instrument and/or the surgical hub comprises an override, wherein the user is allowed to override the lockout in certain pre-defined conditions. Such pre-defined conditions include an emergency, the surgical instrument is currently in use during a surgical procedure where the inability to use the surgical instrument would result in harm to the patient, and a single use override to allow for one additional use of the surgical instrument at the discretion of the user. In various instances, an override is also available to allow a user to perform a secondary end effector function that is unrelated to a primary end effector function. For example, if a surgical instrument prevents the jaws of the end effector from being articulated, the user may activate the override to allow the surgical instrument to articulate the end effector.

A surgical system can adapt a control program configured to operate a surgical instrument in response to a detected instrument actuation parameter, an energy generator parameter, and/or a user input. A determined status of the surgical instrument is used in combination with the user input to adapt the control program. The determined status of the surgical instrument can include whether an end effector is in its open configuration, whether an end effector is in its closed configuration and/or whether a tissue impedance is detectable, for example. The determined status of the surgical instrument can include more than one detected characteristic. For example, the determined status of the surgical instrument can be assessed using a combination of two or more measures, a series of ordered operations, and/or interpretations of a familiar user input based on its situational usage. The control program is configured to adjust various functions of the surgical instrument such as the power level, an incremental step up or step down of power, and/or various motor control parameters, for example.

A surgical system comprises a surgical instrument including a combination electrosurgical functionality, wherein the surgical instrument includes an end effector comprising a first jaw and a second jaw with electrodes disposed thereon. The electrosurgical instrument comprises one or more power generators configured to supply power to the electrodes to energize the electrodes. More specifically, energy delivery to patient tissue supported between the first jaw and the second jaw is achieved by the electrodes which are configured to deliver energy in a monopolar mode, bipolar mode, and/or a combination mode with alternating or blended bipolar and monopolar energies. As described in greater detail herein, the surgical system can adapt a level of energy power activation of the one or more generators based on various monitored parameters of the surgical instrument.

The surgical system is configured to adapt energy power activation based on instrument monitored parameters. In various instances, the surgical system can monitor the sequence in which various surgical instrument functions are activated. The surgical system can then automatically adjust various operating parameters based on the activation of surgical instrument functions. For example, the surgical system can monitor the activation of rotation and/or articulation controls and prevent the ability for the surgical instrument to deliver energy to patient tissue while such secondary non-clamp controls are in use.

In various instances, the surgical system can adapt instrument power levels to compensate for detected operating parameters such as inadequate battery and/or motor drive power levels, for example. The detection of inadequate battery and/or motor drive power levels can indicate to the surgical system that clamp strength of the end effector is impacted and/or impaired, thereby resulting in undesirable control over the patient tissue positioned therebetween, for example.

The surgical system can record operating parameters of the surgical instrument during periods of use that are associated with a particular intended function. The surgical system can then use the recorded operating parameters to adapt energy power levels and/or surgical instrument modes, for example, when the surgical system identifies that the particular intended function is being performed. Stated another way, the surgical system can automatically adjust energy power levels and/or surgical instrument modes with stored preferred operating parameters when a desired function of the surgical instrument is identified and/or the surgical instrument can adjust energy power levels and/or surgical instrument modes in an effort to support and compliment the desired function. For example, a surgical system can supplement a detected lateral loading on the shaft with application of monopolar power, as detected lateral loading on the shaft often results from abrasive dissection with the end effector in its closed configuration. The surgical system decided to apply monopolar power, as the surgical system is aware, through previous procedures and/or through information stored in the memory, that monopolar power results in improved dissection. In various instances, the surgical system is configured to apply the monopolar power proportionate to increases in the detected lateral load.

The surgical system can adapt a control program configured to operate a surgical instrument in response to a detected end effector parameter. As shown in FIG. 167, a surgical instrument can utilize measured tissue conductance to automatically modify a gap clamp control program. Tissue conductance is measured at two frequencies such as 50 kHz and 5 MHz, for example. Low frequency conductance (GE) is driven by extracellular fluid, whereas high frequency conductance (GI) is driven by intracellular fluid. The intracellular fluid levels change through as cells become damaged, for example. The end effector is configurable in an open configuration and a closed configuration. Thus, as the end effector is motivated from its open configuration toward its closed configuration, the jaws of the end effector compress the tissue positioned therebetween. During the tissue compression, changes in the conductance between the two frequencies can be detected and/or recorded. The surgical system is configured to adapt the control program to control end effector clamp compression based on the ratio of low frequency conductance (GE) to high frequency conductance (GI). The surgical system adapts the control program until a discrete pre-determined point and/or until an inflection point is approached, whereby the pre-determined point and/or the inflection point indicate that cellular damage could be near.

More specifically, FIG. 167 is a graphical representation 29000 of relationships between measured tissue conductance 29100, a ratio of low frequency conductance to high frequency conductance 29200, dimension of jaw aperture 29300, and jaw motor force 29400 over the duration 29010 of a jaw clamp stroke. At the beginning of the jaw clamp stroke, measured tissue conductance is at its lowest as the jaws of the end effector initially come into contact with patient tissue, and the jaw aperture 29300 is at its largest value when the end effector is in its open configuration. Due, at least in part, to the small amount of resistance provided against the jaws from the tissue positioned therebetween, the jaw motor force is low at the beginning of the jaw clamp stroke. Prior to compression, but after contact between the patient tissue and the jaws of the end effector, the low frequency conductance 29110 increases indicating the presence of extracellular fluid within the captured tissue. Similarly, prior to compression, but after contact between the patient tissue and the jaws of the end effector, the high energy conductance 29120 increases indicating the presence of intracellular fluid.

As the end effector begins to move toward its closed configuration, the jaws of the end effector begin to clamp the tissue positioned therebetween, and thus, the jaw aperture 29300 continues to decrease. The tissue begins to be compressed by the jaws; however until fluid begins to expel from the compressed tissue, the patient tissue is not desirable to be sealed by the surgical instrument. The jaw motor force continues to increase during the jaw clamp stroke, as increased resistance is expelled against the end effector jaws by the captured tissue.

After the initial expulsion of extracellular fluid causes a decrease in the low frequency conductance (GE) 29110, the low frequency conductance (GE) 29110 remains relatively constant during the jaw clamp stroke. The high frequency conductance (GI) 29120 remains relatively constant during the jaw clamp stroke until after the patient tissue is sealed. As the tissue continues to be compressed after the seal is completed, intracellular tissue damage occurs and the intracellular fluid is expelled. At such point, the high frequency conductance 29120 decreases, causing a spike in the ratio 29210 of low frequency conductance to high frequency conductance. A tissue damage threshold 29220 is predetermined to alert a user and/or automatically prompt the surgical system to modify operational parameters when the spike in the ratio 29210 of low frequency conductance to high frequency conductance reaches and/or exceeds the tissue damage threshold 29220. At such point, the surgical system is configured to modify the control program to stop motivating the jaws of the end effector toward the closed configuration of the end effector and/or begin motivating the jaws of the end effector back toward the open configuration of the end effector. In various instances, the surgical system is configured to modify the control program to reduce the jaw clamp force. Such adaptation of the control program prevents additional tissue damage.

A surgical system is configured to modify a control program based on cooperative dual inputs. More specifically, a surgical system can vary a motor actuation rate based on a user input and pre-defined settings. For example, the more force that a user applies to a handle control, the faster the motor is actuated to trigger the system. In various instances, a handle control can be used to communicate different commands to the surgical system depending on its situational usage. More specifically, the surgical system can monitor and/or record a particular user input. The particular user input can be analyzed for its length, duration, and/or any suitable characteristic that can be used to distinguish the input. For example, a handle of a surgical instrument can include a trigger, wherein the trigger is configured to control shaft rotation. In various instances, faster actuation of the trigger corresponds to an increase in the rate at which the shaft is rotated; however, the maximum force (current) threshold of the motor remains constant. In other instances, faster actuation of the triggers corresponds to an increase in force being applied while a rotation speed threshold remains the same. Such control can be further differentiated by the shaft rotation speed being increased based on the duration that a user actuates the trigger while the force is based on the rate at which the trigger is actuated.

In various instances, motor actuation control is based on a combination of a pre-defined setting and a detection of an instrument operating parameter and/or a user control parameter. FIG. 168 is a graphical representation 29500 of the relationship between actual jaw closure speed 29520 and a trigger speed indicated by a user input 29510. The jaw closure speed 29520 resulting solely from a corresponding user input 29510 is represented by a first line 29530. As the user input trigger speed 29510 increases, the jaw closure speed 29520 also increases. Such a relationship 29530 is determined without the consideration of any additional parameters. The jaw closure speed 29520 resulting from a corresponding user input 29510 and a determination of thick tissue positioned between the jaws of the end effector is represented by a second line 29540. As the user input trigger speed 29510 increases, the jaw closure speed 29520 also increases; however, the jaw closure speed 29520 is less than if the user input trigger speed was being considered alone. The additional consideration of tissue thickness slows the jaw closure speed down in order to prevent damage to the patient tissue and/or the surgical instrument, for example.

A surgical system comprises numerous components. For example, the surgical system comprises numerous handheld surgical instruments, a surgical hub, and a surgical robot. In various instances, each component of the surgical system is in communication with the other components and can issue commands and/or alter a control program based on at least one monitored parameter and/or a user input. The surgical system comprises means to determine which system is in charge and which system makes portions of operational decisions. This designation can be changed based on situational awareness, the occurrence of pre-determined events, and/or the exceedance of thresholds. In various instances, a command protocol can be established within the surgical system to indicate a type of command each component is able to issue and/or to which components within the surgical system the issuing component can direct a command.

The command protocol can use pre-defined thresholds to determine when a control hand-off is warranted. For example, the surgical system comprises a generator and a handheld surgical instrument including various controls therein. At the beginning of a surgical procedure, the generator is initially in control and adjusts the power based on detected impedance. The generator uses the detected impedance and/or the current power level to command a pressure control within a handle of the surgical instrument to follow specific pressure needs. At a point during the surgical procedure, a lower impedance threshold is exceeded indicative that the generator algorithm has detected an electrical short. The generator passes control to the pressure control within the handle by instructing the pressure control to determine if tissue is still positioned between the jaws of the end effector. The pressure control is then able to determine an appropriate tissue compression and can communicate what power level and/or energy modality is most appropriate for the detected tissue.

The control protocol can be determined based on a consensus reached by a plurality of the components within the surgical system. For example, three components within the surgical system detect a first value relating to a monitored parameter while two components within the surgical system detect a second value relating to the same monitored parameter, wherein the first value and the second value are different. The group of three components comprise more components than the group of two components, and thus, the first value of the monitored parameter controls. Each component within the surgical system can be assigned a positioned within a hierarchy. The hierarchy can be established based on reliability of the particular component and/or the capabilities of the particular component. A first component detects a first value relating to a monitored parameter, and a second component detects a second value relating to the same monitored parameter, wherein the first value is different than the second value. The second component "outranks" the first component within the hierarchy of the surgical system, and thus, the second value of the monitored parameter detected by the second component controls.

FIGS. 169-172 depict an electrosurgical instrument 30100 comprising a first jaw 30110, a second jaw 30120, and a monopolar wedge electrode 30130. The first jaw 30110 and the second jaw 30120 are movable between an open position and a closed position and are configured to grasp tissue T therebetween. Each of the first jaw 30110 and the second jaw 30120 comprises an electrode that is electrically coupled to a power generator. Example suitable power generators 900, 1100 are described above in connection with FIGS. 1 and 2. The power generator is configured to supply power to cause the electrodes of the first and second jaws 30110, 30120 to cooperatively deliver bipolar energy to the grasped tissue to seal, coagulate, and/or cauterize the tissue in a bipolar tissue-treatment cycle.

In use, the first jaw 30110 and the second jaw 30120 may deflect away from each other at their distal ends when the tissue T is grasped therebetween. When the tissue T is grasped, the tissue T exerts a force on the first jaw 30110 and the second jaw 30120 causing the jaws to deflect away from each other. More specifically, the gap B between the first jaw 30110 and the second jaw 30120 toward the distal end of the jaws may be greater than the gap A between the first jaw 30110 and the second jaw 30120 toward the proximal end of the jaws when tissue T is grasped between the first jaw 30110 and the second jaw 30120.

Further to the above, the end effector 30100 of the electrosurgical instrument 30100 further includes monopolar wedge electrode 30130 is electrically connected to the power generator (e.g. power generators 900, 1100) and configured to cut the tissue T positioned between the first jaw 30110 and the second jaw 30120 when energized by the power generator. In the illustrated embodiment, the monopolar wedge electrode 30130 is affixed to the second jaw 30120; however, other embodiments are envisioned where the monopolar wedge electrode 30130 is affixed to the first jaw 30110. The monopolar wedge electrode 30130 is thinner at its proximal end and thicker at its distal end (see FIG. 172) to compensate for the variable gap defined between the first jaw 30110 and the second jaw 30120. In other words, the monopolar wedge electrode 30130 comprises a wedge shape. As previously discussed, the variable gap defined between the jaws 30110, 30120 is due, at least in part, to the deflection of the jaws 30110, 30120 when tissue is grasped therebetween. In at least one embodiment, the monopolar wedge electrode 30130 comprises a compliant flex circuit substrate 30132. The compliant flex circuit substrate 30132 is configured to bend and/or flex longitudinally to compensate for the deflection of the first jaw 30110 and the second jaw 30120 when tissue is grasped between the first and second jaws 30110, 30120.

In various examples, the monopolar wedge electrode 30130 includes an electrically conductive member 30134 disposed centrally along a length of the compliant flex circuit substrate 30132. In the illustrated example, the electrically conductive member 30134 is disposed onto the compliant flex circuit substrate 30132 where at least a portion thereof is exposed through a top surface of the compliant flex circuit substrate 30132. In certain examples, portions of the electrically conductive member 30134 are exposed while other portions are covered by the compliant flex circuit substrate 30132.

In examples where the jaws 30110, 30120 comprise a curved shape, the monopolar wedge electrode 30130 extends longitudinally in a similar curved profile. Furthermore, the monopolar wedge electrode 30130 graduates from a larger width to a smaller width as it extends longitudinally. Accordingly, a first width of the monopolar wedge electrode 30130 near a proximal end thereof is greater than a second width near a distal end thereof, as illustrated in FIG. 171. In other examples, a first width of a monopolar wedge electrode near a proximal end thereof can be smaller than a second width near a distal end thereof.

In the illustrated example, the distal end of the electrically conductive member 30134 is proximal to the distal end of the compliant flex circuit substrate 30132, and the distal end of the compliant flex circuit substrate 30132 is proximal to the distal end of the jaw 30130. In other examples, however, the distal ends of the jaw 30130, the electrically conductive member 30134 and the compliant flex circuit substrate 30132 are united at one position.

FIGS. 173-175 depict an electrosurgical instrument 30200 comprising a first jaw 30210, a second jaw 30220, and a monopolar electrode 30230. The first jaw 30210 and the second jaw 30220 are movable between an open position and a closed position, wherein tissue is configured to be positioned therebetween. The first jaw 30210 and the second jaw 30220 are comprised of metal and can be coated with a dielectric material. In at least one embodiment, the first jaw 30210 and the second jaw 30220 are comprised of stainless steel and are coated with a shrink tube. In various aspects, the jaws 30210, 30220 define bipolar electrodes that are electrically isolated from the monopolar electrode 30230.

The first jaw 30210 comprises a first compliant member 30240 positioned around the first jaw 30210 and the second jaw 30220 comprises a second compliant member 30250 positioned around the second jaw 30220. The compliant members 30240, 30250 comprise a deformable dielectric material that is compressible to enhance contact with tissue when tissue is positioned between the first jaw 30210 and the second jaw 30220. In at least one embodiment, the compliant members 30240, 30250 comprise silicone and/or rubber.

Further to the above, the monopolar electrode 30230 is utilized to cut tissue positioned between the first jaw 30210 and the second jaw 30220 when the monopolar electrode 30230 is energized by a power generator (e.g. generators 1100, 900). The monopolar electrode 30230 comprises a wire that extends along the first jaw 30210 and into the first compliant member 30240. The monopolar electrode 30230 exits the first compliant member 20140 through a proximal opening 30242 in the first compliant member 30240, extends along the exterior of the first compliant member 30240, and then re-enters the first compliant member 20140 through a distal opening 30244 in the first compliant member 30240. This arrangement permits a central portion 30232 of the monopolar electrode 30230 to bend and/or flex when tissue is grasped between the first jaw 30210 and the second jaw 30220. Further, the central portion 30232 of the monopolar electrode 30230 is reinforced by the first compliant member 30240 along its length. Stated another way, the first compliant member 30240 applies a biasing force to the central portion 30232 of the monopolar electrode 30230 toward the second jaw 30220. The first compliant member 30240 increases the pressure exerted by the monopolar electrode 30230 on the tissue to improve the cutting ability of the monopolar electrode 30230 when the first jaw 30210 and the second jaw 30220 grasp tissue therebetween.

In various aspects, the monopolar electrode 30230 can be comprised of a metal such as, for example, stainless steel, titanium, or any other suitable metal. The exposed surface of the monopolar electrode 30230 can have a bare metal finish, or can be coated with a thin dielectric material such as, for example, PTFE. In various aspects, the coating can be skived to reveal a thin metal strip defining an electrically conductive surface.

FIG. 176 depicts a surgical instrument 30300 comprising a first jaw 30310, a second jaw 30320, and a monopolar electrode 30330. The first jaw 30310 and the second jaw 30320 are movable between an open position and a closed position to grasp tissue T therebetween. The first jaw 30310 comprises a first bipolar electrode and the second jaw 30320 comprises a second bipolar electrode. The first and second bipolar electrodes cooperate to delivery bipolar energy to cauterize and/or seal tissue grasped between the first and second jaws 30310, 30320 in a bipolar tissue-treatment cycle.

Further to the above, the first jaw 30310 comprises a first tissue contacting surface 30314 and the second jaw 30320 comprises a second tissue contacting surface 30324. The first jaw 30310 comprises a first recess 30312 configured to receive a first compliant or biasing member 30340 therein. The first biasing member 30340 is configured to bias the tissue T toward the second jaw 30320 when the tissue T is grasped between the first jaw 30310 and the second jaw 30320. The second jaw comprises a second recess 30322 configured to receive a second compliant or biasing member 30350 and the monopolar electrode 30330 therein. The second biasing member 30350 is configured to bias the monopolar electrode 30330 and the tissue T toward the first jaw 30310 when the tissue T is grasped between the first jaw 30310 and the second jaw 30320.

Further to the above, the first recess 30312 and the second recess 30322 are sized and shaped to receive the first biasing member 30340, the second biasing member 30350, and the monopolar electrode 30330 to ensure the first jaw 30310 and the second jaw 30320 can be fully closed. In other words, when the first jaw 30310 and the second jaw 30320 are in the closed position, the first tissue-contacting surface 30314 and the second tissue-contacting surface 30324 contact one another when no tissue T is positioned therebetween. However, other embodiments are envisioned where a gap is defined between the first tissue-contacting surface 30314 and the second tissue-contacting surface 30324 when the first jaw 30310 and the second jaw 30320 are in the closed position when tissue T is positioned therebetween and/or when tissue T is not positioned therebetween. In any event, the first recess 30312 and the second recess 30322 are sized and/or shaped such that the monopolar electrode 30330 extends above the second tissue-contacting surface 30324 and into the first recess 30312 of the first jaw 30310 to increase the ability of the first jaw 30310 and the second jaw 30320 to fully close. The first and second recesses 30312, 30322 comprise an electrically isolative material to electrically isolate the monopolar electrode 30330 from the first and second jaws 30310, 30320. However, other embodiments are envisioned where the first and second recesses 30312, 30322 do not electrically isolate the monopolar electrode 30330 from the first and second jaws 30310, 30320. The monopolar electrode 30330 comprises an independent wiring connection to the control housing of the surgical instrument 30300. The independent wiring connection allows the monopolar electrode 30330 to be energized independent of the first and second electrodes of the first and second jaws 30310, 30320 to permit cutting and/or sealing operations to be performed independent of one another. In at least one embodiment, the control housing of the surgical instrument 30300 prevents the monopolar electrode 30330 from being energized until the first and second electrodes of the first and second jaws 30310, 30320 have been energized to prevent cutting of tissue T that has not been cauterized and/or sealed.

FIG. 177 illustrates a surgical end effector 30400 for use with an electrosurgical instrument. The end effector 30400 comprises a first jaw including a first bipolar electrode

30410, a second jaw including a second bipolar electrode 30420, and a monopolar electrode 30430. The first bipolar electrode 30410 and the second bipolar electrode 30420 are at least partially surrounded by a compliant member and/or a compliant insulator 30440. The compliant insulator 30440 can comprise rubber, silicone, Polytetrafluoroethylene (PTFE) tubing, and/or combinations thereof. The monopolar electrode 30430 is affixed to the compliant insulator 30440 of the first bipolar electrode 30410. Thus, the monopolar electrode 30430 is electrically insulated from the first bipolar electrode 30410. In at least one embodiment, the compliant insulator 30440 surrounding the first electrode 30410 comprises a rigid, or at least substantially rigid, PTFE tubing and the second compliant insulator 30440 surrounding the second electrode 30420 comprises a silicone and/or rubber material. Other embodiments are envisioned with different combinations of PTFE tubing, rubber, and/or silicone, positioned at least partially around the first bipolar electrode 30410 and the second bipolar electrode 30420, for example.

FIG. 178 illustrates a surgical end effector 30500 for use with an electrosurgical instrument. The surgical end effector comprises a first jaw 30510 and a second jaw 30520 movable between open and closed positions to grasp tissue therebetween. The first jaw 30510 is at least partially surrounded by a first compliant member 30514 and the second jaw 30520 is at least partially surrounded by a second compliant member 30524. The first compliant member 30514 is almost completely surrounded by a first bipolar electrode 30512 and the second compliant member 30524 is almost completely surrounded by a second bipolar electrode 30522. More specifically, the first bipolar electrode 30512 surrounds the first compliant member 30514 except for a gap portion 30516 where a monopolar electrode 30530 is affixed to the first compliant member 30514. Further, the second bipolar electrode 30522 surrounds the second compliant member 30524 except for a gap portion 30526 facing the first jaw 30510. The gap portion 30526 in the second jaw 30520 permits the monopolar electrode 30530 extending from the first complaint member 30514 to experience biasing forces from both the first and second compliant members 30514, 30524 when the first jaw 30510 and the second jaw 30520 grasp tissue in the closed position. The first complaint member 30514 and the second compliant member 30524 comprise an electrically insulative material to electrically isolate the monopolar electrode 30530 from the first bipolar electrode 30512 and the second bipolar electrode 30522. The first and second complaint members 30514, 30524 can comprise rubber, silicone, PTFE tubing, and/or combinations thereof.

FIG. 179 illustrates a surgical end effector 30600 for use with an electrosurgical instrument. The surgical end effector 30600 comprises a first jaw 30610 and a second jaw 30620 movable between open and closed positions to grasp tissue therebetween. The first jaw 30610 is at least partially surrounded by a first compliant member 30614 and the second jaw 30620 is at least partially surrounded by a second compliant member 30624. The first compliant member 30614 is almost completely surrounded by a first bipolar electrode 30612 and the second compliant member 30624 is almost completely surrounded by a second bipolar electrode 30622. In other words, the first bipolar electrode 30612 surrounds the first compliant member 30614 except for a gap portion 30616 where a monopolar electrode 30630 is affixed to the first compliant member 30614. Further, the second bipolar electrode 30622 surrounds the second compliant member 30624 except for a gap portion 30626.

Further to the above, the gap portions 30616, 30626 in the first and second bipolar electrodes 30612, 30622 permit the monopolar electrode 30630 extending from the first complaint member 30614 to contact the second compliant member 30624 when the first jaw 30610 and the second jaw 30620 are in the closed position. Further, the gap portions 30616, 30626 are offset to permit the first bipolar electrode 30612 to contact the second compliant member 30624 and the second bipolar electrode 30622 to contact the first compliant member 30614 when the jaws 30610, 30620 are closed with no tissue positioned therebetween. Unlike the electrodes 30512, 30533, the electrodes 30612, 30622 are not mirror images of each other. Instead, the electrode 30612 is offset with the electrode 30622 causing the gap portions 30616, 30610 to also be offset with one another. This arrangement prevents circuit shorting.

In any event, when the first jaw 30610 and the second jaw 30620 are closed, the monopolar electrode 30630 is positioned between the first compliant member 30614 and the second compliant member 30624 to provide a spring bias or biasing force to the monopolar electrode 30630 when tissue is grasped between the jaws 30610, 30620. In other words, the monopolar electrode 30630 experiences biasing forces from both the first compliant member 30614 and the second compliant member 30624 when the first jaw 30610 and the second jaw 30620 are closed around tissue. The biasing forces from the compliant members 30614, 30624 facilitate cutting of tissue when the monopolar electrode 30630 is energized.

Further to the above, in at least one embodiment, the first complaint member 30614 and the second compliant member 30624 comprise electrically insulative material to electrically isolate the monopolar electrode 30630 from the first bipolar electrode 30612 and the second bipolar electrode 30622. In at least one embodiment, the first and second complaint members 30614, 30624 can comprise rubber, silicon, PTFE tubing, and/or combinations thereof.

FIG. 180 illustrates a surgical end effector 30700 for use with an electrosurgical instrument. The end effector 30700 comprises a first jaw 30710 and a second jaw 30720 movable between open and closed positions to grasp tissue therebetween. The first jaw 30710 defines a first bipolar electrode and the second jaw 30720 defines a second bipolar electrode that are configured to cooperate to delivery bipolar energy to cauterize and/or seal tissue grasped between the first and second jaws 30710, 30720. Further, the first jaw 30710 comprises a first longitudinal recess 30712 comprising a first compliant member 30714 affixed therein. The second jaw 30720 comprises a second longitudinal recess 30722 comprising a second compliant member 30724 affixed therein. The surgical end effector 30700 further comprises a monopolar electrode 30730 affixed to the first compliant member 30714. The first compliant member 30714 and the second compliant member 30724 permit the monopolar electrode 30730 extending from the first complaint member 30714 to experience biasing forces from both the first and second compliant members 30714, 30724 when the first jaw 30710 and the second jaw 30720 grasp tissue in the closed position. The first complaint member 30714 and the second compliant member 30724 comprise electrically insulative material to electrically isolate the monopolar electrode 30730 from the first electrode of the first jaw 30710 and the second electrode of the second jaw 30720. The first and second complaint members 30714, 30724 can comprises rubber, silicone, PTFE tubing, and/or combinations thereof.

FIG. 181 illustrates a surgical end effector for use with an electrosurgical instrument. The end effector 30800 comprises a first jaw 30810 and a second jaw 30820 movable between an open position and a closed position to grasp tissue therebetween. The first jaw 30810 defines a first bipolar electrode and the second jaw 30820 defines a second bipolar electrode. As discussed above, the first and second bipolar electrodes are configured to cooperate to delivery bipolar energy to cauterize and/or seal tissue positioned between the first and second jaws 30810, 30820. Further, the first jaw 30810 comprises a longitudinal recess 30812 comprising a compliant member 30814 affixed therein. In at least one embodiment, the second jaw 30820 comprises stainless steel coated with PTFE shrink tube. The surgical end effector 30800 further comprises a monopolar electrode 30830 affixed to the compliant member 30814 of the first jaw 30810. The compliant member 30814 provides a biasing force to the monopolar electrode 30830 when the first jaw 30810 and the second jaw 30820 grasp tissue therebetween. The biasing force of the compliant member 30814 enhances contact between the monopolar electrode 30830 and the tissue during cutting operations. The complaint member 30814 comprises an electrically insulative material to electrically isolate the monopolar electrode 30830 from the first electrode of the first jaw 30810. The complaint member 30814 can comprise rubber, silicone, PTFE tubing, and/or combinations thereof.

FIG. 182 illustrates an alternative surgical end effector 30800' to the surgical end effector 30800. The end effector 30800' is similar to the end effector 30800; however, the monopolar electrode 30830 is affixed to the second jaw 30820. When tissue is positioned between the first jaw 30810 and the second jaw 30820, the compliant member 30814 applies a biasing force through the tissue to the monopolar electrode 30830 affixed to the second jaw 30820.

FIG. 183 illustrates a surgical end effector 30900 for use with an electrosurgical instrument. The surgical end effector 30900 defines an end effector axis EA extending longitudinally along the length of the end effector 30900. The surgical end effector 30900 comprises a first jaw 30910 and a second jaw 30920 movable between an open position and a closed position to grasp tissue therebetween. The first jaw 30910 comprises a first honeycomb lattice structure 30912 surrounded by a first diamond-like coating 30914. The second jaw 30920 comprises a second honeycomb lattice structure 30922 surrounded by a second diamond-like coating 30924. The diamond-like coatings 30914, 30924 may be any of the diamond-like coatings described herein, for example. The first honeycomb lattice structure 30912 and the second honeycomb lattice structure 30922 comprise the same geometric array and material. However, other embodiments are envisioned where the first honeycomb lattice structure 30912 and the second honeycomb lattice structure 30922 comprise different geometric arrays and materials which comprise more or less air pockets, as described herein. The first diamond-like coating 30914 and the second diamond-like coating 30924 comprise the same material. However, other embodiments are envisioned where the first diamond-like coating 30914 and the second diamond-like coating 30924 comprise different materials.

Further to the above, the end effector 30900 further comprises a first bipolar electrode 30940 affixed to the first diamond-like coating 30914 of the first jaw 30910 on a first lateral side of the end effector axis EA. The first bipolar electrode 30940 extends longitudinally along a length of the end effector 30900. The second jaw 30920 comprises a compliant member 30960 affixed within a cutout portion 30926 defined in the second jaw 30920. The end effector 30900 further comprises a second bipolar electrode 30950 affixed to the compliant member 30960 on a second lateral side of the end effector axis EA. The second bipolar electrode 30950 extends longitudinally along a length of the end effector 30900. The electrodes 30940, 30950 cooperate to deliver a bipolar energy to tissue grasped between the jaws 30910, 30920. Further, the electrodes 30940, 30950 are offset from one another to prevent incidental contact between them in the closed position, which can form a short circuit.

Further, the end effector 30900 comprises a monopolar electrode 30930 affixed to the compliant member 30960 and positioned intermediate the first bipolar electrode 30940 and the second bipolar electrode 30950. The monopolar electrode 30930 extends longitudinally along a length of the end effector 30900 and, in at least one embodiment, is aligned with the end effector axis EA.

As discussed herein, the first bipolar electrode 30940 and the second bipolar electrode 30950 are configured to cauterize and/or seal tissue when tissue is positioned between the first and second jaws 30910, 30920 by delivering bipolar energy to the tissue in a bipolar energy cycle. Further, the monopolar electrode 30930 is configured to cut the tissue by delivering monopolar energy to the tissue in a monopolar energy cycle.

Further to the above, the compliant member 30960 is compressible and exerts pressure on tissue positioned between the first jaw 30910 and the second jaw 30920. More specifically, the pressure exerted by the jaws 30910, 30920 on the tissue in the region directly above the compliant member 30960 is greater than the pressure exerted on the tissue in the regions adjacent to the compliant member 30960 (i.e., the regions where the compliant member 30960 is not present). In at least one embodiment, the compliant member 30960 comprises an elastomeric and/or plastic honeycomb structure that insulates the second bipolar electrode 30950 and the monopolar electrode 30930 from the second diamond-like coating 30924 and honeycomb lattice structure 30922 of the second jaw 30920. The compliant member 30960 holds the second bipolar electrode 30950 and the monopolar electrode 30930 in place and provides a biasing force to the monopolar electrode 30930 and the second bipolar electrode 30950 toward the first jaw 30910 when tissue is grasped between the first and second jaws 30910, 30920.

Further to the above, the first and second diamond-like coatings 30914, 30924 are electrically conductive and thermally insulative. However, other embodiments are envisioned where the first and second diamond-like coatings 30914, 30924 are electrically insulative and/or thermally insulative. The first and second honeycomb lattice structures 30912, 30922 comprise air pockets which provide thermal insulation for the first and second jaws 30910, 30920. The first and second honeycomb lattice structures 30912, 30922 provide an additional spring bias to the tissue when the tissue is positioned between the first and second jaws 30910, 30920. In at least one embodiment, the first and second honeycomb lattice structures 30912, 30922 allow the first and second jaws 30910, 30920 to flex and/or bend when tissue is grasped therebetween. In any event, the spring forces of the first and second honeycomb lattice structures 30912, 30922 and the compliant member 30960 provide consistent pressure to the tissue when the tissue is grasped between the first and second jaws 30910, 30920.

In various aspects, one or more of the Diamond-Like coatings (DLC) 30914, 30924 are comprised of an amorphous carbon-hydrogen network with graphite and diamond bondings between the carbon atoms. The DLC coatings 30914, 30924 can form films with low friction and high hardness characteristics around the first and second honeycomb lattice structures 30912, 30922. The DLC coatings 30914, 30924 can be doped or undoped, and are generally in the form of amorphous carbon (a-C) or hydrogenated amorphous carbon (a-C:H) containing a large fraction of sp3 bonds. Various surface coating technologies can be utilized to form the DLC coatings 30914, 30924 such as the surface coating technologies developed by Oerlikon Balzers. In at least one example, the DLC coatings 30914, 30924 are generated using Plasma-assisted Chemical Vapor Deposition (PACVD).

In various aspects, one or both of the DLC coatings can be substituted with a coating comprising Titanium Nitride, Chromium Nitride, Graphit iC™, or any other suitable coating.

Still referring to FIG. 183, the electrodes 30940, 30950 are offset such that a plane extending along the axis EA and transecting the monopolar electrode 30930 extends between the electrodes 30940, 30950. Further, in the illustrated examples, the electrodes 30930, 30940, 30950 protrude from the outer surface of the jaws 30910, 30920. In other examples, however, one or more of the electrodes 30930, 30940, 30950 can be embedded into the jaws 30910, 30920 such that their outer surfaces are flush with the outer surface of the jaws 30910, 30920.

A number of the end effectors described in connection with FIGS. 169-183 are configured to coagulate, cauterize, seal, and/or cut tissue grasped by the end effector in a tissue treatment cycle that includes delivery of bipolar energy and/or monopolar energy to the tissue. The bipolar energy and the monopolar energy can be delivered separately, or in combination, to the tissue. In one example, the monopolar energy is delivered to the tissue after bipolar energy delivery to the tissue is terminated.

FIG. 184 is a graph depicting an alternative example of a tissue treatment cycle 31000 that delivers bipolar energy, in a bipolar energy cycle, and monopolar energy, in a monopolar energy cycle, to the tissue. The tissue treatment cycle 31000 includes a bipolar-only phase 31002, a blended energy phase 31004, and a monopolar-only phase 31006. The tissue treatment cycle 31000 can be implemented by an electrosurgical system including a generator (e.g. generators 1100, 900) coupled to an electrosurgical instrument that includes an end effector (e.g. end effectors of FIGS. 169-183), for example.

The graph of FIG. 184 depicts power (W) on the y-axis and time on the x-axis. The power values provided in the graph and in the following description are thereof are non-limiting examples of the power levels that can be utilized with the tissue treatment cycle 31000. Other suitable power levels are contemplated by the present disclosure. The graph depicts a bipolar power curve 31010 and a monopolar power curve 31014. Further, a blended power curve 31012 represents simultaneous application of the monopolar and bipolar energies to the tissue.

Referring still to FIG. 184, an initial tissue contacting stage is depicted between to and which takes place prior to application of any energy to the tissue. The jaws of the end effector are positioned on opposite sides of the tissue to be treated. Bipolar energy is then applied to the tissue throughout a tissue coagulation stage starting at $t_1$ and terminating at $t_4$. During a feathering segment $(t_1-t_2)$, bipolar energy application is increased to a predetermined power value (e.g. 100 W) and is maintained at the predetermined power value through the remainder of the feathering segment $(t_1-t_2)$ and a tissue-warming segment $(t_2-t_3)$. During a sealing segment $(t_3-t_4)$, the bipolar energy application is gradually reduced. Bipolar energy application is terminated at the end of the sealing segment $(t_3-t_4)$, and prior to the beginning of the cutting/transecting stage.

Further to the above, monopolar energy application to the tissue is activated during the tissue coagulation stage. In the example illustrated in FIG. 184, activation of the monopolar energy commences at the end of the feathering segment and the beginning of the tissue-warming segment, at time $t_2$. Like bipolar energy, the monopolar energy application to the tissue is gradually increased to a predetermined power level (e.g. 75 W) that is maintained for the remainder of the tissue-warming segment and an initial portion of the sealing segment.

During the sealing segment $(t_3-t_4)$ of the tissue coagulation stage, the monopolar energy application to the tissue gradually increases in power as bipolar energy application to the tissue gradually decreases in power. In the illustrated example, the bipolar energy application to the tissue is stopped at the end of the tissue coagulation cycle $(t_4)$. The beginning of the tissue transecting stage is ushered by an inflection point in the monopolar power curve 31014 at $t_4$ where the previous gradual increase in monopolar energy, experienced during the sealing segment $(t_3-t_4)$, is followed by a step up to a predetermined maximum threshold power level (e.g. 150 W) sufficient to transect the coagulated tissue. The maximum power threshold is maintained for a predetermined time period that ends with the return of the monopolar power level to zero.

Accordingly, the tissue treatment cycle 31000 is configured to deliver three different energy modalities to a tissue treatment region at three consecutive time periods. The first energy modality, which includes bipolar energy but not monopolar energy, is applied to the tissue treatment region from $t_1$ to $t_2$, during the feathering segment. The second energy modality, which is a blended energy modality that includes a combination of monopolar energy and bipolar energy, is applied to the tissue treatment region from $t_2$ to $t_4$, during the tissue-warming segment and tissue-sealing segment. Lastly, the third energy modality, which includes monopolar energy but not bipolar energy, is applied to the tissue from $t_4$ to $t_5$, during the cutting segment. Furthermore, the second energy modality comprises a power level that is the sum of the power levels of monopolar energy and bipolar energy. In at least one example, the power level of the second energy modality includes a maximum threshold (e.g. 120 W). In various aspects, the monopolar energy and the bipolar energy can be delivered to an end effector from two different electrical generators.

The blended power curve 31012, applied during the blended energy phase 31004, represents a combination of bipolar energy and monopolar energy application to the tissue. During the tissue warming segment $(t_2-t_3)$, the blended power curve 31012 rises as monopolar power is activated, at $t_2$, and increased, while the bipolar power is maintained at a constant, or at least substantially constant, level through the remainder of the tissue warming segment $(t_2, t_3)$ and the beginning of the tissue sealing segment $(t_3-t_4)$. During the sealing segment $(t_3-t_4)$, the blended power curve 31012 is maintained at a constant, or at least substantially constant, level by gradually decreasing the bipolar power level as the monopolar power level is increased.

In various aspects, the bipolar and/or monopolar power levels of the tissue treatment cycle 31000 can be adjusted based on one or more measured parameters including tissue impedance, jaw motor velocity, jaw motor force, jaws aperture of an end effector and/or current draw of the motor effecting end effector closure.

In accordance with at least one embodiment, a monopolar electrode for cutting patient tissue comprises a monopolar camming lobe electrode and a wire attached thereto. The monopolar camming lobe electrode is initially located at a distal end of an end effector of an electrosurgical instrument. When the clinician desires to cut patient tissue, the monopolar camming lobe electrode is energized (i.e., via a power generator, as discussed herein) and pulled on by the wire attached thereto. The wire first induces the camming lobe electrode to rotate upward into the tissue gap along the centerline of the end effector and is then pulled from the distal end to the proximal end to cut the patient tissue. In other words, the camming lobe electrode acts like a pivoting cutting blade of a surgical instrument if the pivoting cutting blade was located at the distal end and then pulled proximally. Further, in at least one embodiment, the wire attached to the camming lobe electrode is offset from the rotational center of the camming lobe electrode such that when the wire is pulled proximally, the camming lobe electrode is initially rotated into an upright position. The camming lobe electrode exerts a force vertically against the opposite side of the end effector jaw from where the camming lobe electrode is positioned. In such an arrangement, the camming lobe electrode may be initially concealed from the tissue gap between the jaws of the end effector until the wire initially pulls on the camming lobe electrode to rotate the camming lobe electrode into its upright position. Since the camming lobe electrode is initially concealed, the load the camming lobe is exerting against the other jaw of the end effector is independent of the tissue gap. In other words, the camming lobe electrode will either stand substantially upright prior to beginning distal to proximal motion or the camming lobe electrode will stand partially up prior to beginning distal to proximal motion. The amount the camming lobe electrode is rotated toward its upright position is dependent upon the amount of tissue positioned between the jaws of the end effector and the stiffness of the tissue. For example, stiffer tissue resists the camming lobe electrode from rotating into its upright position more than softer tissue before the camming lobe electrode begins to move from the distal end toward the proximal end.

FIG. 185 depicts an electrosurgical instrument 40100 comprising a housing, a shaft 40110 extending from the housing, and an end effector 40120 extending from the shaft 40110. An articulation joint 40130 rotatably connects the shaft 40110 and the end effector 40120 to facilitate articulation of the end effector 40120 relative to the shaft 40110. A circuit board 40140 is located in the housing of the instrument 40100. However, other embodiments are envisioned with the circuit board 40140 positioned in any suitable location. In at least one example, the circuit board 40140 is a printed circuit board. The printed circuit board 40140 includes a connection plug 40142 for connecting the printed circuit board 40140 to a wiring assembly 40150. The wiring assembly 40150 extends from the printed circuit board 40140 through the shaft 40110 and into the end effector 40120. The wiring assembly 40150 is configured to monitor at least one function of the end effector 40120 and relay monitored information to the printed circuit board 40140. The wiring assembly 40150 can monitor functions of the end effector including the compression rate of the jaws of the end effector 40120 and/or the heat cycle of the end effector 40120, for example. In the illustrated example, the wiring assembly 40150 comprises a sensor 40122 positioned in the end effector 40120. The sensor 40122 monitors at least one function of the end effector 40120.

In various aspects, the sensor 40122 may comprise any suitable sensor, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor. In various aspects, the circuit board 40140 comprises a control circuit that includes a microcontroller with a processor and a memory unit. The memory unit may store one or more algorithms and/or look-up tables to recognize certain parameters of the end effector 40120 and/or tissue grasped by the end effector 40120 based on measurements provided by the sensor 40122.

Further to the above, the wiring assembly 40150 may comprise several flexible, rigid, and/or stretchable portions as part of a flexible circuit to allow the wiring assembly 40150 to flex, bend, and/or stretch across various part boundaries and/or joints of the surgical instrument 40100. For example, as the wiring assembly 40150 crosses a part boundary or joint an inextensible flexible plastic substrate (i.e., polyimide, peek, transparent conductive polyester film) transitions to a flexible silicone, or elastomeric substrate, and then back to the inextensible flexible substrate on the other side of the joint. The metallic conductor within the wiring assembly 40150 remains continuous but stretchable over the part boundary and/or joint. This arrangement enables the entire circuit to be flexible with local portions being flexible in at least two planes. Thus, the portions of the wiring assembly 40150 that span across part boundaries and/or joints allow local relative motions without tearing the wiring assembly 40150, or a loss in its continuity. The wiring assembly 40150 is fixed around the local movement zones to protect the wiring assembly 40150 from excessive strain and/or distortion.

Further to the above, in the present embodiment, the wiring assembly 40150 comprises a first elastic portion 40152, a proximal rigid portion 40154, a second elastic portion 40156, and a distal rigid portion 40158. The proximal rigid portion 40154 is positioned in the elongate shaft 40110 and the distal rigid portion 40158 is positioned in the end effector 40120. The first elastic portion 40152 is positioned between the printed circuit board 40140 and the proximal rigid portion 40154. The second elastic portion 40156 is positioned between the proximal rigid portion 40154 and the distal rigid portion 40158. Other embodiments are envisioned where the wiring assembly 40150 comprises more or less than two elastic portions. The rigid portions 40154, 40158 may be fixed to the shaft 40110 and end effector 40120, respectively, with an adhesive 40105, for example. However, any suitable attachment means may be utilized. The elastic portions 40152, 40156 further comprise a resilient portion (i.e., for bending and/or flexing) and a stretchable portion (i.e. for stretching). In at least one embodiment, the resilient portion comprise a first substrate, or layer, and the stretchable portions comprise a second substrate, or layer. The first and second substrates comprise different materials. However, other embodiments are envisioned where the first and second substrates comprise the same material in different configurations.

Further to the above, the wiring assembly 40150 further comprises an electrical trace, or conductor 40160, spanning the entire length of the wiring assembly 40150 and configured to carry electrical energy between the printed circuit board 40140 and the end effector 40120. Referring primarily to FIGS. 186 and 187, the conductor 40160 comprises a stretchable portion 40162 spanning the elastic portions 40152, 40156. The stretchable portion 40162 comprises a snaking, oscillating, and/or zig-zag pattern which allows the stretchable portion 40162 to stretch when the elastic portions 40152, 40156 are extended as illustrated in FIG. 187. When the elastic portions 40152, 40156 are returned to their relaxed and/or natural state, the stretchable portion 40162 is returned to its snaking, oscillating, and/or zig-zag pattern as illustrated in FIG. 186.

Further to the above, in at least one embodiment, the conductor 40160 may be used in high current applications such as RF treatment energy where the conductor 40160 comprises a copper conductor that is printed into the wiring assembly 40150 in a snaking, oscillating, and/or zig-zag pattern. Other embodiments are envisioned where the stretchable portions 40162 of the conductor 40160 spanning the elastic portions 40152, 40156 comprise conductive links that interlock to allow the stretchable portion 40162 to stretch across the joint.

FIG. 188 illustrates an electrosurgical instrument 40200 comprising a shaft 40210, a translating member 40220, and a flex circuit and/or wiring harness 40230. The wiring harness 40230 may be similar to the wiring assembly 40150. The translating member 40220 may be a knife drive rod for incising patient tissue, an articulation cable, and/or a rigid articulation member of the instrument 40200, for example. However, the translating member 40220 may be any translating member as described herein. In any event, the translating member 40220 is configured to translate relative to the shaft 40210 and comprises a ferrous element 40222 that translates with the translating member 40220. The ferrous element 40222 may be attached to or housed within the translating member 40220, for example. The wiring harness 40230 is fixed within the shaft 40210 and comprises a linear inductive sensor 40232 configured to detect the linear position of the ferrous element 40222 and thus the linear position of the translating member 40220. More specifically, the linear inductive sensor 40232 is configured to generate an electrical field which the ferrous element 40222 disrupts. The linear inductive sensor 40232 is integrated into the wiring harness 40230 to provide robust protection from external elements and fluids.

In various aspects, the sensor 40232 can be a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor. In various aspects, a control circuit a includes a microcontroller with a processor and a memory unit that stores one or more algorithms and/or look-up tables to recognize certain parameters of the surgical instrument 40200 and/or tissue treated by the surgical instrument 40200 based on measurements provided by the sensor 40232.

FIGS. 189 and 190 illustrate an electrosurgical instrument 40300 comprising a shaft 40310, a translating member 40320, and a flex circuit or wiring harness 40330. The translating member 40320 is configured to translate relative to the shaft 40310 to perform an end effector function. The translating member 40320 may be a knife drive rod for incising patient tissue, an articulation cable, and/or a rigid articulation member of the instrument 40300, for example. However, the translating member may be any translating member described herein, for example. In any event, the wiring harness 40330 comprises a conductor 40331, a body portion 40332, and an elastic portion 40334 which extends from the body portion 40332. The body portion 40332 is fixed to the shaft 40310 and comprises a first sensor 40340 configured to measure a function of an end effector of the surgical instrument 40300. The elastic portion 40334 is attached to the translating member 40320 and comprises a second sensor 40350. The second sensor 40350 is positioned at the end of the elastic portion 40334 where the elastic portion 40334 attaches to the translating member 40320. Thus, the second sensor 40350 translates with the translating member 40320. The second sensor 40350 is configured to measure the stress and/or strain within the translating member 40320. However, other embodiments are envisioned where the second sensor is configured to measure the position, velocity, and/or acceleration of the translating member 40320.

In various aspects, a control circuit a includes a microcontroller with a processor and a memory unit that stores one or more algorithms and/or look-up tables to recognize certain parameters of the surgical instrument 40300 and/or tissue treated by the surgical instrument 40300 based on measurements provided by the sensors 40340, 40350.

Further to the above, the elastic portion 40334 is similar to the elastic portions 40152, 40156 discussed herein with respect to FIGS. 185-187. More specifically, the elastic portion 40334 comprises resilient and/or stretchable portions which allow the elastic portion 40334 to bend, flex, and/or stretch relative to the body portion 40332 of the wiring harness 40330. Such an arrangement allows the second sensor 40350 to be integral to the wiring harness 40330 without the detected measurements of the second sensor 40350 being impacted by the movement of the translating member 40320 relative to the wiring harness 40330.

FIGS. 191-198 depict an electrosurgical instrument 40400 comprising a handle 40410, a shaft 40420 extending from the handle 40410, and a distal head or end effector 40430 extending from the shaft 40420. The handle 40410 comprises a trigger 40412 an electric motor assembly 40411 including a motor 40411a driven by a motor driver/controller 40422b configured to drive the motor 40411a per input from a control circuit 40413, and in response to actuation motions of the trigger 40412. In various aspects, the control circuit 40413 includes a microcontroller 40414 that has a processor 40415 and a memory unit 40417. A power source 40418 is coupled to the motor controller 40411b for powering the motor and to the microcontroller 40414.

The shaft 40420 defines a shaft axis SA and comprises an end effector drive member, such as the end effector drive member 40419. The end effector drive member 40419 is operably responsive to the electric motor 40411a in the handle 40410 and is configured to perform at least two end effector functions. The end effector 40430 is configured to be selectively locked and unlocked from the shaft 40420, as discussed herein. More specifically, when the end effector 40430 is locked to the shaft 40420, the end effector 40430 cannot be rotated and/or articulated relative to the shaft 40420, and the end effector drive member 40419 is configured to open and close jaws of the end effector 40430. Further, when the end effector 40430 is unlocked from the shaft 40420, the end effector can be rotated and/or articulated relative to the shaft 40420 and the end effector drive member 40419 rotates the end effector 40430 about the shaft axis SA when the end effector drive member 40419 is actuated by the electric motor.

The instrument 40400 further comprises a manual toggle member or rocker member 40440, an elongate shaft 40450, and a pull cable 40460. The elongate shaft 40450 is crimped to the pull cable 40460 such that the elongate shaft 40450 and pull cable 40460 move together along the shaft axis SA.

The rocker member 40440 comprises a slot 40442 defined therein which is configured to receive the elongate shaft 40450. The rocker member 40440 and elongate shaft 40450 are mounted within the handle 40410 and portions of the rocker member 40440 extending laterally beyond each side of the handle 40410 to allow the rocker member 40440 to be manually actuated by a clinician. The rocker member 40440 further comprises a pin 40444 extending into the slot 40442. The pin 40444 extends into a V-shaped groove 40452 defined in the outer diameter of the elongate shaft 40450. The elongate shaft 40450 is biased, such as by a spring, away from the rocker member 40440 (i.e., biased distally).

In use, when the rocker member 40440 is rotated in a clockwise direction CW the pin 40444 slides within a first side of the V-shaped groove 40452 and retracts the elongate shaft 40450 toward the rocker member 40440 (i.e., proximally). When the rocker member 40440 is rotated in a counter-clockwise direction CCW the pin 40444 slides within a second side of the V-shaped groove 40452, opposite from the first side, and retracts the elongate shaft 40450 toward the rocker member 40440 (i.e., proximally). Referring to FIG. 196, when the rocker member 40440 is centered, the elongate shaft 40450 is in its distal most position (i.e., farthest away from the rocker member 40440). Referring to FIGS. 197 and 198, when the rocker member 40440 is rotated in either the clockwise direction CW or the counter-clockwise direction CCW, the elongate shaft 40450 is retracted toward the rocker member 40440 (i.e., proximally).

Figure 54:
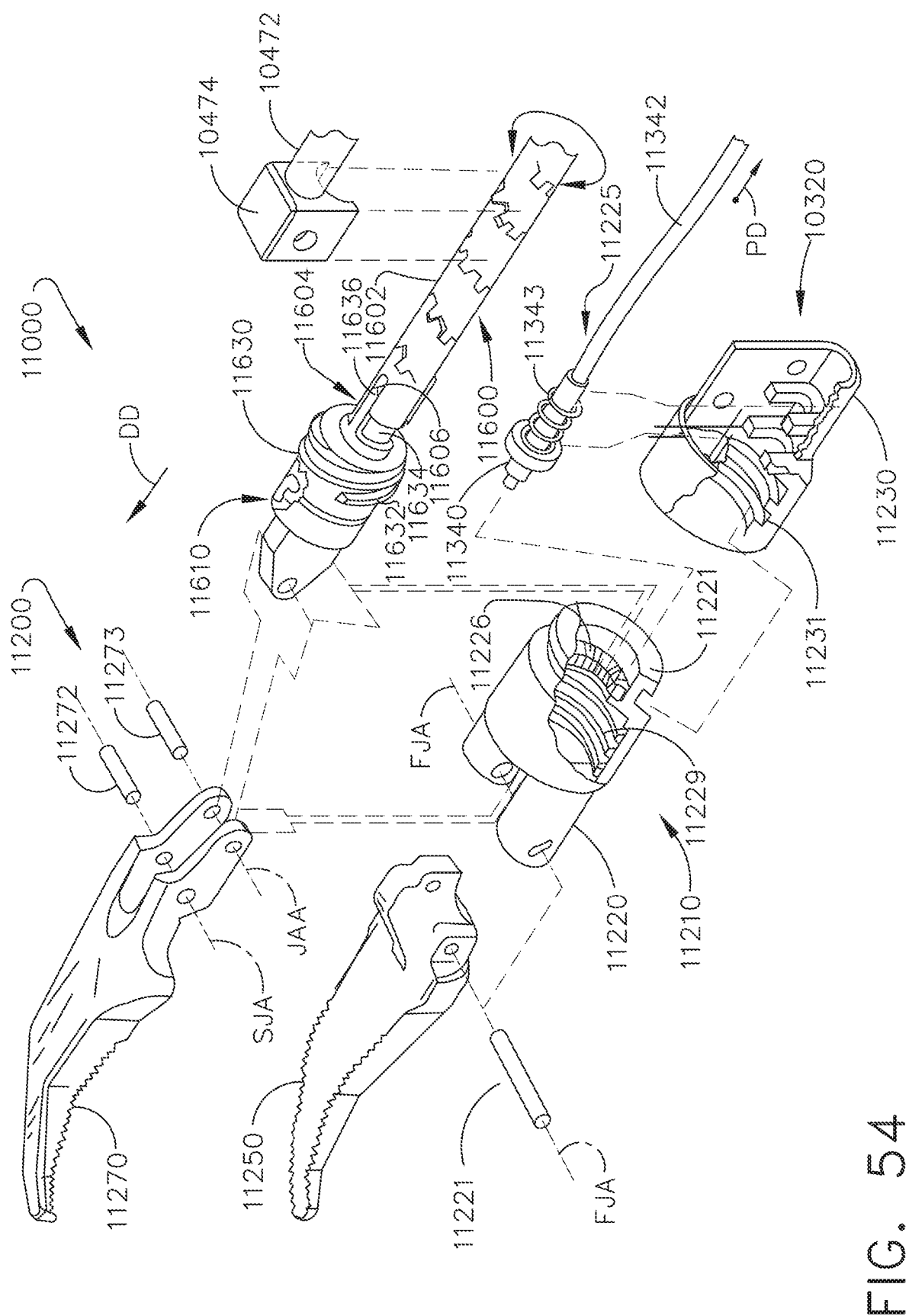
FIG. 54 is an exploded perspective assembly view of a portion of the surgical instrument of FIG. 52.
Figure 55:
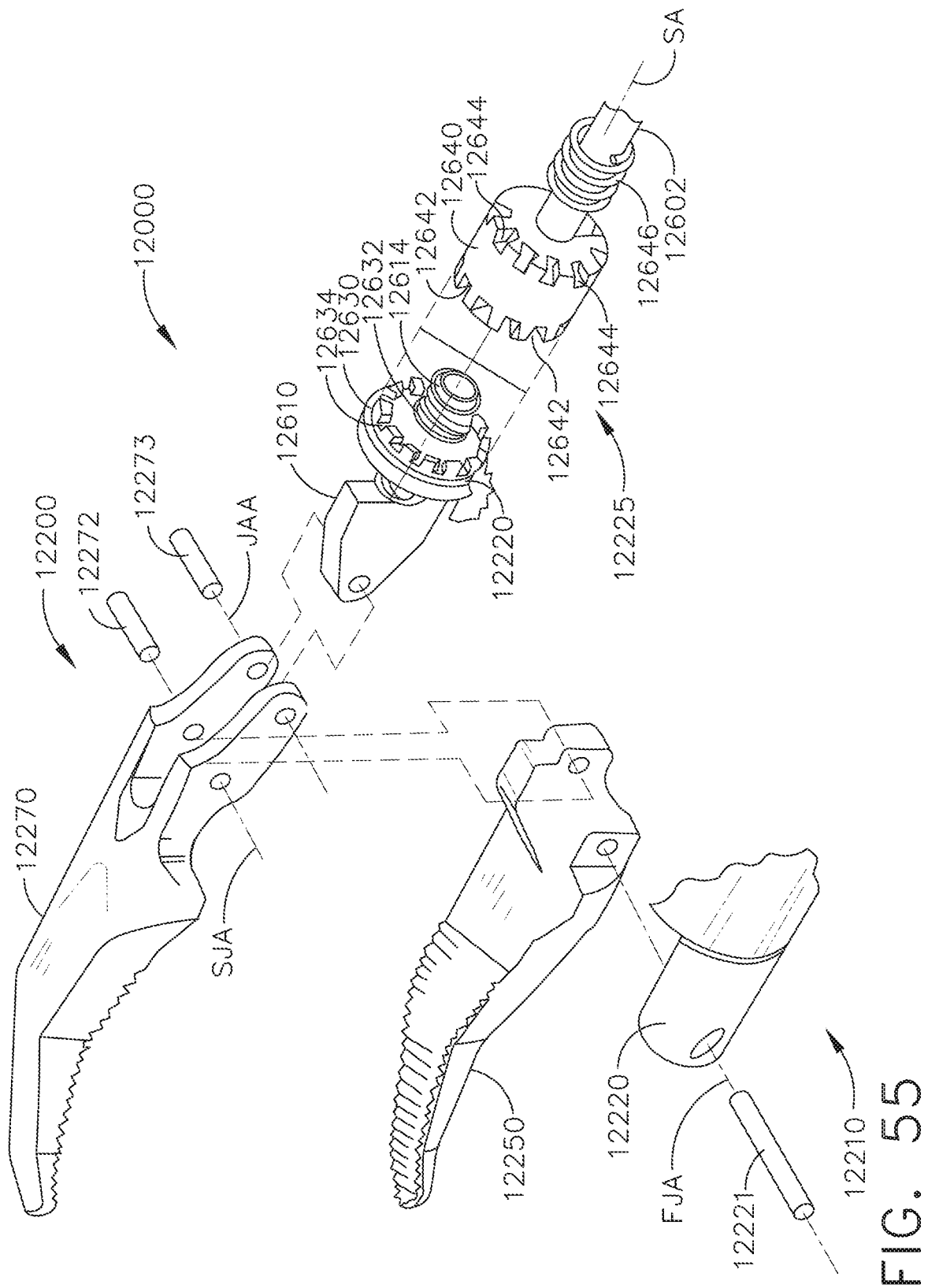
FIG. 55 is an exploded perspective assembly view of a portion of another surgical instrument, in accordance with at least one aspect of the present disclosure.
Figure 56:
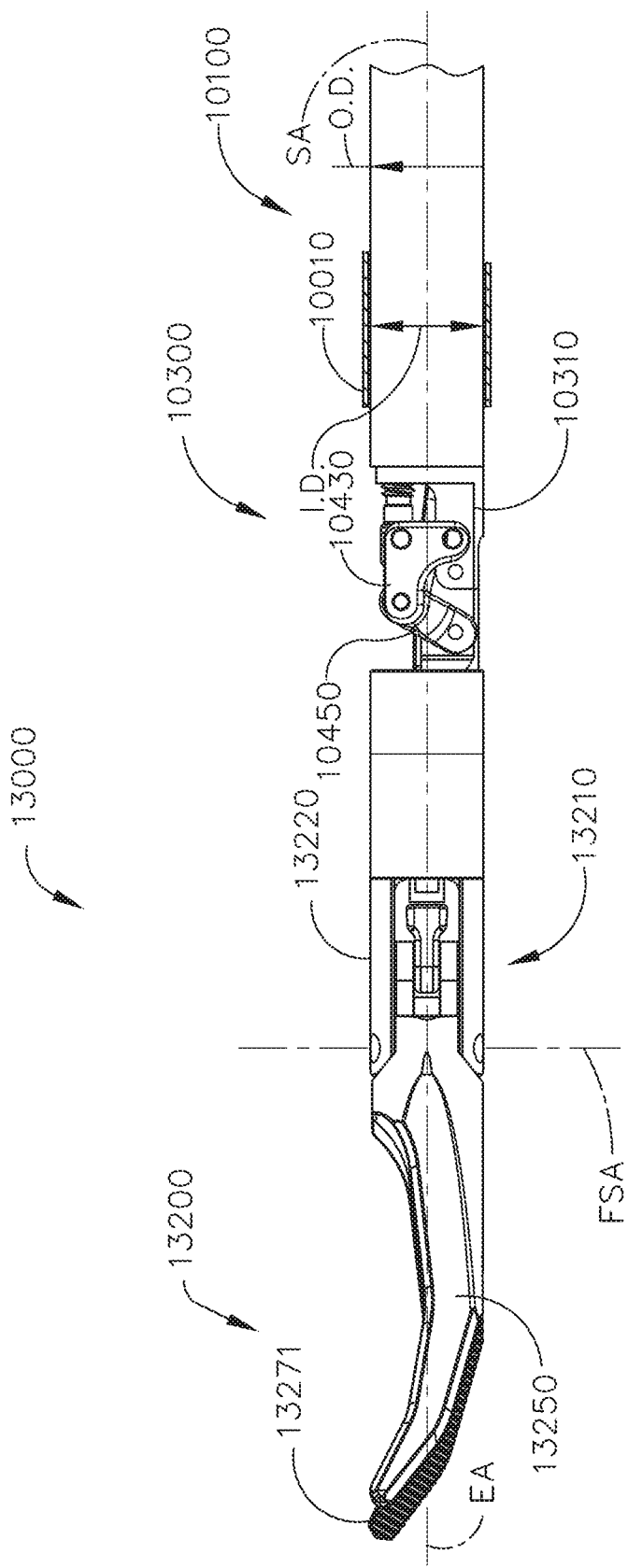
FIG. 56 is a side elevational view of a portion of another surgical instrument with a surgical end effector thereof in an unarticulated position and jaws of the surgical end effector in a partially closed position, in accordance with at least one aspect of the present disclosure.
Figure 57:
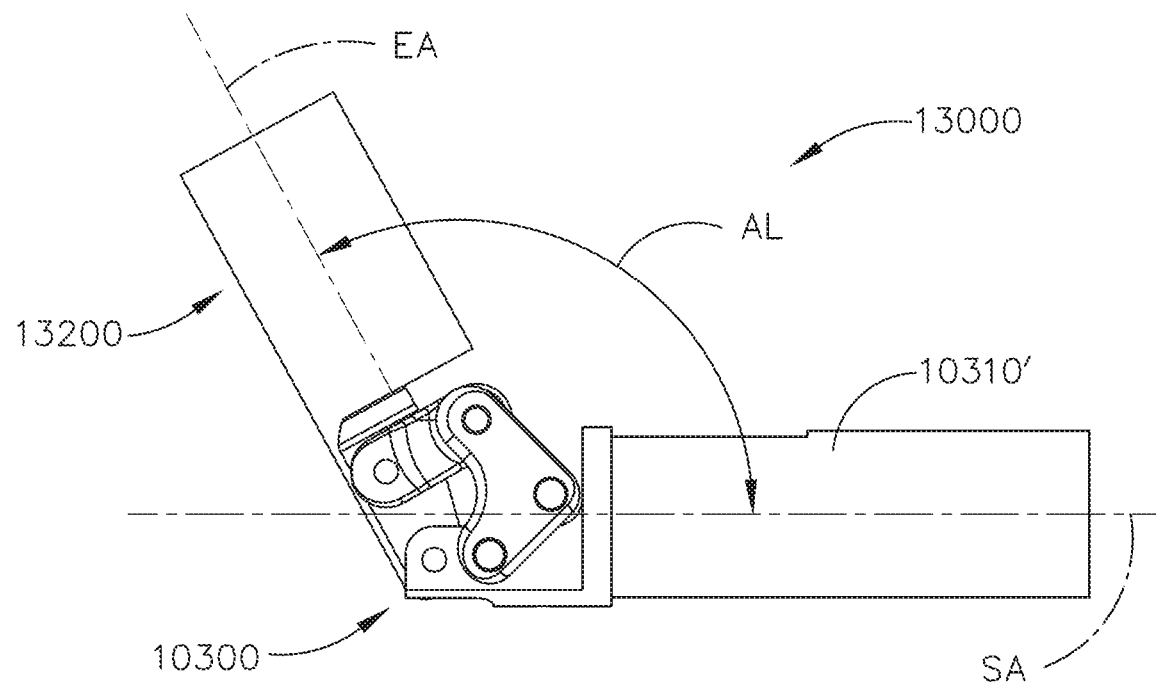
FIG. 57 is a partial side elevational view of a portion of an articulation joint of the surgical instrument of FIG. 56 articulated in a first direction.
Figure 58:
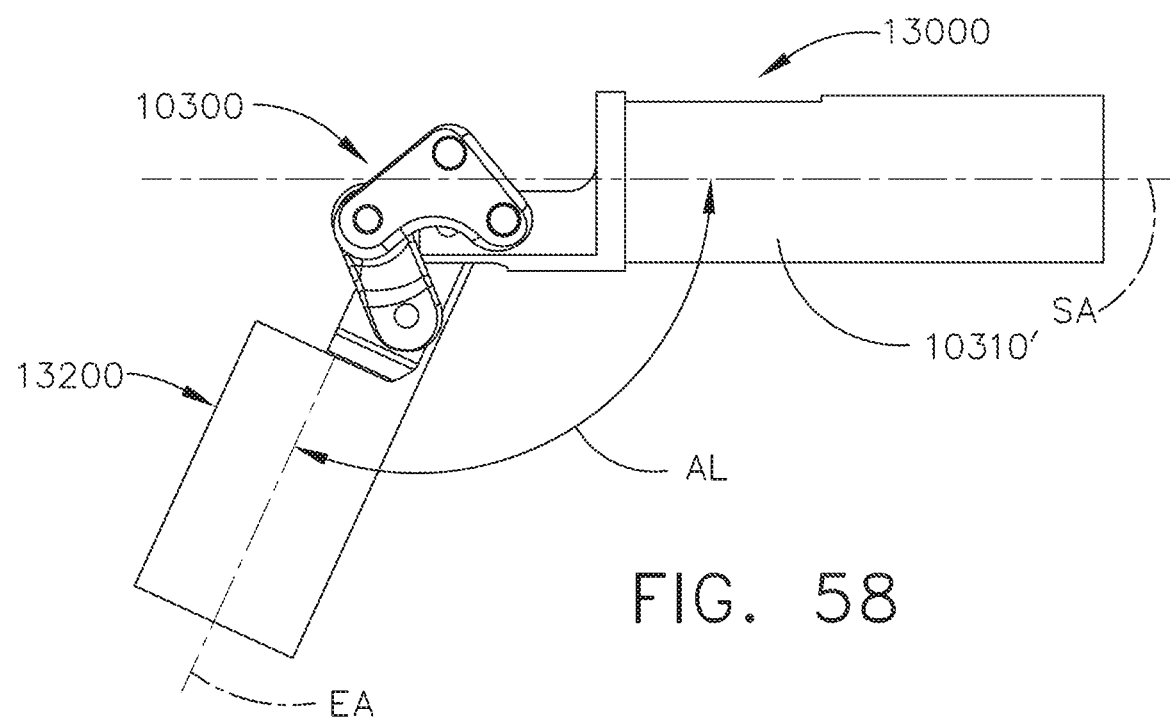
FIG. 58 is another partial side elevational view of the articulation joint of FIG. 56 articulated in a second direction.
Figure 59:
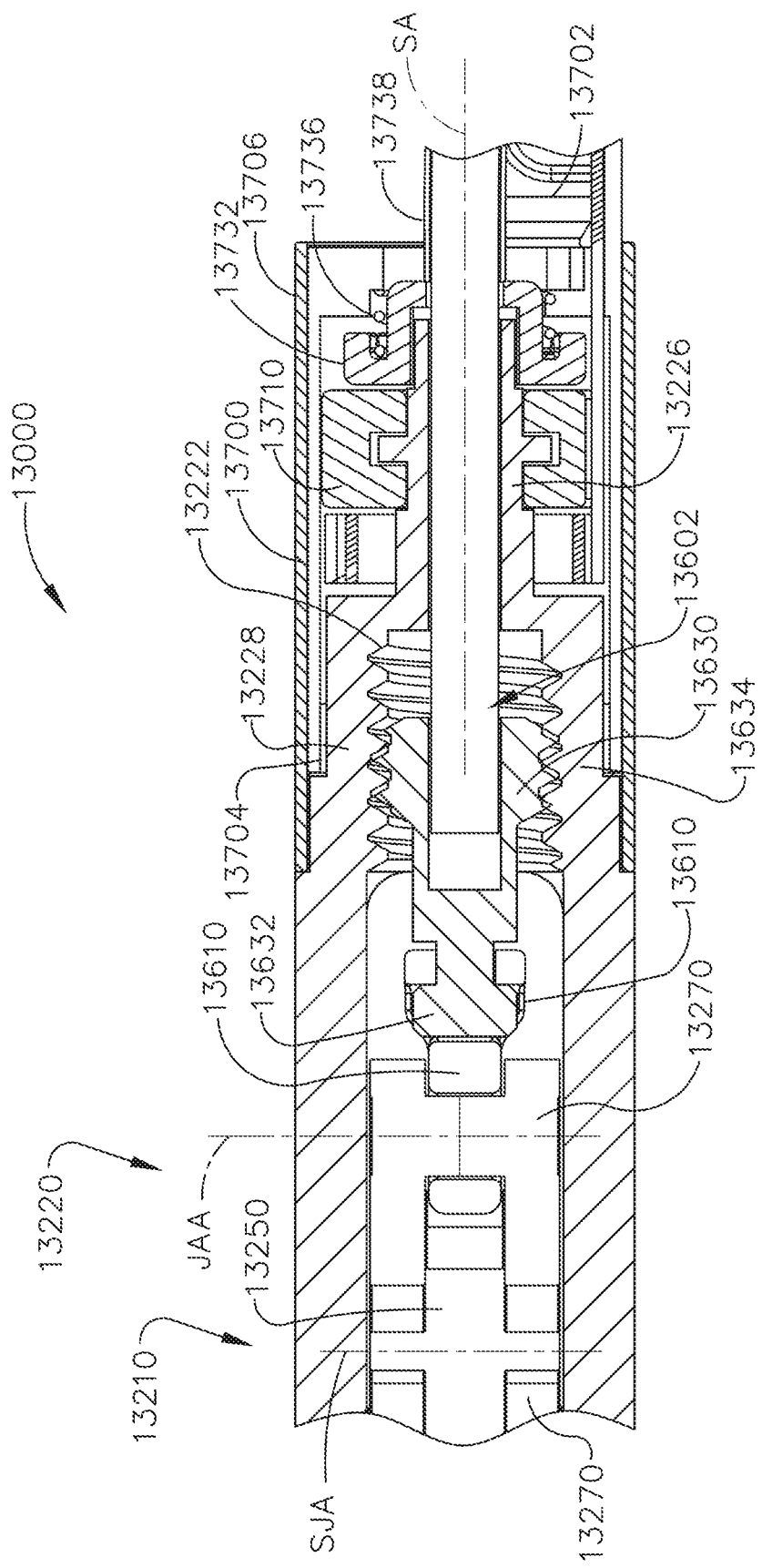
FIG. 59 is a partial cross-sectional side view of a portion of the surgical instrument of FIG. 56.
Figure 60:
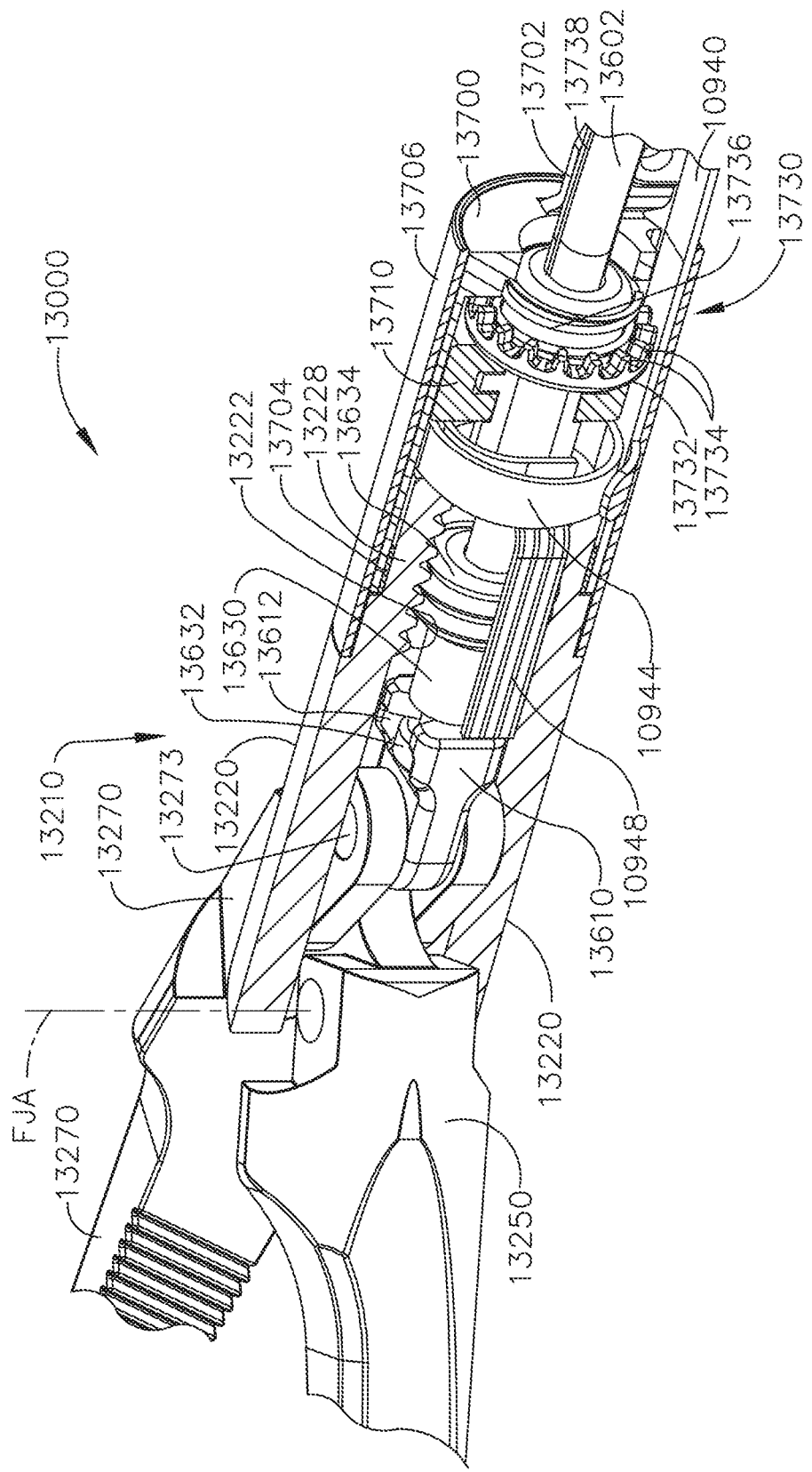
FIG. 60 is a partial perspective view of a portion of the surgical instrument of FIG. 56.
Figure 61:
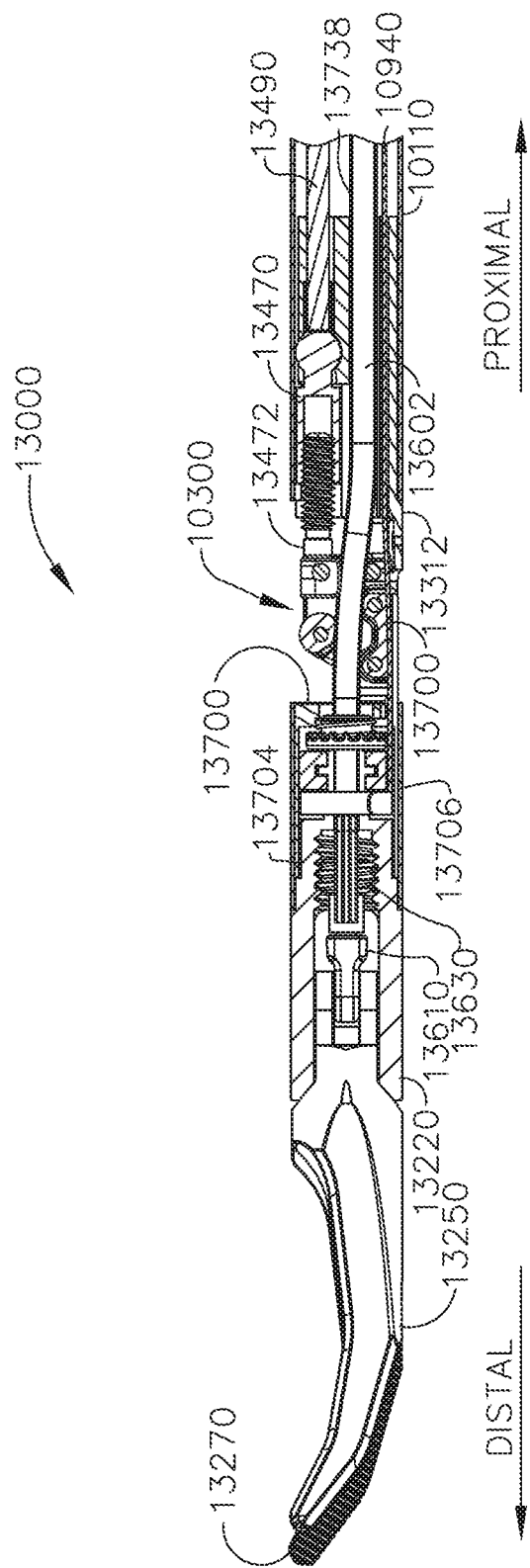
FIG. 61 is a cross-sectional side view of a portion of the surgical instrument of FIG. 56.
Figure 62:
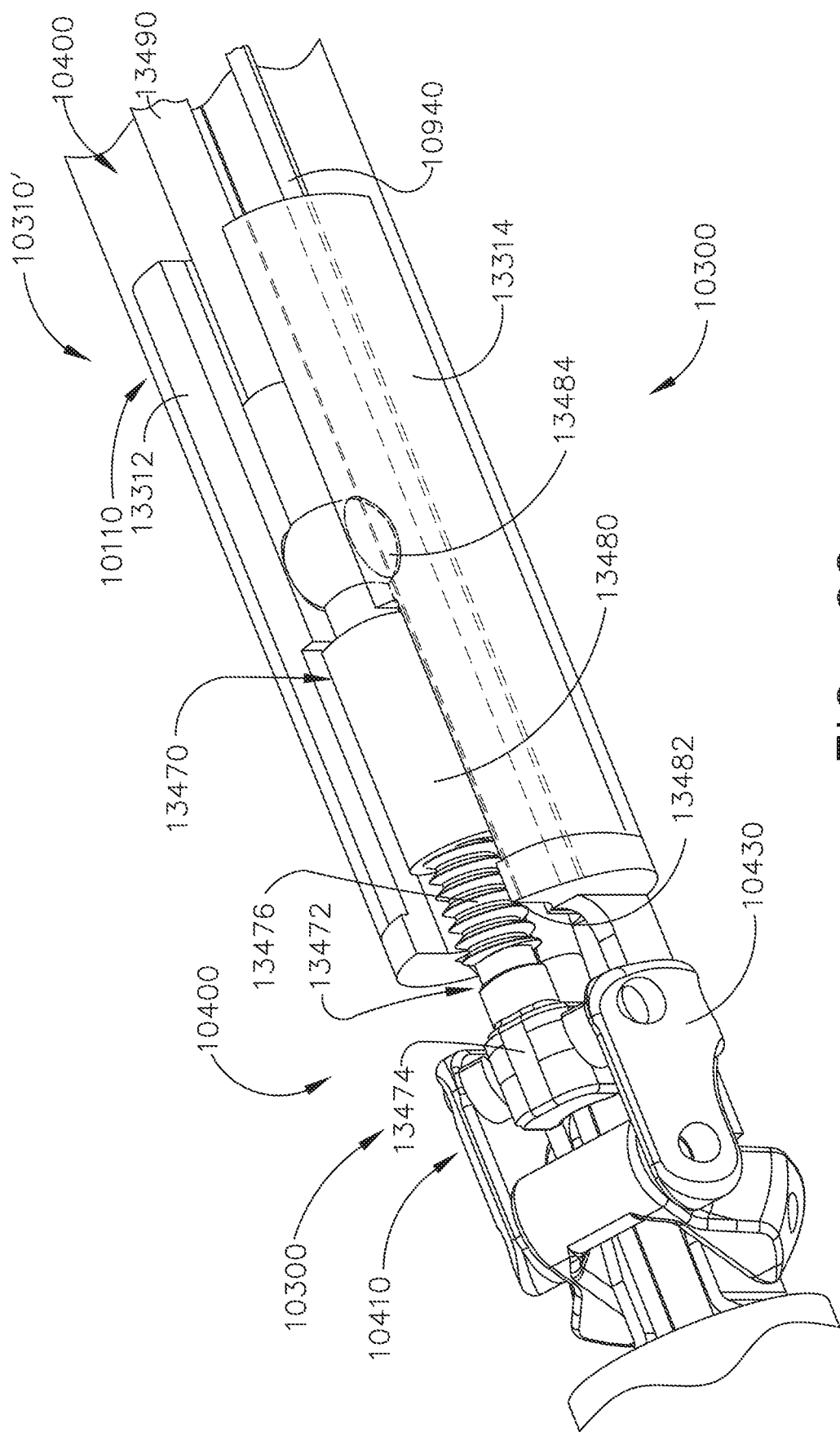
FIG. 62 is a partial perspective view of a portion of the surgical instrument of FIG. 56.
Figure 69:
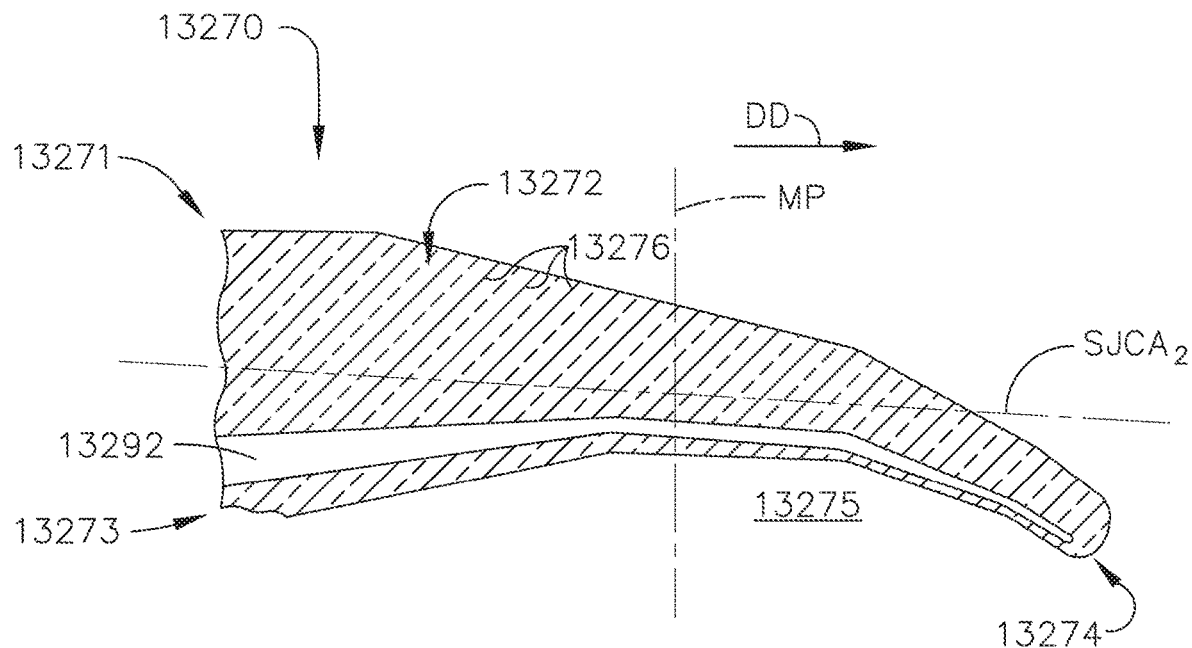
FIG. 69 is a cross-sectional view of a portion of a second jaw embodiment, in accordance with at least one aspect of the present disclosure.
Figure 68:
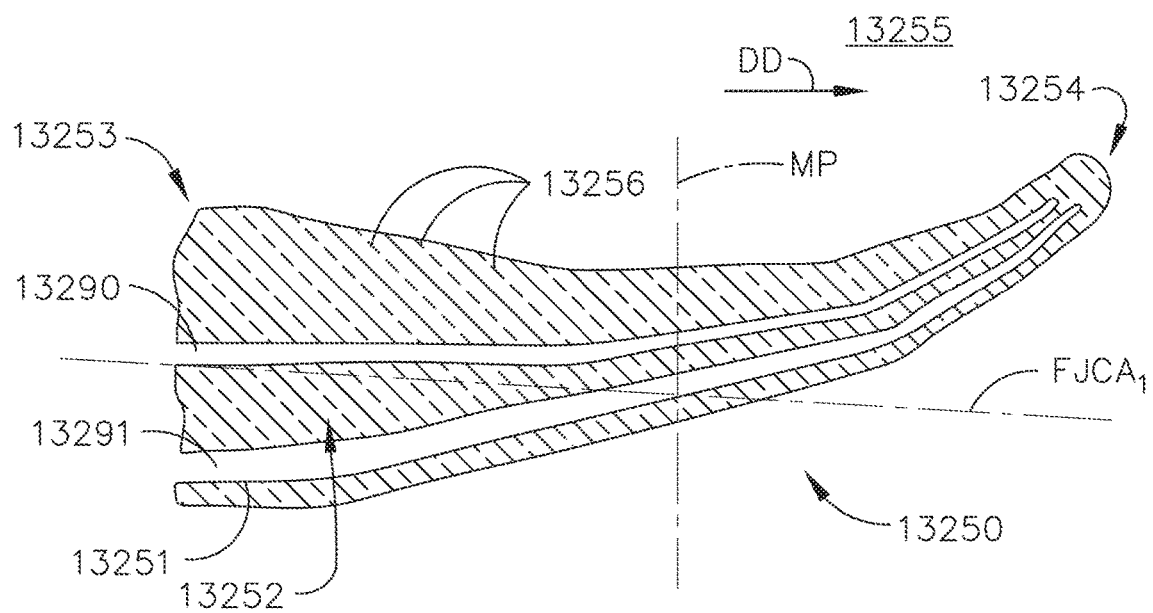
FIG. 68 is a cross-sectional view of a portion of a first jaw embodiment, in accordance with at least one aspect of the present disclosure.
Figure 70:
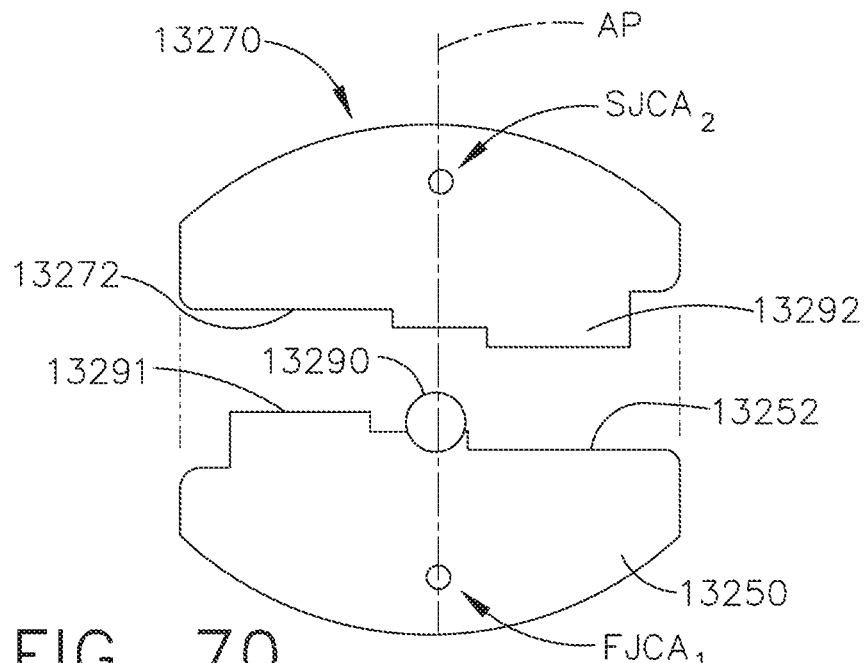
FIG. 70 is a cross-sectional end view of portions of a first jaw and a second jaw in alignment in a closed position, in accordance with at least one aspect of the present disclosure.
Figure 71:
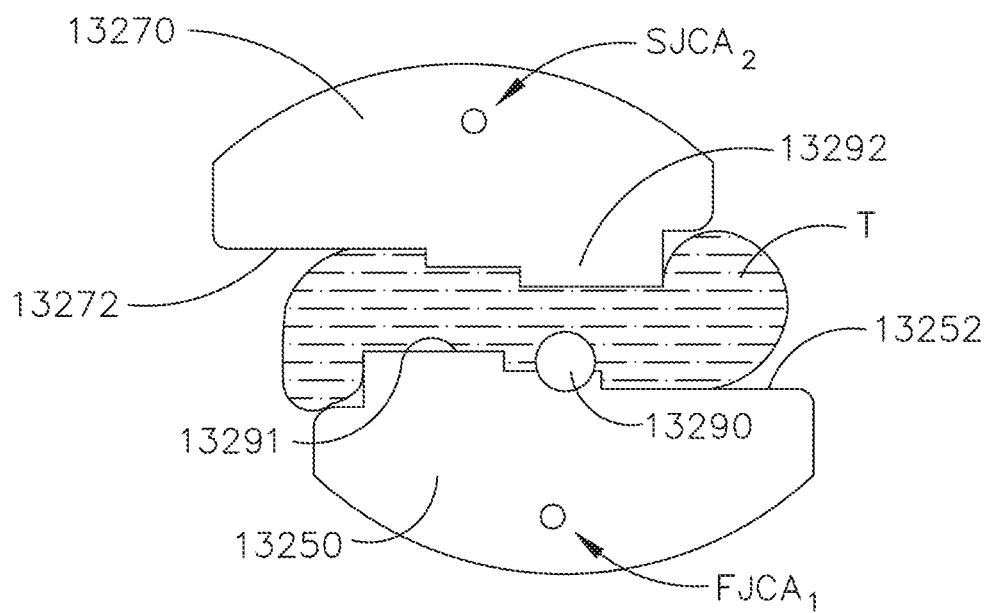
FIG. 71 is another cross-sectional end view of the first jaw and second jaw of FIG. 70 out of alignment while closing onto tissue.
Figure 72:
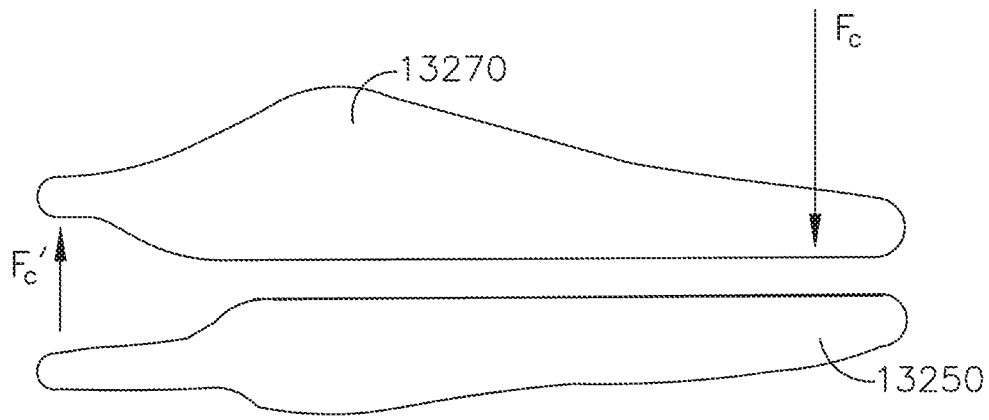
FIG. 72 is a diagrammatic depiction of a first jaw and a second jaw in a closed position, in accordance with at least one aspect of the present disclosure.
Figure 73:
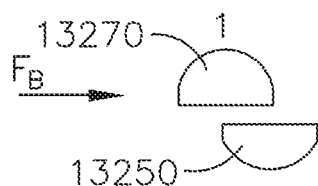
FIG. 73 is a cross-sectional end view of portions of the first jaw and second jaw of FIG. 72 out of alignment during closing.
Figure 74:
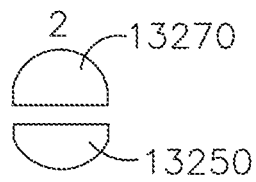
FIG. 74 is a cross-sectional end view of portions of the first jaw and the second jaw of FIG. 72 in alignment in a closed position.
Figure 75:
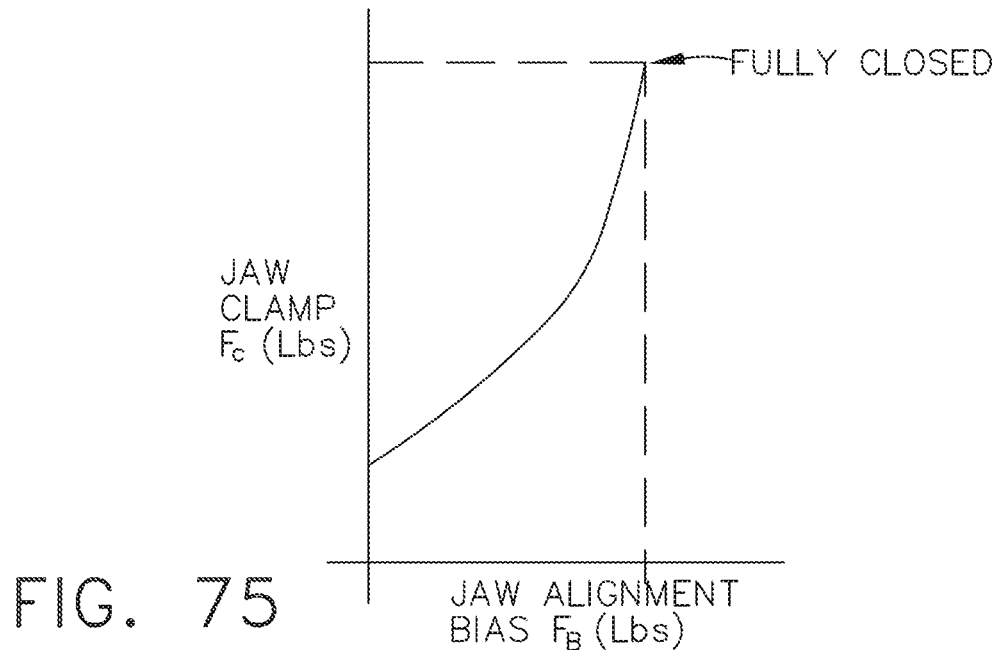
FIG. 75 is a graphical comparison between a jaw clamping force required to close a first jaw and a second jaw and an amount of jaw biasing force required to move the first and second jaws into alignment with each other as the first and second jaws move from an open position to a fully closed position, in accordance with at least one aspect of the present disclosure.
Figure 78:
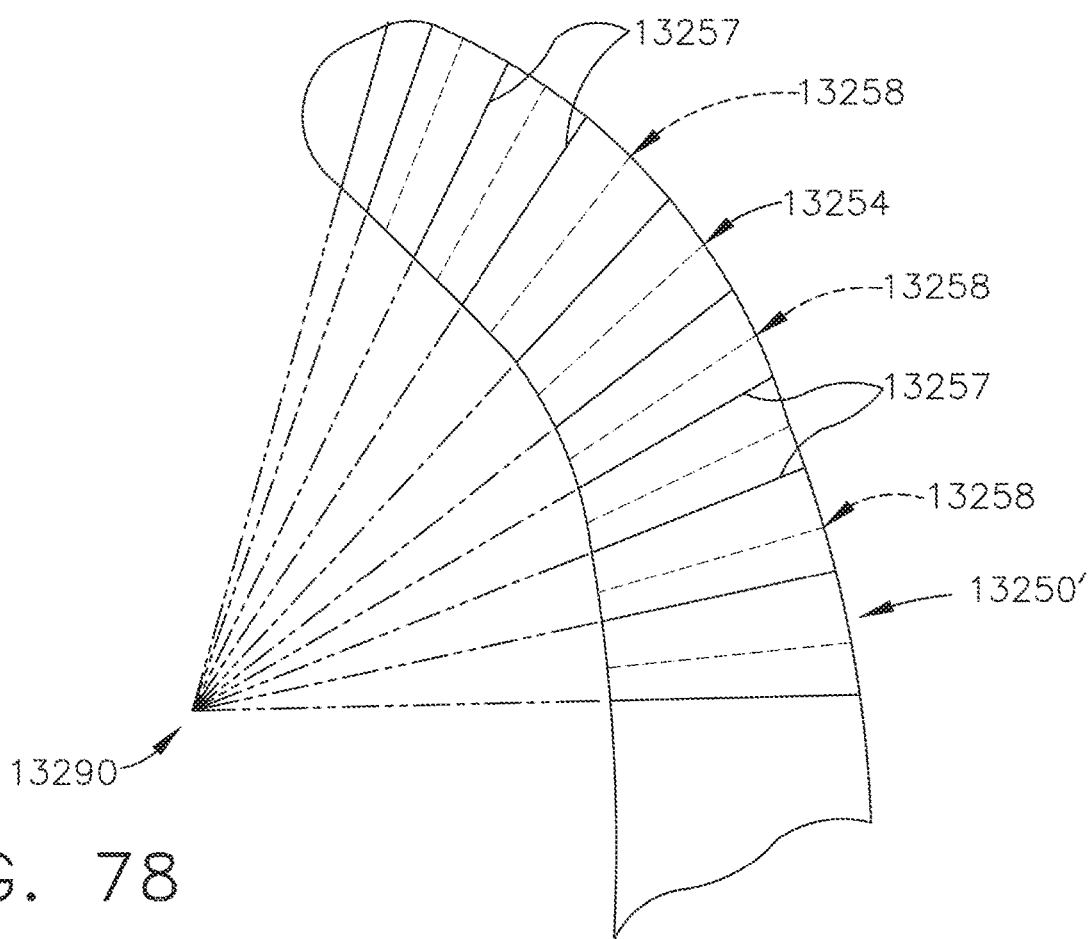
FIG. 78 is a top view of another first jaw, in accordance with at least one aspect of the present disclosure.
Figure 76:
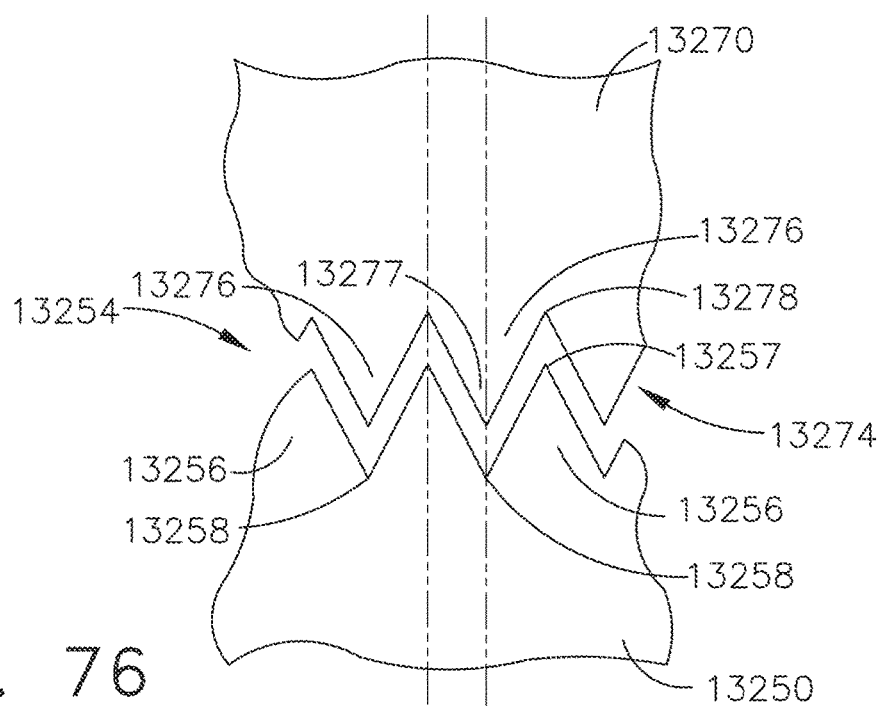
FIG. 76 is a partial cross-sectional view of a portion of a first jaw and a corresponding portion of a second jaw when the first jaw and second jaw are in a closed position, in accordance with at least one aspect of the present disclosure.
Figure 79:
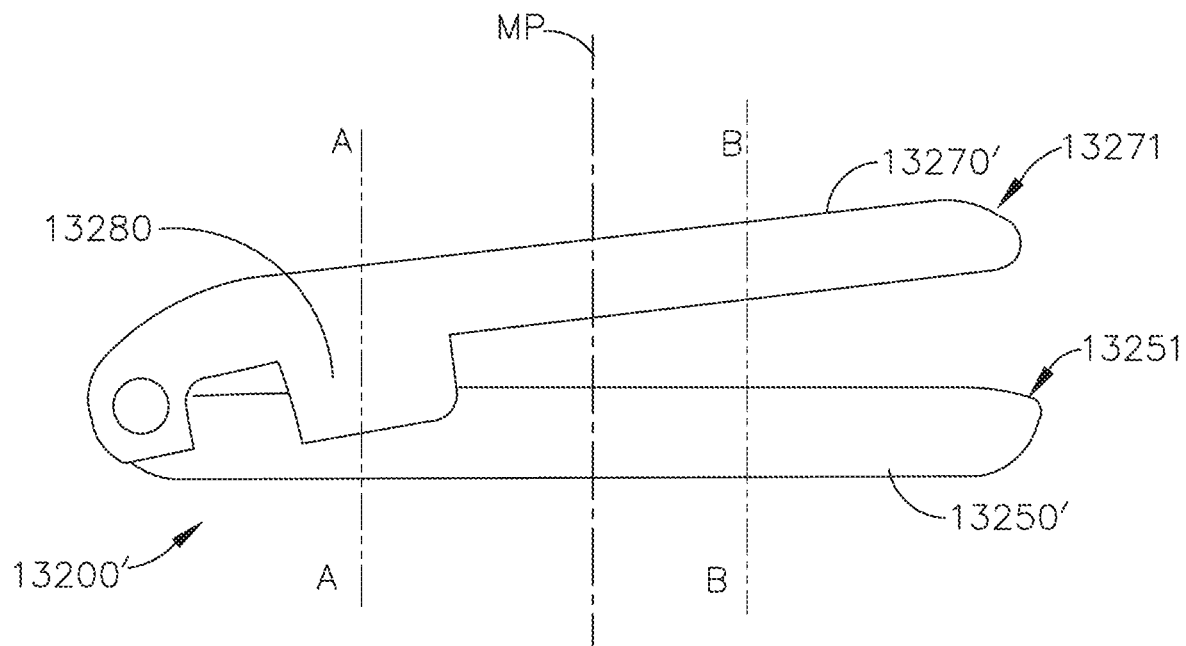
FIG. 79 is a diagrammatical side view of a surgical end effector embodiment with jaws thereof in an open position, in accordance with at least one aspect of the present disclosure.
Figure 80:
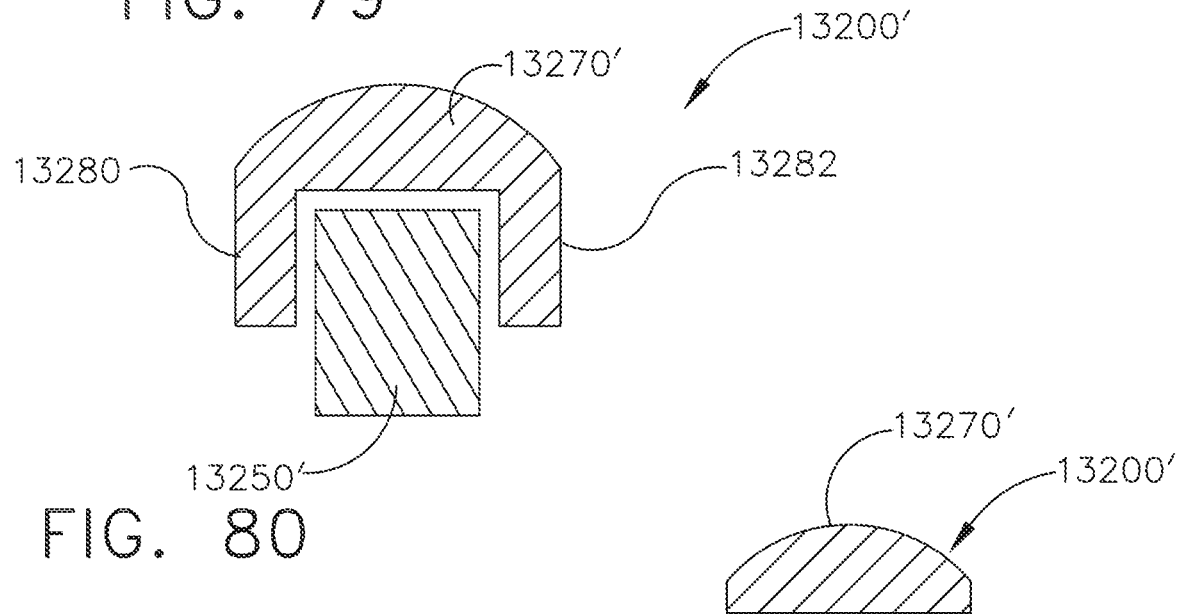
FIG. 80 is a cross-sectional end view of the surgical end effector of FIG. 79 taken along line A-A in FIG. 79.
Figure 81:
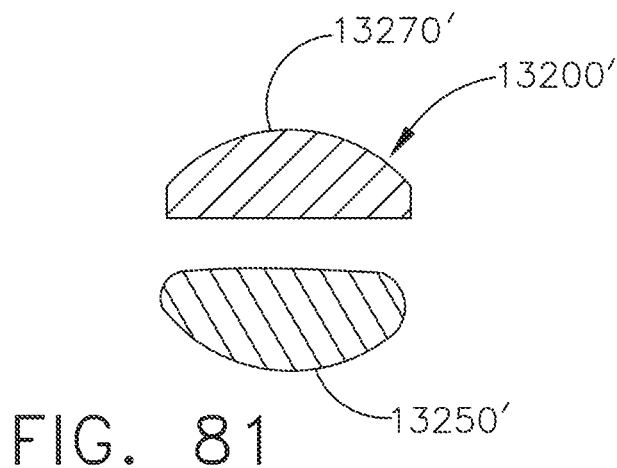
FIG. 81 is another cross-sectional end view of the surgical end effector of FIG. 79 taken along line B-B in FIG. 79.
Figure 82:
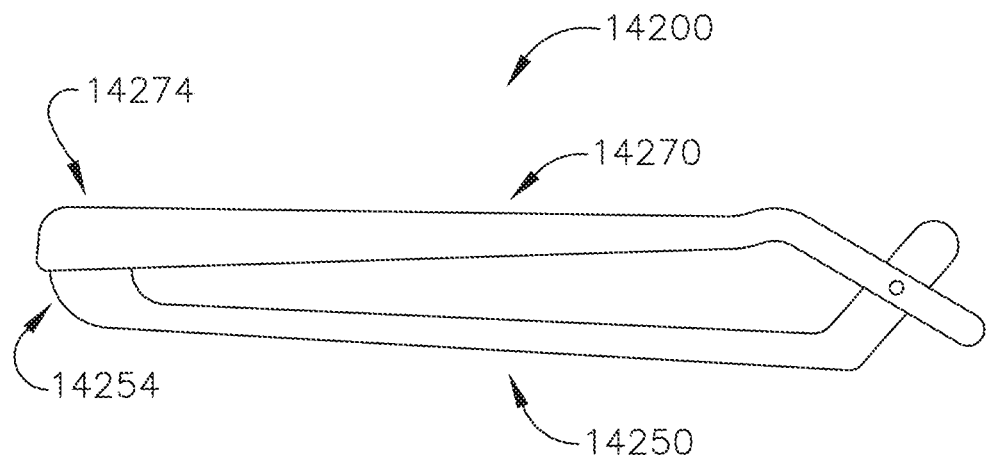
FIG. 82 is a side elevational view of another surgical end effector embodiment with jaws thereof in a closed position, in accordance with at least one aspect of the present disclosure.
Figure 83:
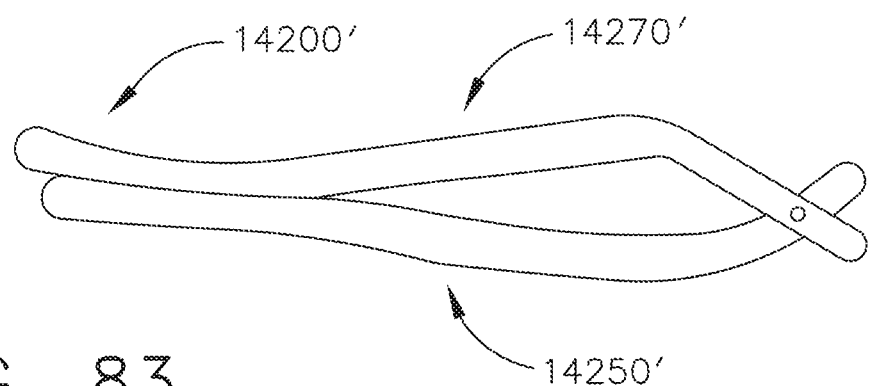
FIG. 83 is a side elevational view of another surgical end effector embodiment with jaws thereof in a closed position, in accordance with at least one aspect of the present disclosure.
Figure 84:
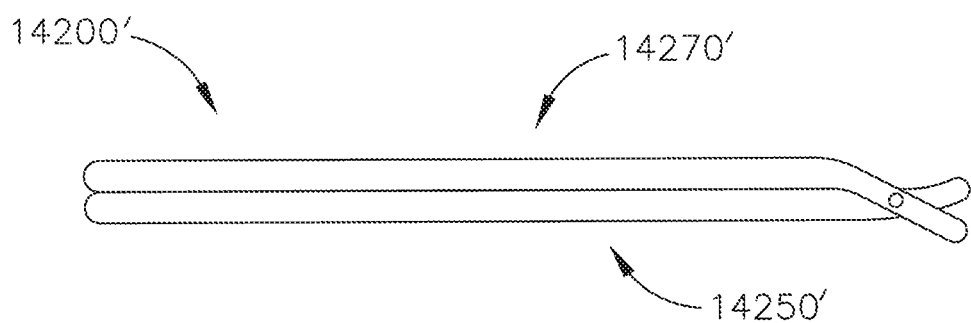
FIG. 84 is a side elevational view of the surgical end effector of FIG. 83 illustrating the jaws thereof in a fully closed position.
Figure 85:
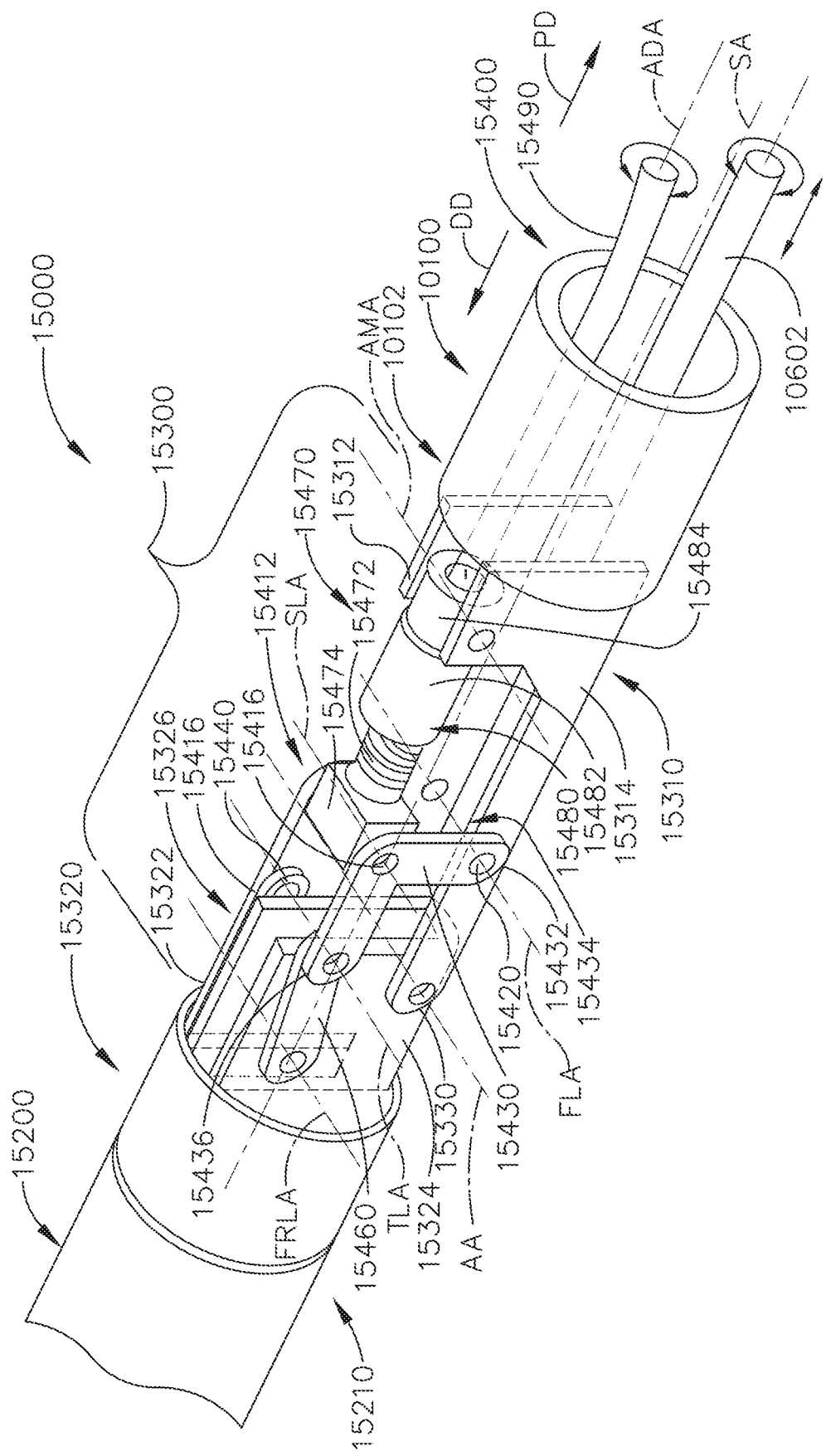
FIG. 85 is a partial perspective view of a portion of a surgical instrument, in accordance with at least one aspect of the present disclosure.
Figure 86:
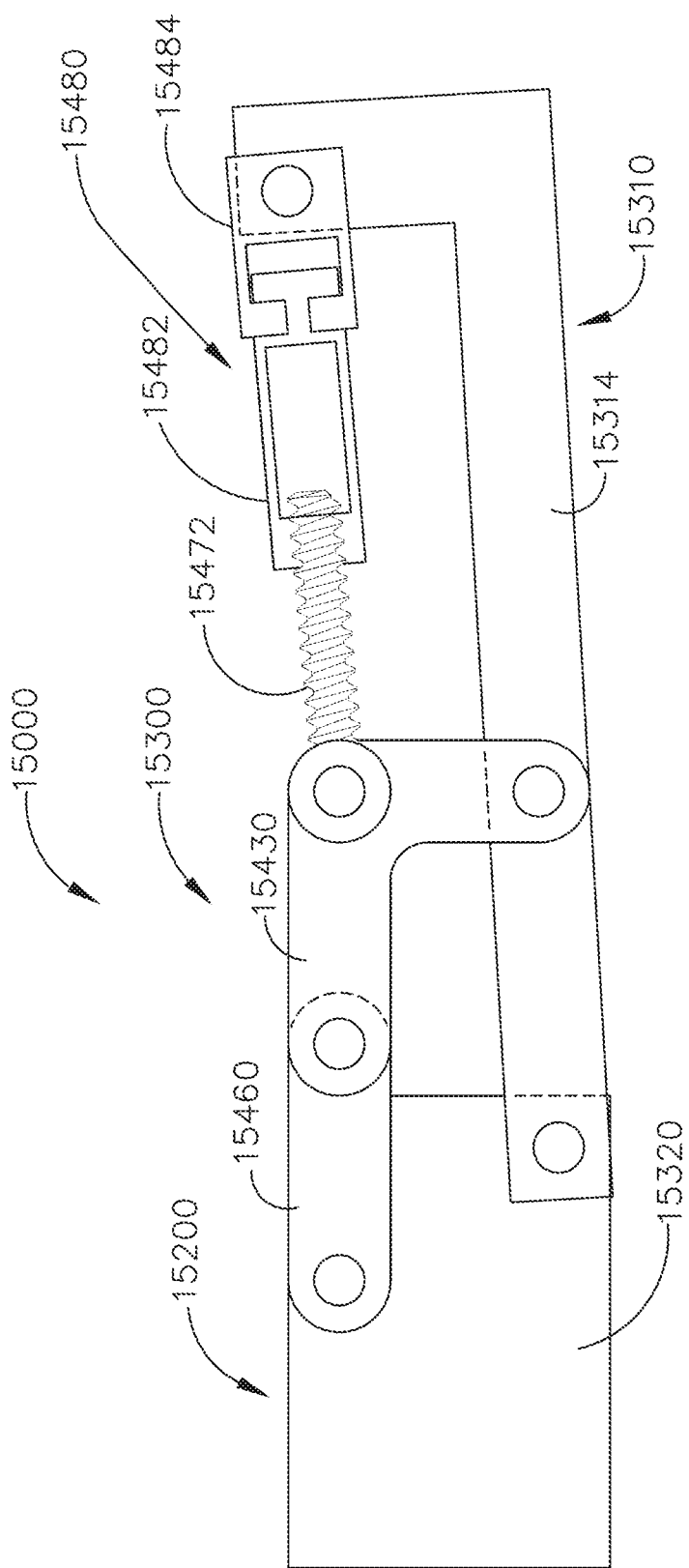
FIG. 86 is a side elevational view of a portion of the surgical instrument of FIG. 85.
Figure 87:
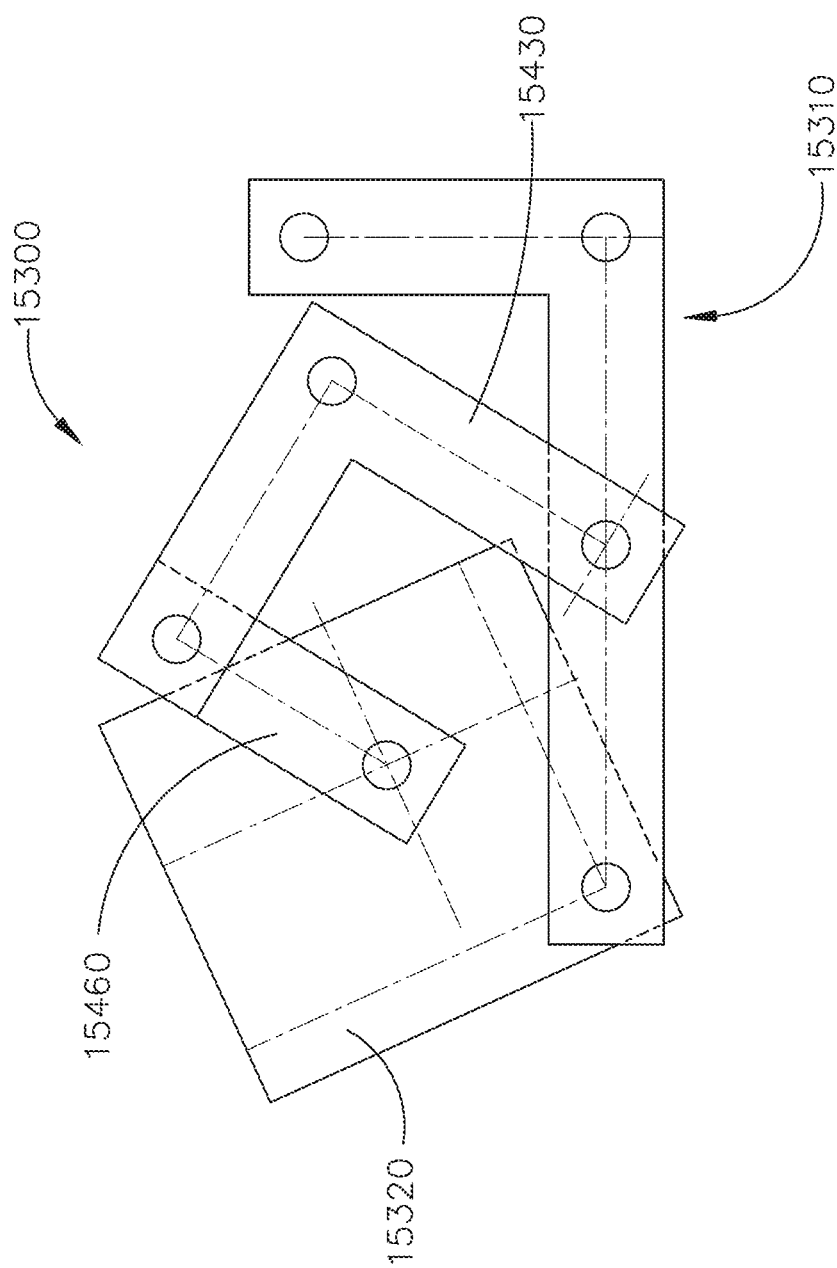
FIG. 87 is a finite element analysis of an articulation joint of the surgical instrument of FIG. 85 articulated in a first direction.
Figure 88:
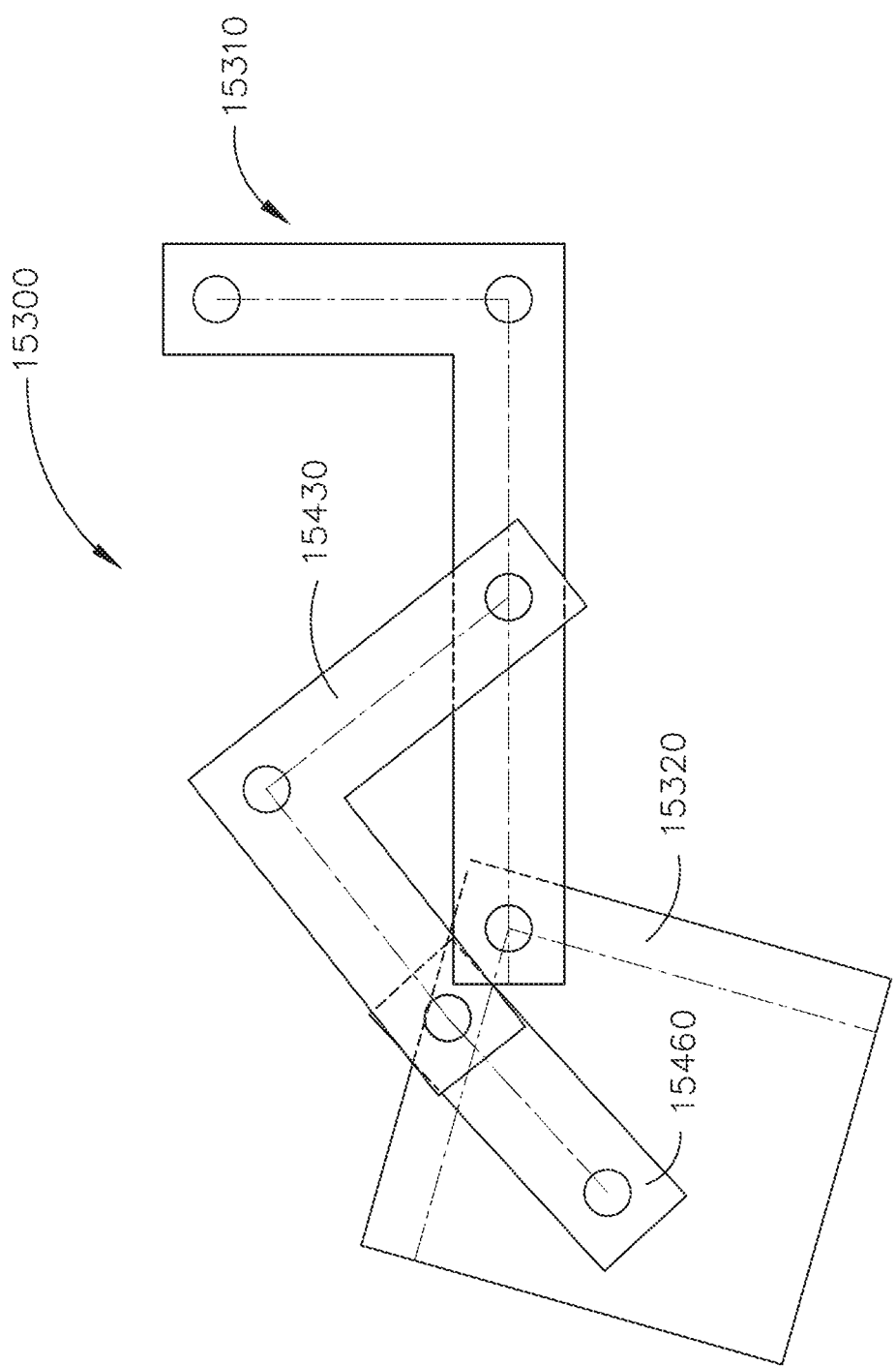
FIG. 88 is another finite element analysis of the articulation joint of the surgical instrument of FIG. 85 articulated in a second direction.
Figure 91:
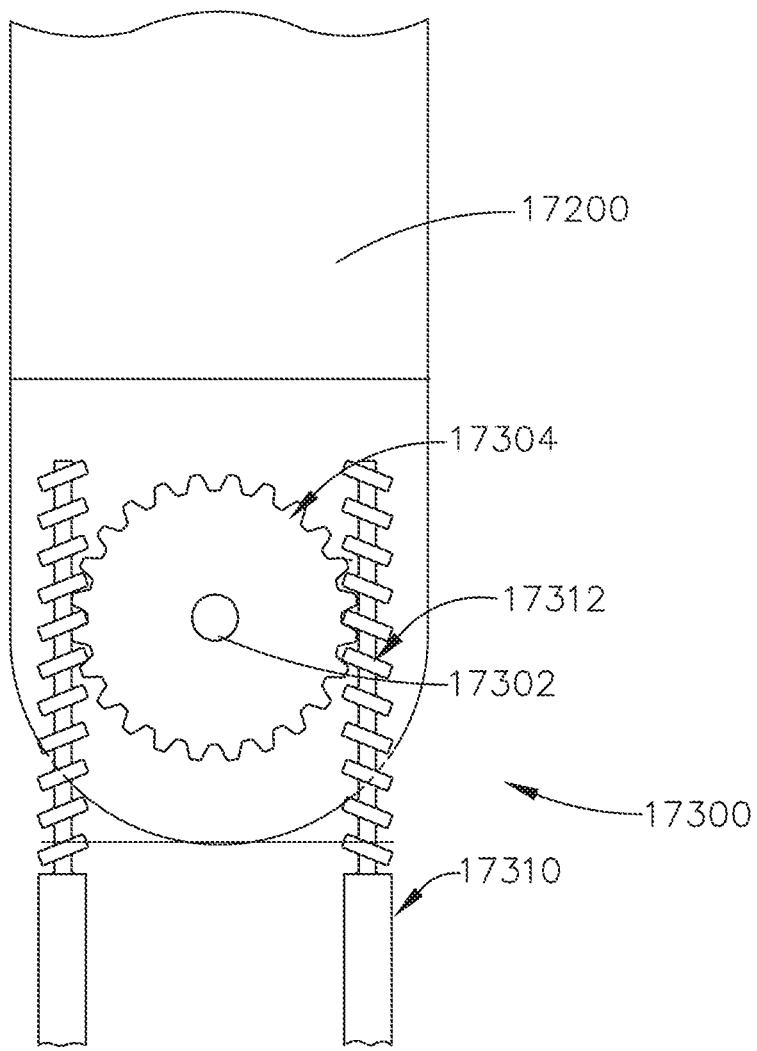
FIG. 91 is a partial view of another surgical instrument with a surgical end effector in an unarticulated position, in accordance with at least one aspect of the present disclosure.
Figure 92:
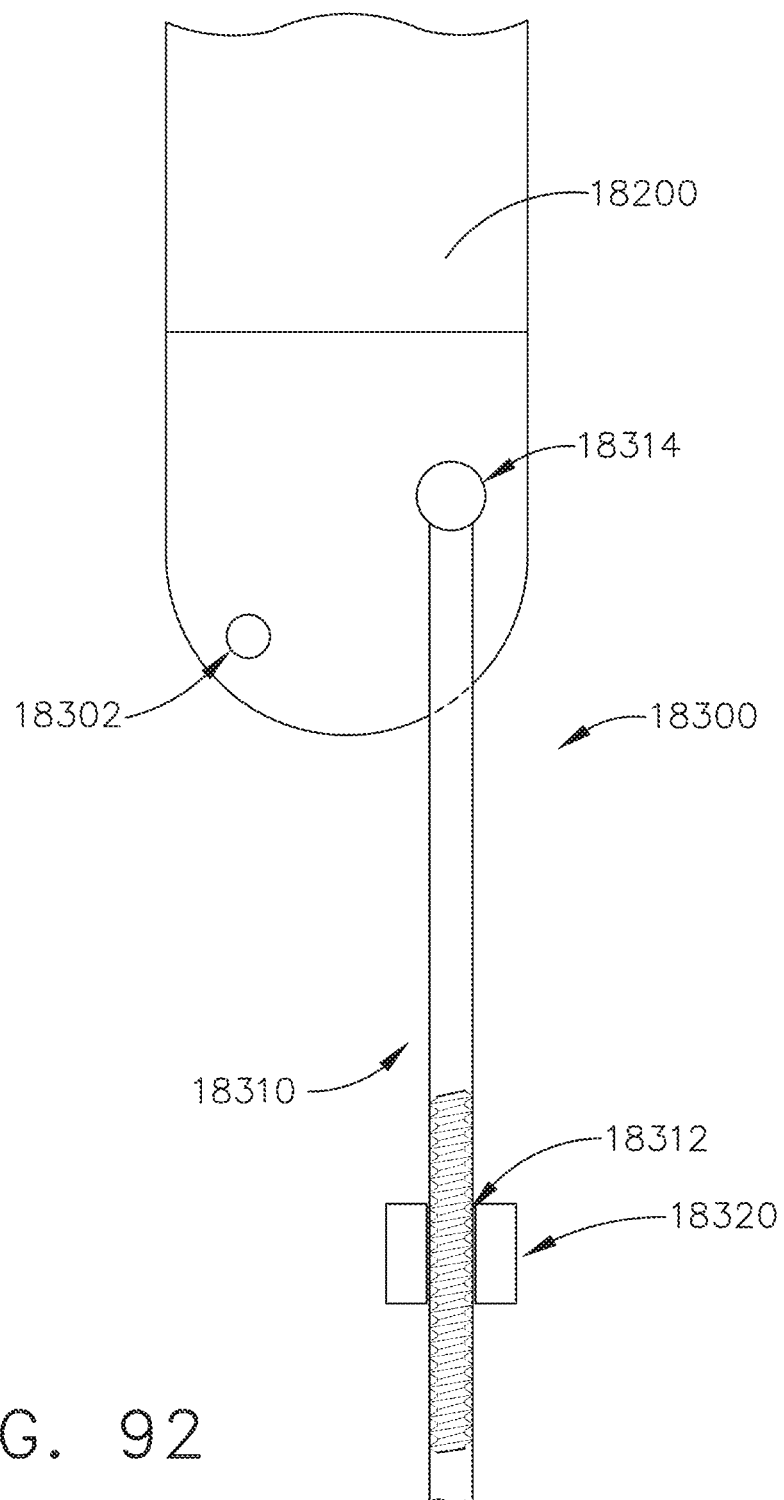
FIG. 92 is a partial view of another surgical instrument with a surgical end effector in an unarticulated position, in accordance with at least one aspect of the present disclosure.

As discussed above, the elongate shaft 40450 is crimped to the pull cable 40460. Thus, the pull cable 40460 is retracted when the rocker member 40440 is rotated in either the clockwise direction CW or the counter-clockwise direction CCW. The pull cable 40460 may be similar to the unlocking cable 11342 illustrated in FIG. 54. More specifically, the pull cable 40460, when retracted, (i.e., moved proximally) unlocks the end effector 40430 to permit the end effector 40430 to be rotated and/or articulated relative to the shaft 40420. Thus, when the rocker member 40440 is rotated in either the clockwise direction CW or the counter-clockwise direction CCW, the end effector 40430 is unlocked to allow for rotation and/or articulation of the end effector 40430.

Further to the above, the rocker member 40440 further comprises a downwardly extending post 40446 configured to engage a first switch 40447 and a second switch 40448 positioned on either side of the downwardly extending post 40446. The first switch 40447 and the second switch 40448 are configured to activate an articulation motor positioned within the handle 40410. More specifically, when the rocker member 40440 is rotated in the clockwise direction CW, the pull cable 40460 is retracted to unlock the end effector 40430 and the post 40446 engages the first switch 40447 resulting in rotation of the motor 40411a in a first direction which causes an articulation drive assembly 40417 to articulate the end effector 40430 to the right, for example. When the rocker member 40440 is rotated in the counter-clockwise direction CCW, the pull cable 40460 is retracted to unlock the end effector 40430. The post 40446 engages the second switch 40448 which results in the rotation of the motor 40411a in a second direction, opposite the first direction, thereby causing the articulation drive assembly 40417 to articulate the end effector 40430 to the left.

Further to the above, when the rocker member 40440 is centered, as illustrated in FIG. 193, neither the first switch 40447 nor the second switch 40448 are activated. The pull cable 40460 is in its distal most position corresponding to the end effector 40430 being locked, as discussed above. In various aspect, any suitable shifter or clutch mechanism can be configured to shift the drive member 40419 between an operable engagement with the articulation drive assembly 40417 and an operable engagement with a closure/firing assembly 40421. The shifter mechanism can be motivated by the rocker member 40440 such that the drive member 40419 is operably coupled to the closure/firing drive assembly 40421 when the rocker member 40440 is centered, and is operably coupled to the articulation drive assembly 40417 when the rocker member 40440 is rotated either the clockwise direction CW or the counter-clockwise direction CCW from the centered position.

When the end effector 40430 is locked, rotation of the electric motor in the handle 40410 results in rotation of the end effector drive member 40419 to cause the closure/firing drive assembly 40421 to move the pair of jaws of the end effector 40430 between the open and closed positions. However, other embodiments are envisioned where rotation of the end effector drive member 40419 translates a firing member through the end effector 40430 when the end effector 40430 is locked. In any event, when the rocker member 40440 is rotated in either the clockwise direction CW or the counter-clockwise direction CCW, the end effector 40430 is unlocked which allows for rotation of the end effector 40430 about the shaft axis SA. More specifically, when the end effector 40430 is unlocked, and the end effector drive member 40419 is actuated by the electric motor 40411a in the handle 40410, the end effector 40430 is rotated about the shaft axis SA relative to the shaft 40420.

Further to the above, other embodiments are envisioned with more than one articulation motor where the articulation motors are operably responsive to the first switch 40447 and the second switch 40448. Such an arrangement facilitates articulation of the end effector 40430 about multiple axes if a double articulation joint is employed between the end effector 40430 and the shaft 40420, for example. Other embodiments are also envisioned with separate motors dedicated to closure, firing, and/or articulation.

In various aspects, the motor driver 40411b is configured to operate the electric motor 40411a in a plurality of operating states based on input from the processor 40416. For example, when the end effector drive member 40419 is opening and closing the jaws of the end effector 40430 (i.e., the distal head or end effector 40430 is locked), the electric motor is in a first operating mode. When the electric motor 40411a is in the first operating mode, the end effector drive member 40419 is operated at a first speed, at a first rate, with a first amount of torque, and/or with a first amount of acceleration to open and close the jaws of the end effector 40430. When the end effector drive member 40419 is rotating the end effector 40430 about the shaft axis SA (i.e., the distal head or end effector 40430 is unlocked) the electric motor 40411a is in a second operating mode. When the electric motor 40411a is in the second operating mode, the end effector drive member 40419 is operated at a second speed, at a second rate, with a second amount of torque, and/or with a second amount of acceleration to rotate the end effector 40430.

In at least one embodiment, the first operating mode and the second operating mode are different and comprise different combinations of control parameters to drive the end effector drive member 40419 at different speeds, torques, and/or accelerations, for example. In at least one embodiment, the second operating mode (i.e., distal head rotation) comprises a lower max torque limit, a graduated acceleration to allow precise adjustments, and/or a lower max torque velocity than the first operating mode, for example. In contrast, the end effector drive member 40419 comprises a higher torque limit, comprises no, or limited, graduation of acceleration, and/or rotates at a faster speed in the first operating mode, for example.

In various aspects, the memory 40415 stores program instructions that, when executed by the processor 40416, cause the processor 40416 to select one of the first operating mode or the second operating mode. Various combinations of control parameters to drive the end effector drive member 40419 at different speeds, torques, and/or accelerations, for example, can be selected by the processor 40416 from a lookup table, algorithm, and/or equation stored in the memory 40415.

Further to the above, referring to FIG. 194, the control circuit 40413 controls the speed, torque, and/or accelerations of the articulation motor. The articulation motor is activated by the first switch 40447 and the second switch 40448 to articulate the end effector 40430 relative to the shaft axis SA, as discussed above. In at least one embodiment, the first switch 40447 and the second switch 40448 are adaptively controlled. The microcontroller 40414 can be in signal communication with the first switch 40447 and the second switch 40448 to provide proportional speed control of the motor 40411a to articulate the end effector 40430 based on the manual movements of the rocker member 40440. More specifically, the distance and/or or force by which the first switch 40447 or the second switch 40448 is depressed is directly proportional to the speed, torque, and/or acceleration with which the end effector 40430 is articulated. Alternatively, in certain examples, the switches 40447 and 40448 are directly in communication with the motor driver 40411b.

As illustrated in FIG. 194, various embodiments are envisioned wherein the surgical instrument 40400 comprises a transmission, a shiftable motor drive, and/or a shifter 40427 to lock two drive mechanisms together, such as the end effector drive shaft 40419 and the articulation drive assembly 40417 which drives articulation of the end effector 40430, for example, or lock the end effector drive shaft 40419 and the closure/firing drive assembly 40421. In such an arrangement, the surgical instrument 40400 comprises a single electric motor 40411a to drive articulation of the end effector 40430, rotate the end effector 40430 about the shaft axis SA, and open and close the jaws of the end effector 40430. More specifically, the shifter 40427 switches the single electric motor between engagement with the articulation drive assembly 40417 and the closure/firing drive assembly 40421.

In accordance with at least one embodiment, handle user controls of the motors and/or end-effector motions of a surgical instrument are in signal communication with a control system of the surgical instrument. The control system is housed within the handle and couples user trigger feedback to the motor driven feedback of the end-effector to provide proportionate, but not direct, control of the end-effector. In at least one embodiment, the control system provides indirect open loop control of the end-effector with an alternative means for providing clamp level feedback to the user. The surgical instrument comprises tactile feedback and a trigger sweep correlation. Further, the surgical instrument comprises feedback systems to the control system for monitoring alternative compression or pressure in the jaws to compensate for the removal of tactile feedback. In such an arrangement, the manual user inputs drive the jaws independent of the stroke of the trigger. In at least one embodiment, a smaller trigger that is finger sized with spring returns is utilized to improve the maneuverability of the manual controls and the handle. Further, in at least one embodiment, modular attachment of an electrical backbone to the surgical instrument is employed when a new single use shaft is introduced.

FIG. 200 illustrates a graph 40500 of a power schematic of a surgical system 40550 (FIG. 199) comprising an electrosurgical instrument 40551 and a power source (e.g. a power generator) 40552 configured to supply power to the electrosurgical instrument 40551. The electrosurgical instrument 40551 comprises an integrated, or self-contained, power source that works in concert with the separate power generator 40552 to power motors and other components of the electrosurgical instrument 40551. The integrated power source comprises a charge accumulator device such as a rechargeable, non-removable battery 40553, for example. The battery 40553 is configured to begin recharging as soon as the battery 40553 is attached to the power output from the generator 40552. The integrated power source can begin recharging during use within the procedure, for example. The integrated power source, or rechargeable battery, draws a constant power level from the power output generator 40552 regardless of the power being expended by the motors, controllers, and/or sensors until the rechargeable battery 40553 is charged to a maximum predetermined level. The battery 40553 can be simultaneously discharging to operate the controls or motors of the electrosurgical instrument 40551 and charging via the power output generator 40552. The battery 40553 continues to charge until it reaches a predetermined level in between user requested operations during generator initialization or in wait state in-between uses. If the battery 40553 drains to a minimum predetermined level, the user is notified that they have to wait an amount of time until the battery 40553 is charged above a minimum threshold level before the electrosurgical instrument 40551 can be used again.

Further to the above, the graph 40500 of FIG. 200 includes graphs 40502, 40504, 40506, 40508 including Y-axes representing various parameters of the surgical system 40550 plotted against time t on the X-axis. Graph 40502 depicts on the Y-axis power in Watts (W) supplied by a generator 40552 to a power source (e.g. internal charge accumulator such as a rechargeable battery 40553) of the electrosurgical instrument. Graph 40504 depicts on the Y-axis the charge level of the battery 40553 as a percentage of a maximum charge level threshold. Graph 40506 depicts on the Y-axis power in Watts (W) drawn from the battery 40553 by components of the surgical instrument 40551 such as, for example, a motor 40554. Graph 40508 depicts on the Y-axis motor velocity limits set as a percentage of a maximum motor-velocity threshold.

In the illustrated example, the electrosurgical instrument 40551 is connected to the generator 40552 at a time $t_0$. The generator 40552 charges the rechargeable battery 40553 at a constant recharge rate ($S_1$) until the charge level of the battery 40553 reaches a maximum threshold at 100%, which is achieved at $t_1$. The power supply by the generator 40552 is automatically started upon connecting the surgical instrument 40551 to the generator 40552, and is automatically stopped once the charge level reaches the maximum threshold. In various examples, the surgical system 40550 includes a control circuit 40555 that comprises a charge meter 40556 for detecting the charge level of the battery 40553, and a switching mechanism for deactivating the power supply to the surgical instrument 40551 when the charge level reaches the maximum threshold. In at least one example, the battery can be charged at a constant rate of 15 W. The generator will automatically stop charging the battery 40553 when the battery charge level has reached 100%.

Further, at time $t_2$, the motor 40554 is activated to cause an end effector 40557 of the surgical instrument 40551 to perform one or more functions. The motor 40554 draws power from the battery 40553 causing the battery 40553 to discharge at a rate $S_2$. The battery 40553 continues to charge while discharging power to the motor 40554. Accordingly, the rate of discharge $S_2$ is derived from a combination of the rate of discharge of the battery 40553 caused by the motor draw of power from the battery and the rate of charge of the battery 40553 by power supplied to the battery 40553 by the generator 40552, which occur concurrently, or simultaneously, until the motor 40554 is deactivated. Once the power draw by the motor 40554 is stopped, the battery 40553 returns to recharging at the constant rate $S_1$.

In the illustrated example, the motor 40553 is activated at first and second instances 40501, 40503, as depicted in Graph 40506, to open and close the jaws of the end effector 40557 to grasp tissue, for example. A clinician may open and close the jaws a number of times to achieve a good grasp of the tissue. At the end of the second instance 40503 of the motor activation, the battery 40553 returns to recharging at the constant rate $S_1$ up to the 100% charge level achieved at $t_3$, at which point the power supplied by the generator 40552 to the battery 40553 is stopped. Further, a third instance 40505 of the motor activation, to articulate the end effector 40557, causes the battery 40553 to discharge at a rate $S_3$ from time $t_0$ to time $t_5$. The end effector closure/opening and articulation can be driven by the same or different motors that draw power from the battery 40553.

Further, as depicted in graphs 40504, 40506, fourth, fifth, sixth, and seventh instances 40507, 40509, 40511, 40513 of motor activations cause the charge level of the battery 40553 to reach and cross a first predetermined minimum threshold (e.g. 40%) and a second predetermined minimum threshold (e.g. 20%). A motor driver/controller 40558 of the electrosurgical instrument 40551, which is in signal communication with the generator 40552 and the battery 40553, maintains the motor velocity limit at 100% until the battery charge level is reduced to the first predetermined threshold level. When the charge level of the battery 40553 is reduced to a first predetermined level, for example 40% at time $t_6$, the motor controller 40558 reduces the motor velocity limit (e.g. to 50%) to conserve battery power. Accordingly, when the battery charge level is at 40% and the jaws of the end effector 40557 are actuated, the instrument will close the jaws of the end effector 40557 at first a reduced speed, which causes the time period $t_b$ of the motor activation instance 40509 to greater than the time period $t_a$ of the motor activation instance 40507. Further, when the charge level is reduced to a second predetermined level, for example 20% at time $t_7$, the motor controller 40558 reduces the velocity limit of the motor to 25% to further conserve the battery power. When the battery charge level is at 20% and the jaws of the end effector 40557 are actuated, the instrument clamps the jaws of the end effector 40557 at a second reduced speed that is less than the first reduced speed, which causes the time period $t_c$ of the motor activation instance 40513 to greater than the time period $t_b$ of the motor activation instance 40509. Accordingly, the motor controller 40558 causes the motor to perform similar functions at different speeds based on corresponding charge levels of the battery 40553 supplying power to the motor 40554.

Further, when the charge level of the battery 40553 is reduced to a predetermined minimum level, for example 10% at time $t_8$, the motor velocity limit is reduced to zero and the surgical instrument alerts the clinician to wait until the battery 40553 is charged above a predetermined minimum level, for example 40% at time $t_9$. When the battery 40553 has been re-charged from 10% to 40% and the jaws of the end effector 40557 are actuated at a motor activation instance 40515, the surgical instrument 40551 will move the jaws of the end effector 40557 at the first reduced speed for a time period $t_d$ that is less than the time period ta. Upon completion of the activation instance 40515, at the end of the time period $t_d$, the battery 40553 commences recharging at the constant recharging rate $S_1$ until it reaches the maximum charge level at $t_{10}$ at which point the power supply from the generator 40552 to the battery 40553 is stopped.

FIG. 199 is a simplified schematic diagram of the surgical system 40550 that includes a control circuit 40550 that has a microcontroller 40560 including a processor 40561 and a memory 40562 that stores program instructions. When the program instructions are executed, the program instructions cause the processor 40561 to detect a charge level of the battery 40553. In at least one example, the processor 40561 is in communication with a charge meter 40556 configured to measure the charge level of the battery 40553. Further, detecting that the charge level of the battery 40553 is equal to or less than a first minimum charge level threshold (e.g. 40%) while the motor 40554 is in operation causes the processor to reduce a maximum velocity limit of the motor 40554 to a first maximum threshold. In at least one example, the processor 4056 is in communication with a motor driver 40558 configured to control the velocity of the motor 40554. In such example, the processor 40561 signals the motor driver 40558 to reduce the motor velocity limit of the motor 40554 to first maximum threshold. Alternatively, in other examples, the processor 40561 may directly control the maximum motor velocity limit.

Further, detecting that the charge level of the battery 40561 is equal to or less than a second minimum charge level threshold (e.g. 20%) while the motor 40554 is in operation causes the processor to reduce the maximum velocity limit of the motor 40554 to a second maximum threshold less than the first maximum threshold. In addition, detecting that the charge level of the battery 40553 is equal to or less than a third minimum charge level threshold (e.g. 10%) while the motor 40554 is in operation causes the processor to reduce the maximum velocity limit of the motor 40554 to zero or stop the motor 40554. The processor 40561 may prevent the restart of the motor 40554 until the minimum charge level is equal to or greater than a predetermined threshold such as, for example, the second minimum charge level threshold (e.g. 20%).

In certain examples, the processor 40561 may further employ one or more feedback systems 40563 to issue an alert to a clinician. In certain instances, the feedback systems 40563 may comprise one or more visual feedback systems such as display screens, backlights, and/or LEDs, for example. In certain instances, the feedback systems 40563 may comprise one or more audio feedback systems such as speakers and/or buzzers, for example. In certain instances, the feedback systems 40563 may comprise one or more haptic feedback systems, for example. In certain instances, the feedback systems 40563 may comprise combinations of visual, audio, and/or haptic feedback systems, for example.

Further to the above, in at least one embodiment, the internal battery is charged in-between surgical procedures and/or during surgical procedures by an external charge accumulation device, or by an external battery attached to the surgical instrument. In at least one embodiment, the external battery comprises disposable batteries which are introduced into the sterile field in sterile packaging and attached to the surgical instrument to supplement the internal battery and/or to replace the internal battery, for example. In at least one embodiment, the external battery is the sole operational power source for controlling the mechanical operating systems while radio frequency (RF) power for the therapeutic treatment of tissue is supplied by the power generator, for example. In such an arrangement, the external battery is connected to the surgical instrument when the internal battery is insufficient to power the device. More specifically, the external battery is used cooperatively with the internal battery rather than in place of it. Further, in at least one embodiment, the external battery comprises disposable batteries which are connected to the internal battery of the surgical instrument when the surgical instrument is not performing a surgical procedure to charge the internal battery. The external battery is then disconnected from the surgical instrument for later use by the clinician if supplemental power is required.

FIG. 201 illustrates a surgical system 40600 comprising a surgical instrument 40610, a monopolar power generator 40620, and a bipolar power generator 40630. In the illustrated embodiment, the monopolar power generator 40620 is electrically coupled directly to a motor 40650 of the surgical instrument 40610 and the bipolar power generator 40630 is electrically coupled directly to the battery 40640. The bipolar power generator 40630 is configured to charge the battery 40640 which in turn supplies power to the motor 40650. The monopolar power generator 40620 is configured to supply power directly to the motor 40650 and charge the battery 40640. More specifically, an additional electrical connection 40660 is supplied between the monopolar power generator 40620 and the battery to allow the monopolar power generator 40620 to supply power to the motor 40650 while also supplying power to the battery 40640 to charge the battery 40640. The monopolar power generator 40620 and the bipolar power generator 40630 are configured to output DC power to the battery 40640 and the motor 40650.

In various aspects, the surgical instrument 40610 includes an end effector 40611. The motor 40650 is operably coupled to the end effector 40611, and can be activated to cause the end effector 40611 to perform a plurality of functions such as, for example, causing at least one of the jaws of 40613, 40614 of the end effector 40611 to move to transition the end effector 40611 between an open configuration, as illustrated in FIG. 201, and a closed configuration to grasp tissue therebetween. Further, the end effector 40611 extends distally from a shaft 40615, and is articulatable relative to the shaft 40611 about a longitudinal axis extending centrally through the shaft 40615 by actuation motions generated by the motor 40650.

In addition, the surgical instrument 40610 further includes a power supply assembly 40616 that routes power from the generators 40620 and 40630 to the motor 40650 and/or the battery 40640. In at least one example, the power supply assembly 40616 separately receives a first power from the generator 40620 and a second power from the generator 40630. The power supply assembly 40616 is configured to route the second power to the battery 40640 to charge the battery at a constant rate (S1) up to a maximum predetermined charge level. The power supply assembly 40616 is further configured to route the first power to the electric motor 40650 and the battery 40640. In the illustrated example, the motor 40650 is concurrently, or simultaneously, powered by the battery 40640 and the generator 40620.

FIG. 202 illustrates a graph 40700 of the battery charge percentage and the motor torque of the surgical system 40600. Line 40710 represents the battery charge percentage of the battery 40640 if only the bipolar power generator 40630 is utilized with the surgical instrument 40610. Line 40720 represents the combined battery charge percentage when both the monopolar power generator 40620 and the bipolar power generator 40630 are utilized with the surgical instrument 40610. When both the monopolar power generator 40620 and the bipolar power generator 40630 are used to charge the battery 40640, the battery 40640 is charged faster than if only one of the monopolar power generator 40620 and the bipolar power generator 40630 were used to charge the battery 40640. Further, line 40730 represents the motor torque of the motor 40650 if only the bipolar power generator 40630 is utilized with the surgical instrument 40610. Line 40740 represents the motor torque of the motor 40650 when both the monopolar power generator 40620 and the bipolar power generator 40630 are utilized with the surgical instrument 40610. When both the monopolar power generator 40620 and the bipolar power generator 40630 are used to power the motor 40650, the motor 40650 can produce more torque as compared to if only one of the monopolar power generator 40620 and the bipolar power generator 40630 were used to power the motor 40650.

Further to the above, other embodiments are envisioned where the monopolar power generator 40620 is configured to supply power only to the motor 40650 and the bipolar power generator 40630 is configured to charge the battery 40640 which in turn supplies additional power to the motor 40650 (i.e., the monopolar power generator 40620 does not charge the battery 40640). Further, other embodiments are envisioned where both the monopolar power generator 40620 and the bipolar power generator 40630 are used solely to charge the battery 40640 which in turn supplies power to the motor 40650, for example. In such an arrangement, both the monopolar power generator 40620 and the bipolar power generator 40630 could be synchronized to charge the battery 40640 in unison which is in turn used to operate the motor 40650. In at least one embodiment, more than one motor may be utilized to drive the end effector 40611 of the surgical instrument 40610. In such an arrangement, the monopolar power generator 40620 can supply power to one of the motors and the bipolar power generator 40630 can supply power to another of the motors. Further, both the monopolar power generator 40620 and the bipolar power generator 40630 are used to charge the battery 40640 which in turn can be used to power the motors. However, other embodiments are envisioned where only one of the monopolar power generator 40620 and the bipolar power generator 40630 are used to charge the battery 40640.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method for performing an electrosurgical procedure using an electrosurgical instrument, the method comprising:
   articulating an end effector of the electrosurgical instrument relative to a shaft of the electrosurgical instrument, wherein the end effector is articulated toward a target tissue;
   causing the end effector to transition to a closed configuration, wherein the target tissue is grasped by jaws of the end effector in the closed configuration;
   reversibly moving an electrode by the target tissue relative to the jaws of the end effector; and
   performing an energy treatment cycle to coagulate and cut the target tissue, wherein the energy treatment cycle comprises:
   executing a tissue-feathering segment by applying a bipolar energy to the target tissue;
   executing a tissue-warming segment following the tissue-feathering segment by continuing to apply the bipolar energy while additionally applying a monopolar energy to the target tissue, thereby applying an energy blend of the bipolar energy and the monopolar energy to the target tissue, wherein the monopolar energy is applied to the target tissue through the electrode;
   executing a tissue-sealing segment following the tissue-warming segment by continuing to apply the energy blend to the target tissue while increasing a monopolar power level of a monopolar generator and decreasing a bipolar power level of a bipolar generator; and
   executing a tissue-cutting segment following the tissue-sealing segment by discontinuing the bipolar energy but continuing to apply the monopolar energy to the target tissue.

2. The method of claim 1, wherein articulating the end effector stretches portions of a flexible wiring assembly of the electrosurgical instrument.

3. The method of claim 1, wherein articulating the end effector moves portions of a flexible wiring assembly of the electrosurgical instrument.

4. The method of claim 1, wherein executing the tissue-feathering segment by applying the bipolar energy comprises gradually raising the bipolar power level of the bipolar generator.

5. The method of claim 1, wherein applying the energy blend comprises simultaneously applying the bipolar energy and the monopolar energy to the target tissue.

6. The method of claim 1, wherein executing the tissue-cutting segment by continuing to apply the monopolar energy to the target tissue comprises stepping up the monopolar power level of the monopolar generator.

7. The method of claim 1, wherein discontinuing the bipolar energy comprises:
   gradually decreasing the bipolar power level of the bipolar generator to a non-therapeutic power level; or
   gradually decreasing the bipolar power level of the bipolar generator until the application of the bipolar energy is terminated.

8. The method of claim 1, wherein executing the tissue-sealing segment following the tissue-warming segment by continuing to apply the energy blend to the target tissue comprises gradually decreasing the bipolar power level of the bipolar generator while gradually increasing the monopolar power level of the monopolar generator.

9. A method for performing an electrosurgical procedure using an electrosurgical instrument including an end effector, the method comprising:
   applying a bipolar energy to a target tissue grasped by the end effector in a tissue-feathering segment;
   continuing to apply the bipolar energy while additionally applying a monopolar energy to the target tissue, thereby applying an energy blend of the bipolar energy and the monopolar energy to the target tissue in a tissue-warming segment following the tissue-feathering segment;
   continuing to apply the energy blend to the target tissue while increasing a monopolar power level of a monopolar generator and decreasing a bipolar power level of a bipolar generator in a tissue-sealing segment following the tissue-warming segment; and discontinuing the bipolar energy but continuing to apply the monopolar energy to the target tissue in a tissue-cutting segment following the tissue-sealing segment.

10. The method of claim 9, further comprising articulating the end effector relative to a shaft of the electrosurgical instrument, thereby stretching portions of a flexible wiring assembly of the electrosurgical instrument.

11. The method of claim 9, further comprising articulating the end effector relative to a shaft of the electrosurgical instrument, thereby moving portions of a flexible wiring assembly of the electrosurgical instrument.

12. The method of claim 9, wherein applying the bipolar energy in the tissue-feathering segment comprises gradually raising the bipolar power level of the bipolar generator.

13. The method of claim 9, wherein applying the energy blend comprises simultaneously applying the bipolar energy and the monopolar energy to the target tissue.

14. The method of claim 9, wherein applying the monopolar energy to the target tissue in the tissue-cutting segment comprises stepping up the monopolar power level of the monopolar generator.

15. The method of claim 9, wherein discontinuing the bipolar energy comprises:
   gradually decreasing the bipolar power level of the bipolar generator to a non-therapeutic power level; or
   gradually decreasing the bipolar power level of the bipolar generator until the application of the bipolar energy is terminated.

16. The method of claim 9, wherein continuing to apply the energy blend in the tissue-sealing segment comprises gradually decreasing the bipolar power level of the bipolar generator while gradually increasing the monopolar power level of the monopolar generator during the tissue-sealing segment.

17. A method for operating an electrosurgical system in a tissue treatment cycle applied to a target tissue by an electrosurgical instrument of the electrosurgical system, the method comprising:
   gradually increasing a bipolar power level of a bipolar generator of the electrosurgical system to a predetermined bipolar power level in a first portion of a tissue-feathering segment of the tissue treatment cycle;
   maintaining the predetermined bipolar power level in a second portion of the tissue-feathering segment;
   gradually increasing a monopolar power level of a monopolar generator of the electrosurgical system to a predetermined monopolar power level in a first portion of a tissue-warming segment of the tissue treatment cycle;
   maintaining the predetermined bipolar power level and the predetermined monopolar power level in a second portion of the tissue-warming segment;
   gradually increasing the monopolar power level of the monopolar generator from the predetermined monopolar power level to beyond the predetermined monopolar power level while gradually decreasing the bipolar power level of the bipolar generator from the predetermined bipolar power level to below the predetermined bipolar power level in a tissue-sealing segment of the tissue treatment cycle; and
   stepping up the monopolar power level of the monopolar generator in a tissue-cutting segment of the tissue treatment cycle.

* * * * *